(12) United States Patent
Zetterberg et al.

(10) Patent No.: US 11,939,349 B2
(45) Date of Patent: *Mar. 26, 2024

(54) GALACTOSIDE INHIBITOR OF GALECTINS

(71) Applicant: GALECTO BIOTECH AB, Copenhagen (DK)

(72) Inventors: Fredrik Zetterberg, Copenhagen (DK); Kristoffer Peterson, Lund (SE); Karl Jansson, Lund (SE)

(73) Assignee: GALECTO BIOTECH AB, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/869,107

(22) Filed: Jul. 20, 2022

(65) Prior Publication Data
US 2022/0380401 A1    Dec. 1, 2022

Related U.S. Application Data

(63) Continuation of application No. 17/295,556, filed as application No. PCT/EP2019/081539 on Nov. 15, 2019, now Pat. No. 11,447,517.

(30) Foreign Application Priority Data

Nov. 21, 2018   (EP) ..................... 18207503
Oct. 4, 2019    (EP) ..................... 19201571

(51) Int. Cl.
*A61K 31/7052*   (2006.01)
*C07H 19/056*    (2006.01)
*C07H 19/23*     (2006.01)
*C07H 19/24*     (2006.01)

(52) U.S. Cl.
CPC ....... *C07H 19/056* (2013.01); *A61K 31/7052* (2013.01); *C07H 19/23* (2013.01); *C07H 19/24* (2013.01)

(58) Field of Classification Search
None
See application file for complete search history.

(56) References Cited

U.S. PATENT DOCUMENTS 11,072,626 B2 *   7/2021   Jalagam ............... C07H 19/052
11,447,517 B2 *   9/2022   Zetterberg ............ A61P 11/00
2017/0349619 A1  12/2017   Brimert et al.

FOREIGN PATENT DOCUMENTS

WO   2016/120403 A1   8/2016
WO   2018/011094 A1   1/2018
WO   2019/075045 A1   4/2019

OTHER PUBLICATIONS

Rajput Vishal Kumar et al: "Synthesis and evaluation of iminocoumaryl and coumaryl derivatized glycosides as galectin antagonists", Bioorganic & Medicinal Chemistry Letters, Pergamon, Amsterdam, NL, vol. 24, No. 15, Jun. 9, 2014 (Jun. 9, 2014), pp. 3516-3520.

Almkvist, J., Faldt, J., Dahlgren, C., Leffler, H., and Karlsson, A. (2001) Lipopolysaccharide—induced gelatinase granule mobilization primes neutrophils for activation by galectin-3 and f-Met-Leu-Phe. Infect. Immun. vol. 69: 832-837.

Barondes, S. H., Cooper, D. N. W., Gitt, M. A., and Leffler, H. (1994). Galectins. Structure and function of a large family of animal lectins. J. Biol. Chem. 269:20807-20810.

Blois, S.M., Ilarregui, J.M., Tometten, M., Garcia, M., Orsal, A.S., Cordo-Russo, R., Toscano, M.A., Bianco, G.A., Kobelt, P., Handjiski, B., et al. (2007). A pivotal role for galectin-1 in fetomaternal tolerance. Nat Med 13: 1450-1457.

Chen, W.-S., Leffler H., Nilsson, U. J., Panjwani, N. (2012). Targeting Galectin-1 and Galectin-3 Attenuates VEGF-A-Induced Angiogenesis; Mol. Biol. Cell (suppl), Abstract No. 2695.

Cumpstey, I., Carlsson, S., Leffler, H. and Nilsson, U. J. (2005) Synthesis of a phenyl thio-ß-D-galactopyranoside library from 1,5-difluoro-2,4-dinitrobenzene: discovery of efficient and selective monosaccharide inhibitors of galectin-7. Org. Biomol. Chem. 3: 1922-1932.

Cumpstey, I., Sundin, A., Leffler, H. and Nilsson, U. J. (2005) C2-Symmetrical thiodigalactoside bis-benzamido derivatives as high-affinity inhibitors of galectin-3: Efficient lectin inhibition through double arginine-arene interactions. Angew. Chem. Int. Ed. 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. Chem. Eur. J. 14: 4233-4245.

Dam, T.K., and Brewer, C.F. (2008). Effects of clustered epitopes in multivalent ligand-receptor interactions. Biochemistry 47: 8470-8476.

Delacour, D., Greb, C., Koch, A., Salomonsson, E., Leffler, H., Le Bivic, A., and Jacob, R. (2007). Apical Sorting by Galectin-3-Dependent Glycoprotein Clustering. Traffic 8: 379-388.

Delaine, T., Cumpstey, I., Ingrassia, L., Le Mercier, M., Okechukwu, P., Leffler, H., Kiss, R., and Nilsson, U.J. (2008). Galectin-Inhibitory Thiodigalactoside Ester Derivatives Have Anti-Migratory Effects in Cultured Lung and Prostate Cancer Cells. J Med Chem 51; 8109-8114.

Demotte, N., Wieers, G., van der Smissen, P., Moser, M., Schmidt, C., Thielemans, K., et al., "A Galectin-3 Ligand Corrects the Impaired Function of Human CD4 and CD8 Tumor-Infiltrating Lymphocytes and Favors Tumor Rejection in Mice" (2010). Cancer Res. 70; 7476-7488.

(Continued)

*Primary Examiner* — Traviss C McIntosh, III
(74) *Attorney, Agent, or Firm* — Maier & Maier, PLLC

(57) ABSTRACT

A compound of the general formula (1). The compound of formula (1) is suitable for use in a method for treating a disorder relating to the binding of a galectin, such as galectin-3 to a ligand in a mammal, such as a human. Also, a method for treatment of a disorder relating to the binding of a galectin, such as galectin-3 to a ligand in a mammal, such as a human.

16 Claims, No Drawings

(56) References Cited

OTHER PUBLICATIONS

Farkas, I.; Szabo, I. F.; Bognar, R.; Anderle, D. Carbohydr. "Synthesis of 1,2-trans-glycopyranosyl chlorides using the dichloromethyl methyl ether-boron trifluoride etherate reagent" Res. 1976, 48, 136-138.
Garner, O.B., and Baum, L.G. (2008). Galectin-glycan lattices regulate cell-surface glycoprotein organization and signalling. Biochem Soc Trans 36: 1472-1477.
Giguere, D., Patnam, R., Bellefleur, M.- A., St.-Pierre, C., Sato, S., and Roy, R. (2006). Carbohydrate triazoles and soxazoles as inhibitors of galectins-1 and -3. Chem Commun: 2379-2381.
Glinsky, G.V., Price, J.E., Glinsky, V.V., Mossine, V.V., Kiriakova, G., and Metcalf, J.B. "Inhibition of Human Breast Cancer Metastasis in Nude Mice by Synthetic Glycoamines" (1996). Cancer Res 56: 5319-5324.
Glinsky, V.V., Kiriakova, G., Glinskii, O.V., Mossine, V.V., Mawhinney, T.P., Turk, J.R., Glinskii, A.B., Huxley, V.H., Price, J.E., and Glinsky, G.V. (2009). Synthetic Galectin-3 Inhibitor Increases Metastatic Cancer Cell Sensitivity to Taxol-Induced Apoptosis In Vitro and In Vivo. Neoplasia 11; 901-909.
Huflejt, M. E. and Leffler, H. (2004) Galectin-4 in normal tissues and cancer. Glycoconj. J. 20: 247-255.
Ingrassia et al. (2006) A Lactosylated Steroid Contributes in Vivo Therapeutic Benefits in Experimental Models of Mouse Lymphoma and Human Glioblastoma. J. Med. CHem. 49: 1800-1807.
John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast Cancer. Clin. Cancer Res. 9: 2374-2383.
Kouo, T., Huang, L., Pucsek, A.B., Cao, M., Solt, S., Armstrong, T., Jaffee, E. (2015) "Galectin-3 Shapes Antitumor Immune Responses by Suppressing CD8 T Cells via LAG-3 and Inhibiting Expansion of Plasmacytoid Dendritic Cells" Cancer Immonol. Res. 3: 412-23.
Lau, K.S., and Dennis, J.W. (2008). N-Glycans in cancer progression. Glycobiology 18: 750-760.
Lau, K.S., Partridge, E.A., Grigorian, A., Silvescu, C.I., Reinhold, V.N., Demetriou, M., and Dennis, J.W. (2007). Complex N-glycan number and degree of branching cooperate to regulate cell proliferation and differentiation. Cell 129: 123-134.
Leffler, H. and Barondes, S. H. (1986) Specificity of binding of three soluble rat lung lectins to substituted and unsubstituted mammalian B-galactosides. J. Biol. Chem. 261:10119-10126.
Leffler, H. Galectins "Structure and Function—A Synopsis" Springer Verlag, Heidelberg, 2001 pp. 57-83.
Leffler, H., Carlsson, S., Hedlund, M., Qian, Y. and Poirier, F. (2004) Introduction to galectins. Glycoconj. J. 19: 433-440.
Vishal K. Rajput et al: "A Selective Galactose-Coumarin-Derived Galectin-3 Inhibitor Demonstrates Involvement of Galectin-3-glycan Interactions in a Pulmonary Fibrosis Model", Journal of Medicinal Chemistry, vol. 59, No. 17, Aug. 23, 2016 (Aug. 23, 2016), pp. 8141-8147.
Lin, C.- I., Whang, E.E., Donner, D.B., Jiang, X., Price, B.D., Carothers, A.M., Delaine, T., Leffler, H., Nilsson, U.J., Nose, V., et al. (2009). Galectin-3 Targeted Therapy with a Small Molecule Inhibitor Activates Apoptosis and Enhances Both Chemosensitivity and Radiosensitivity in Papillary Thyroid Cancer. Mol Cancer Res 7: 1655-1662.
MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. J. Immun. 180; 2650-2658.
Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1-driven lung fibrosis by Galectin-3. Am. J. Resp. Crit. Care Med., in press.
Massa, S. M., Cooper, D. N. W., Leffler, H., Barondes, S. H. (1993) L-29, an endogenous lectin, binds to glycoconjugate ligands with positive cooperativity. Biochemistry 32: 260-267.
Melero, I., Berman, D.M., Aznar, M.A., Korman, A.J., Gracia, J.L.P., Haanen, J. "Evolving synergistic combinations of targeted immunotherapies to combat cancer" (2015) Nature Reviews Cancer, 15: 457-472.
Partridge, E.A., Le Roy, C., Di Guglielmo, G.M., Pawling, J., Cheung, P., Granovsky, M., Nabi, I.R., Wrana, J.L., and Dennis, J.W. (2004). Regulation of cytokine receptors by Golgi N-glycan processing and endocytosis. Science 306: 120-124.
Perone, M.J., Bertera, S., Shufesky, W.J., Divito, S.J., Montecalvo, A., Mathers, A.R., Larregina, A.T., Pang, M., Seth, N., Wucherpfennig, K.W., et al. (2009). Suppression of autoimmune diabetes by soluble galectin-1. J Immunol 182: 2641-2653.
Pienta, K.J., Naik, H., Akhtar, A., Yamazaki, K., Replogle, T.S., Lehr, J., Donat, T.L., Tait, L., Hogan, V., and Raz, A. (1995). Inhibition of spontaneous metastasis in a rat prostate cancer model by oral administration of modified citrus pectin. J Natl Cancer Inst 87, 348-353.
Ramos-Soriano, J.; Niss, U.; Angulo, J.; Angulo, M.; Moreno-Vargas, A. J.; Carmona, A. T.; Ohlson, S.; Robina, I. "Synthesis, Biological Evaluation, WAC and NMR Studies of S-Galactosides and Non-Carbohydrate Ligands of Cholera Toxin Based on Polyhydroxyalkylfuroate Moieties" Chem. Eur. J. 2013, 19, 17989-18003.
Ruvolo, P.P. Biochim. Biophys Acta.Molecular cell research (2015) E-pub ahead of print, title: Galectin-3 as a guardian of the tumor microenvironment, published on-line Apr. 8, 2015: (http://www.sciencedirect.com/science/article/pii/S0167488915002700).
Saegusa, J., Hsu, D.K., Chen, H.Y., Yu, L., Fermin, A., Fung, M.A., and Liu, F.T. (2009). Galectin-3 is critical for the development of the allergic inflammatory response in a mouse model of atopic dermatitis. Am J Pathol 174: 922-931.
Salameh, B. A., Leffler, H. and Nilsson, U. J. "3-(1,2,3-Triazol-1-yl)-1-thio-galactosides as small, efficient, and hydrolytically stable inhibitors of galectin-3" (2005) Bioorg. Med. Chem. Lett. 15: 3344-3346.
Salameh, B.A., Cumpstey, I., Sundin, A., Leffler, H., and Nilsson, U.J. (2010). 1H-1,2,3-Triazol-1-yl thiodigalactoside derivatives as high affinity galectin-3 inhibitors. Bioorg Med Chem 18: 5367-5378.
Salomonsson, E., Larumbe, A., Tejler, J., Tullberg, E., Rydberg, H., Sundin, A., Khabut, A., Frejd, T., Lobsanov, Y.D., Rini, J.M., Nilsson, U.J., and Leffler, H (2010). Monovalent interactions of galectin-1. Biochemistry 49: 9518-9532.
Shah, P.; Jogani, V.; Bagchi, T.; Misra, A. Role of Caco-2 Cell Monolayers in Prediction of Intestinal Drug Absorption. Biotechnol. Prog. 2006, 22 (1), 186-198.
Sörme, P., Qian, Y., Nyholm, P.-G., Leffler, H., Nilsson, U. J. (2002) Low micromolar inhibitors of galectin-3 based on 3'-derivatization of N-acetyllactosamine. ChemBioChem 3:183-189.
Sörme, P., Kahl-Knutsson, B., Wellmar, U., Nilsson, U. J., and Leffler H. (2003a) Fluorescence polarization to study galectin-ligand interactions. Meth. Enzymol.362: 504-512.
Sörme, P., Kahl-Knutsson, B., Wellmar, U., Magnusson, B.-G., Leffler H., and Nilsson, U. J. (2003b) Design and synthesis of galectin inhibitors. Meth. Enzymol.363: 157-169.
Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47.
Thijssen, V.L., Poirer, F., Baum, L.G., and Griffioen, A.W. (2007). Galectins in the tumor endothelium: opportunities for combined cancer therapy. Blood 110: 2819-2827.
Toscano, M.A., Bianco, G.A., Ilarregui, J.M., Croci, D.O., Correale, J., Hernandez, J.D., Zwirner, N.W., Poirier, F., Riley, E.M., Baum, L.G., et al. (2007). Differential glycosylation of TH1, TH2 and TH-17 effector cells selectively regulates susceptibility to cell death. Nat Immunol 8: 825-834.
International Search Report dated Jan. 7, 2020 in corresponding application No. PCT/EP2019/081539; 5 pgs.
Denis Gigure et al: "Inhibitory potential of chemical substitutions at bioinspired sites of—galactopyranose on neoglycoprotein/cell surface binding of two classes of medically relevant lectins", Bioorganic & Medicinal Chemistry : A Tetrahedron Publication for the Rapid Dissemination of Full Original Research Papers and Critical Reviews

(56) References Cited

OTHER PUBLICATIONS on Biomolecular Chemistry, Medicinal Chemistry and Related Disciplines, Els ev i er, NL, vol. 19, No. 10, Mar. 9, 2011 (Mar. 9, 2011), pp. 3280-3287.

Geoffrey Masuyer et al: "Inhibition mechanism of human galectin-7 by a novel galactose-benzylphosphate Inhibitor", FEBS Journal, vol. 279, No. 2, Nov. 30, 2011 (Nov. 30, 2011), pp. 193-202.

* cited by examiner

GALACTOSIDE INHIBITOR OF GALECTINS

CROSS-REFERENCE TO RELATED APPLICATIONS

This application is Continuation of U.S. patent application Ser. No. 17/295,556, filed on May 20, 2021, which claims the benefit of International Patent Application Number PCT/EP2019/081539, filed Nov. 15, 2019, the contents of which are incorporated herein by reference in its entirety.

FIELD

The present invention relates to novel compounds, the use of said compounds as medicament and for the manufacture of a medicament for the treatment of inflammation; fibrosis; scarring; keloid formation; aberrant scar formation; surgical adhesions; septic shock; cancers; autoimmune diseases; metabolic disorders; heart disease; heart failure; pathological angiogenesis; eye diseases; atherosclerosis; metabolic diseases; asthma and other interstitial lung diseases; and liver disorders in mammals. The invention also relates to pharmaceutical compositions comprising said novel compounds.

BACKGROUND

Galectins are proteins with a characteristic carbohydrate recognition domain (CRD) (Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Lepur et al., 2012). These were the first discovered galectins and are abundant in many tissues.

There are now over 5700 publications on galectins in PubMed, with most, as mentioned above, about galectins-1 (>1400) and -3 (>2800). Strong evidence suggests roles for galectins in e.g. inflammation and cancer, and development (Blidner et al., 2015, Ebrahim et al., 2014).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004; Arthur et al., 2015). They can also function in all these compartments; for galectin-3, solid evidence published in well respected journals support roles in RNA splicing in the nucleus, inhibition of apoptosis in the cytosol, accumulation around disrupted vesicles, association with microtubule organizing center of cilia, and a variety of extracellular effects on cell signaling and adhesion (Elola et al. 2015, Funasaka et al., 2014, Aits et al., 2015, Clare et al., 2014). Other galectins also may act in the cytosol by enhancing apoptosis and regulating the cell cycle and differentiation in certain cells. Most galectins act also extracellularly by cross-linking glycoproteins (e.g. laminin, integrins, and IgE receptors) possibly forming supramolecular ordered arrays (Elola et al., 2015) and may thereby modulate cell adhesion and induce intracellular signals. Related to this, recent years have seen the emergence of a molecular mechanism of these galectin functions involving a formation of microdomains (lattices) within membranes, (Elola et al., 2015) which in turn affects intracellular trafficking and cell surface presentation of glycoprotein receptors. This has been documented in cell culture, in null mutant mice, and animals treated with galectin or galectin inhibitors.

Potential Therapeutic Use of Galectin-3 Inhibitors

Galectin-3 has been implicated in diverse phenomena and, hence, inhibitors may have multiple uses (Blanchard et al., 2014). It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation

A pro-inflammatory role of galectin-3 is indicated by its induction in cells at inflammatory sites, a variety of effects on immune cells (e.g. oxidative burst in neutrophils and chemotaxis in monocytes), and decrease of the inflammatory response, mainly in neutrophils and macrophages, in null mutant mice (Blidner et al., 2015, Arthur et al., 2015). Importantly, recent studies have identified galectin-3 as a key rate-limiting factor in macrophage M2 differentiation and myofibroblast activation, which influences the development of fibrosis (Mackinnon et al., 2008; Mackinnon et al., 2012, Li et al., 2014).

Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of certain receptors (Elola et al., 2015), such as the TGF-β receptor (MacKinnon, 2012), which in turn regulates alternative macrophage differentiation into M2 macrophages and myofibroblast activation.

Hence, as galectin-3 is a good candidate for being an endogenous enhancer of TGF-β signaling and alternative macrophage differentiation and myofibroblast activation, galectin-3 inhibitors may be very useful in treating fibrosis and adverse tissue remodeling.

Treatment of Cancer

A large number of immunohistochemical studies show changed expression of certain galectins in cancer (Thijssen et al, 2015; Ebrahim et al., 2014) and for example galectin-3 is now an established histochemical marker of thyroid cancer. The direct evidence for a role of galectin-3 in cancer comes mainly from mouse models. In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. Further, recent evidence have shown that galectin-3 plays a critical role in the tumor microenvironment (Ruvolo, 2015). Galectin-3 is also believed to regulate the interaction between the tumor cells and immune cells, such as T-lymphocytes (T-cells), and inhibition of galectin-3 has been shown to restore T-cell activity (Demotte et al. 2010, Kouo et al. 2015, Menero et al. 2015). From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Blanchard et al., 2015).

Also other galectins are frequently over-expressed in low differentiated cancer cells, or induced in specific cancer types (Thijssen et al, 2015; Ebrahim et al. 2014). Galectin-1 induces apoptosis in activated T-cells and has a remarkable immunosuppressive effect on autoimmune disease in vivo (Blidner et al., 2015). Therefore, the over-expression of these galectins in cancers might help the tumor to defend itself against the T-cell response raised by the host.

Null mutant mice for galectins-1, -3, -7 and -9 have been established and are healthy and reproduce apparently normally in animal house conditions. However, further studies have revealed subtle phenotypes under different type of challenge, mainly in function of immune cells (Blidner et al., 2015), but also other cells types (Viguier et al., 2014). The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Treatment of Angiogenesis

Vascular endothelial growth factors (VEGFs) signaling through VEGF receptor-2 (VEGFR-2) is the primary angiogenic pathway. Studies have been published demonstrating that both galectin-1 (Gal-1) and galectin-3 (Gal-3) are important modulators for VEGF/VEGFR-2 signaling pathway (Croci et al., 2014). It has also been published that a galectin inhibitor, TDX, is expected have efficacy against pathological angiogenesis. (Chen 2012)

Known Inhibitors

Natural Ligands

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or LacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

Cluster molecules having up to four lactose moieties showed a strong multivalency effect when binding to galectin-3, but not to galectin-1 and galectin-5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules.

Thiodigalactoside is known to be a synthetic and hydrolytically stable, yet polar inhibitor, approximately as efficient as N-acetyllactosamine (Leffler and Barondes, 1986). N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 μM, which is a 20-fold improvement in comparison with the natural N-acetyllactosamine disaccharide (Sarme et al., 2002; Sarme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed (Cumpstey et al., 2005b; Cumpstey et al., 2008; Salameh et al., 2010; WO/2005/113569 and US2007185041; WO/2005/113568, U.S. Pat. No. 7,638,623 B2, T. Delaine, 2016, ChemBioChem 10.1002/cbic.201600285)) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

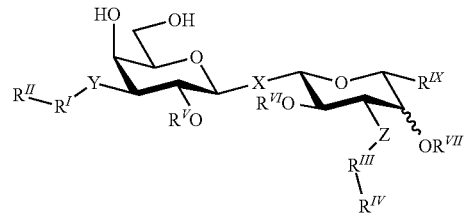

as described in WO/2005/113568, and

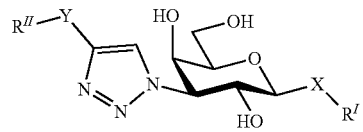

as described in WO/2005/113569, in which $R^1$ can be a D-galactose.

In recently published US20140099319, WO2014067986 and (T. Delaine, 2016, ChemBioChem 10.1002/cbic.201600285) are disclosed a compound of formula

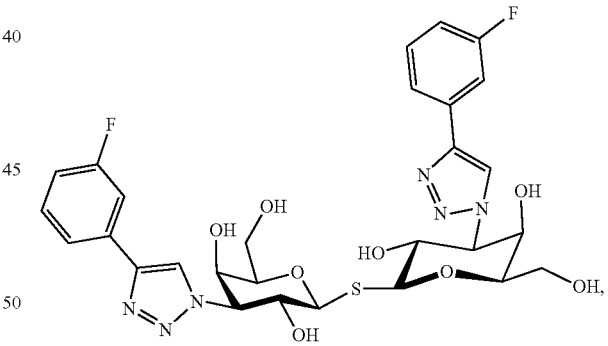

having fluorine (F) in the meta position on both the phenyl rings in relation to the triazole rings. This compound has been shown to be a promising drug candidate for lung fibrosis, and in particular is very selective on galectin-3 with high affinity.

A series of small C1 or C1 and C3-substituted galactopyranosides have been disclosed showing affinity towards galectin-3 and 1. The beta-D-galactopyranosides were reported as having affinity in the same range or less than lactose, which has a Kd of about 91 μM towards galectin-3 and 190 μM towards galectin-1. (Giguere, D et. al. 2011, 2008, 2006).

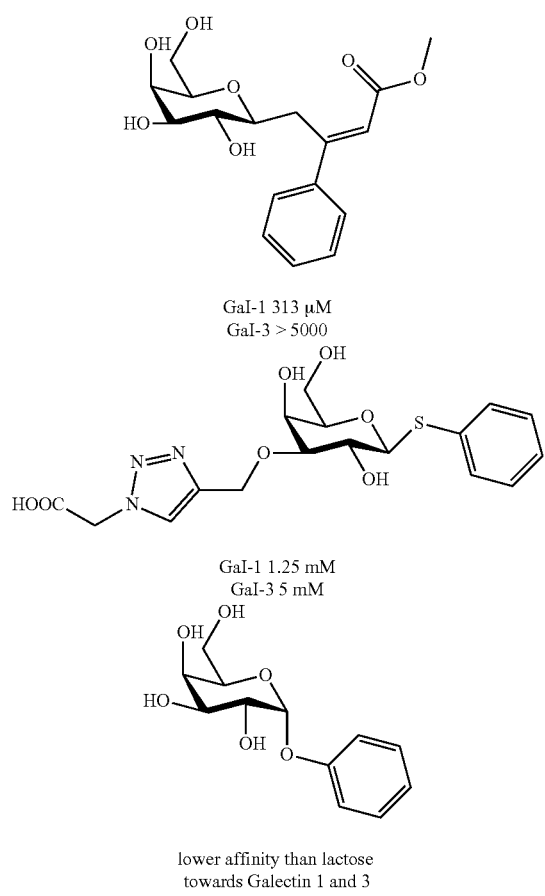

Gal-1 313 µM
Gal-3 > 5000

Gal-1 1.25 mM
Gal-3 5 mM lower affinity than lactose
towards Galectin 1 and 3

There is no disclosure or mentioning of corresponding alpha-anomers having affinity towards galectin-3 or galectin-1 better than lactose.

SUMMARY

The compounds of the present invention are novel α-D-galactopyranose compounds that unexpectedly have shown very high affinity for galectin-3 and are considered novel potent drug candidates. Some of these compounds have very good PK properties for e.g. oral administration, such as low clearance and high bioavailability. Furthermore, introduction of small alkyl substituents, such as straight and/or linear alkyls to the galactoside 2-OH such as compounds of formula (1) results in low or no efflux combined with a high uptake.

In broad aspect the present invention concerns a D-galactopyranose compound of formula (1)

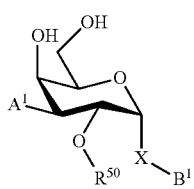

(1)

wherein
the pyranose ring is α-D-galactopyranose,
$A^1$ is selected from

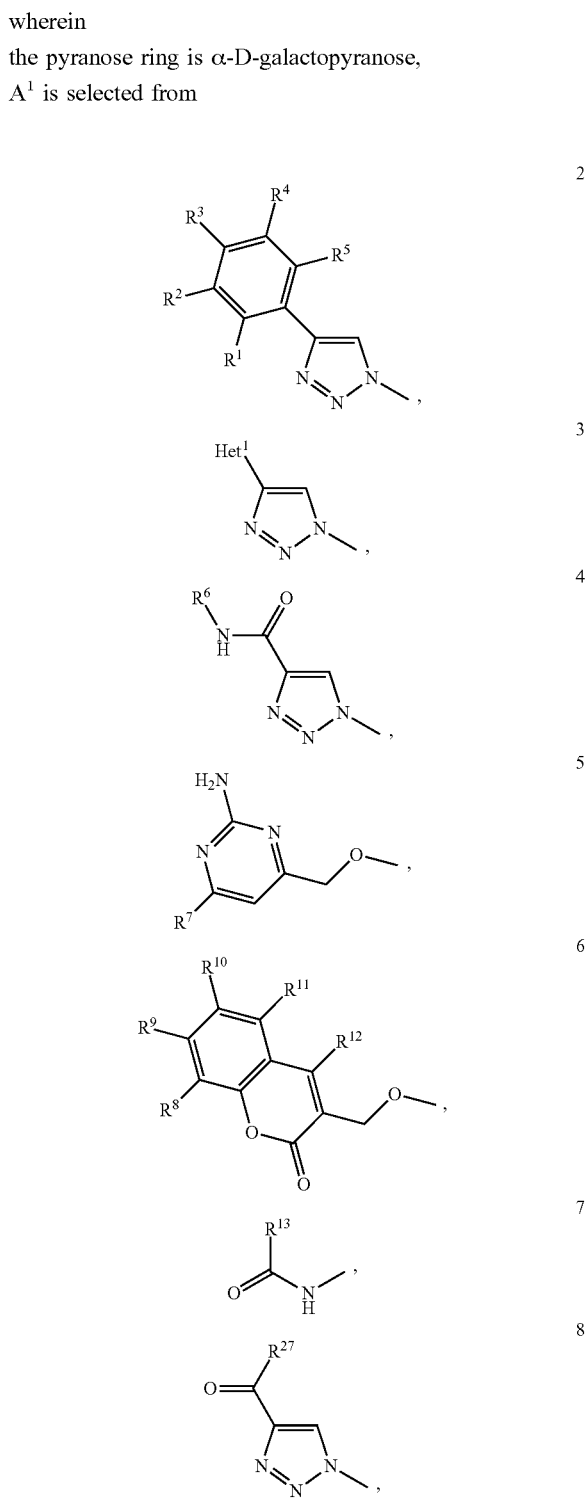

wherein $Het^1$ is selected from a five or six membered heteroaromatic ring, optionally substituted with a group selected from Br; F; Cl; I; CN; $NR^{19}R^{20}$, wherein $R^{19}$ and $R^{20}$ are independently selected from H, $C_{1-3}$ alkyl, cyclopropyl, iso-propyl, —C(═O)—$R^{21}$, wherein $R^{21}$ is selected from H and $C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; $OC_{1-3}$ alkyl optionally substituted with a F; and $SC_{1-3}$ alkyl optionally substituted with a F;

wherein $R^1$-$R^5$ are independently selected from H, CN, $NH_2$, Br, Cl, I, F, methyl optionally substituted with a F, $SCH_3$ optionally substituted with a F, and $OCH_3$ optionally substituted with a F;

wherein $R^6$ is selected from $C_{1-6}$ alkyl optionally substituted with a halogen, branched $C_{3-6}$ alkyl and $C_{3-7}$ cycloalkyl;

wherein $R^7$ is selected from a five or six membered heteroaromatic ring, optionally substituted with a group selected from Br, F, Cl, methyl optionally substituted with a F, and $OCH_3$ optionally substituted with a F, and a phenyl optionally substituted with a group selected from Br, F, Cl, methyl optionally substituted with a F, and $OCH_3$ optionally substituted with a F;

wherein $R^8$-$R^{12}$ are independently selected from H, F, methyl optionally substituted with a F, and $OCH_3$ optionally substituted with a F;

wherein $R^{13}$ is a five or six membered heteroaromatic ring optionally substituted with a group selected from H, OH, F, methyl optionally substituted with a F, and $OCH_3$ optionally substituted with a F, or an aryl, such as phenyl or naphthyl, optionally substituted with a group selected from H, OH, F, methyl optionally substituted with a F, and $OCH_3$ optionally substituted with a F;

$X^1$ is selected from S, SO, $SO_2$, O, C=O, and $CR^7R^8$ wherein $R^7$ and $R^8$ are independently selected from hydrogen, OH, or halogen;

wherein $R^{27}$ is selected from a $C_{1-6}$ alkyl, branched $C_{3-6}$ alkyl, $C_{1-6}$ alkoxy and branched $C_{3-6}$ alkoxy;

$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{15}$—CONH— wherein $R^{15}$ is selected from $C_{1-3}$ alkyl and cyclopropyl; b) an aryl, such as phenyl or naphthyl, optionally substituted with a group selected from a halogen; CN; —COOH; —$CONR^{22}R^{23}$, wherein $R^{22}$ and $R^{23}$ are independently selected from H, $C_{1-3}$ alkyl, cyclopropyl, and iso-propyl, or $R^{22}$ and $R^{23}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{28}R^{29}$, wherein $R^{28}$ and $R^{29}$ are independently selected from H, $C_{1-3}$ alkyl and isopropyl; OH; and $R^{16}$—CONH— wherein $R^{16}$ is selected from $C_{1-3}$ alkyl and cyclopropyl; c) a $C_{5-7}$ cycloalkyl, optionally substituted with a substituent selected from a halogen, CN, methyl optionally substituted with a F, $OCH_3$ optionally substituted with a F, $OCH_2CH_3$ optionally substituted with a F, OH, and $R^{17}$—CONH— wherein $R^{17}$ is selected from $C_{1-3}$ alkyl and cyclopropyl; and d) a heterocycle, such as heteroaryl or heterocycloalkyl, optionally substituted with a group selected from a halogen; a spiro heterocycle such as N-(2-oxa)-6-azaspiro[3.3]heptanyl; CN; —COOH; —$CONR^{24}R^{25}$, wherein $R^{24}$ and $R^{25}$ are independently selected from H, $C_{1-3}$ alkyl, cyclopropyl, and iso-propyl or $R^{24}$ and $R^{25}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{30}R^{31}$, wherein $R^{30}$ and $R^{31}$ are independently selected from H, $C_{1-3}$ alkyl and isopropyl; OH; $R^{18}$—CONH— wherein $R^{18}$ is selected from $C_{1-3}$ alkyl and cyclopropyl; a pyrimidinyl optionally substituted with a substituent selected from CN, a halogen, methyl optionally substituted with a F, $OCH_3$ optionally substituted with a F, $OCH_2CH_3$ optionally substituted with a F, OH, and $R^{71}$—CONH— wherein $R^{71}$ is selected from $C_{1-3}$ alkyl and cyclopropyl; a pyridinyl optionally substituted with a substituent selected from CN, a halogen, methyl optionally substituted with a F, $OCH_3$ optionally substituted with a F, $OCH_2CH_3$ optionally substituted with a F, OH, and $R^{72}$—CONH— wherein $R^{72}$ is selected from $C_{1-3}$ alkyl and cyclopropyl; a tetrahydropyridinyl optionally substituted with a substituent selected from CN, a halogen, methyl optionally substituted with a F, $OCH_3$ optionally substituted with a F, $OCH_2CH_3$ optionally substituted with a F, OH, and $R^{73}$—CONH— wherein $R^{73}$ is selected from $C_{1-3}$ alkyl and cyclopropyl; a pyrrolinyl optionally substituted with a substituent selected from CN, a halogen, methyl optionally substituted with a F, $OCH_3$ optionally substituted with a F, $OCH_2CH_3$ optionally substituted with a F, OH, and $R^{74}$—CONH— wherein $R^{74}$ is selected from $C_{1-3}$ alkyl and cyclopropyl; an oxazolyl optionally substituted with a substituent selected from CN, a halogen, methyl optionally substituted with a F, $OCH_3$ optionally substituted with a F, $OCH_2CH_3$ optionally substituted with a F, OH, and $R^{75}$—CONH— wherein $R^{75}$ is selected from $C_{1-3}$ alkyl and cyclopropyl; a thiazolyl optionally substituted with a substituent selected from CN, a halogen, methyl optionally substituted with a F, $OCH_3$ optionally substituted with a F, $OCH_2CH_3$ optionally substituted with a F, OH, and $R^{76}$—CONH— wherein $R^{76}$ is selected from $C_{1-3}$ alkyl and cyclopropyl; and a $C_{2-4}$ alkynyl, e) a $C_{1-6}$ alkyl or branched $C_{3-6}$ alkyl;

$R^{50}$ is selected from the group consisting of a) $C_{1-6}$ alkyl optionally substituted with one or more halogen, CN, $OR^{51}$, $NR^{52}R^{53}$, and $CONH_2$, wherein $R^{51}$ is selected from the group consisting of H, CN, a halogen, methyl optionally substituted with a F, $OCH_3$ optionally substituted with a F, $OCH_2CH_3$ optionally substituted with a F, OH, and $R^{54}$—CONH— wherein $R^{54}$ is selected from $C_{1-3}$ alkyl and cyclopropyl, $R^{52}$ is selected from the group consisting of H, CN, a halogen, methyl optionally substituted with a F, $OCH_3$ optionally substituted with a F, $OCH_2CH_3$ optionally substituted with a F, OH, and $R^{55}$—CONH— wherein $R^{55}$ is selected from $C_{1-3}$ alkyl and cyclopropyl, and $R^{53}$ is selected from the group consisting of H, CN, a halogen, methyl optionally substituted with a F, $OCH_3$ optionally substituted with a F, $OCH_2CH_3$ optionally substituted with a F, OH, and $R^{56}$—CONH— wherein $R^{56}$ is selected from $C_{1-3}$ alkyl and cyclopropyl, b) branched $C_{3-6}$ alkyl optionally substituted with one or more halogen, CN, OR$^{57}$, NR$^{58}$R$^{59}$, and CONH$_2$, wherein R$^{57}$ is selected from the group consisting of H, CN, a halogen, methyl optionally substituted with a F, OCH$_3$ optionally substituted with a F, OCH$_2$CH$_3$ optionally substituted with a F, OH, and R$^{60}$—CONH— wherein R$^{60}$ is selected from C$_{1-3}$ alkyl and cyclopropyl, R$^{58}$ is selected from the group consisting of H, CN, a halogen, methyl optionally substituted with a F, OCH$_3$ optionally substituted with a F, OCH$_2$CH$_3$ optionally substituted with a F, OH, and R$^{61}$—CONH— wherein R$^{61}$ is selected from C$_{1-3}$ alkyl and cyclopropyl, and R$^{59}$ is selected from the group consisting of H, CN, a halogen, methyl optionally substituted with a F, OCH$_3$ optionally substituted with a F, OCH$_2$CH$_3$ optionally substituted with a F, OH, and R$^{62}$—CONH— wherein R$^{62}$ is selected from C$_{1-3}$ alkyl and cyclopropyl, and c) cyclic C$_{3-6}$ alkyl optionally substituted with one or more halogen, CN, OR$^{63}$, NR$^{64}$R$^{65}$, and CONH$_2$, wherein R$^{63}$ is selected from the group consisting of H, CN, a halogen, methyl optionally substituted with a F, OCH$_3$ optionally substituted with a F, OCH$_2$CH$_3$ optionally substituted with a F, OH, and R$^{66}$—CONH— wherein R$^{66}$ is selected from C$_{1-3}$ alkyl and cyclopropyl, R$^{64}$ is selected from the group consisting of H, CN, a halogen, methyl optionally substituted with a F, OCH$_3$ optionally substituted with a F, OCH$_2$CH$_3$ optionally substituted with a F, OH, and R$^{67}$—CONH— wherein R$^{67}$ is selected from C$_{1-3}$ alkyl and cyclopropyl, and R$^{65}$ is selected from the group consisting of H, CN, a halogen, methyl optionally substituted with a F, OCH$_3$ optionally substituted with a F, OCH$_2$CH$_3$ optionally substituted with a F, OH, and R$^{68}$—CONH— wherein R$^{68}$ is selected from C$_{1-3}$ alkyl and cyclopropyl; or a pharmaceutically acceptable salt or solvate thereof.

In an embodiment the present invention concerns a D-galactopyranose compound of formula (1)

(1)

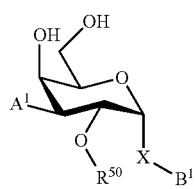

wherein
the pyranose ring is α-D-galactopyranose,
A$^1$ is selected from

2

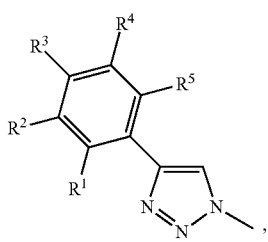

3

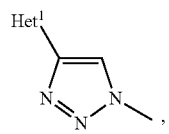

-continued

4

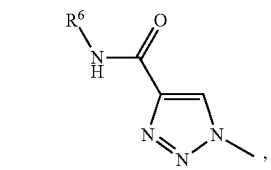

5

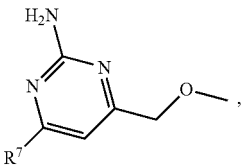

6

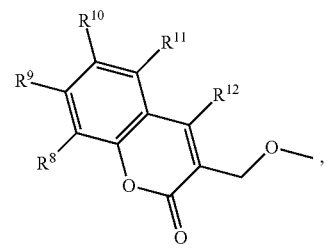

7

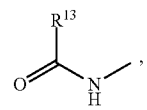

8

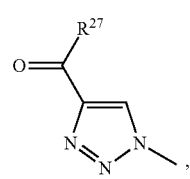

wherein Het$^1$ is selected from a five or six membered heteroaromatic ring, optionally substituted with a group selected from Br; F; Cl; I; CN; NR$^{19}$R$^{20}$, wherein R$^{19}$ and R$^{20}$ are independently selected from H, C$_{1-3}$ alkyl, cyclopropyl, iso-propyl, —C(=O)—R$^{21}$, wherein R$^{21}$ is selected from H and C$_{1-3}$ alkyl; C$_{1-3}$ alkyl, optionally substituted with a F; cyclopropyl, optionally substituted with a F; iso-propyl, optionally substituted with a F; O-cyclopropyl optionally substituted with a F; O-iso-propyl optionally substituted with a F; OC$_{1-3}$ alkyl optionally substituted with a F; and SC$_{1-3}$ alkyl optionally substituted with a F;

wherein R$^1$-R$^5$ are independently selected from H, CN, NH$_2$, Br, Cl, I, F, methyl optionally substituted with a F, SCH$_3$ optionally substituted with a F, and OCH$_3$ optionally substituted with a F;

wherein R$^6$ is selected from C$_{1-6}$ alkyl optionally substituted with a halogen, branched C$_{3-6}$ alkyl and C$_{3-7}$ cycloalkyl;

wherein R$^7$ is selected from a five or six membered heteroaromatic ring, optionally substituted with a group selected from Br, F, Cl, methyl optionally substituted with a F, and OCH$_3$ optionally substituted with a F, and a phenyl optionally substituted with a group selected from Br, F, Cl, methyl optionally substituted with a F, and OCH$_3$ optionally substituted with a F;

wherein R$^8$-R$^{12}$ are independently selected from H, F, methyl optionally substituted with a F, and OCH$_3$ optionally substituted with a F;

wherein $R^{13}$ is a five or six membered heteroaromatic ring optionally substituted with a group selected from H, OH, F, methyl optionally substituted with a F, and OCH$_3$ optionally substituted with a F, or an aryl, such as phenyl or naphthyl, optionally substituted with a group selected from H, OH, F, methyl optionally substituted with a F, and OCH$_3$ optionally substituted with a F;

$X^1$ is selected from S, SO, SO$_2$, O, C=O, and CR$^7$R$^8$ wherein $R^7$ and $R^8$ are independently selected from hydrogen, OH, or halogen;

wherein $R^{27}$ is selected from a C$_{1-6}$ alkyl, branched C$_{3-6}$ alkyl, C$_{1-6}$ alkoxy and branched C$_{3-6}$ alkoxy;

$B^1$ is selected from a) a C$_{1-6}$ alkyl or branched C$_{3-6}$ alkyl substituted with a five or six membered heteroaromatic ring, optionally substituted with a substituent selected from CN, a halogen, methyl optionally substituted with a F, OCH$_3$ optionally substituted with a F, OCH$_2$CH$_3$ optionally substituted with a F, OH, and $R^{14}$—CONH— wherein $R^{14}$ is selected from C$_{1-3}$ alkyl and cyclopropyl; or a C$_{1-6}$ alkyl substituted with a phenyl, optionally substituted with a substituent selected from CN, a halogen, methyl optionally substituted with a F, OCH$_3$ optionally substituted with a F, OCH$_2$CH$_3$ optionally substituted with a F, OH, and $R^{15}$—CONH— wherein $R^{15}$ is selected from C$_{1-3}$ alkyl and cyclopropyl; b) an aryl, such as phenyl or naphthyl, optionally substituted with a group selected from a halogen; CN; —COOH; —CONR$^{22}$R$^{23}$, wherein $R^{22}$ and $R^{23}$ are independently selected from H, C$_{1-3}$ alkyl, cyclopropyl, and iso-propyl, or $R^{22}$ and $R^{23}$ together with the nitrogen may form a heterocycloalkyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{28}$R$^{29}$, wherein $R^{28}$ and $R^{29}$ are independently selected from H, C$_{1-3}$ alkyl and isopropyl; OH; and $R^{16}$—CONH— wherein $R^{16}$ is selected from C$_{1-3}$ alkyl and cyclopropyl; c) a C$_{5-7}$ cycloalkyl, optionally substituted with a substituent selected from a halogen, CN, methyl optionally substituted with a F, OCH$_3$ optionally substituted with a F, OCH$_2$CH$_3$ optionally substituted with a F, OH, and $R^{17}$—CONH— wherein $R^{17}$ is selected from C$_{1-3}$ alkyl and cyclopropyl; and d) a heterocycle, such as heteroaryl or heterocycloalkyl, optionally substituted with a group selected from a halogen; a spiro heterocycle such as N-(2-oxa)-6-azaspiro[3.3]heptanyl; CN; —COOH; —CONR$^{24}$R$^{25}$, wherein $R^{24}$ and $R^{25}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{30}$R$^{31}$, wherein $R^{30}$ and $R^{31}$ are independently selected from H, C$_{1-3}$ alkyl and isopropyl; OH; and $R^{18}$—CONH— wherein $R^{18}$ is selected from C$_{1-3}$ alkyl and cyclopropyl; e) a C$_{1-6}$ alkyl or branched C$_{3-6}$ alkyl;

$R^{50}$ is selected from the group consisting of a) C$_{1-6}$ alkyl optionally substituted with one or more halogen, CN, OR$^{51}$, NR$^{52}$R$^{53}$, and CONH$_2$, wherein $R^{51}$ is selected from the group consisting of H, CN, a halogen, methyl optionally substituted with a F, OCH$_3$ optionally substituted with a F, OCH$_2$CH$_3$ optionally substituted with a F, OH, and $R^{54}$—CONH— wherein $R^{54}$ is selected from C$_{1-3}$ alkyl and cyclopropyl, $R^{52}$ is selected from the group consisting of H, CN, a halogen, methyl optionally substituted with a F, OCH$_3$ optionally substituted with a F, OCH$_2$CH$_3$ optionally substituted with a F, OH, and $R^{55}$—CONH— wherein $R^{55}$ is selected from C$_{1-3}$ alkyl and cyclopropyl, and $R^{53}$ is selected from the group consisting of H, CN, a halogen, methyl optionally substituted with a F, OCH$_3$ optionally substituted with a F, OCH$_2$CH$_3$ optionally substituted with a F, OH, and $R^{56}$—CONH— wherein $R^{56}$ is selected from C$_{1-3}$ alkyl and cyclopropyl, b) branched C$_{3-6}$ alkyl optionally substituted with one or more halogen, CN, OR$^{57}$, NR$^{58}$R$^{59}$, and CONH$_2$, wherein $R^{57}$ is selected from the group consisting of H, CN, a halogen, methyl optionally substituted with a F, OCH$_3$ optionally substituted with a F, OCH$_2$CH$_3$ optionally substituted with a F, OH, and $R^{60}$—CONH— wherein $R^{60}$ is selected from C$_{1-3}$ alkyl and cyclopropyl, $R^{58}$ is selected from the group consisting of H, CN, a halogen, methyl optionally substituted with a F, OCH$_3$ optionally substituted with a F, OCH$_2$CH$_3$ optionally substituted with a F, OH, and $R^{61}$—CONH— wherein $R^{61}$ is selected from C$_{1-3}$ alkyl and cyclopropyl, and $R^{59}$ is selected from the group consisting of H, CN, a halogen, methyl optionally substituted with a F, OCH$_3$ optionally substituted with a F, OCH$_2$CH$_3$ optionally substituted with a F, OH, and $R^{62}$—CONH— wherein $R^{62}$ is selected from C$_{1-3}$ alkyl and cyclopropyl, and c) cyclic C$_{3-6}$ alkyl optionally substituted with one or more halogen, CN, OR$^{63}$, NR$^{64}$R$^{65}$, and CONH$_2$, wherein $R^{63}$ is selected from the group consisting of H, CN, a halogen, methyl optionally substituted with a F, OCH$_3$ optionally substituted with a F, OCH$_2$CH$_3$ optionally substituted with a F, OH, and $R^{66}$—CONH— wherein $R^{66}$ is selected from C$_{1-3}$ alkyl and cyclopropyl, $R^{64}$ is selected from the group consisting of H, CN, a halogen, methyl optionally substituted with a F, OCH$_3$ optionally substituted with a F, OCH$_2$CH$_3$ optionally substituted with a F, OH, and $R^{67}$—CONH— wherein $R^{67}$ is selected from C$_{1-3}$ alkyl and cyclopropyl, and $R^{65}$ is selected from the group consisting of H, CN, a halogen, methyl optionally substituted with a F, OCH$_3$ optionally substituted with a F, OCH$_2$CH$_3$ optionally substituted with a F, OH, and $R^{68}$—CONH— wherein $R^{68}$ is selected from C$_{1-3}$ alkyl and cyclopropyl; or a pharmaceutically acceptable salt or solvate thereof.

In an embodiment of the present invention A1 is selected from formula 2 wherein $R^1$-$R^5$ are independently selected from H, Cl, F, methyl optionally substituted with a fluorine (F), and OCH$_3$ optionally substituted with a F.

In another embodiment of the present invention A1 is selected from formula 2 wherein $R^1$ and $R^5$ are selected from H and $R^2$-$R^4$ are selected from F.

In a further embodiment of the present invention A1 is selected from formula 2 wherein $R^1$ and $R^5$ are selected from H and $R^2$-$R^4$ are selected from one or more H, F, Cl, and methyl, such as 3 F, 1 F, 1H and one methyl, 2 F and 1 Cl, 2 F and one methyl.

In a further embodiment of the present invention A1 is selected from formula 2 wherein $R^2$ and $R^3$ are F and $R^1$, $R^4$ and $R^5$ are H, or wherein $R^2$ and $R^4$ are F and $R^1$, $R^3$ and $R^5$ are H, or wherein $R^2$ is F and $R^1$, $R^3$-$R^5$ are H, or wherein $R^2$ and $R^4$ are F, $R^3$ is OCH$_3$, and $R^1$ and $R^5$ are H.

In a further embodiment of the present invention A1 is selected from formula 2 wherein $R^1$-$R^5$ are independently selected from H and F, provided that at least one of $R^1$-$R^5$ is F. Preferably from one to five, such as three or five, of $R^1$-$R^5$ are independently selected from F.

In a further embodiment of the present invention A1 is selected from formula 2 wherein $R^1$ and $R^5$ are selected from H and $R^2$-$R^4$ are independently selected from one or more from the group consisting of F, Cl, and Methyl.

In a further embodiment of the present invention A1 is selected from formula 2 wherein $R^1$, $R^4$ and $R^5$ are selected from H and $R^2$-$R^3$ are independently selected from one or two from the group consisting of F, Cl, and Methyl.

In a still further embodiment of the present invention A1 is selected from formula 3 wherein $Het^1$ is selected from a six membered heteroaromatic ring, optionally substituted with a group selected from Br, F, and Cl. Typically, $Het^1$ is selected from a pyridinyl substituted with a F, such as 3 F.

In a further embodiment of the present invention A1 is selected from formula 3 wherein $Het^1$ is selected from a pyridinyl, optionally substituted with a group selected from H, CN, Br, Cl, I, F, methyl optionally substituted with a F, $OCH_3$ optionally substituted with a F, and $SCH_3$ optionally substituted with a F; or a pyrimidyl, optionally substituted with a group selected from H, CN, Br, Cl, I, F, methyl optionally substituted with a F, $OCH_3$ optionally substituted with a F, and $SCH_3$ optionally substituted with a F.

In a further embodiment of the present invention A1 is selected from formula 4 wherein $R^6$ is selected from $C_{1-6}$ alkyl and branched $C_{3-6}$ alkyl. Typically, $R^6$ is $C_{1-6}$ alkyl, such as $CH_3$, $CH_2CH_3$, $CH_2CH_2CH_3$ and isopropyl, e.g. $CH_3$, or isopropyl.

In a further embodiment of the present invention A1 is selected from formula 4 wherein $R^6$ is selected from $C_{1-6}$ alkyl substituted with a halogen, such as one, two or three F, e.g. $CH_2CF_3$.

In a still further embodiment of the present invention A1 is selected from formula 5 wherein $R^7$ is selected from phenyl optionally substituted with a group selected from Br, F, Cl, methyl optionally substituted with a F, and $OCH_3$ optionally substituted with a F.

In a further embodiment of the present invention A1 is selected from formula 5 wherein $R^7$ is selected from phenyl substituted with a Cl.

In a still further embodiment of the present invention A is selected from formula 6 wherein $R^8$-$R^{12}$ are independently selected from H and F. Typically, $R^8$-$R^{12}$ are all H, or $R^{10}$-$R^{11}$ are F and $R^8$, $R^9$, and $R^{12}$ are H.

In a further embodiment of the present invention A1 is selected from formula 7 wherein $R^{13}$ is an aryl, such as phenyl or naphthyl, optionally substituted with a group selected from F. Typically, $R^{13}$ is phenyl, optionally substituted with one, two or three F.

In a further embodiment of the present invention A1 is selected from formula 8 wherein $R^{27}$ is selected from a $C_{1-6}$ alkyl, branched $C_{3-6}$ alkyl, $C_{1-6}$ alkoxy and branched $C_{3-6}$ alkoxy. Typically, $R^{27}$ is selected from a $C_{1-6}$ alkyl and $C_{1-6}$ alkoxy.

In a further embodiment of the present invention X1 is selected from S, SO, $SO_2$, and O. Preferably X is selected from S, SO, and $SO_2$. In a further embodiment X1 is selected from S and $SO_2$, such as S.

In a still further embodiment of the present invention B1 is selected from a $C_{1-6}$ alkyl substituted with a phenyl, optionally substituted with a group selected from Br, F, Cl, methyl optionally substituted with a F, and $OCH_3$ optionally substituted with a F.

In a further embodiment of the present invention B1 is selected from a $C_{1-6}$ alkyl substituted with a phenyl, such as benzyl or $CH_2$—$CH_2$-phenyl.

In a still further embodiment of the present invention B1 is selected from a $C_{1-6}$ alkyl substituted with a phenyl, said phenyl substituted with a group selected from Cl, such as benzyl substituted with one or two Cl, or —$CH_2$—$CH_2$-phenyl substituted with one Cl.

In a further embodiment of the present invention B1 is selected from a $C_{1-6}$ alkyl.

In a still further embodiment of the present invention B1 is selected from an aryl, such as phenyl or naphthyl, optionally substituted with one or more substituents selected from a halogen (e.g. Cl, F, Br, I), methyl optionally substituted with a F, $OCH_3$ optionally substituted with a F, $OCH_2CH_3$ optionally substituted with a F, OH, and $R^{16}$—CONH— wherein $R^{16}$ is selected from $C_{1-3}$ alkyl and cyclopropyl.

In a further embodiment of the present invention B1 is selected from an aryl, such as phenyl or naphthyl, optionally substituted with one or more substituents selected from I, COOH and $CONH_2$.

In a further embodiment of the present invention B1 is selected from an aryl, such as phenyl or naphthyl, optionally substituted with one or more substituents selected from $NR^{28}R^{29}$, wherein $R^{28}$ and $R^{29}$ are independently selected from H, $C_{1-3}$ alkyl and isopropyl.

In a still further embodiment of the present invention B1 is selected from an aryl, such as phenyl or naphthyl, optionally substituted with one or more substituents selected from CN.

In a further embodiment of the present invention B1 is selected from an aryl, optionally substituted with a group selected from a Cl; Br; CN; —$CONR^{22}R^{23}$, wherein $R^{22}$ and $R^{23}$ are independently selected from H and $C_{1-3}$ alkyl, or $R^{22}$ and $R^{23}$ together with the nitrogen may form a heterocycloalkyl.

In a further embodiment of the present invention B1 is selected from an unsubstituted phenyl.

In a still further embodiment of the present invention B1 is selected from an unsubstituted naphthyl.

In a further embodiment of the present invention B1 is selected from a phenyl substituted with one, two or three substituents selected from Cl, F, Br, CN, methyl, OH, $CF_3$, $OCH_2CH_3$, $OCH_3$, $OCF_3$, $R^{16}$—CONH— wherein $R^{16}$ is selected from $C_{1-3}$ alkyl, such as methyl. Such as a phenyl substituted with two substituents selected from Cl, F, Br, CN. Such as a phenyl substituted with three substituents selected from Cl, F, and CN.

In a still further embodiment of the present invention B1 is selected from a phenyl substituted with one, two or three substituents selected from Cl, F, Br, I CN, methyl, OH, $CF_3$, $OCH_2CH_3$, $OCH_3$, $OCF_3$, COOH, $CONH_2$, and $R^{16}$—CONH— wherein $R^{16}$ is selected from $C_{1-3}$ alkyl, such as methyl. Such as a phenyl substituted with one substituent selected from I, COOH, and $CONH_2$.

In a further embodiment of the present invention B1 is selected from a phenyl substituted with one, two or three substituents selected from a Cl, Br, CN, —$CONR^{22}R^{23}$, wherein $R^{22}$ and $R^{23}$ are independently selected from H and $C_{1-3}$ alkyl, or $R^{22}$ and $R^{23}$ together with the nitrogen may form a heterocyclobutyl or heterocyclohexyl.

In a further embodiment of the present invention B1 is selected from a heterocycle, such as heteroaryl or heterocycloalkyl, optionally substituted with one or more substituents selected from a halogen (e.g. Cl, F, Br, I); methyl optionally substituted with a F; $OCH_3$ optionally substituted with a F; $OCH_2CH_3$ optionally substituted with a F; $CONH_2$; OH; $NR^{30}R^{31}$, wherein $R^{30}$ and $R^{31}$ are independently selected from H, $C_{1-3}$ alkyl and isopropyl; and $R^{18}$—CONH— wherein $R^{18}$ is selected from $C_{1-3}$ alkyl and cyclopropyl.

In a still further embodiment of the present invention B1 is selected from a heterocycle, such as heteroaryl or heterocycloalkyl, optionally substituted with one or more substituents selected from a halogen (e.g. Cl, F, Br, I); methyl optionally substituted with a F; $OCH_3$ optionally substituted with a F; $OCH_2CH_3$ optionally substituted with a F; OH; and $R^{18}$—CONH— wherein $R^{18}$ is selected from $C_{1-3}$ alkyl and cyclopropyl.

In a further embodiment of the present invention B1 is selected from a heterocycle, such as heteroaryl or heterocycloalkyl, optionally substituted with one or more substituents selected from $CONH_2$; OH; Cl; Br; and $CF_3$.

In a still further embodiment of the present invention B1 is selected from a heterocycle, such as heteroaryl or heterocycloalkyl, optionally substituted with one or more substituents selected from CN.

In a further embodiment of the present invention B1 is selected from a heterocycle, such as heteroaryl or heterocycloalkyl, optionally substituted with one to three substituents selected from $CONH_2$; OH; CN; Cl; Br; and $CF_3$.

In a still further embodiment of the present invention B1 is selected from an unsubstituted pyridinyl.

In a further embodiment of the present invention B1 is selected from a pyridinyl substituted with a group independently selected from a Cl, Br, methyl, $CF_3$, $OCH_3$, N-(2-oxa)-6-azaspiro[3.3]heptanyl, OH, $NH_2$, $CONH_2$, —$CONR^{24}R^{25}$, wherein $R^{24}$ and $R^{25}$ together with the nitrogen may form a heterocycloalkyl, CN, ethynyl, pyrimidinyl, pyridinyl, tetrahydropyridinyl, pyrrolidinyl, oxazolyl, thiazolyl.

In a further embodiment of the present invention B1 is selected from a pyridinyl substituted with one to three, such as two, substituents selected from Cl, Br, $CF_3$ and CN.

In a still further embodiment of the present invention B1 is selected from a pyridinyl substituted with one to three, such as one or two, substituents selected from $CONH_2$, and OH.

In a further embodiment of the present invention B1 is selected from a pyridinyl substituted with one to three, such as one, substituents selected from $NR^{30}R^{31}$, wherein $R^{30}$ and $R^{31}$ are independently selected from H, $C_{1-3}$ alkyl and isopropyl.

In a further embodiment of the present invention B1 is selected from a pyridazinyl substituted with one to three, such as two, substituents selected from Cl, OH, $OCH_3$, and CN.

In a still further embodiment of the present invention B1 is selected from a thiophenyl substituted with one to three, such as one, substituents selected from halogen, such as Cl.

In a further embodiment of the present invention B1 is selected from a $C_{5-7}$ cycloalkyl, optionally substituted with one or more substituents selected from a halogen (e.g. Cl, F, Br, I), methyl optionally substituted with a F, $OCH_3$ optionally substituted with a F, $OCH_2CH_3$ optionally substituted with a F, OH, and $R^{17}$—CONH— wherein $R^{17}$ is selected from $C_{1-3}$ alkyl and cyclopropyl.

In a still further embodiment of the present invention B1 is a cyclohexyl optionally substituted with one or more substituents selected from a halogen.

In a further embodiment of the present invention B1 is a cyclohexyl.

In a still further embodiment of the present invention B1 is a cyclohexyl substituted with one or two substituents selected from a halogen, such as 2 F.

In a further embodiment of the present invention $R^{50}$ is selected from the group consisting of a) $C_{1-6}$ alkyl optionally substituted with one or more halogen, CN, $OR^{51}$, $NR^{52}R^{53}$, and $CONH_2$, wherein $R^{51}$ is selected from the group consisting of H, CN, a halogen, methyl optionally substituted with a F, $OCH_3$ optionally substituted with a F, $OCH_2CH_3$ optionally substituted with a F, OH, and $R^{54}$. CONH— wherein $R^{54}$ is selected from $C_{1-3}$ alkyl and cyclopropyl, $R^{52}$ is selected from the group consisting of H, CN, a halogen, methyl optionally substituted with a F, $OCH_3$ optionally substituted with a F, $OCH_2CH_3$ optionally substituted with a F, OH, and $R^{55}$—CONH— wherein $R^{55}$ is selected from $C_{1-3}$ alkyl and cyclopropyl, and $R^{53}$ is selected from the group consisting of H, CN, a halogen, methyl optionally substituted with a F, $OCH_3$ optionally substituted with a F, $OCH_2CH_3$ optionally substituted with a F, OH, and $R^{56}$—CONH— wherein $R^{56}$ is selected from $C_{1-3}$ alkyl and cyclopropyl, b) branched $C_{3-6}$ alkyl optionally substituted with one or more halogen, CN, $OR^{57}$, $NR^{58}R^{59}$, and $CONH_2$, wherein $R^{57}$ is selected from the group consisting of H, CN, a halogen, methyl optionally substituted with a F, $OCH_3$ optionally substituted with a F, $OCH_2CH_3$ optionally substituted with a F, OH, and $R^{60}$—CONH— wherein $R^{60}$ is selected from $C_{1-3}$ alkyl and cyclopropyl, $R^{58}$ is selected from the group consisting of H, CN, a halogen, methyl optionally substituted with a F, $OCH_3$ optionally substituted with a F, $OCH_2CH_3$ optionally substituted with a F, OH, and $R^{61}$—CONH— wherein $R^{61}$ is selected from $C_{1-3}$ alkyl and cyclopropyl, and $R^{59}$ is selected from the group consisting of H, CN, a halogen, methyl optionally substituted with a F, $OCH_3$ optionally substituted with a F, $OCH_2CH_3$ optionally substituted with a F, OH, and $R^{62}$—CONH— wherein $R^{62}$ is selected from $C_{1-3}$ alkyl and cyclopropyl, In a still further embodiment of the present invention $R^{50}$ is selected from a) $C_{1-4}$ alkyl optionally substituted with at least one from the group consisting of halogen, $NR^{52}R^{53}$ wherein $R^{52}$ and $R^{53}$ are independently selected from the group consisting of H and $C_{1-4}$ alkyl, such as methyl, and $OR^{51}$ wherein $R^{51}$ is selected from the group consisting of H and methyl, or b) branched $C_{3-4}$ alkyl optionally substituted with at least one from the group consisting of halogen, $OR^{57}$ and wherein $R^{57}$ is selected from the group consisting of H and methyl.

In a further embodiment of the present invention, the compound is selected from the group consisting of:
5-Bromopyridin-3-yl 3-deoxy-3-[4-(3,4,5-trifluorophenyl)-1H-1,2,3-triazol-1-yl]-2-O-methyl-1-thio-α-D-galactopyranoside,
5-Bromo-2-cyano-pyridin-3-yl 3-deoxy-3-[4-(3-fluoro-4-methylphenyl)-1H-1,2,3-triazol-1-yl]-2-O-methyl-1-thio-α-D-galactopyranoside,
4-Bromo-N,N-dimethyl-benzamide-2-yl 3-deoxy-3-[4-(3,4,5-trifluorophenyl)-1H-1,2,3-triazol-1-yl]-2-O-methyl-1-thio-α-D-galactopyranoside,
4-Bromo-N,N-dimethyl-benzamide-2-yl 3-[4-(4-chloro-3,5-difluorophenyl)-1H-1,2,3-triazol-1-yl]-3-deoxy-2-O-methyl-1-thio-α-D-galactopyranoside,
5-Bromopyridin-3-yl 3-deoxy-3-[4-(3,4,5-trifluorophenyl)-1H-1,2,3-triazol-1-yl]-2-O-(1,1,1-trifluoro-2-hydroxy-prop-3-yl)-1-thio-α-D-galactopyranoside,
2-(N-piperidinyl-carbonyl)-5-chloro-phenyl 3-[4-(4-chloro-3,5-difluorophenyl)-1H-1,2,3-triazol-1-yl]-3-deoxy-2-O-methyl-1-thio-α-D-galactopyranoside,
4-Chloro-N,N-dimethyl-benzamide-2-yl 3-[4-(4-chloro-3,5-difluorophenyl)-1H-1,2,3-triazol-1-yl]-3-deoxy-2-O-trifluoromethyl-1-thio-α-D-galactopyranoside, 4-Chloro-N,N-dimethyl-benzamide-2-yl 3-deoxy-2-O-trifluoromethyl-3-[4-(3,4,5-trifluorophenyl)-1H-1,2,3-triazol-1-yl]-1-thio-α-D-galactopyranoside, 5-Chloro-2-(N,N-dimethylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside, 5-Chloro-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-2-cyano-pyridin-3-yl 3-deoxy-3-[4-(3,5-difluoro-4-methylphenyl)-1H-1,2,3-triazol-1-yl]-2-O-methyl-1-thio-α-D-galactopyranoside, 5-Chloro-2-cyano-pyridin-3-yl 3-deoxy-3-[4-(3-fluoro-4-methyl-phenyl)-1H-1,2,3-triazol-1-yl]-2-O-methyl-1-thio-α-D-galactopyranoside, 5-Chloro-2-cyano-phenyl 3-deoxy-3-[4-(3,5-difluoro-4-methylphenyl)-1H-1,2,3-triazol-1-yl]-2-O-methyl-1-thio-α-D-galactopyranoside, 5-Chloro-2-cyano-pyridin-3-yl 3-deoxy-2-O-2,2,2,-trifluoroethyl-3-[4-(3,4,5-trifluoro-phenyl)-1H-1,2,3-triazol-1-yl]-1-thio-α-D-galactopyranoside, 5-Chloro-2-cyano-pyridin-3-yl 3-deoxy-2-O-ethyl-3-[4-(3,4,5-trifluoro-phenyl)-1H-1,2,3-triazol-1-yl]-1-thio-α-D-galactopyranoside, 5-Bromopyridin-3-yl 3-deoxy-3-[4-(3,4,5-trifluorophenyl)-1H-1,2,3-triazol-1-yl]-2-O-ethyl-1-thio-α-D-galactopyranoside, 5-Bromopyridin-3-yl 3-deoxy-3-[4-(3,4,5-trifluorophenyl)-1H-1,2,3-triazol-1-yl]-2-O-isopropyl-1-thio-α-D-galactopyranoside, 5-Bromopyridin-3-yl 3-deoxy-3-[4-(3,4,5-trifluorophenyl)-1H-1,2,3-triazol-1-yl]-2-O-(2-fluoroethyl)-1-thio-α-D-galactopyranoside, 5-Bromopyridin-3-yl 3-deoxy-3-[4-(3,4,5-trifluorophenyl)-1H-1,2,3-triazol-1-yl]-2-O-[2-(methylamino)ethyl]-1-thio-α-D-galactopyranoside, 3,4-Dichlorophenyl 3-[4-(4-chloro-3,5-difluorophenyl)-1H-1,2,3-triazol-1-yl]-3-deoxy-2-O-(2-hydroxyethyl)-1-thio-α-D-galactopyranoside, 5-Chloro-6-cyano-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-6-cyano-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyrimidin-5-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-3-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(1,2,3,6-tetrahydropyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(3-pyrrolin-3-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(oxazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 2,5-Bis(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloropyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloropyridin-3-yl 3-deoxy-3-[4-(3-fluoro-4-methylphenyl)-1H-1,2,3-triazol-1-yl]-2-O-methyl-1-thio-α-D-galactopyranoside, 5-Bromopyridin-3-yl 3-deoxy-3-[4-(3-fluoro-4-methylphenyl)-1H-1,2,3-triazol-1-yl]-2-O-methyl-1-thio-α-D-galactopyranoside, 5-Chloropyridin-3-yl 3-[4-(4-chloro-3-fluorophenyl)-1H-1,2,3-triazol-1-yl]-3-deoxy-2-O-methyl-1-thio-α-D-galactopyranoside, 5-Bromopyridin-3-yl 3-[4-(4-chloro-3-fluorophenyl)-1H-1,2,3-triazol-1-yl]-3-deoxy-2-O-methyl-1-thio-α-D-galactopyranoside, 6-Trifluoromethyl-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside, 2-(N-azetidinyl-carbonyl)-5-chlorophenyl 3-[4-(4-chloro-3,5-difluorophenyl)-1H-1,2,3-triazol-1-yl]-3-deoxy-2-O-methyl-1-thio-α-D-galactopyranoside, 2-(N-azetidinyl-carbonyl)-5-chlorophenyl 3-deoxy-3-[4-(3-fluoro-4-methylphenyl)-1H-1,2,3-triazol-1-yl]-2-O-methyl-1-thio-α-D-galactopyranoside, 5-Chloropyridin-3-yl 3-deoxy-3-[4-(3,4,5-trifluorophenyl)-1H-1,2,3-triazol-1-yl]-2-O-methyl-1-thio-α-D-galactopyranoside, 5-Chloropyridin-3-yl 3-deoxy-3-[4-(6-fluoro-5-methylpyridin-2-yl)-1H-1,2,3-triazol-1-yl]-2-O-methyl-1-thio-α-D-galactopyranoside, 5-Chloropyridin-3-yl 3-[4-(5-chloro-6-methylpyridin-2-yl)-1H-1,2,3-triazol-1-yl]-3-deoxy-2-O-methyl-1-thio-α-D-galactopyranoside, 3-Chloro-2-cyanopyridin-5-yl 3-deoxy-3-[4-(3,4,5-trifluorophenyl)-1H-1,2,3-triazol-1-yl]-2-O-methyl-1-thio-α-D-galactopyranoside, 5-Chloro-2-cyanopyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-2-cyanopyridin-3-yl 3-[4-(4-chloro-3-fluorophenyl)-1H-1,2,3-triazol-1-yl]-3-deoxy-2-O-methyl-1-thio-α-D-galactopyranoside, 2-Cyano-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromo-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromo-2-cyanopyridin-3-yl 3-[4-(4-chloro-3-fluorophenyl)-1H-1,2,3-triazol-1-yl]-3-deoxy-2-O-methyl-1-thio-α-D-galactopyranoside, 5-Chloro-2-(N-azetidinylcarbamoyl)-3-pyridyl 3-[4-(4-chloro-3,5-difluorophenyl)-1H-1,2,3-triazol-1-yl]-3-deoxy-2-O-methyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside, 5-Ethynylpyridin-3-yl 3-[4-(4-chloro-3,5-difluorophenyl)-1H-1,2,3-triazol-1-yl]-3-deoxy-2-O-methyl-1-thio-α-D-galactopyranoside, and 5-Chloro-2-cyanopyridin-3-yl 3-[4-(5-chloro-6-fluoropyridin-2-yl)-1H-1,2,3-triazol-1-yl]-3-deoxy-2-O-methyl-1-thio-α-D-galactopyranoside; or a pharmaceutically acceptable salt or solvate thereof.

In a still further embodiment of the present invention, the compound is selected from the group consisting of:

2-Cyano-5-ethynylpyridin-3-yl 3-[4-(4-chloro-3,5-difluorophenyl)-1H-1,2,3-triazol-1-yl]-3-deoxy-2-O-methyl-1-thio-α-D-galactopyranoside, 2-Cyano-5-ethynylpyridin-3-yl 3-deoxy-3-[4-(3,5-difluoro-4-methylphenyl)-1H-1,2,3-triazol-1-yl]-2-O-methyl-1-thio-α-D-galactopyranoside, 5-Cyano-6-trifluoromethylpyridin-3-yl 3-[4-(4-chloro-3,5-difluorophenyl)-1H-1,2,3-triazol-1-yl]-3-deoxy-2-O-methyl-1-thio-α-D-galactopyranoside, 5-Cyanopyridin-3-yl 3-deoxy-3-[4-(3,4,5-trifluorophenyl)-1H-1,2,3-triazol-1-yl]-2-O-methyl-1-thio-α-D-galactopyranoside, 5-Cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromo-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside, 5-Bromo-2-(N-azetidinylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside, 5-Bromo-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside, 2-(N-azetidinyl-carbonyl)-5-bromophenyl 3-deoxy-3-[4-(3,4,5-trifluorophenyl)-1H-1,2,3-triazol-1-yl]-2-O-methyl-1-thio-α-D-galactopyranoside, 2-(N-azetidinyl-carbonyl)-5-bromophenyl 3-deoxy-3-[4-(3,4,5-trifluorophenyl)-1H-1,2,3-triazol-1-yl]-2-O-ethyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside, 5-Chloro-2-(N-azetidinylcarbamoyl)-3-pyridyl 3-[4-(4-chloro-3,5-difluorophenyl)-1H-1,2,3-triazol-1-yl]-3-deoxy-2-O-ethyl-1-thio-α-D-galactopyranoside, 2-(N-azetidinyl-carbonyl)-5-chlorophenyl 3-deoxy-3-[4-(3,4,5-trifluorophenyl)-1H-1,2,3-triazol-1-yl]-2-O-methyl-1-thio-α-D-galactopyranoside, and 3,4-Dichlorophenyl 3-[4-(4-chloro-3,5-difluorophenyl)-1H-1,2,3-triazol-1-yl]-3-deoxy-2-O-methyl-1-thio-α-D-galactopyranoside; or a pharmaceutically acceptable salt or solvate thereof.

In a further aspect the present invention relates to a compound of formula (1) for use as a medicine.

In a still further aspect the present invention relates to a pharmaceutical composition comprising the compound of any one of the previous claims and optionally a pharmaceutically acceptable additive, such as a carrier and/or excipient.

In a further aspect the present invention relates to a compound of formula (1) of the present invention for use in a method for treating a disorder relating to the binding of a galectin-3 to a ligand in a mammal, such as a human. In a further embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistens; obesity; Diastolic HF; asthma and other interstitial lung diseases, including Hermansky-Pudlak syndrome, mesothelioma; liver disorders, such as non-alcoholic steatohepatitis or non-alcoholic fatty liver disease.

In a still further aspect the present invention relates to a method for treatment of a disorder relating to the binding of a galectin-3 to a ligand in a mammal, such as a human, wherein a therapeutically effective amount of at least one compound of formula (1) of the present invention is administered to a mammal in need of said treatment. In a further embodiment of the present invention, the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistens; obesity; Diastolic HF; asthma and other interstitial lung diseases, including Hermansky-Pudlak syndrome, mesothelioma; liver disorders, such as non-alcoholic steatohepatitis or non-alcoholic fatty liver disease.

Another aspect of the present invention concerns combination therapy involving administering a compound of formula (1) of the present invention together with a therapeutically active compound different from the compound of formula (1) (interchangeable with "a different therapeutically active compound"). In one embodiment the present invention relates to a combination of a compound of formula (1) and a different therapeutically active compound for use in treatment of a disorder relating to the binding of a galectin-3 to a ligand in a mammal. Such disorders are disclosed below.

In an embodiment of the present invention, a therapeutically effective amount of at least one compound of formula (1) of the present invention is administered to a mammal in need thereof in combination with a different therapeutically active compound. In a further embodiment, said combination of a compound of formula (1) together with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistens; obesity; Diastolic HF; asthma and other interstitial lung diseases, including Hermansky-Pudlak syndrome, mesothelioma; liver disorders, such as non-alcoholic steatohepatitis or non-alcoholic fatty liver disease.

A non-limiting group of cancers given as examples of cancers that may be treated, managed and/or prevented by administration of a compound of formula (1) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (1) of the present invention and at least one additional therapeutic agent demonstrates therapeutic synergy. In some aspects of the methods of the present invention, a measurement of response to treatment observed after administering both at least one compound of formula (1) of the present invention and the additional therapeutic agent is improved over the same measurement of response to treatment observed after administering either the at least one compound of formula (1) of the present invention or the additional therapeutic agent alone.

A further aspect of the present invention concerns combination therapy involving administering a compound of formula (1) of the present invention together with an anti-fibrotic compound different form the compound of formula (1) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, PAT-1251 and PBI-4050.

A still further aspect of the present invention concerns combination therapy involving administering a compound of formula (1) in combination with a further conventional cancer treatment such as chemotherapy or radiotherapy, or treatment with immunostimulating substances, gene therapy, treatment with antibodies and treatment using dendritic cells, to a mammal in need thereof.

In an embodiment the compound of formula (1) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (1) is administered together with at least one additional therapeutic agent selected from a checkpoint inhibitor. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO. These are known targets and some of these targets are described in Melero et al., Nature Reviews Cancer (2015). Examples of check point inhibitors administered together with the compound of formula (1) are Anti-PD-1: Nivolumab, Pembrolizumab, Cemiplimab. Anti-PD-L1: Atezolizumab, Avelumab, Durvalumab and one Anti-CTLA-4: Ipilimumab. Each one of these check point inhibitors can be made the subject of an embodiment in combination with any one of the compounds of formula (1).

In some embodiments of the present invention the compound of formula (1) is administered together with at least one additional therapeutic agent selected from an inhibitor of indoleamine-2,3-dioxygenase (IDO).

In some embodiments of the present invention the compound of formula (1) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (1) is administered together with at least one additional therapeutic agent selected from one or more inhibitors of the PD-1/PD-L pathway. In some embodiments, the one or more inhibitors of the PD-1/PD-L pathway are selected from one or more antibodies against PD-1, PD-L1, and/or PD-L2.

In a still further aspect the present invention relates to a process of preparing a compound of formula 1 or a pharmaceutically acceptable salt or solvate thereof comprising the step a comprising the step a1-a3):

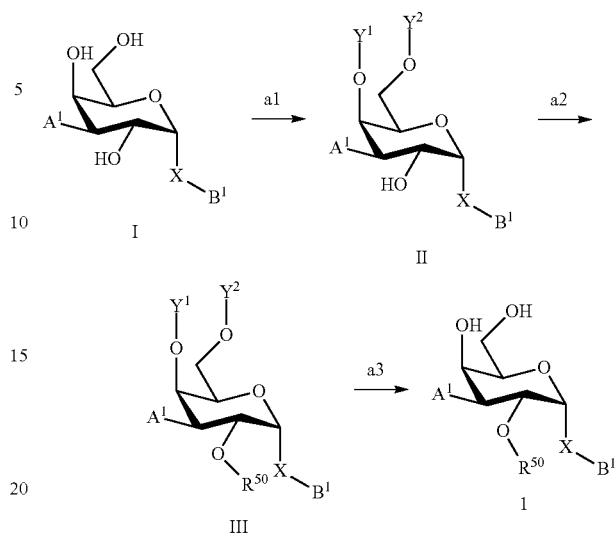

a1) Protecting a compound of the structure I using a protecting group to form a compound of formula II wehrein the OH in the 4 and 6- position is protected by a protective group denoted $Y^1$ and $Y^2$. One example could be reacting I with benzaldehyde dimethylacetal in the prescence an acid such as p-toluenesulphonic acid to give a compound of formula II where Y1 and Y2 is defined as benzylidene.
a2) Reacting a compound of formula II with an $R^{50}$-$L^1$ wherein $L^1$ is a leaving group such as a halide or sulfonate in the presence of a base to give a compound of formula III. One example could be reacting a compound of formula II with methyliodide in the presence of NaH.
a3) Reacting a compoung of formula III with chemical that removes the protective group to give a compound of the formula 1. One example could be when a compound of formula III where Y1 and Y2 is a bensylidene is reacted with an acid such as trifluoroacetic acid to give a compound of formula (1)

DETAILED DESCRIPTION

The present compounds of formula (1) differ from prior art compounds in particular in that the pyranose ring is α-D-galactopyranose and that the C2 carbon has an optionally substituted alkoxy attached that has the potential of reducing polarity of that position. Reduced polarity correlates in general with good uptake. It is important to emphasize that alpha and beta anomers are very different isomers and it is by no means considered to be obvious to the skilled person to expect same or similar activity of both anomers. Consequently, alpha and beta anomers do not in general posses the same activity, and this is common knowledge to the skilled person. In general, the compounds of formula (1) are believed to be >10 fold better with respect to galectin-3 affinity compared to the corresponding beta-anomers.

In a broad aspect the present invention relates to a D-galactopyranose compound of formula (1)

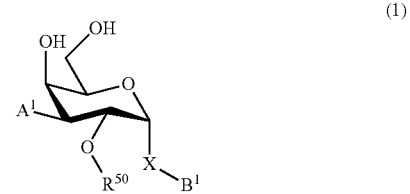

(1)

wherein
the pyranose ring is α-D-galactopyranose,
$A^1$ is selected from

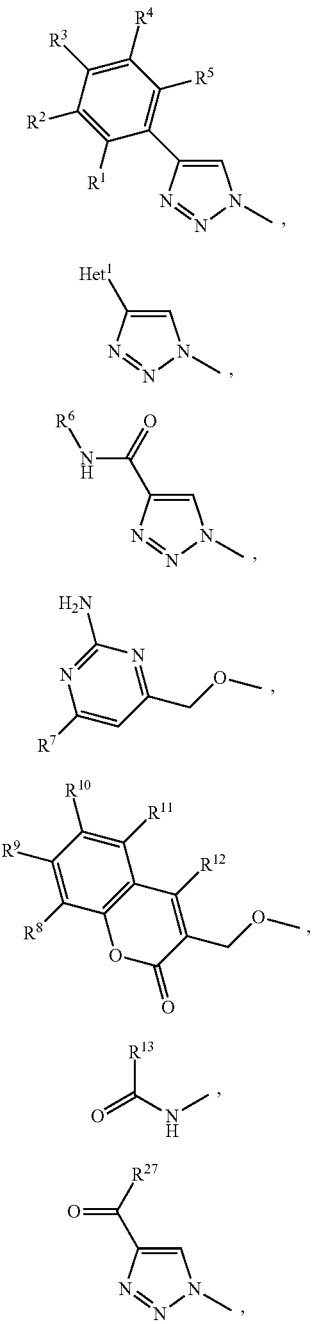

wherein $Het^1$ is selected from a five or six membered heteroaromatic ring, optionally substituted with a group selected from Br; F; Cl; I; CN; $NR^{19}R^{20}$, wherein $R^{19}$ and $R^{20}$ are independently selected from H, $C_{1-3}$ alkyl, cyclopropyl, iso-propyl, —C(=O)—$R^{21}$, wherein $R^{21}$ is selected from H and $C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; $OC_{1-3}$ alkyl optionally substituted with a F; and $SC_{1-3}$ alkyl optionally substituted with a F;

wherein $R^1$-$R^5$ are independently selected from H, CN, $NH_2$, Br, Cl, I, F, methyl optionally substituted with a F, $SCH_3$ optionally substituted with a F, and $OCH_3$ optionally substituted with a F;

wherein $R^6$ is selected from $C_{1-6}$ alkyl optionally substituted with a halogen, branched $C_{3-6}$ alkyl and $C_{3-7}$ cycloalkyl;

wherein $R^7$ is selected from a five or six membered heteroaromatic ring, optionally substituted with a group selected from Br, F, Cl, methyl optionally substituted with a F, and $OCH_3$ optionally substituted with a F, and a phenyl optionally substituted with a group selected from Br, F, Cl, methyl optionally substituted with a F, and $OCH_3$ optionally substituted with a F;

wherein $R^8$-$R^{12}$ are independently selected from H, F, methyl optionally substituted with a F, and $OCH_3$ optionally substituted with a F;

wherein $R^{13}$ is a five or six membered heteroaromatic ring optionally substituted with a group selected from H, OH, F, methyl optionally substituted with a F, and $OCH_3$ optionally substituted with a F, or an aryl, such as phenyl or naphthyl, optionally substituted with a group selected from H, OH, F, methyl optionally substituted with a F, and $OCH_3$ optionally substituted with a F;

$X^1$ is selected from S, SO, $SO_2$, O, C=O, and $CR^7R^8$ wherein $R^7$ and $R^8$ are independently selected from hydrogen, OH, or halogen;

wherein $R^{27}$ is selected from a $C_{1-6}$ alkyl, branched $C_{3-6}$ alkyl, $C_{1-6}$ alkoxy and branched $C_{3-6}$ alkoxy;

$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{15}$—CONH— wherein $R^{15}$ is selected from $C_{1-3}$ alkyl and cyclopropyl; b) an aryl, such as phenyl or naphthyl, optionally substituted with a group selected from a halogen; CN; —COOH; —$CONR^{22}R^{23}$, wherein $R^{22}$ and $R^{23}$ are independently selected from H, $C_{1-3}$ alkyl, cyclopropyl, and iso-propyl, or $R^{22}$ and $R^{23}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{28}R^{29}$, wherein $R^{28}$ and $R^{29}$ are independently selected from H, $C_{1-3}$ alkyl and isopropyl; OH; and $R^{16}$—CONH— wherein $R^{16}$ is selected from $C_{1-3}$ alkyl and cyclopropyl; c) a $C_{5-7}$ cycloalkyl, optionally substituted with a substituent selected from a halogen, CN, methyl optionally substituted with a F, $OCH_3$ optionally substituted with a F, $OCH_2CH_3$ optionally substituted with a F, OH, and $R^{17}$—CONH— wherein $R^{17}$ is selected from $C_{1-3}$ alkyl and cyclopropyl; and d) a heterocycle, such as heteroaryl or heterocycloalkyl, optionally substituted with a group selected from a halogen; CN; —COOH; —CONR$^{24}$R$^{25}$, wherein R$^{24}$ and R$^{25}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{30}$R$^{31}$, wherein R$^{30}$ and R$^{31}$ are independently selected from H, C$_{1-3}$ alkyl and isopropyl; OH; and R$^{18}$—CONH— wherein R$^{18}$ is selected from C$_{1-3}$ alkyl and cyclopropyl; e) a C$_{1-6}$ alkyl or branched C$_{3-6}$ alkyl;

R$^{50}$ is selected from the group consisting of a) C$_{1-6}$ alkyl optionally substituted with one or more halogen, CN, OR$^{51}$, NR$^{52}$R$^{53}$, and CONH$_2$, wherein R$^{51}$ is selected from the group consisting of H, CN, a halogen, methyl optionally substituted with a F, OCH$_3$ optionally substituted with a F, OCH$_2$CH$_3$ optionally substituted with a F, OH, and R$^{54}$—CONH— wherein R$^{54}$ is selected from C$_{1-3}$ alkyl and cyclopropyl, R$^{52}$ is selected from the group consisting of H, CN, a halogen, methyl optionally substituted with a F, OCH$_3$ optionally substituted with a F, OCH$_2$CH$_3$ optionally substituted with a F, OH, and R$^{55}$—CONH— wherein R$^{55}$ is selected from C$_{1-3}$ alkyl and cyclopropyl, and R$^{53}$ is selected from the group consisting of H, CN, a halogen, methyl optionally substituted with a F, OCH$_3$ optionally substituted with a F, OCH$_2$CH$_3$ optionally substituted with a F, OH, and R$^{56}$—CONH— wherein R$^{56}$ is selected from C$_{1-3}$ alkyl and cyclopropyl, b) branched C$_{3-6}$ alkyl optionally substituted with one or more halogen, CN, OR$^{57}$, NR$^{58}$R$^{59}$, and CONH$_2$, wherein R$^{57}$ is selected from the group consisting of H, CN, a halogen, methyl optionally substituted with a F, OCH$_3$ optionally substituted with a F, OCH$_2$CH$_3$ optionally substituted with a F, OH, and R$^{60}$—CONH— wherein R$^{60}$ is selected from C$_{1-3}$ alkyl and cyclopropyl, R$^{58}$ is selected from the group consisting of H, CN, a halogen, methyl optionally substituted with a F, OCH$_3$ optionally substituted with a F, OCH$_2$CH$_3$ optionally substituted with a F, OH, and R$^{61}$—CONH— wherein R$^{61}$ is selected from C$_{1-3}$ alkyl and cyclopropyl, and R$^{59}$ is selected from the group consisting of H, CN, a halogen, methyl optionally substituted with a F, OCH$_3$ optionally substituted with a F, OCH$_2$CH$_3$ optionally substituted with a F, OH, and R$^{62}$—CONH— wherein R$^{62}$ is selected from C$_{1-3}$ alkyl and cyclopropyl, and c) cyclic C$_{3-6}$ alkyl optionally substituted with one or more halogen, CN, OR$^{63}$, NR$^{64}$R$^{65}$, and CONH$_2$, wherein R$^{63}$ is selected from the group consisting of H, CN, a halogen, methyl optionally substituted with a F, OCH$_3$ optionally substituted with a F, OCH$_2$CH$_3$ optionally substituted with a F, OH, and R$^{66}$—CONH— wherein R$^{66}$ is selected from C$_{1-3}$ alkyl and cyclopropyl, R$^{64}$ is selected from the group consisting of H, CN, a halogen, methyl optionally substituted with a F, OCH$_3$ optionally substituted with a F, OCH$_2$CH$_3$ optionally substituted with a F, OH, and R$^{67}$—CONH— wherein R$^{67}$ is selected from C$_{1-3}$ alkyl and cyclopropyl, and R$^{65}$ is selected from the group consisting of H, CN, a halogen, methyl optionally substituted with a F, OCH$_3$ optionally substituted with a F, OCH$_2$CH$_3$ optionally substituted with a F, OH, and R$^{68}$—CONH— wherein R$^{68}$ is selected from C$_{1-3}$ alkyl and cyclopropyl; or a pharmaceutically acceptable salt or solvate thereof.

In an embodiment A1 is selected from formula 2 wherein R$^1$-R$^5$ are independently selected from H, F, methyl optionally substituted with a F, and OCH$_3$ optionally substituted with a F. In further embodiments A1 is selected from formula 2 wherein R$^1$ and R$^5$ are selected from H and R$^2$-R$^4$ are selected from F or wherein R$^1$-R$^5$ are all F or wherein R$^2$ and R$^3$ are F and R$^1$, R$^4$ and R$^5$ are H, or wherein R$^2$ and R$^4$ are F and R$^1$, R$^3$ and R$^5$ are H, or wherein R$^2$ is F and R$^1$, R$^3$-R$^5$ are H, or wherein R$^2$ and R$^4$ are F, R$^3$ is OCH$_3$, and R$^1$ and R$^5$ are H. In a further embodiment A1 is selected from formula 2 wherein R$^1$ and R$^5$ are H and R$^2$-R$^4$ are independently selected from methyl, Cl and F, such as R$^2$ and R$^4$ are F and R$^3$ is methyl or R$^2$ and R$^4$ are F and R$^3$ is Cl. In a further embodiment A1 is selected from formula 2 wherein R$^1$, R$^4$ and R$^5$ are H and R$^2$ and R$^3$ are independently selected from methyl, F, and Cl, such as R$^2$ is F and R$^3$ is Cl, or R$^2$ is F and R$^3$ is methyl, or R$^2$ is methyl and R$^3$ is Cl.

In another embodiment A1 is selected from formula 3 wherein Het$^1$ is selected from a six membered heteroaromatic ring, optionally substituted with a group selected from CN, Br, Cl, I, F, methyl optionally substituted with a F, OCH$_3$ optionally substituted with a F, and SCH$_3$ optionally substituted with a F. In a further embodiment A1 is selected from formula 3 wherein Het$^1$ is selected from a pyridinyl, optionally substituted with a group selected from CN, Br, Cl, I, F, methyl optionally substituted with a F, OCH$_3$ optionally substituted with a F, and SCH$_3$ optionally substituted with a F. In a further embodiment A1 is selected from formula 3 wherein Het$^1$ is selected from a pyridinyl substituted with a group independently selected from F, Cl, and methyl, such as pyridinyl substituted with two group selected from F, Cl, and methyl. In a still further embodiment A1 is selected from formula 3 wherein Het$^1$ is selected from a pyrimidyl, optionally substituted with a group selected from CN, Br, Cl, I, F, methyl optionally substituted with a F, OCH$_3$ optionally substituted with a F, and SCH$_3$ optionally substituted with a F.

In a still further embodiment X1 is selected from S, SO, SO$_2$, and O, such as S, SO, and SO$_2$, preferably S.

In a further embodiment B1 is selected from a heterocycle, such as heteroaryl or heterocycloalkyl, optionally substituted with a group selected from a halogen; CN; methyl optionally substituted with a F; OCH$_3$ optionally substituted with a F; OCH$_2$CH$_3$ optionally substituted with a F; OH; CONH$_2$; NR$^{30}$R$^{31}$, wherein R$^{30}$ and R$^{31}$ are independently selected from H, C$_{1-3}$ alkyl and isopropyl; and R$^{18}$—CONH— wherein R$^{18}$ is selected from C$_{1-3}$ alkyl and cyclopropyl. In a preferred embodiment B1 is selected from a pyridinyl optionally substituted with a group selected from Cl, Br, CF$_3$, OCH$_3$, OH, NH$_2$, CONH$_2$, and CN. In one example B1 is selected from a pyridinyl substituted with a group independently selected from CF$_3$ and CH$_3$, such as one CF$_3$ and one CH$_3$. In another example B1 is selected from a pyridinyl substituted with a group independently selected from CF$_3$ and CN, such as one CF$_3$ and one CN. In a more preferred embodiment B1 is pyridinyl substituted with a halogen, such as Br or Cl, in particular one Br or one Cl. In a preferred embodiment B1 is pyridinyl substituted with an alkynyl, such as C$_{2-4}$ alkynyl, preferably one ethynyl. In a further embodiment of the present invention B1 is selected from a pyridinyl substituted with a group independently selected from a Cl, CN, and N-(2-oxa)-6-azaspiro[3.3]heptanyl, such as one Cl, one CN and one N-(2-oxa)-6-azaspiro[3.3]heptanyl. In another embodiment B1 is selected from a pyridinyl substituted with two groups selected from one Cl and one CN. In a further embodiment of the present invention B1 is selected from a pyridinyl substituted with a group independently selected from a methyl and CN, such as one methyl and one CN. In another embodiment B1 is selected from a pyridinyl substituted with two groups selected from one Br and one CN. In a still further embodiment B1 is selected from a pyridinyl substituted with a group independently selected from Cl, pyrimidinyl, pyridinyl, tetrahydropyridinyl, pyrrolidinyl, oxazolyl, and thiazolyl, such as two substituents independently selected from Cl, pyrimidinyl, pyridinyl, tetrahydropyridinyl, pyrrolidinyl, oxazolyl, and thiazolyl; Typically, one substituent is Cl and the other is selected from pyrimidinyl, pyridinyl, tetrahydropyridinyl, pyrrolidinyl, oxazolyl, and thiazolyl. In a further embodiment B1 is selected from a pyridinyl substituted with one or two thiazolyl, such as two thiazolyl. In a further embodiment B1 is selected from a pyridinyl substituted with a group independently selected from Cl, Br and —$CONR^{24}R^{25}$, wherein $R^{24}$ and $R^{25}$ together with the nitrogen form a heterocycloalkyl. In a still further embodiment B1 is selected from a pyridinyl substituted with two groups independently selected from Cl, Br and —$CONR^{24}R^{25}$, wherein $R^{24}$ and $R^{25}$ together with the nitrogen form a heterocyclobutyl. Typically, B1 is selected from a pyridinyl substituted with two groups selected from one Cl, and one —$CONR^{24}R^{25}$, wherein $R^{24}$ and $R^{25}$ together with the nitrogen form a heterocyclobutyl, or B1 is selected from a pyridinyl substituted with two groups selected from one Br, and one —$CONR^{24}R^{25}$, wherein $R^{24}$ and $R^{25}$ together with the nitrogen form a heterocyclobutyl. In a preferred embodiment B1 is pyridinyl substituted with a group independently selected from CN and $C_{2-4}$ alkynyl, such as one CN and one ethynyl. In a further embodiment of the present invention B1 is selected from a pyridinyl substituted with a CN, such as one CN.

In a further embodiment B1 is selected from a phenyl substituted with a group independently selected from a halogen, such as Cl, typically two Cl. In a still further embodiment B1 is selected from a phenyl substituted with a group independently selected from halogen and —$CONR^{22}R^{23}$, wherein $R^{22}$ and $R^{23}$ are independently selected from H, $C_{1-3}$ alkyl, cyclopropyl, and iso-propyl, or $R^{22}$ and $R^{23}$ together with the nitrogen may form a heterocycloalkyl, such as a phenyl substituted with a group independently selected from Cl, Br and —$CONR^{22}R^{23}$, wherein $R^{22}$ and $R^{23}$ together with the nitrogen may form a heterocycloalkyl, such as a heterocyclobutyl or heterocyclohexyl. Typically, B1 is selected from a phenyl substituted with one Cl and one heterocycloalkyl, such as a heterocyclobutyl or heterocyclohexyl, or B1 is selected from a phenyl substituted with one Br and one heterocycloalkyl, such as a heterocyclobutyl or heterocyclohexyl.

In a further embodiment $R^{50}$ is selected from $C_{1-4}$ alkyl or branched $C_{3-6}$ alkyl optionally substituted with at least one from the group consisting of halogen and $OR^{51}$ wherein $R^{51}$ is selected from the group consisting of H, CN, a halogen, methyl optionally substituted with a F, $OCH_3$ optionally substituted with a F, $OCH_2CH_3$ optionally substituted with a F, OH, and $R^{54}$—CONH— wherein $R^{54}$ is selected from $C_{1-3}$ alkyl and cyclopropyl. In one embodiment $R^{50}$ is selected from branched $C_{3-6}$ alkyl, such as isopropyl.

In a still further embodiment $R^{50}$ is selected from $C_{1-4}$ alkyl, $C_{1-4}$ alkyl substituted with at least one from the group consisting of halogen and $OR^{51}$ wherein $R^{51}$ is selected from the group consisting of H, CN, a halogen, methyl optionally substituted with a F, $OCH_3$ optionally substituted with a F, $OCH_2CH_3$ optionally substituted with a F, OH, and $R^{54}$—CONH— wherein $R^{54}$ is selected from $C_{1-3}$ alkyl and cyclopropyl. In one embodiment $R^{50}$ is selected from $C_{1-4}$ alkyl, such as methyl or ethyl. In another embodiment $R^{50}$ is selected from $C_{1-4}$ alkyl substituted with at least one from the group consisting of halogen, $NRS^2R^{53}$, wherein $R^{52}$ and $R^{53}$ are independently selected from the group consisting H and methyl, and OH, such as 3F and one OH. In a still further embodiment $R^{50}$ is selected from $C_{1-4}$ alkyl, such as ethyl, substituted with a halogen, such as one F. In a further embodiment $R^{50}$ is selected from $C_{1-4}$ alkyl, such as ethyl, substituted with a OH, such as one OH. In a still further embodiment $R^{50}$ is selected from $C_{1-4}$ alkyl, such as ethyl, substituted with a $NH_2$, $NHCH_3$ or $N(CH_3)_2$, such as $NHCH_3$. In a further embodiment $R^{50}$ is selected from $C_{1-4}$ alkyl, such as methyl, substituted with a halogen, such as F.

In a further embodiment the compound of formula (1) is selected from the group consisting of:
5-Bromopyridin-3-yl 3-deoxy-3-[4-(3,4,5-trifluorophenyl)-1H-1,2,3-triazol-1-yl]-2-O-methyl-1-thio-α-D-galactopyranoside,
5-Bromo-2-cyano-pyridin-3-yl 3-deoxy-3-[4-(3-fluoro-4-methylphenyl)-1H-1,2,3-triazol-1-yl]-2-O-methyl-1-thio-α-D-galactopyranoside,
4-Bromo-N,N-dimethyl-benzamide-2-yl 3-deoxy-3-[4-(3,4,5-trifluorophenyl)-1H-1,2,3-triazol-1-yl]-2-O-methyl-1-thio-α-D-galactopyranoside,
4-Bromo-N,N-dimethyl-benzamide-2-yl 3-[4-(4-chloro-3,5-difluorophenyl)-1H-1,2,3-triazol-1-yl]-3-deoxy-2-O-methyl-1-thio-α-D-galactopyranoside,
5-Bromopyridin-3-yl 3-deoxy-3-[4-(3,4,5-trifluorophenyl)-1H-1,2,3-triazol-1-yl]-2-O-(1,1,1-trifluoro-2-hydroxy-prop-3-yl)-1-thio-α-D-galactopyranoside,
2-(N-piperidinyl-carbonyl)-5-chloro-phenyl 3-[4-(4-chloro-3,5-difluorophenyl)-1H-1,2,3-triazol-1-yl]-3-deoxy-2-O-methyl-1-thio-α-D-galactopyranoside,
4-Chloro-N,N-dimethyl-benzamide-2-yl 3-[4-(4-chloro-3,5-difluorophenyl)-1H-1,2,3-triazol-1-yl]-3-deoxy-2-O-trifluoromethyl-1-thio-α-D-galactopyranoside,
4-Chloro-N,N-dimethyl-benzamide-2-yl 3-deoxy-2-O-trifluoromethyl-3-[4-(3,4,5-trifluorophenyl)-1H-1,2,3-triazol-1-yl]-1-thio-α-D-galactopyranoside,
5-Chloro-2-(N,N-dimethylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside,
5-Chloro-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside,
5-Chloro-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside,
5-Chloro-2-cyano-pyridin-3-yl 3-deoxy-3-[4-(3,5-difluoro-4-methylphenyl)-1H-1,2,3-triazol-1-yl]-2-O-methyl-1-thio-α-D-galactopyranoside,
5-Chloro-2-cyano-pyridin-3-yl 3-deoxy-3-[4-(3-fluoro-4-methyl-phenyl)-1H-1,2,3-triazol-1-yl]-2-O-methyl-1-thio-α-D-galactopyranoside,
5-Chloro-2-cyano-phenyl 3-deoxy-3-[4-(3,5-difluoro-4-methylphenyl)-1H-1,2,3-triazol-1-yl]-2-O-methyl-1-thio-α-D-galactopyranoside,
5-Chloro-2-cyano-pyridin-3-yl 3-deoxy-2-O-2,2,2,-trifluoroethyl-3-[4-(3,4,5-trifluoro-phenyl)-1H-1,2,3-triazol-1-yl]-1-thio-α-D-galactopyranoside,
5-Chloro-2-cyano-pyridin-3-yl 3-deoxy-2-O-ethyl-3-[4-(3,4,5-trifluoro-phenyl)-1H-1,2,3-triazol-1-yl]-1-thio-α-D-galactopyranoside,
5-Bromopyridin-3-yl 3-deoxy-3-[4-(3,4,5-trifluorophenyl)-1H-1,2,3-triazol-1-yl]-2-O-ethyl-1-thio-α-D-galactopyranoside, 5-Bromopyridin-3-yl 3-deoxy-3-[4-(3,4,5-trifluorophenyl)-1H-1,2,3-triazol-1-yl]-2-O-isopropyl-1-thio-α-D-galactopyranoside, 5-Bromopyridin-3-yl 3-deoxy-3-[4-(3,4,5-trifluorophenyl)-1H-1,2,3-triazol-1-yl]-2-O-(2-fluoroethyl)-1-thio-α-D-galactopyranoside, 5-Bromopyridin-3-yl 3-deoxy-3-[4-(3,4,5-trifluorophenyl)-1H-1,2,3-triazol-1-yl]-2-O-[2-(methylamino)ethyl]-1-thio-α-D-galactopyranoside, 3,4-Dichlorophenyl 3-[4-(4-chloro-3,5-difluorophenyl)-1H-1,2,3-triazol-1-yl]-3-deoxy-2-O-(2-hydroxyethyl)-1-thio-α-D-galactopyranoside, 5-Chloro-6-cyano-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-6-cyano-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyrimidin-5-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-3-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(1,2,3,6-tetrahydropyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(3-pyrrolin-3-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(oxazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 2,5-Bis(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloropyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloropyridin-3-yl 3-deoxy-3-[4-(3-fluoro-4-methylphenyl)-1H-1,2,3-triazol-1-yl]-2-O-methyl-1-thio-α-D-galactopyranoside, 5-Bromopyridin-3-yl 3-deoxy-3-[4-(3-fluoro-4-methylphenyl)-1H-1,2,3-triazol-1-yl]-2-O-methyl-1-thio-α-D-galactopyranoside, 5-Chloropyridin-3-yl 3-[4-(4-chloro-3-fluorophenyl)-1H-1,2,3-triazol-1-yl]-3-deoxy-2-O-methyl-1-thio-α-D-galactopyranoside, 5-Bromopyridin-3-yl 3-[4-(4-chloro-3-fluorophenyl)-1H-1,2,3-triazol-1-yl]-3-deoxy-2-O-methyl-1-thio-α-D-galactopyranoside, 6-Trifluoromethyl-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside, 2-(N-azetidinyl-carbonyl)-5-chlorophenyl 3-[4-(4-chloro-3,5-difluorophenyl)-1H-1,2,3-triazol-1-yl]-3-deoxy-2-O-methyl-1-thio-α-D-galactopyranoside, 2-(N-azetidinyl-carbonyl)-5-chlorophenyl 3-deoxy-3-[4-(3-fluoro-4-methylphenyl)-1H-1,2,3-triazol-1-yl]-2-O-methyl-1-thio-α-D-galactopyranoside, 5-Chloropyridin-3-yl 3-deoxy-3-[4-(3,4,5-trifluorophenyl)-1H-1,2,3-triazol-1-yl]-2-O-methyl-1-thio-α-D-galactopyranoside, 5-Chloropyridin-3-yl 3-deoxy-3-[4-(6-fluoro-5-methylpyridin-2-yl)-1H-1,2,3-triazol-1-yl]-2-O-methyl-1-thio-α-D-galactopyranoside, 5-Chloropyridin-3-yl 3-[4-(5-chloro-6-methylpyridin-2-yl)-1H-1,2,3-triazol-1-yl]-3-deoxy-2-O-methyl-1-thio-α-D-galactopyranoside, 3-Chloro-2-cyanopyridin-5-yl 3-deoxy-3-[4-(3,4,5-trifluorophenyl)-1H-1,2,3-triazol-1-yl]-2-O-methyl-1-thio-α-D-galactopyranoside, 5-Chloro-2-cyanopyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-2-cyanopyridin-3-yl 3-[4-(4-chloro-3-fluorophenyl)-1H-1,2,3-triazol-1-yl]-3-deoxy-2-O-methyl-1-thio-α-D-galactopyranoside, 2-Cyano-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromo-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromo-2-cyanopyridin-3-yl 3-[4-(4-chloro-3-fluorophenyl)-1H-1,2,3-triazol-1-yl]-3-deoxy-2-O-methyl-1-thio-α-D-galactopyranoside, 5-Chloro-2-(N-azetidinylcarbamoyl)-3-pyridyl 3-[4-(4-chloro-3,5-difluorophenyl)-1H-1,2,3-triazol-1-yl]-3-deoxy-2-O-methyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-thio-α-D-galactopyranoside, 5-Ethynylpyridin-3-yl 3-[4-(4-chloro-3,5-difluorophenyl)-1H-1,2,3-triazol-1-yl]-3-deoxy-2-O-methyl-1-thio-α-D-galactopyranoside, and 5-Chloro-2-cyanopyridin-3-yl 3-[4-(5-chloro-6-fluoropyridin-2-yl)-1H-1,2,3-triazol-1-yl]-3-deoxy-2-O-methyl-1-thio-α-D-galactopyranoside; or a pharmaceutically acceptable salt or solvent thereof. Typically, the compound of formula (1) is selected from the group consisting of:

5-Bromopyridin-3-yl 3-deoxy-3-[4-(3,4,5-trifluorophenyl)-1H-1,2,3-triazol-1-yl]-2-O-methyl-1-thio-α-D-galactopyranoside, 5-Bromo-2-cyano-pyridin-3-yl 3-deoxy-3-[4-(3-fluoro-4-methylphenyl)-1H-1,2,3-triazol-1-yl]-2-O-methyl-1-thio-α-D-galactopyranoside, 4-Bromo-N,N-dimethyl-benzamide-2-yl 3-deoxy-3-[4-(3,4,5-trifluorophenyl)-1H-1,2,3-triazol-1-yl]-2-O-methyl-1-thio-α-D-galactopyranoside, 4-Bromo-N,N-dimethyl-benzamide-2-yl 3-[4-(4-chloro-3,5-difluorophenyl)-1H-1,2,3-triazol-1-yl]-3-deoxy-2-O-methyl-1-thio-α-D-galactopyranoside, 5-Bromopyridin-3-yl 3-deoxy-3-[4-(3,4,5-trifluorophenyl)-1H-1,2,3-triazol-1-yl]-2-O-(1,1,1-trifluoro-2-hydroxy-prop-3-yl)-1-thio-α-D-galactopyranoside, 2-(N-piperidinyl-carbonyl)-5-chloro-phenyl 3-[4-(4-chloro-3,5-difluorophenyl)-1H-1,2,3-triazol-1-yl]-3-deoxy-2-O-methyl-1-thio-α-D-galactopyranoside, 4-Chloro-N,N-dimethyl-benzamide-2-yl 3-[4-(4-chloro-3,5-difluorophenyl)-1H-1,2,3-triazol-1-yl]-3-deoxy-2-O-trifluoromethyl-1-thio-α-D-galactopyranoside, 4-Chloro-N,N-dimethyl-benzamide-2-yl 3-deoxy-2-O-trifluoromethyl-3-[4-(3,4,5-trifluorophenyl)-1H-1,2,3-triazol-1-yl]-1-thio-α-D-galactopyranoside, 5-Chloro-2-(N,N-dimethylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside, 5-Chloro-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-2-cyano-pyridin-3-yl 3-deoxy-3-[4-(3,5-difluoro-4-methylphenyl)-1H-1,2,3-triazol-1-yl]-2-O-methyl-1-thio-α-D-galactopyranoside, 5-Chloro-2-cyano-pyridin-3-yl 3-deoxy-3-[4-(3-fluoro-4-methyl-phenyl)-1H-1,2,3-triazol-1-yl]-2-O-methyl-1-thio-α-D-galactopyranoside, 5-Chloro-2-cyano-phenyl 3-deoxy-3-[4-(3,5-difluoro-4-methylphenyl)-1H-1,2,3-triazol-1-yl]-2-O-methyl-1-thio-α-D-galactopyranoside, 5-Chloro-2-cyano-pyridin-3-yl 3-deoxy-2-O-2,2,2,-trifluoroethyl-3-[4-(3,4,5-trifluoro-phenyl)-1H-1,2,3-triazol-1-yl]-1-thio-α-D-galactopyranoside, 5-Chloro-2-cyano-pyridin-3-yl 3-deoxy-2-O-ethyl-3-[4-(3,4,5-trifluoro-phenyl)-1H-1,2,3-triazol-1-yl]-1-thio-α-D-galactopyranoside, 5-Bromopyridin-3-yl 3-deoxy-3-[4-(3,4,5-trifluorophenyl)-1H-1,2,3-triazol-1-yl]-2-O-ethyl-1-thio-α-D-galactopyranoside, 5-Bromopyridin-3-yl 3-deoxy-3-[4-(3,4,5-trifluorophenyl)-1H-1,2,3-triazol-1-yl]-2-O-isopropyl-1-thio-α-D-galactopyranoside, 5-Bromopyridin-3-yl 3-deoxy-3-[4-(3,4,5-trifluorophenyl)-1H-1,2,3-triazol-1-yl]-2-O-(2-fluoroethyl)-1-thio-α-D-galactopyranoside, 5-Bromopyridin-3-yl 3-deoxy-3-[4-(3,4,5-trifluorophenyl)-1H-1,2,3-triazol-1-yl]-2-O-[2-(methylamino)ethyl]-1-thio-α-D-galactopyranoside, 3,4-Dichlorophenyl 3-[4-(4-chloro-3,5-difluorophenyl)-1H-1,2,3-triazol-1-yl]-3-deoxy-2-O-(2-hydroxyethyl)-1-thio-α-D-galactopyranoside, 5-Chloro-6-cyano-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-6-cyano-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyrimidin-5-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-3-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(1,2,3,6-tetrahydropyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(3-pyrrolin-3-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(oxazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 2,5-Bis(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloropyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloropyridin-3-yl 3-deoxy-3-[4-(3-fluoro-4-methylphenyl)-1H-1,2,3-triazol-1-yl]-2-O-methyl-1-thio-α-D-galactopyranoside, 5-Bromopyridin-3-yl 3-deoxy-3-[4-(3-fluoro-4-methylphenyl)-1H-1,2,3-triazol-1-yl]-2-O-methyl-1-thio-α-D-galactopyranoside, 5-Chloropyridin-3-yl 3-[4-(4-chloro-3-fluorophenyl)-1H-1,2,3-triazol-1-yl]-3-deoxy-2-O-methyl-1-thio-α-D-galactopyranoside, 5-Bromopyridin-3-yl 3-[4-(4-chloro-3-fluorophenyl)-1H-1,2,3-triazol-1-yl]-3-deoxy-2-O-methyl-1-thio-α-D-galactopyranoside, 6-Trifluoromethyl-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside, 2-(N-azetidinyl-carbonyl)-5-chlorophenyl 3-[4-(4-chloro-3,5-difluorophenyl)-1H-1,2,3-triazol-1-yl]-3-deoxy-2-O-methyl-1-thio-α-D-galactopyranoside, 2-(N-azetidinyl-carbonyl)-5-chlorophenyl 3-deoxy-3-[4-(3-fluoro-4-methylphenyl)-1H-1,2,3-triazol-1-yl]-2-O-methyl-1-thio-α-D-galactopyranoside, 5-Chloropyridin-3-yl 3-deoxy-3-[4-(3,4,5-trifluorophenyl)-1H-1,2,3-triazol-1-yl]-2-O-methyl-1-thio-α-D-galactopyranoside, 5-Chloropyridin-3-yl 3-deoxy-3-[4-(6-fluoro-5-methylpyridin-2-yl)-1H-1,2,3-triazol-1-yl]-2-O-methyl-1-thio-α-D-galactopyranoside, 5-Chloropyridin-3-yl 3-[4-(5-chloro-6-methylpyridin-2-yl)-1H-1,2,3-triazol-1-yl]-3-deoxy-2-O-methyl-1-thio-α-D-galactopyranoside, 3-Chloro-2-cyanopyridin-5-yl 3-deoxy-3-[4-(3,4,5-trifluorophenyl)-1H-1,2,3-triazol-1-yl]-2-O-methyl-1-thio-α-D-galactopyranoside, 5-Chloro-2-cyanopyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-2-cyanopyridin-3-yl 3-[4-(4-chloro-3-fluorophenyl)-1H-1,2,3-triazol-1-yl]-3-deoxy-2-O-methyl-1-thio-α-D-galactopyranoside, 2-Cyano-5-methylpyridn-3-yl 3-[4-(4-chloro-3,5-difluorophenyl)-1H-1,2,3-triazol-1-yl]-3-deoxy-2-O-methyl-1-thio-α-D-galactopyranoside, 5-Bromo-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromo-2-cyanopyridin-3-yl 3-[4-(4-chloro-3-fluorophenyl)-1H-1,2,3-triazol-1-yl]-3-deoxy-2-O-methyl-1-thio-α-D-galactopyranoside, 5-Chloro-2-(N-azetidinylcarbamoyl)-3-pyridyl 3-[4-(4-chloro-3,5-difluorophenyl)-1H-1,2,3-triazol-1-yl]-3-deoxy-2-O-methyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside, 5-Ethynylpyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-2-cyanopyridin-3-yl 3-[4-(5-chloro-6-fluoropyridin-2-yl)-1H-1,2,3-triazol-1-yl]-3-deoxy-2-O-methyl-1-thio-α-D-galactopyranoside, 2-Cyano-5-ethynylpyridin-3-yl 3-[4-(4-chloro-3,5-difluorophenyl)-1H-1,2,3-triazol-1-yl]-3-deoxy-2-O-methyl-1-thio-α-D-galactopyranoside, 2-Cyano-5-ethynylpyridin-3-yl 3-deoxy-3-[4-(3,5-difluoro-4-methylphenyl)-1H-1,2,3-triazol-1-yl]-2-O-methyl-1-thio-α-D-galactopyranoside, 5-Cyano-6-trifluoromethylpyridin-3-yl 3-[4-(4-chloro-3,5-difluorophenyl)-1H-1,2,3-triazol-1-yl]-3-deoxy-2-O-methyl-1-thio-α-D-galactopyranoside, 5-Cyanopyridin-3-yl 3-deoxy-3-[4-(3,4,5-trifluorophenyl)-1H-1,2,3-triazol-1-yl]-2-O-methyl-1-thio-α-D-galactopyranoside, 5-Cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromo-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside, 5-Bromo-2-(N-azetidinylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside, 5-Bromo-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside, 2-(N-azetidinyl-carbonyl)-5-bromophenyl 3-deoxy-3-[4-(3,4,5-trifluorophenyl)-1H-1,2,3-triazol-1-yl]-2-O-methyl-1-thio-α-D-galactopyranoside, 2-(N-azetidinyl-carbonyl)-5-bromophenyl 3-deoxy-3-[4-(3,4,5-trifluorophenyl)-1H-1,2,3-triazol-1-yl]-2-O-ethyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside, 5-Chloro-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside, 5-Chloro-2-(N-azetidinylcarbamoyl)-3-pyridyl 3-[4-(4-chloro-3,5-difluorophenyl)-1H-1,2,3-triazol-1-yl]-3-deoxy-2-O-ethyl-1-thio-α-D-galactopyranoside, 2-(N-azetidinyl-carbonyl)-5-chlorophenyl 3-deoxy-3-[4-(3,4,5-trifluorophenyl)-1H-1,2,3-triazol-1-yl]-2-O-methyl-1-thio-α-D-galactopyranoside, and 3,4-Dichlorophenyl 3-[4-(4-chloro-3,5-difluorophenyl)-1H-1,2,3-triazol-1-yl]-3-deoxy-2-O-methyl-1-thio-α-D-galactopyranoside.

In a further embodiment A1 is selected from formula (2) wherein $R^1$-$R^5$ are independently selected from H, CN, NH$_2$, F, methyl optionally substituted with a fluorine (F), and OCH$_3$ optionally substituted with a F. In a further embodiment $R^1$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment $R^1$ is selected from H and F. In a further embodiment $R^2$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment $R^2$ is selected from F. In a further embodiment $R^3$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment $R^3$ is selected from H, OCH$_3$ and F. In a further embodiment $R^4$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment $R^4$ is selected from H and F. In a further embodiment $R^5$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment $R^5$ is selected from H and F.

In another embodiment A1 is selected from formula (3) wherein Het$^1$ is selected from a five or six membered heteroaromatic ring, optionally substituted with a group selected from Br; F; Cl; CN; NR$^{19}$R$^{20}$, wherein R$^{19}$ and R$^{20}$ are independently selected from H, C$_{1-3}$ alkyl, cyclopropyl, iso-propyl, —C(=O)—R$^{21}$, wherein R$^{21}$ is selected from H and C$_{1-3}$ alkyl; methyl optionally substituted with a F; and OCH$_3$ optionally substituted with a F. In a further embodiment A is selected from formula (3) wherein Het$_1$ is selected from a five or six membered heteroaromatic ring, optionally substituted with a group selected from Br, F, Cl, methyl optionally substituted with a F, and OCH$_3$ optionally substituted with a F. In a further embodiment Het$^1$ is selected from a five membered heteroaromatic ring. In a further embodiment Het$^1$ is selected from a five membered heteroaromatic ring substituted with a group selected from Br, F, Cl, methyl, CF$_3$, OCH$_3$ and OCF$_3$.

In a further embodiment Het$^1$ is selected from a six membered heteroaromatic ring.

In a further embodiment Het$^1$ is selected from a six membered heteroaromatic ring substituted with a group selected from Br, F, Cl, methyl, CF$_3$, OCH$_3$ and OCF$_3$. In a further embodiment Het$^1$ is selected from a six membered heteroaromatic ring substituted with a group selected from Br, F, and Cl.

In a further embodiment Het$^1$ is selected from pyridinyl, pyrimidinyl, pyrazinyl, pyridazyl, oxazoyl, thiazoyl, thiadiazoly, oxadiazoyl, thiophenyl, and imidazolyl optionally substituted with a group selected from Br, F, Cl, methyl, CF$_3$, OCH$_3$ and OCF$_3$. In a further embodiment Het$^1$ is selected from pyridinyl substituted with a group selected from Br, F, and Cl. In a further embodiment Het$^1$ is selected from pyridinyl substituted with a group selected from F, such as one, two or three F, typically 3 F.

In a further embodiment A1 is selected from formula (4) wherein $R^6$ is selected from $C_{1-6}$ alkyl, branched $C_{3-6}$ alkyl and $C_{3-7}$ cycloalkyl. In an embodiment $R^6$ is a $C_{1-6}$ alkyl, such as methyl or ethyl. In another embodiment $R^6$ is a cyclopropyl, cyclopentyl or cyclohexyl.

In a further embodiment A1 is selected from formula (4) wherein $R^6$ is selected from $C_{1-6}$ alkyl substituted with a halogen. In a further embodiment $R^6$ is a $C_{1-3}$ alkyl substituted with one, two or three halogens, such as one, two or three F, e.g. $CH_2CF_3$.

In a further embodiment A1 is selected from formula (5) wherein $R^7$ is selected from a five or six membered heteroaromatic ring, optionally substituted with a group selected from Br, F, Cl, methyl optionally substituted with a F, and $OCH_3$ optionally substituted with a F, and a phenyl optionally substituted with a group selected from Br, F, Cl, methyl optionally substituted with a F, and $OCH_3$ optionally substituted with a F. In a further embodiment $R^7$ is selected from a five membered heteroaromatic ring. In a further embodiment $R^7$ is selected from a five membered heteroaromatic ring substituted with a group selected from Br, F, Cl, methyl, $CF_3$, $OCF_3$ and $OCH_3$. In a further embodiment $R^7$ is selected from a six membered heteroaromatic ring. In a further embodiment $R^7$ is selected from a six membered heteroaromatic ring substituted with a group selected from Br, F, Cl, methyl, $CF_3$, $OCF_3$ and $OCH_3$, such as 1, 2 or 3 selected from Br, F, Cl, methyl, $CF_3$, $OCF_3$ and $OCH_3$. In a further embodiment $R^7$ is selected from a phenyl. In a further embodiment $R^7$ is selected from a phenyl substituted with a group selected from Br, F, Cl, methyl, $CF_3$, $OCF_3$ and $OCH_3$, such as 1, 2 or 3 selected from Br, F, Cl, methyl, $CF_3$, $OCF_3$ and $OCH_3$. In a further embodiment $R^7$ is selected from a phenyl substituted with a group selected from $C_1$.

In a further embodiment A1 is selected from formula (6) wherein $R^8$-$R^{12}$ are independently selected from H, F, methyl optionally substituted with a fluorine (F), and $OCH_3$ optionally substituted with a F. In a further embodiment $R^8$-$R^{12}$ are independently selected from H and F. In a further embodiment $R^8$-$R^{12}$ are H. In a further embodiment $R^8$-$R^{12}$ are independently selected from H and F, provided that at least two of $R^8$-$R^{12}$ are F. In a further embodiment $R^{10}$-$R^{11}$ are F and $R^8$, $R^9$ and $R^{12}$ are H. In a further embodiment $R^8$ is selected from H, F, methyl optionally substituted with a fluorine (F), and $OCH_3$ optionally substituted with a F, such as H, F, methyl, $CF_3$, $OCF_3$ and $OCH_3$. In a further embodiment $R^9$ is selected from H, F, methyl optionally substituted with a fluorine (F), and $OCH_3$ optionally substituted with a F, such as H, F, methyl, $CF_3$, $OCF_3$ and $OCH_3$. In a further embodiment $R^{10}$ is selected from H, F, methyl optionally substituted with a fluorine (F), and $OCH_3$ optionally substituted with a F, such as H, F, methyl, $CF_3$, $OCF_3$ and $OCH_3$. In a further embodiment $R^{11}$ is selected from H, F, methyl optionally substituted with a fluorine (F), and $OCH_3$ optionally substituted with a F, such as H, F, methyl, $CF_3$, $OCF_3$ and $OCH_3$. In a further embodiment $R^{12}$ is selected from H, F, methyl optionally substituted with a fluorine (F), and $OCH_3$ optionally substituted with a F, such as H, F, methyl, $CF_3$, $OCF_3$ and $OCH_3$, typically H or methyl.

In a further embodiment A1 is selected from formula (7) wherein $R^{13}$ is a five or six membered heteroaromatic ring optionally substituted with a group selected from H, OH, F, methyl optionally substituted with a fluorine (F), and $OCH_3$ optionally substituted with a F, or an aryl, such as phenyl or naphthyl, optionally substituted with a group selected from H, OH, F, methyl optionally substituted with a fluorine (F), and $OCH_3$ optionally substituted with a F. In an embodiment $R^{13}$ is a five membered heteroaromatic ring. In another embodiment $R^{13}$ is a five membered heteroaromatic ring substituted with a group selected from H, OH, F, methyl, $CF_3$, $OCF_3$ and $OCH_3$, such as 1, 2 or 3 selected from OH, F, methyl, $CF_3$, $OCF_3$ and $OCH_3$. In an embodiment $R^{13}$ is a six membered heteroaromatic ring. In an embodiment $R^{13}$ is a six membered heteroaromatic ring substituted with a group selected from H, OH, F, methyl, $CF_3$, $OCF_3$ and $OCH_3$, such as 1, 2 or 3 selected from OH, F, methyl, $CF_3$, $OCF_3$ and $OCH_3$. In a further embodiment $R^{13}$ is a phenyl or naphthyl. In a further embodiment $R^{13}$ is a phenyl substituted with a group selected from H, OH, F, $CF_3$, $OCF_3$ and $OCH_3$, such as 1, 2 or 3 selected from OH, F, methyl, $CF_3$, $OCF_3$ and $OCH_3$. In a further embodiment $R^{13}$ is a phenyl substituted with a group selected from F, such as one, two or three F. In a further embodiment $R^{13}$ is a naphthyl substituted with a group selected from H, OH, F, $CF_3$, $OCF_3$ and $OCH_3$, such as 1, 2 or 3 selected from OH, F, methyl, $CF_3$, $OCF_3$ and $OCH_3$.

In a further embodiment A1 is selected from formula (8) wherein $R^{27}$ is selected from a $C_{1-6}$ alkyl, branched $C_{3-6}$ alkyl, $C_{1-6}$ alkoxy and branched $C_{3-6}$ alkoxy. In a further embodiment $R^{27}$ is selected from a $C_{1-6}$ alkyl, such as $C_{1-4}$ alkyl, e.g. methyl, ethyl, propyl. In a further embodiment $R^{27}$ is selected from a $C_{1-6}$ alkoxy, such as $C_{1-4}$ alkoxy, e.g. methoxy, ethoxy, propoxy.

In a still further embodiment X1 is selected from S, SO, $SO_2$, O, C=O, and $CR^7R^8$ wherein $R^7$ and $R^8$ are independently selected from hydrogen, OH, or halogen (e.g. F, Cl, Br). In a further embodiment X1 is selected from S. In a further embodiment X1 is selected from SO. In a further embodiment X1 is selected from $SO_2$. In a further embodiment X1 is selected from O. In a further embodiment X1 is selected from C=O. In a further embodiment X1 is selected from $CR^7R^8$ wherein $R^7$ and $R^8$ are independently selected from hydrogen, OH, F, Cl, and Br, such as $CH_2$, CHF, CHCl, CHBr, CHOH, $CF_2$, $CCl_2$ and $CBr_2$.

In a still further embodiment B1 is selected from a $C_{1-6}$ alkyl or branched $C_{3-6}$ alkyl substituted with a five or six membered heteroaromatic ring, optionally substituted with a substituent selected from a halogen (e.g. Cl, F, Br, I), CN, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl. In a further embodiment B1 is selected from a $C_{1-6}$ alkyl substituted with a five membered heteroaromatic ring. In a further embodiment B is selected from a branched $C_{3-6}$ alkyl substituted with a five membered heteroaromatic ring. In a further embodiment B1 is selected from a $C_{1-6}$ alkyl substituted with a five membered heteroaromatic ring substituted with a substituent selected from CN, Cl, F, Br, I, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl. In a further embodiment B1 is selected from a $C_{1-6}$ alkyl substituted with a five membered heteroaromatic ring substituted with a substituent selected from CN, Cl, F, Br, I, methyl, $CF_3$, $OCH_3$, $OCF_3$, $OCH_2CH_3$, $OCF_2CF_3$, OH, and $R^{14}$—CONH— wherein $R^{14}$ is selected from methyl. In a further embodiment B1 is selected from a branched $C_{3-6}$ alkyl substituted with a five membered heteroaromatic ring substituted with a substituent selected from CN, Cl, F, Br, I, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl. In a further embodiment B1 is selected from a branched $C_{3-6}$ alkyl substituted with a five membered heteroaromatic ring substituted with a substituent, such as 1, 2 or 3, selected from CN, Cl, F, Br, I, methyl, $CF_3$, $OCH_3$, $OCF_3$, $OCH_2CH_3$, $OCF_2CF_3$, OH, and $R^{14}$—CONH— wherein $R^{14}$ is selected from methyl. In a further embodiment B1 is selected from a $C_{1-6}$ alkyl substituted with a phenyl, such as benzyl or $CH_2CH_2$-phenyl. In a further embodiment B1 is selected from a $C_{1-6}$ alkyl substituted with a phenyl substituted with a substituent, such as 1, 2 or 3, selected from CN, Cl, F, Br, I, methyl, $CF_3$, $OCH_3$, $OCF_3$, $OCH_2CH_3$, $OCF_2CF_3$, OH, and $R^{15}$—CONH— wherein $R^{15}$ is selected from methyl. In a further embodiment B1 is selected from a $C_{1-6}$ alkyl substituted with a phenyl substituted with a group selected from Cl, F, Br, methyl, $CF_3$, $OCH_3$, $OCF_3$, such as benzyl substituted with one or two Cl, or $CH_2CH_2$-phenyl substituted with one Cl. In a still further embodiment B1 is selected from a phenyl. In a further embodiment B1 is selected from a naphthyl. In a further embodiment B1 is selected from a naphthyl substituted with a group selected from $NR^{28}R^{29}$, wherein $R^{28}$ and $R^{29}$ are independently selected from H and $C_{1-3}$ alkyl. In a further embodiment B1 is selected from a naphthyl substituted with a group selected from $NR^{28}R^{29}$, wherein $R^{28}$ and $R^{29}$ are independently selected from H and $CH_3$. In a further embodiment B1 is selected from a naphthyl substituted with a group selected from $NR^{28}R^{29}$, wherein $R^{28}$ and $R^{29}$ selected from $CH_3$. In a further embodiment B1 is selected from a phenyl substituted with a group, such as 1, 2 or 3, selected from Cl, F, Br, I, methyl, $CF_3$, $OCH_3$, $OCF_3$, $OCH_2CH_3$, $OCF_2CF_3$, OH, and $R^{16}$—CONH— wherein $R^{16}$ is selected from methyl. In a still further embodiment B1 is selected from a phenyl substituted with a group, such as 1, 2 or 3, selected from Cl, F, Br, I, CN, methyl, $CF_3$, $OCH_3$, $OCF_3$, $OCH_2CH_3$, $OCF_2CF_3$, OH, and $R^{16}$—CONH— wherein $R^{16}$ is selected from methyl. In a further embodiment B1 is selected from a phenyl substituted with a group, such as 1, 2 or 3, selected from COOH and $CONH_2$. In a still further embodiment B1 is selected from a naphthyl substituted with a group, such as 1, 2 or 3, selected from Cl, F, Br, I, methyl, $CF_3$, $OCH_3$, $OCF_3$, $OCH_2CH_3$, $OCF_2CF_3$, OH, and $R^{16}$—CONH— wherein $R^{16}$ is selected from methyl. In a further embodiment B1 is selected from a naphthyl. In a still further embodiment B1 is selected from a naphthyl substituted with a $NR^{28}R^{29}$, wherein $R^{28}$ and $R^{29}$ are independently selected from H, $C_{1-3}$ alkyl and isopropyl, such as naphthyl substituted with a $N(CH_3)_2$.

In a further embodiment B1 is selected from a $C_{5-7}$ cycloalkyl, such as cyclopentyl or cyclohexyl. In a further embodiment B is selected from cyclohexyl. In a still further embodiment B is selected from a $C_{5-7}$ cycloalkyl, such as cyclohexyl, substituted with a group, such as 1, 2 or 3, selected from CN, Cl, F, Br, I, methyl, $CF_3$, $OCH_3$, $OCF_3$, $OCH_2CH_3$, $OCF_2CF_3$, OH, and $R^{17}$—CONH— wherein $R^{17}$ is selected from methyl. In a still further embodiment B1 is selected from a cyclohexyl, substituted with a halogen, such as one or two halogens, typically F.

In a further embodiment of the present invention B1 is selected from a $C_{1-4}$ alkyl. Typically, B is selected from ethyl, propyl and butyl.

In a still further embodiment B1 is selected from a heterocycle, such as heteroaryl or heterocycloalkyl. In a still further embodiment B1 is selected from a heteroaryl substituted with a group, such as 1, 2 or 3, selected from Cl, F, Br, I, methyl $CF_3$, $OCH_3$, $OCF_3$, $OCH_2CH_3$, $OCF_2CF_3$, OH, and $R^{18}$—CONH— wherein $R^{18}$ is selected from methyl. In a further embodiment B1 is selected from a heteroaryl substituted with a group, such as 1, 2 or 3, selected from Cl, F, Br, I, CN, methyl, $CF_3$, $OCH_3$, $OCF_3$, $OCH_2CH_3$, $OCF_2CF_3$, OH, and $R^{18}$—CONH— wherein $R^{18}$ is selected from methyl. In a still further embodiment B1 is selected from a heterocycloalkyl substituted with a group, such as 1, 2 or 3, selected from Cl, F, Br, I, methyl $CF_3$, $OCH_3$, $OCF_3$, $OCH_2CH_3$, $OCF_2CF_3$, OH, and $R^{18}$—CONH— wherein $R^{18}$ is selected from methyl. In a further embodiment B1 is selected from a heteroaryl substituted with a group, such as 1, 2 or 3, selected from $NR^{30}R^{31}$, wherein $R^{30}$ and $R^{31}$ are independently selected from H, $C_{1-3}$ alkyl and isopropyl. Typically, B1 is selected from a pyridinyl substituted with a group, such as 1, 2 or 3, selected from $NH_2$, such as one $NH_2$. In another embodiment B1 is selected from a thiophenyl substituted with a halogen, such as one Cl. In a further embodiment B1 is selected from a pyridazinyl. In a further embodiment B1 is selected from a pyridazinyl substituted with one, two or three, substituents selected from $OCH_3$, CN, OH and Cl.

In a further aspect the present invention relates to a compound of formula (1) of the present invention for use as a medicine.

In a still further aspect the present invention relates to a pharmaceutical composition comprising a compound of formula (1) of the present invention and optionally a pharmaceutically acceptable additive, such as a carrier and/or excipient.

In a further aspect the present invention relates to a compound of formula (1) of the present invention for use in a method for treating a disorder relating to the binding of a galectin-3 to a ligand in a mammal, such as a human. In an embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistens; obesity; Diastolic HF; asthma and other interstitial lung diseases, including Hermansky-Pudlak syndrome, mesothelioma; liver disorders, such as non-alcoholic steatohepatitis or non-alcoholic fatty liver disease.

A non-limiting group of cancers given as examples of cancers that may be treated, managed and/or prevented by administration of a compound of formula (1) include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer. Each of these disorders is considered a single embodiment and may be made the subject of a claim specifically to such disease or disorder.

In a still further aspect the present invention relates to a method for treatment of a disorder relating to the binding of a galectin-3 to a ligand in a mammal, such as a human, wherein a therapeutically effective amount of at least one compound of formula (1) of the present invention is administered to a mammal in need of said treatment. In an embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistens; obesity; Diastolic HF; asthma and other interstitial lung diseases, including Hermansky-Pudlak syndrome, mesothelioma; liver disorders, such as non-alcoholic steatohepatitis or non-alcoholic fatty liver disease.

Each of these disorders are considered a single embodiment and may be made the subject of a claim specifically to such disease or disorder.

The skilled person will understand that it may be necessary to adjust or change the order of steps in the processes a1 to a3, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g. t-butyldimethylsilyl, t-butyldipheylsilyl or trimethylsilyl), AcO(acetoxy), TBS(t-butyldimethylsilyl), TMS(trimethylsilyl), PMB (p-methoxybensyl), and tetrahydropyranyl. Suitable proteting groups for carboxylic acid include ($C_{1-6}$)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)NH$_2$, TIPS.

The protection and deprotection of functional groups may take place before or after any reaction in the above mentioned processes.

Furthermore the skilled person will appreciate, that, in order to obtain compounds of the invention in an alternative, and on some occasions more convenient manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound (1) is on free form. "On free form" as used herein means a compound of formula (1), either an acid form or base form, or as a neutral compound, depending on the substitutents. The free form does not have any acid salt or base salt in addition. In one embodiment the free form is an anhydrate. In another embodiment the free form is a solvate, such as a hydrate.

In a further embodiment the compound (1) is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-x}$ alkyl" as used herein means an alkyl group containing 1-x carbon atoms, e.g. $C_{1-5}$ or $C_{1-6}$, such as methyl, ethyl, propyl, butyl, pentyl or hexyl.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "$C_{5-7}$ cycloalkyl" as used herein means a cyclic alkyl group containing 5-7 carbon atoms, such as cyclopentyl, cyclohexyl, or cycloheptyl.

The term "$C_{2-4}$ alkynyl" as used herein means an alkynyl group containing 2-4 carbon atoms and having one triple bond, such as ethynyl, propynyl, butynyl.

The term "Oxo" as used herein means an oxygen atom with double bonds, also indicated as =O.

The term "CN" as used herein means a nitril.

The term "a five or six membered heteroaromatic ring" as used herein means one five membered heteroaromatic ring or one six membered heteroaromatic ring. The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isooxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoly, oxadiazoyl, and pyridonyl.

The term "a heterocycle, such as heteroaryl or heterocycloalkyl" as used herein means a heterocycle consisting of one or more 3-7 membered ring systems containing one or more heteroatoms and wherein such ring systems may optionally be aromatic. The term "a heteroaryl" as used herein means a mono or bicyclic aromatic ringsystem containing one or more heteroatoms, such as 1-10, e.g. 1-6, selected from O, S, and N, including but not limited to oxazolyl, oxadiazolyl, thiophenyl, thiadiazolyl, thiazolyl, pyridyl, pyrimidinyl, pyridonyl, pyrimidonyl, quinolinyl, azaquionolyl, isoquinolinyl, azaisoquinolyl, quinazolinyl, azaquinazolinyl, bensozazoyl, azabensoxazoyl, bensothiazoyl, or azabensothiazoyl. The term "a heterocycloalkyl" as used herein means a mono or bicyclic 3-7 membered alifatic heterocycle containing one or more heteroatoms, such as 1-7, e.g. 1-5, selected from O, S, and N, including but not limited to piperidinyl, tetrahydropyranyl, tetrahydrothipyranyl, or piperidonyl.

The term "a spiro heterocycle" as used herein means a two-ring system connected by a common carbon atom, and containing from 5 to 12 ring members wherein from 2 to 11 are carbon atoms and at least one is a heteroatom, such as a hetero atom selected from one or more N, S, O; one example is N-(2-oxa)-6-azaspiro[3.3]heptanyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person skilled within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compounds as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention indiverse forms thereof.

Experimental Procedures

| Example | Name | structure | Galectin-3 Kd (µM) |
|---------|------|-----------|--------------------|
| 1 | 5-Bromopyridin-3-yl 3-deoxy-3-[4-(3,4,5-trifluorophenyl)-1H-1,2,3-triazol-1-yl]-2-O-methyl-1-thio-α-D-galactopyranoside | 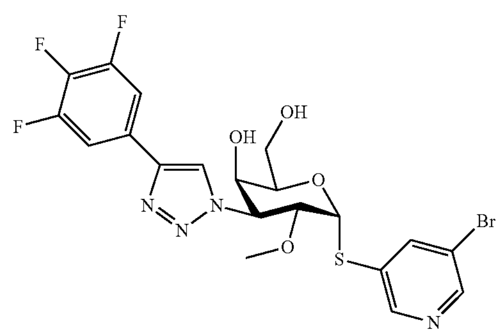 | 0.025 |
| 2 | 5-Bromo-2-cyanopyridin-3-yl 3-deoxy-3-[4-(3-fluoro-4-methylphenyl)-1H-1,2,3-triazol-1-yl]-2-O-methyl-1-thio-α-D-galactopyranoside | 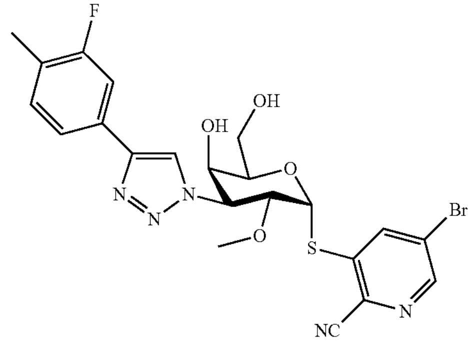 | |

| Example | Name | structure | Galectin-3 Kd (μM) |
|---|---|---|---|
| 3 | 4-Chloro-N,N-dimethyl-benzamide-2-yl 3-deoxy-3-[4-(3,4,5-trifluorophenyl)-1H-1,2,3-triazol-1-yl]-2-O-methyl-1-thio-α-D-galactopyranoside | 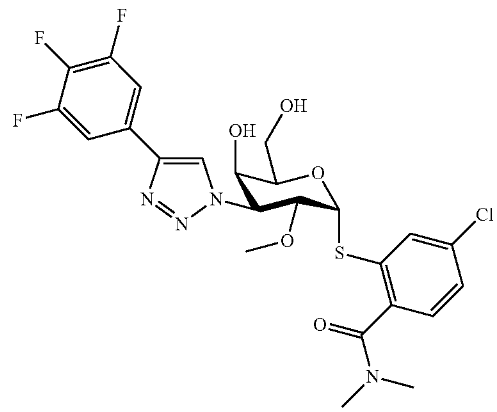 | 0.008 |
| 4 | 4-Chloro-N,N-dimethyl-benzamide-2-yl 3-[4-(4-chloro-3,5-difluorophenyl)-1H-1,2,3-triazol-1-yl]-3-deoxy-2-O-methyl-1-thio-α-D-galactopyranoside | 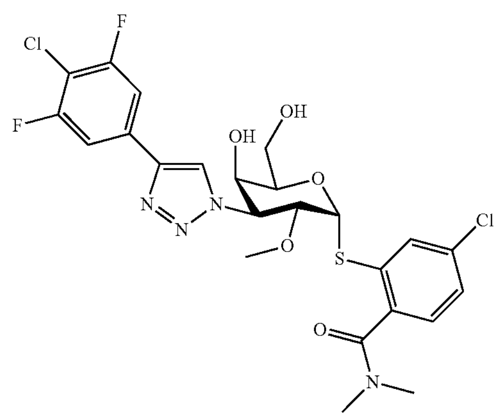 | 0.014 |
| 5 | 5-Bromopyridin-3-yl 3-deoxy-3-[4-(3,4,5-trifluorophenyl)-1H-1,2,3-triazol-1-yl]-2-O-(1,1,1-trifluoro-2-hydroxyprop-3-yl)-1-thio-α-D-galactopyranoside | 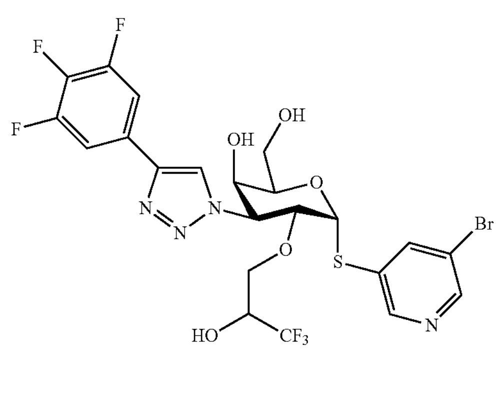 | 0.082 |

| Example | Name | structure | Galectin-3 Kd (μM) |
|---|---|---|---|
| 6 | 2-(N-piperidinyl-carbonyl)-5-chlorophenyl 3-[4-(4-chloro-3,5-difluorophenyl)-1H-1,2,3-triazol-1-yl]-3-deoxy-2-O-methyl-1-thio-α-D-galactopyranoside | 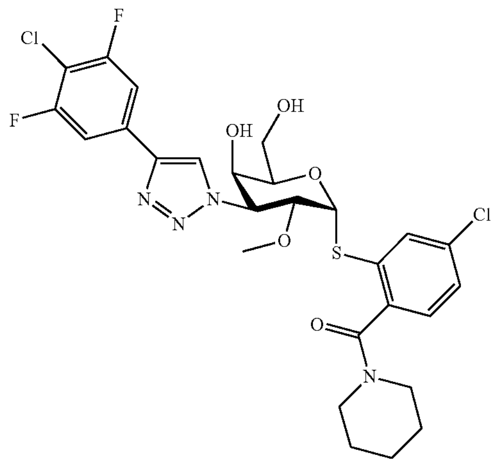 | 0.120 |
| 7 | 4-Chloro-N,N-dimethyl-benzamide-2-yl 3-[4-(4-chloro-3,5-difluorophenyl)-1H-1,2,3-triazol-1-yl]-3-deoxy-2-O-trifluoromethyl-1-thio-α-D-galactopyranoside | 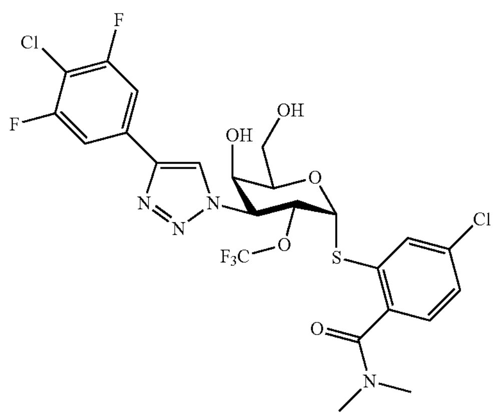 | |
| 8 | 4-Chloro-N,N-dimethyl-benzamide-2-yl 3-deoxy-2-O-trifluoromethyl-3-[4-(3,4,5-trifluorophenyl)-1H-1,2,3-triazol-1-yl]-1-thio-α-D-galactopyranoside | 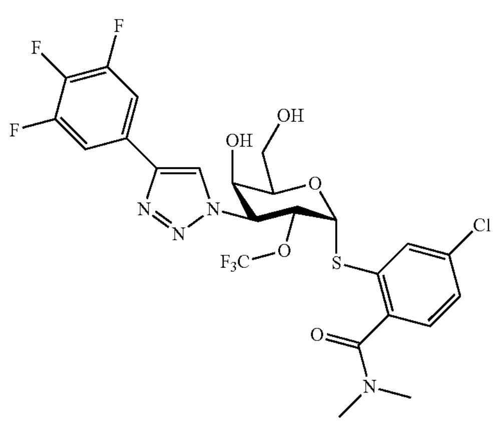 | |

| Example | Name | structure | Galectin-3 Kd (μM) |
|---|---|---|---|
| 9 | 5-Chloro-2-(N,N-dimethylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside | 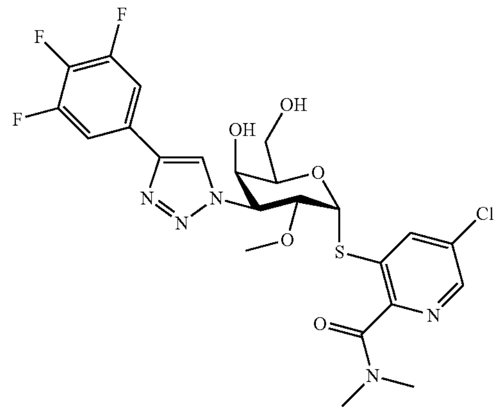 | |
| 10 | 5-Chloro-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside | 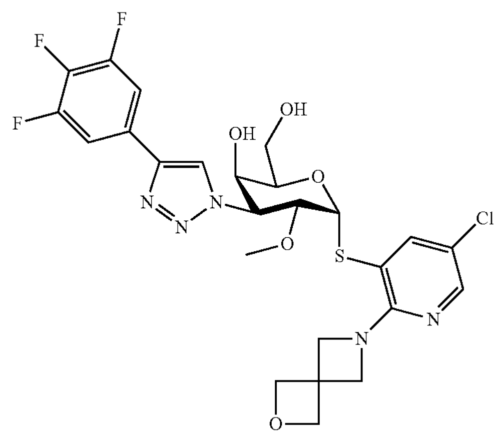 | 0.033 |
| 11 | 5-Chloro-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside | 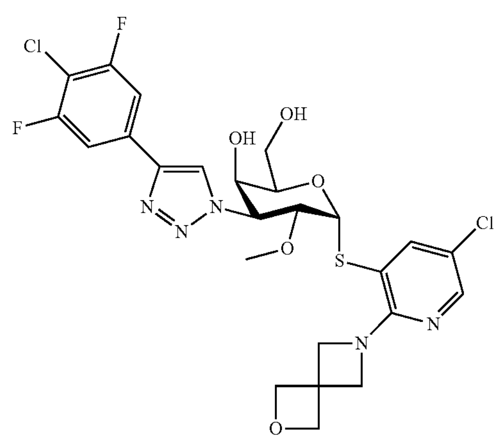 | 0.049 |

| Example | Name | structure | Galectin-3 Kd (μM) |
|---|---|---|---|
| 12 | 5-Chloro-2-cyanopyridin-3-yl 3-deoxy-3-[4-(3,5-difluoro-4-methylphenyl)-1H-1,2,3-triazol-1-yl]-2-O-methyl-1-thio-α-D-galactopyranoside | 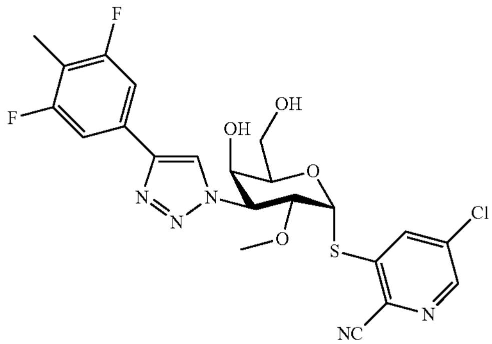 | 0.012 |
| 13 | 5-Chloro-2-cyanopyridin-3-yl 3-deoxy-3-[4-(3-fluoro-4-methylphenyl)-1H-1,2,3-triazol-1-yl]-2-O-methyl-1-thio-α-D-galactopyranoside | 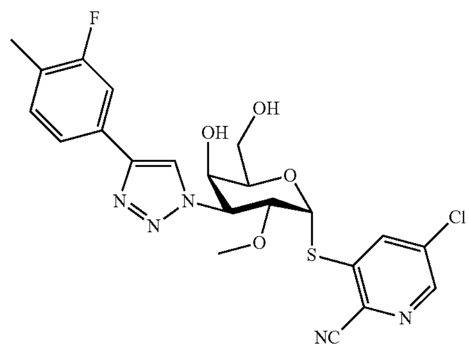 | 0.014 |
| 14 | 5-Chloro-2-cyanophenyl 3-deoxy-3-[4-(3,5-difluoro-4-methylphenyl)-1H-1,2,3-triazol-1-yl]-2-O-methyl-1-thio-α-D-galactopyranoside | 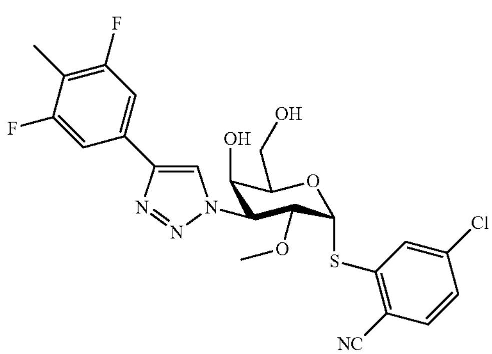 | 0.050 |
| 15 | 5-Chloro-2-cyanopyridin-3-yl 3-deoxy-2-O-(2,2,2-trifluoroethyl)-3-[4-(3,4,5-trifluorophenyl)-1H-1,2,3-triazol-1-yl]-1-thio-α-D-galactopyranoside | 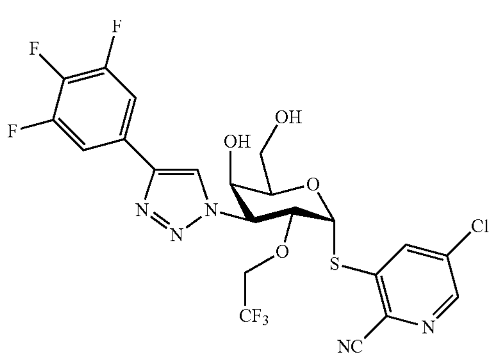 | |

| Example | Name | structure | Galectin-3 Kd (μM) |
|---|---|---|---|
| 16 | 5-Chloro-2-cyanopyridin-3-yl 3-deoxy-2-O-ethyl-3-[4-(3,4,5-trifluoro-phenyl)-1H-1,2,3-triazol-1-yl ]-1-thio-α-D-galactopyranoside | 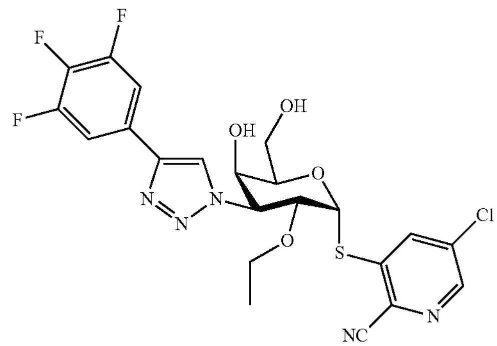 | 0.059 |
| 17 | 5-Bromopyridin-3-yl 3-deoxy-3-[4-(3,4,5-trifluorophenyl)-1H-1,2,3-triazol-1-yl]-2-O-ethyl-1-thio-α-D-galactopyranoside | 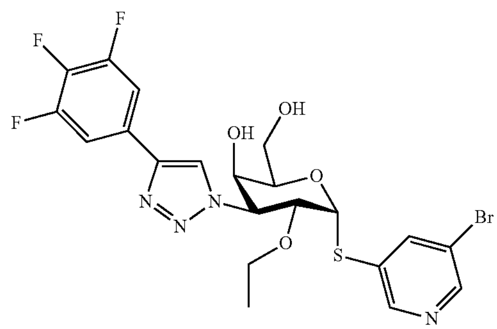 | 0.074 |
| 18 | 5-Bromopyridin-3-yl 3-deoxy-3-[4-(3,4,5-trifluorophenyl)-1H-1,2,3-triazol-1-yl]-2-O-isopropyl-1-thio-α-D-galactopyranoside | 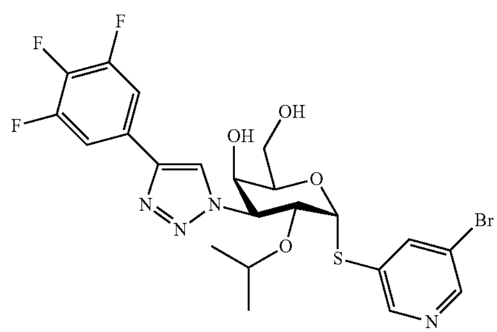 | 0.15 |
| 19 | 5-Bromopyridin-3-yl 3-deoxy-3-[4-(3,4,5-trifluorophenyl)-1H-1,2,3-triazol-1-yl]-2-O-(2-fluoroethyl)-1-thio-α-D-galactopyranoside | 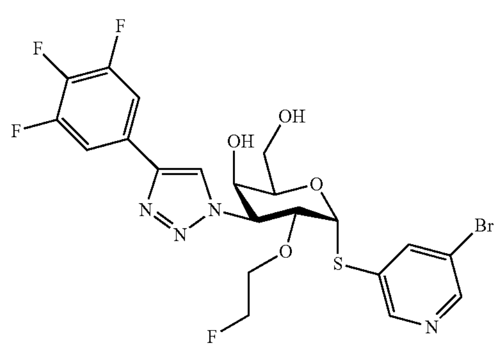 | 0.020 |

| Example | Name | structure | Galectin-3 Kd (μM) |
|---|---|---|---|
| 20 | 5-Bromopyridin-3-yl 3-deoxy-3-[4-(3,4,5-trifluorophenyl)-1H-1,2,3-triazol-1-yl]-2-O-[2-(methylamino)ethyl]-1-thio-α-D-galactopyranoside | 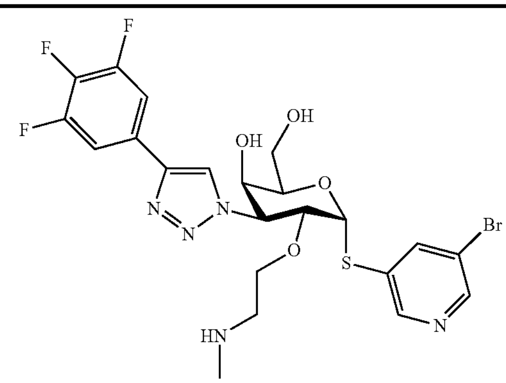 | 0.071 |
| 21 | 3,4-Dichlorophenyl 3-[4-(4-chloro-3,5-difluorophenyl)-1H-1,2,3-triazol-1-yl]-3-deoxy-2-O-(2-hydroxyethyl)-1-thio-α-D-galactopyranoside | 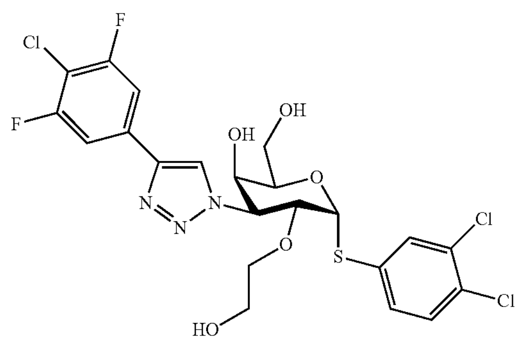 | 0.058 |
| 22 | 5-Chloro-6-cyano-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside | 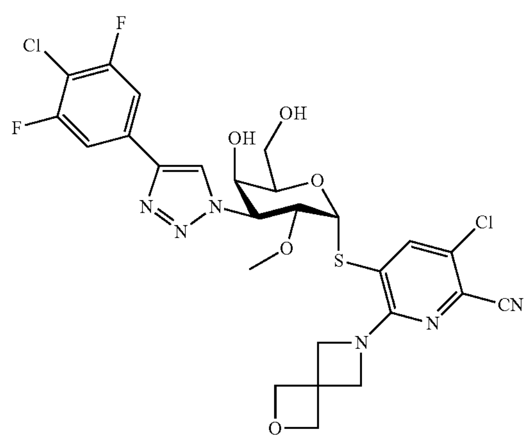 | 0.060 |
| 23 | 5-Chloro-6-cyano-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside | 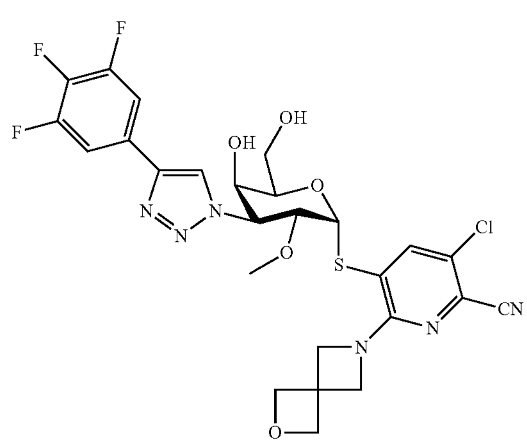 | 0.037 |

-continued

| Example | Name | structure | Galectin-3 Kd (μM) |
|---|---|---|---|
| 24 | 5-Chloro-2-(pyrimidin-5-yl)pyridin-3-yl 3-deoxy-3-[4-(3,4,5-trifluorophenyl)-1H-1,2,3-triazol-1-yl]-2-O-methyl-1-thio-α-D-galactopyranoside | 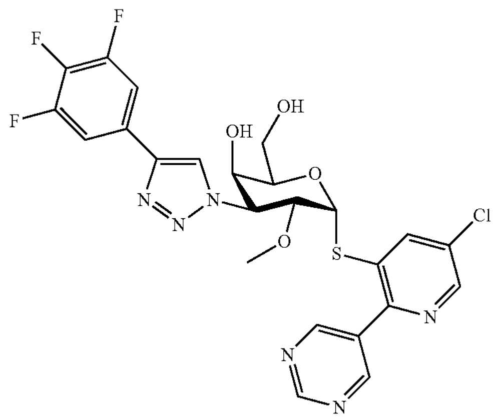 | 0.028 |
| 25 | 5-Chloro-2-(pyridin-2-yl)pyridin-3-yl 3-deoxy-3-[4-(3,4,5-trifluorophenyl)-1H-1,2,3-triazol-1-yl]-2-O-methyl-1-thio-α-D-galactopyranoside | 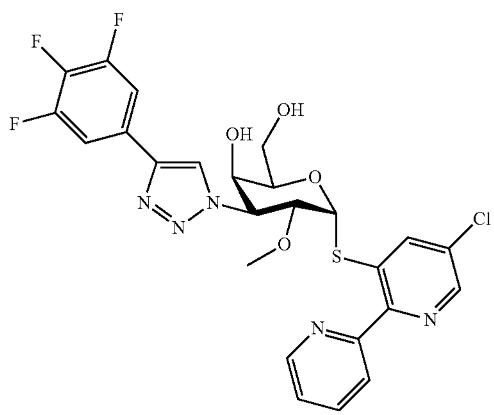 | 0.024 |
| 26 | 5-Chloro-2-(pyridin-3-yl)pyridin-3-yl 3-deoxy-3-[4-(3,4,5-trifluorophenyl)-1H-1,2,3-triazol-1-yl]-2-O-methyl-1-thio-α-D-galactopyranoside | 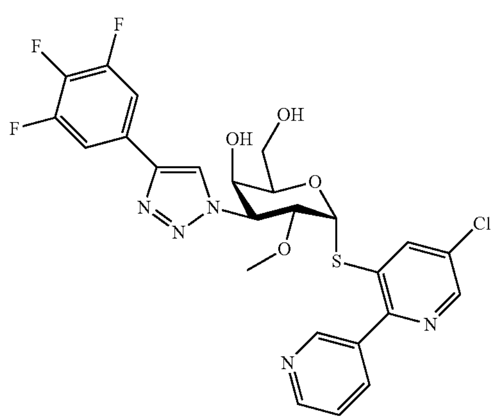 | 0.055 |

-continued

| Example | Name | structure | Galectin-3 Kd (μM) |
|---|---|---|---|
| 27 | 5-Chloro-2-(pyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside | 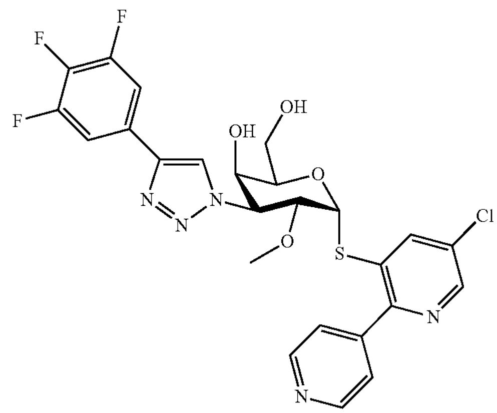 | 0.056 |
| 28 | 5-Chloro-2-(1, 2,3,6-tetrahydropyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside | 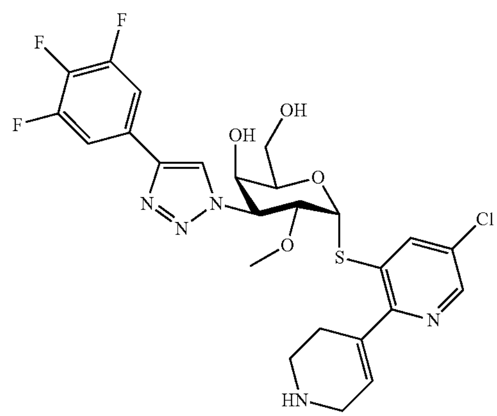 | 0.036 |
| 29 | 5-Chloro-2-(3-pyrrolin-3-yl)pyridin-3-yl 3-deoxy-3-[4-(3,4,5-trifluorophenyl)-1H-1,2,3-triazol-1-yl]-2-O-methyl-1-thio-α-D-galactopyranoside | 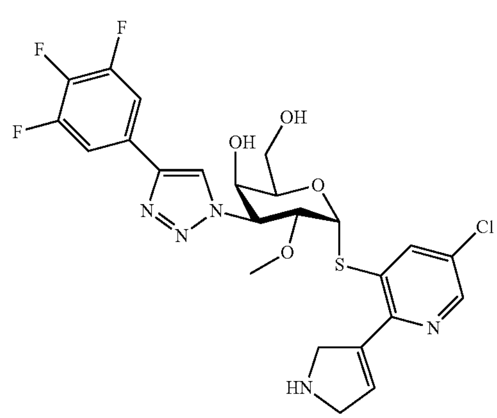 | 0.068 |

-continued

| Example | Name | structure | Galectin-3 Kd (μM) |
|---|---|---|---|
| 30 | 5-Chloro-2-(oxazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside | 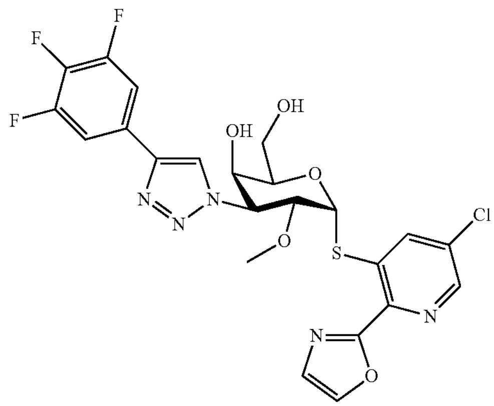 | 0.056 |
| 31 | 5-Chloro-2-(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside | 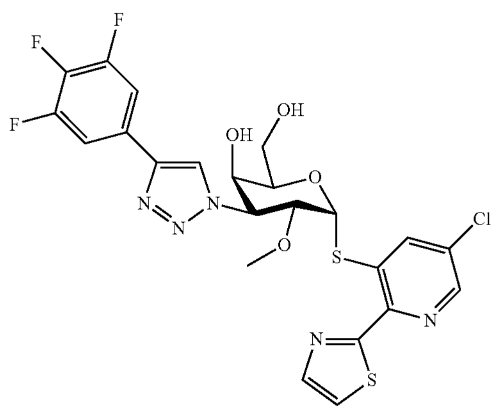 | 0.30 |
| 32 | 2,5-Bis(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside | 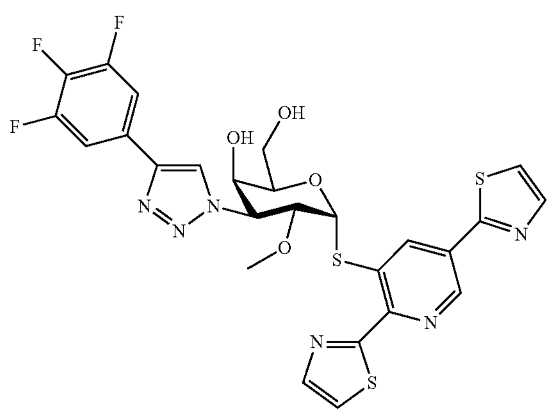 | 0.21 |
| 33 | 5-Chloropyridin-3-yl 3-[4-(4-chloro-3,5-difluorophenyl)-1H-1,2,3-triazol-1-yl]-3-deoxy-2-O-methyl-1-thio-α-D-galactopyranoside | 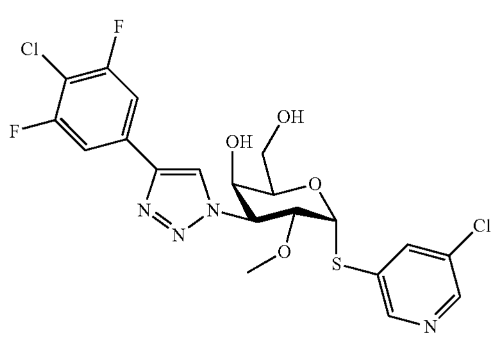 | 0.031 |

-continued

| Example | Name | structure | Galectin-3 Kd (μM) |
|---|---|---|---|
| 34 | 5-Bromopyridin-3-yl 3-[4-(4-chloro-3,5-difluorophenyl)-1H-1,2,3-triazol-1-yl]-3-deoxy-2-O-methyl-1-thio-α-D-galactopyranoside | 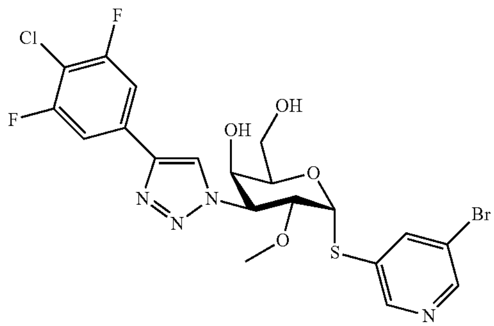 | 0.021 |
| 35 | 5-Chloropyridin-3-yl 3-deoxy-3-[4-(3-fluoro-4-methylphenyl)-1H-1,2,3-triazol-1-yl]-2-O-methyl-1-thio-α-D-galactopyranoside | 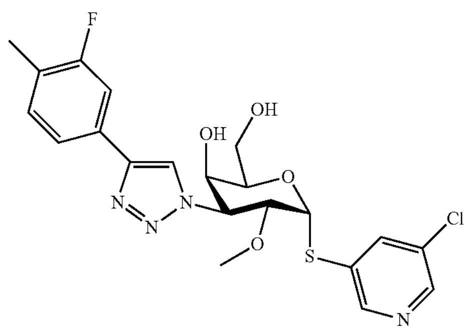 | 0.045 |
| 36 | 5-Bromopyridin-3-yl 3-deoxy-3-[4-(3-fluoro-4-methylphenyl)-1H-1,2,3-triazol-1-yl]-2-O-methyl-1-thio-α-D-galactopyranoside | 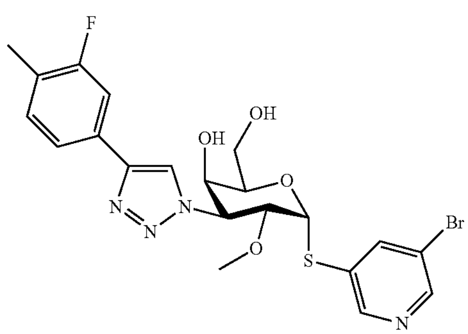 | 0.026 |
| 37 | 5-Chloropyridin-3-yl 3-[4-(4-chloro-3-fluorophenyl)-1H-1,2,3-triazol-1-yl]-3-deoxy-2-O-methyl-1-thio-α-D-galactopyranoside | 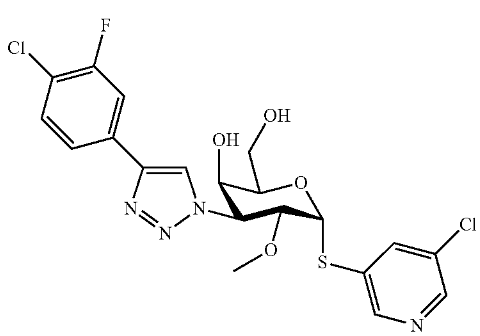 | 0.042 |

-continued

| Example | Name | structure | Galectin-3 Kd (μM) |
|---|---|---|---|
| 38 | 5-Bromopyridin-3-yl 3-[4-(4-chloro-3-fluorophenyl)-1H-1,2,3-triazol-1-yl]-3-deoxy-2-O-methyl-1-thio-α-D-galactopyranoside | 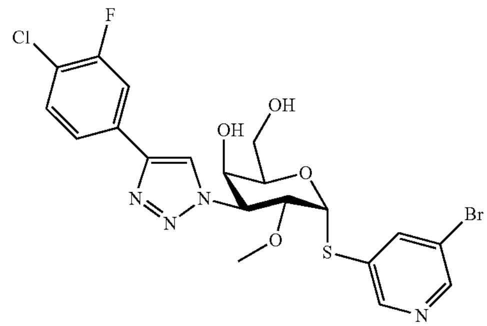 | 0.062 |
| 39 | 6-Trifluoromethyl-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside | 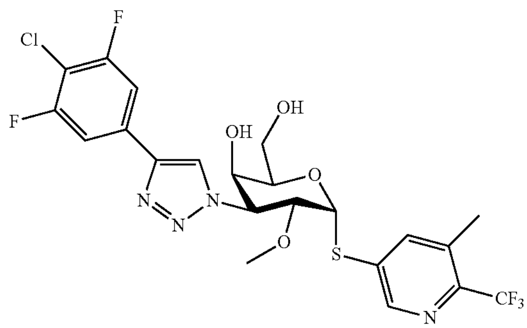 | 0.28 |
| 40 | 2-(N-azetidinyl-carbonyl)-5-chlorophenyl 3-[4-(4-chloro-3,5-difluorophenyl)-1H-1,2,3-triazol-1-yl]-3-deoxy-2-O-methyl-1-thio-α-D-galactopyranoside | 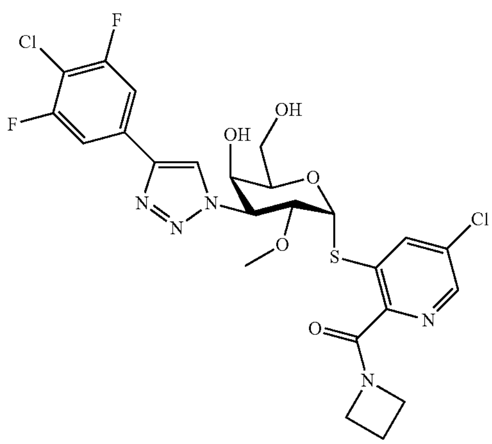 | 0.015 |
| 41 | 2-(N-azetidinyl-carbonyl)-5-chlorophenyl 3-deoxy-3-[4-(3-fluoro-4-methylphenyl)-1H-1,2,3-triazol-1-yl]-2-O-methyl-1-thio-α-D-galactopyranoside | 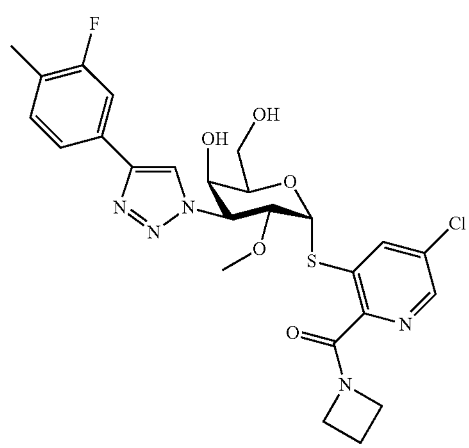 | 0.007 |

-continued

| Example | Name | structure | Galectin-3 Kd (μM) |
|---|---|---|---|
| 42 | 5-Chloropyridin-3-yl 3-deoxy-3-[4-(3,4,5-trifluorophenyl)-1H-1,2,3-triazol-1-yl]-2-O-methyl-1-thio-α-D-galactopyranoside | 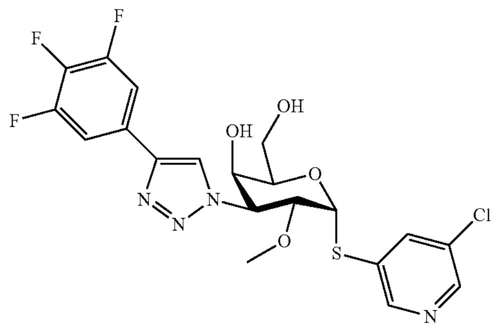 | 0.029 |
| 43 | 5-Chloropyridin-3-yl 3-deoxy-3-[4-(6-fluoro-5-methylpyridin-2-yl)-1H-1,2,3-triazol-1-yl]-2-O-methyl-1-thio-α-D-galactopyranoside | 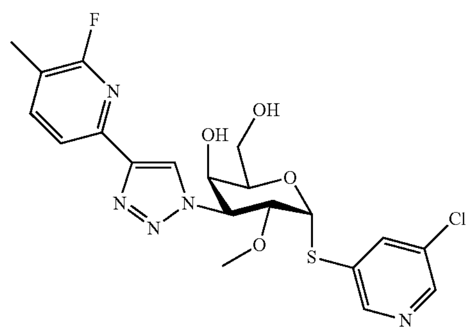 | 0.039 |
| 44 | 5-Chloropyridin-3-yl 3-[4-(5-chloro-6-methylpyridin-2-yl)-1H-1,2,3-triazol-1-yl]-3-deoxy-2-O-methyl-1-thio-α-D-galactopyranoside | 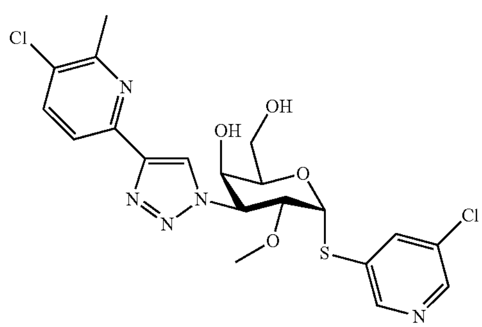 | 0.88 |
| 45 | 3-Chloro-2-cyanopyridin-5-yl 3-deoxy-3-[4-(3,4,5-trifluorophenyl)-1H-1,2,3-triazol-1-yl]-2-O-methyl-1-thio-α-D-galactopyranoside | 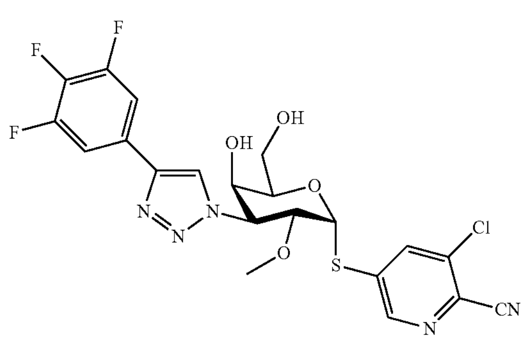 | 0.065 |

-continued

| Example | Name | structure | Galectin-3 Kd (μM) |
|---|---|---|---|
| 46 | 5-Chloro-2-cyanopyridin-3-yl 3-deoxy-3-[4-(3,4,5-trifluorophenyl)-1H-1,2,3-triazol-1-yl]-2-O-methyl-1-thio-α-D-galactopyranoside | 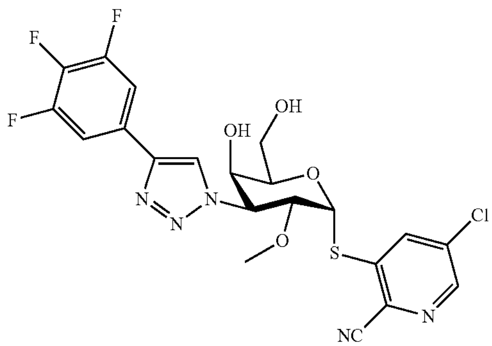 | 0.035 |
| 47 | 5-Chloro-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside | 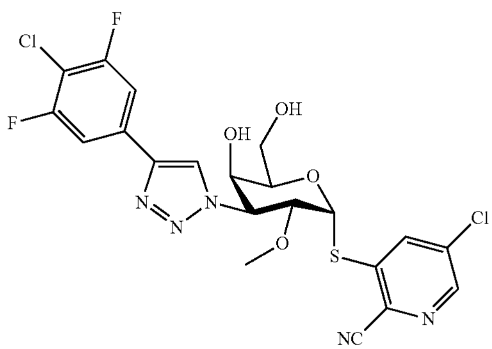 | 0.034 |
| 48 | 5-Chloro-2-cyanopyridin-3-yl 3-[4-(4-chloro-3-fluorophenyl)-1H-1,2,3-triazol-1-yl]-3-deoxy-2-O-methyl-1-thio-α-D-galactopyranoside | 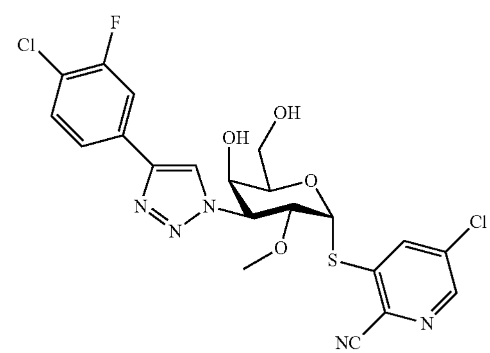 | 0.031 |
| 49 | 2-Cyano-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside | 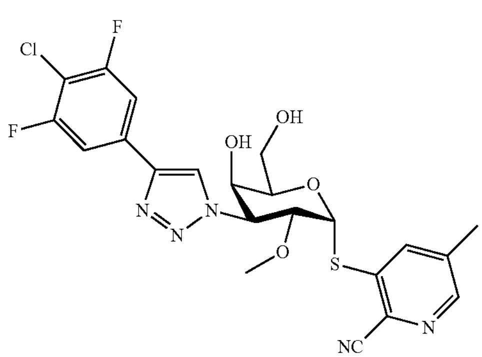 | 0.050 |

-continued

| Example | Name | structure | Galectin-3 Kd (μM) |
|---|---|---|---|
| 50 | 5-Bromo-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside | 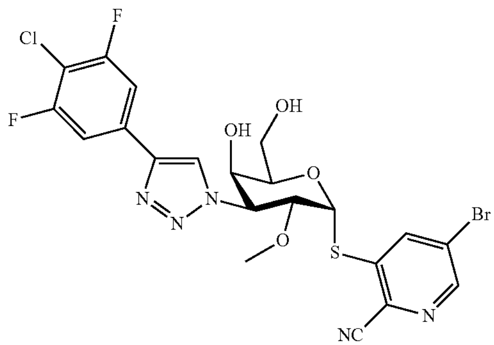 | 0.023 |
| 51 | 5-Bromo-2-cyanopyridin-3-yl 3-[4-(4-chloro-3-fluorophenyl)-1H-1,2,3-triazol-1-yl]-3-deoxy-2-O-methyl-1-thio-α-D-galactopyranoside | 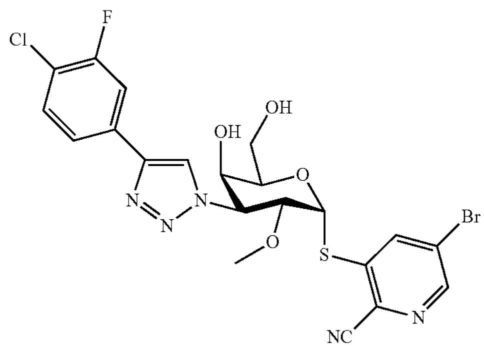 | 0.037 |
| 52 | 5-Chloro-2-(N-azetidinylcarbamoyl)-3-pyridyl 3-[4-(4-chloro-3,5-difluorophenyl)-1H-1,2,3-triazol-1-yl]-3-deoxy-2-O-methyl-1-thio-α-D-galactopyranoside | 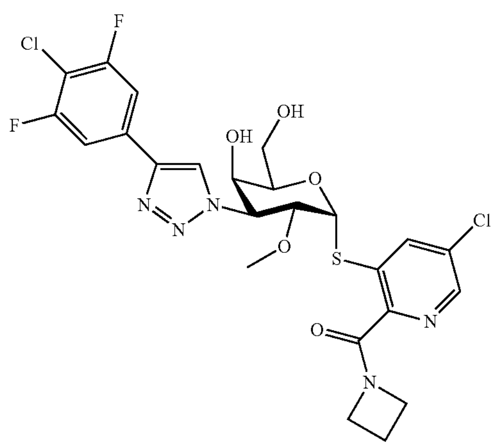 | 0.016 |
| 53 | 5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside | 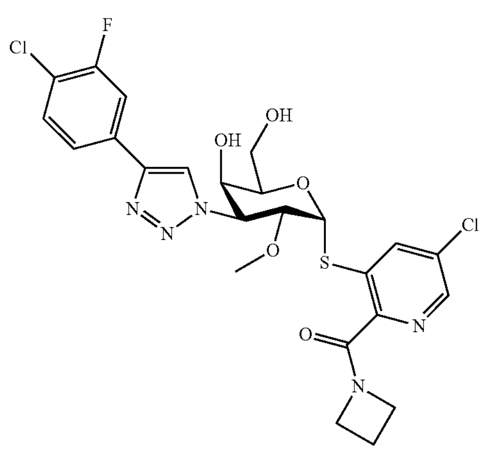 | 0.021 |

-continued

| Example | Name | structure | Galectin-3 Kd (μM) |
|---|---|---|---|
| 54 | 5-Ethynylpyridin-3-yl 3-[4-(4-chloro-3,5-difluorophenyl)-1H-1,2,3-triazol-1-yl]-3-deoxy-2-O-methyl-1-thio-α-D-galactopyranoside | 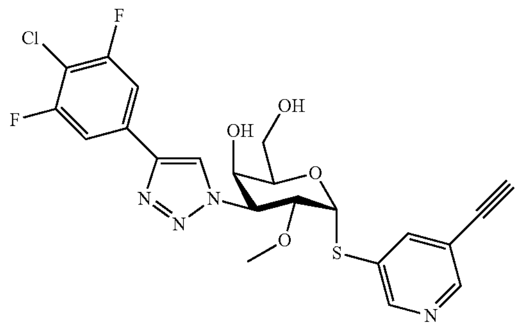 | 0.035 |
| 55 | 5-Chloro-2-cyanopyridin-3-yl 3-[4-(5-chloro-6-fluoropyridin-2-yl)-1H-1,2,3-triazol-1-yl]-3-deoxy-2-O-methyl-1-thio-α-D-galactopyranoside | 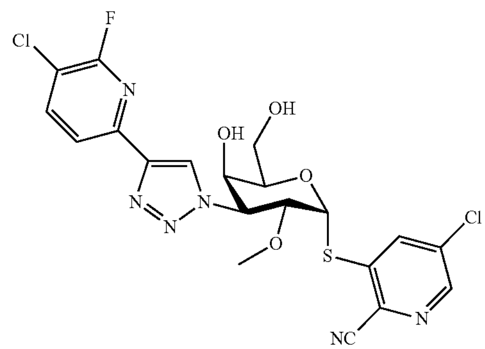 | 0.35 |
| 56 | 2-Cyano-5-ethynylpyridin-3-yl 3-[4-(4-chloro-3,5-difluorophenyl)-1H-1,2,3-triazol-1-yl]-3-deoxy-2-O-methyl-1-thio-α-D-galactopyranoside | 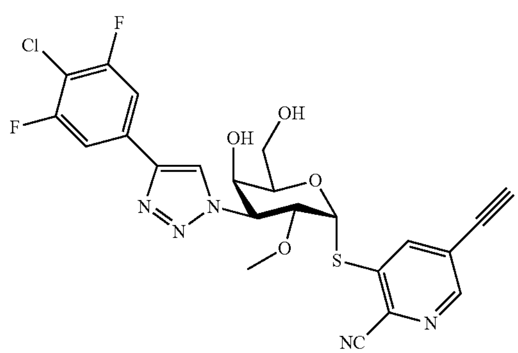 | 0.028 |
| 57 | 2-Cyano-5-ethynylpyridin-3-yl 3-deoxy-3-[4-(3,5-difluoro-4-methylphenyl)-1H-1,2,3-triazol-1-yl]-2-O-methyl-1-thio-α-D-galactopyranoside | 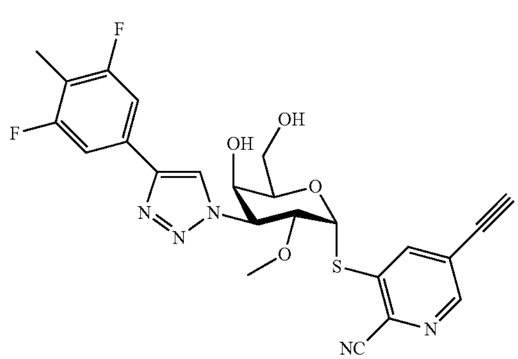 | 0.035 |

-continued

| Example | Name | structure | Galectin-3 Kd (μM) |
|---|---|---|---|
| 58 | 5-Cyano-6-trifluoromethylpyridin-3-yl 3-[4-(4-chloro-3,5-difluorophenyl)-1H-1,2,3-triazol-1-yl]-3-deoxy-2-O-methyl-1-thio-α-D-galactopyranoside | 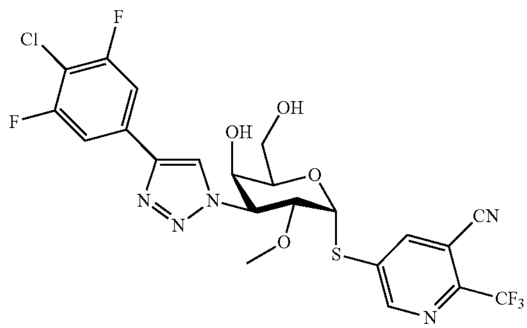 | 0.19 |
| 59 | 5-Cyanopyridin-3-yl 3-deoxy-3-[4-(3,4,5-trifluorophenyl)-1H-1,2,3-triazol-1-yl]-2-O-methyl-1-thio-α-D-galactopyranoside | 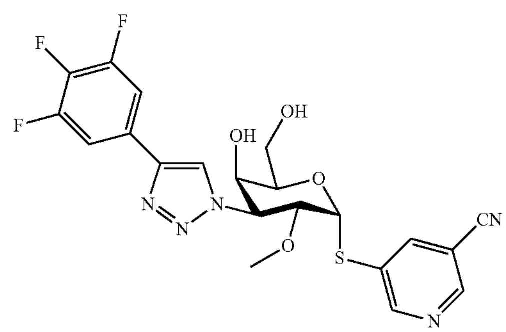 | 0.076 |
| 60 | 5-Cyanopyridin-3-yl 3-[4-(4-chloro-3,5-difluorophenyl)-1H-1,2,3-triazol-1-yl]-3-deoxy-2-O-methyl-1-thio-α-D-galactopyranoside | 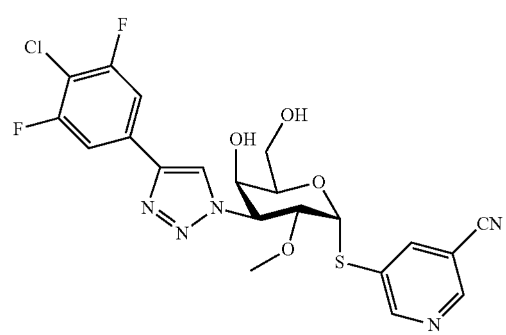 | 0.080 |
| 61 | 5-Bromo-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside | 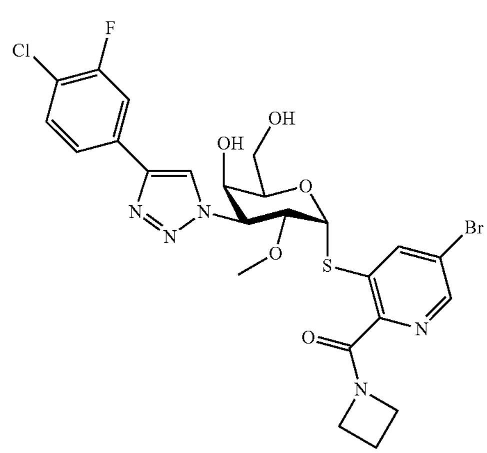 | 0.007 |

-continued

| Example | Name | structure | Galectin-3 Kd (μM) |
|---|---|---|---|
| 62 | 5-Bromo-2-(N-azetidinylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside | 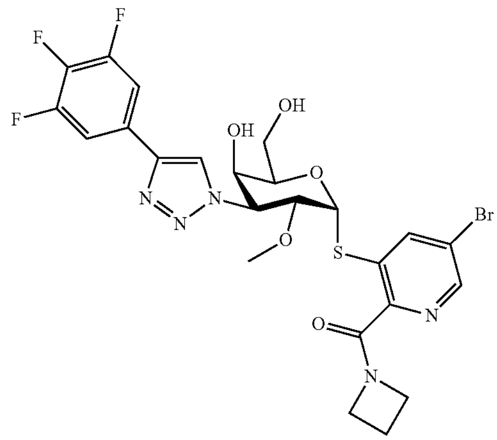 | 0.006 |
| 63 | 5-Bromo-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside | 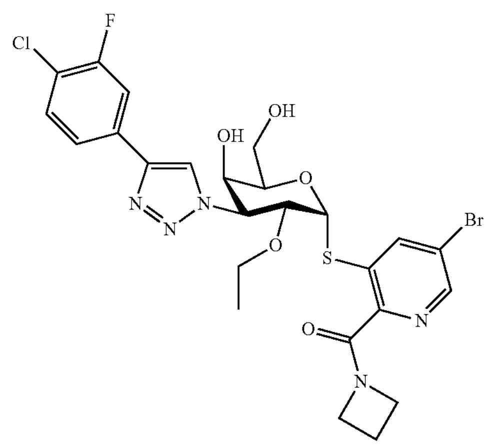 | 0.008 |
| 64 | 2-(N-azetidinyl-carbonyl)-5-bromophenyl 3-deoxy-3-[4-(3,4,5-trifluorophenyl)-1H-1,2,3-triazol-1-yl]-2-O-methyl-1-thio-α-D-galactopyranoside | 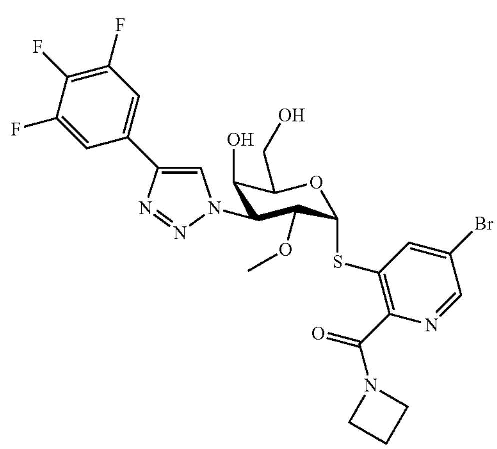 | 0.016 |

| Example | Name | structure | Galectin-3 Kd (μM) |
|---|---|---|---|
| 65 | 2-(N-azetidinyl-carbonyl)-5-bromophenyl 3-deoxy-3-[4-(3,4,5-trifluorophenyl)-1H-1,2,3-triazol-1-yl]-2-O-ethyl-1-thio-α-D-galactopyranoside | 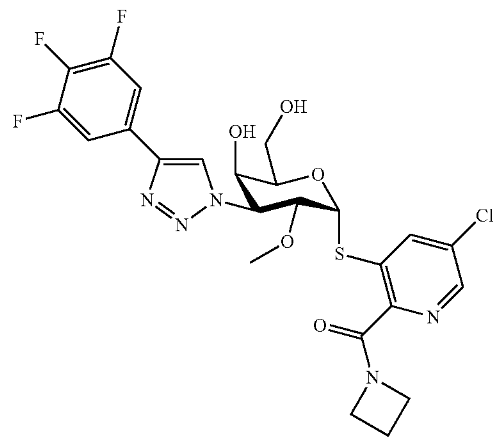 | 0.018 |
| 66 | 5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside | 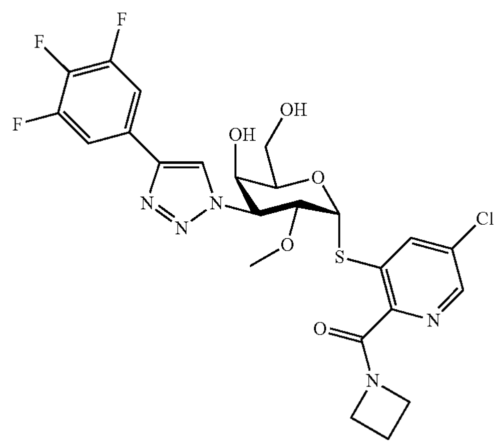 | 0.010 |
| 67 | 5-Chloro-2-(N-azetidinylcarbamoyl)-3-pyridyl 3-deoxy-3-[4-(3,4,5-trifluorophenyl)-1H-1,2,3-triazol-1-yl]-2-O-ethyl-1-thio-α-D-galactopyranoside | 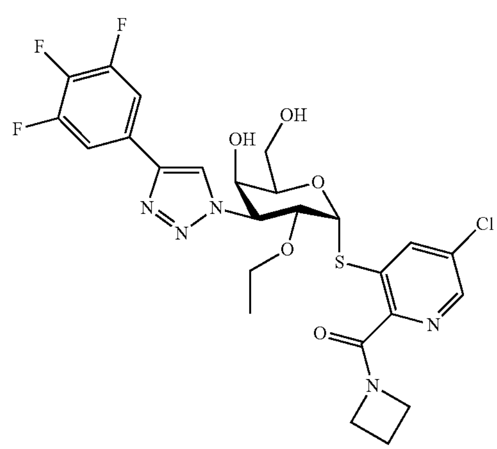 | 0.021 |

-continued

| Example | Name | structure | Galectin-3 Kd (μM) |
|---|---|---|---|
| 68 | 5-Chloro-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside | 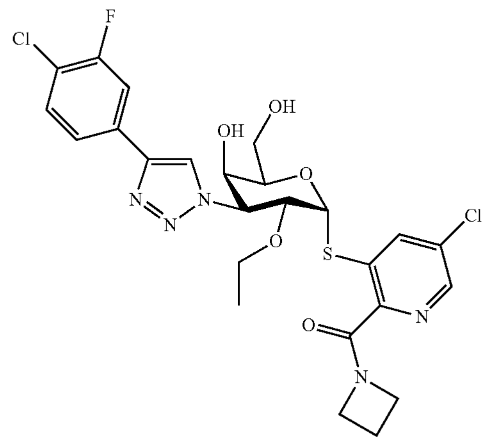 | 0.017 |
| 69 | 5-Chloro-2-(N-azetidinylcarbamoyl)-3-pyridyl 3-[4-(4-chloro-3,5-difluorophenyl)-1H-1,2,3-triazol-1-yl]-3-deoxy-2-O-ethyl-1-thio-α-D-galactopyranoside | 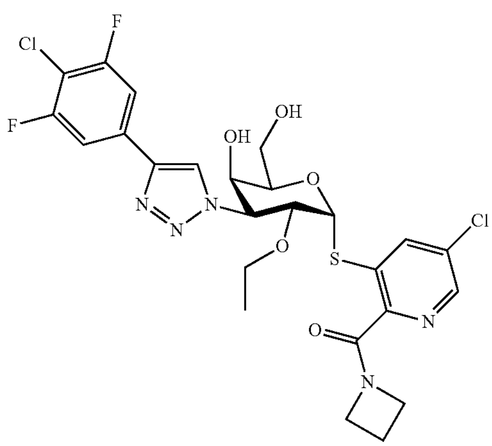 | 0.011 |
| 70 | 2-(N-azetidinyl-carbonyl)-5-chlorophenyl 3-deoxy-3-[4-(3,4,5-trifluorophenyl)-1H-1,2,3-triazol-1-yl]-2-O-methyl-1-thio-α-D-galactopyranoside | 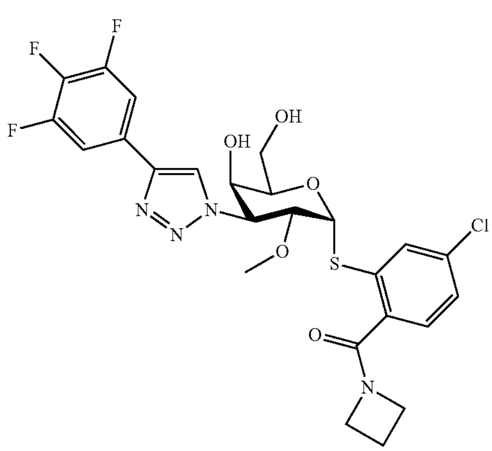 | 0.012 |

| Example | Name | structure | Galectin-3 Kd (μM) |
|---|---|---|---|
| 71 | 3,4-Dichlorophenyl 3-[4-(4-chloro-3,5-difluorophenyl)-1H-1,2,3-triazol-1-yl]-3-deoxy-2-O-methyl-1-thio-α-D-galactopyranoside | 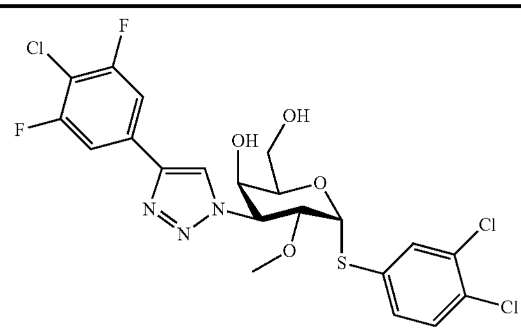 | 0.25 |

Evaluation of Kd Values

The affinity of Example 1-71 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sarme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010). The assay was also adapted to be able to measure the high affinity of compounds for galectin-3 by using the below probe constructed to have high affinity for galectin-3 which made it possible to use a low concentration of galectin-3 (50 nM). 100 nM albumin was included as a carrier to prevent protein loss at such low concentration of galectin.

Uptake of compounds of formula 1 over CACO2 monolayers.

Uptake of a drug over the intestine can be predicted measuring the uptake over a monolayer of CACO-2 cells measured as Papp ($10^{-6}$ cm/s). (Shah, P.; Jogani, V.; Bagchi, T.; Misra, A. Role of Caco-2 Cell Monolayers in Prediction of Intestinal Drug Absorption. *Biotechnol. Prog.* 2006, 22 (1), 186-198.) In general compounds like Ref 1 and 2 where the 2-OH group is unsubstituted have low (Papp<5 $10^{-6}$ cm/s) to medium (Papp=5-10 $10^{-6}$ cm/s) uptake due to efflux from the basolateral to the apical side of the CACO2 membranes. By introduction of small alkyl substituents to the galactoside 2-OH such as compounds of formula (1) results in low or no efflux combined with a high uptake (Papp>10 $10^{-6}$ cm/s) over CACO-2 cells from the apical to the basolateral side of the cells.

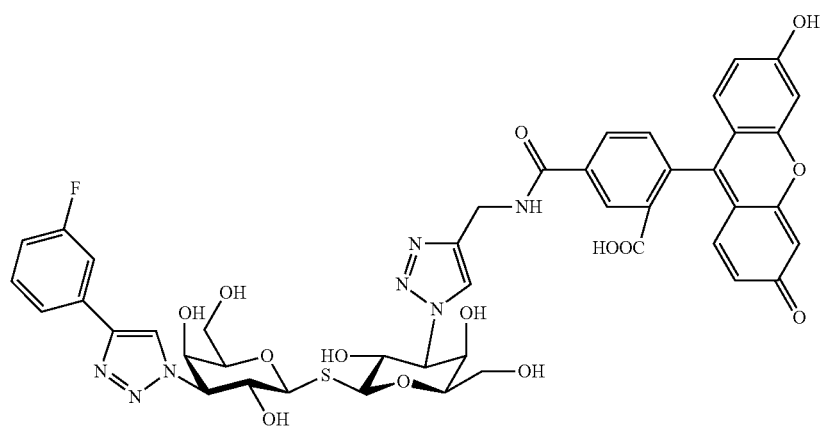

Probe

| Example | CACO-2 A>B Papp (10^-6 cm/s) | CACO-2 B>A Papp (10^-6 cm/s) | Efflux ratio Papp (B>A/A>B) |
|---|---|---|---|
| 35 | 31 | 45 | 1.4 |
| 01 | 30 | 38 | 1.2 |
| 36 | 28 | 32 | 1.1 |
| 43 | 26 | 34 | 1.3 |
| 13 | 18 | 23 | 1.3 |
| Ref 1 | 3 | 30 | 10 |

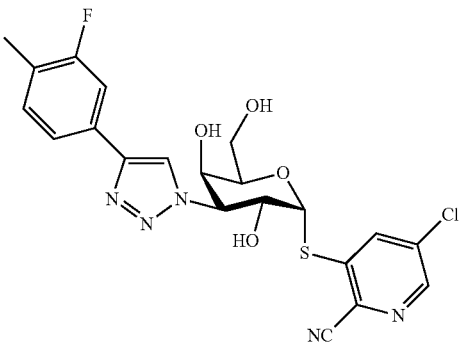

| | | | |
|---|---|---|---|
| Ref 2 | 5 | 46 | 9 |

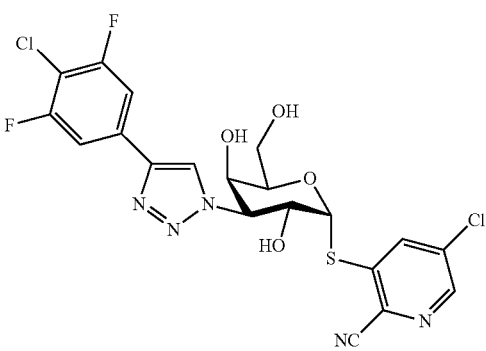

| | | | |
|---|---|---|---|
| Ref 3 | 4 | 36 | 9 |

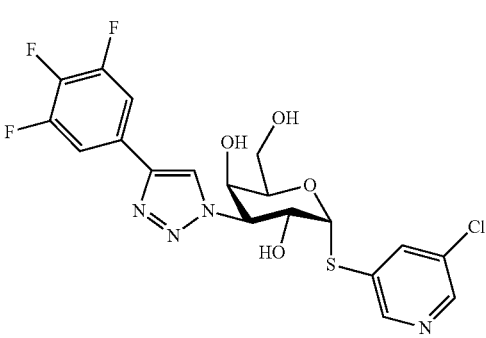

Synthesis of Examples and Intermediates

General Experimental:

Nuclear Magnetic Resonance (NMR) spectra were recorded on a 400 MHz Bruker AVANCE III 500 instrument or a Varian instrument at 400 MHz or a 500 MHz Bruker Avance Neo 500 instrument, at 25° C.

Chemical shifts are reported in ppm (d) using the residual solvent as internal standard. Peak multiplicities are expressed as follow: s, singlet; d, doublet; dd, doublet of doublets; t, triplet; dt, doublet of triplet; q, quartet; p, pentet; m, multiplet; br s, broad singlet. In the case of anomeric mixtures, the shifts of the individual anomers are reported separately and the α/β ratio was calculated based on the integration of the anomeric peaks.

LC-MS were acquired on an Agilent 1200 HPLC coupled with an Agilent MSD mass spectrometer operating in ES (+) ionization mode. Column: XBridge C18 (4.6×50 mm, 3.5 μm) or SunFire C18 (4.6×50 mm, 3.5 μm). Solvent A water+0.1% TFA and solvent B Acetonitrile+0.1% TFA or solvent A water (10 mM Ammonium hydrogen carbonate) and solvent B Acetonitrile. Wavelength: 254 nM. Alternatively, LC-MS were acquired on an Agilent 1100 HPLC coupled with an Agilent MSD mass spectrometer operating in ES (+) ionization mode. Column: Waters symmetry 2.1×30 mm C18 or Chromolith RP-18 2×50 mm. Solvent A water+0.1% TFA and solvent B Acetonitrile+0.1% TFA. Wavelength 254 nm.

GC-MS were acquired on a Shimadzu GCMS-QP2010 Ultra. Column: DB-5 ms: 0.25 mm*30 m*0.25 µm. Injection Temperature: 150° C.; Spilt Ratio: 99:1; He (1.5 ml/min); Inst Method: 50° C. (1 min)/15° C./min/260° C. (1 min); Ion Source Temp: 200° C.; Interface Temp: 250° C.

Preparative HPLC was performed on a Gilson 281. Flow: 20 mL/min Column: X-Select 10 µm 19×250 mm column. Wavelength: 254 nm or 214 nm. Solvent A water (10 mM Ammonium hydrogen carbonate) and solvent B Acetonitrile (Method A). Alternatively, preparative HPLC were acquired on a Gilson system. Flow: 12 ml/min Column: kromasil 100-5-C18 column. Wavelength: 220 nm. Solvent A water+ 0.1% TFA and solvent B Acetonitrile (Method B).

The following abbreviations are used
aq: aqueous
Calcd: Calculated
DCM: dichloromethane
DIEA: N,N-Diisopropylethylamine
DMAP: 4-dimethylaminopyridine
DMF: N,N-dimethylformamide
ESI-MS: Electrospray ionization mass spectrometry
$Et_3N$: triethylamine
EtOAc: ethyl acetate
h: hours
HATU: 1-[Bis(dimethylamino)methylene]-1H-1,2,3-triazolo[4,5-b]pyridinium 3-oxid hexafluorophosphate
HPLC: High Performance liquid chormatography
MeCN: acetonitrile
min: minutes
prep. preparative
PE: petroleum ether
rt: room temperature
SFC: Supercritical Fluid Chromatography
TBS: tert-Butyldimethylsilyl
TBAF: tetrabutylarnmonium fluoride
TFA: trifluoroacetic acid
THF: tetrahydrofuran
TMS: trimethyl silyl
UV: Ultraviolet Synthesis of Examples 1-71 from their Respective Intermediates 1-71

Example 1

5-Bromopyridin-3-yl 3-deoxy-3-[4-(3,4,5-trifluorophenyl)-1H-1,2,3-triazol-1-yl]-2-O-methyl-1-thio-α-D-galactopyranoside

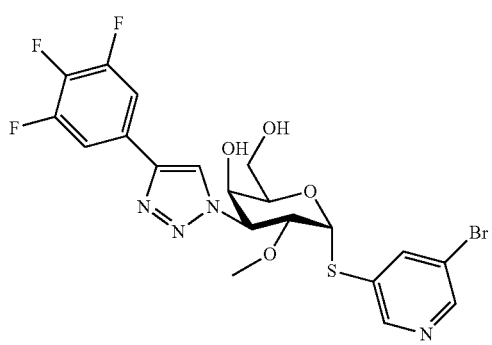

5-Bromopyridin-3-yl 4,6-O-benzylidene-3-deoxy-3-[4-(3,4,5-trifluorophenyl)-1H-1,2,3-triazol-1-yl]-1-thio-α-D-galactopyranoside (150 mg, 0.24 mmol) and NaH (60% in oil, 19 mg, 0.48 mmol) were stirred in DMF (3 mL) for 10 min before the addition of iodomethane (22.5 µL, 0.36 mmol). The mixture was stirred 2 h at 40° C., then diluted with EtOAc and washed twice with water. The organic phase was dried, evaporated and the residue was stirred 1 h in 80% aq TFA (2 mL). The mixture was concentrated and purified by chromatography ($SiO_2$, PE/EtOAc). Further purification by preparative HPLC (Method B) afforded the title compound (50 mg, 38%) as a white powder. ESI-MS m/z calcd for $[C_{20}H_{18}BrF_3N_4O_4S]$ $[M+H]^+$: 547.0; found: 547.1. $^1$H NMR (400 MHz, Methanol-$d_4$) δ 8.71 (d, J=1.7 Hz, 1H), 8.59 (s, 2H), 8.40-8.36 (m, 1H), 7.70-7.62 (m, 2H), 6.28 (d, J=5.3 Hz, 1H), 5.04 (dd, J=11.3, 2.7 Hz, 1H), 4.65 (dd, J=11.3, 5.3 Hz, 1H), 4.46 (t, J=6.0 Hz, 1H), 4.19 (d, J=2.7 Hz, 1H), 3.75-3.66 (m, 2H), 3.41 (s, 3H).

Example 2

5-Bromo-2-cyanopyridin-3-yl 3-deoxy-3-[4-(3-fluoro-4-methylphenyl)-1H-1,2,3-triazol-1-yl]-2-O-methyl-1-thio-α-D-galactopyranoside Example 3

4-Chloro-N,N-dimethyl-benzamide-2-yl 3-deoxy-3-[4-(3,4,5-trifluorophenyl)-1H-1,2,3-triazol-1-yl]-2-O-methyl-1-thio-α-D-galactopyranoside

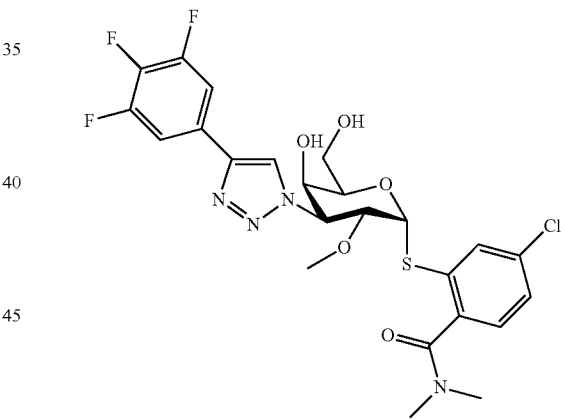

A solution of 4-chloro-N,N-dimethyl-benzamide-2-yl 3-deoxy-3-[4-(3,4,5-trifluorophenyl)-1H-1,2,3-triazol-1-yl]-1-thio-α-D-galactopyranoside (190 mg, 0.34 mmol), benzaldehyde dimethylacetal (207 µL, 1.36 mmol) and p-toluenesulfonic acid monohydrate (5 mg, 0.026 mmol) in MeCN (3.0 mL) were stirred 2 h at rt. The mixture was concentrated and partitioned between EtOAc and water, the organic phase was collected and evaporated. The residue was subjected to chromatography ($SiO_2$, PE/EtOAc) and the obtained material was dissolved in DMF (2.0 mL). Iodomethane (45 µL, 0.72 mmol) followed by NaH (60% in oil, 15 mg, 0.36 mmol) were added and the mixture was stirred 1 h at rt. The mixture was poured onto ice and HCl (0.2 M), the precipitate was isolated by filtration. The precipitate was dissolved in 80% aq TFA (2.0 mL) stirred 1 h at rt before being poured on water and NaOH (20 mL, 2 M). The precipitate was isolated by filtration and purified by chromatography (SiO$_2$, PE/EtOAc) to afford the title compound (24 mg, 12%). ESI-MS m/z calcd for [C$_{24}$H$_{24}$ClF$_3$NO$_5$O$_5$S][M+H]$^+$: 573.1; found: 573.2. $^1$H NMR (400 MHz, Methanol-d$_4$) δ 8.57 (s, 1H), 7.86 (s, 1H), 7.66 (m, 2H), 7.46 (d, J=8.1 Hz, 1H), 7.30 (d, J=8.2 Hz, 1H), 6.19 (bs, 1H), 4.98 (dd, J=11.4, 2.8 Hz, 1H), 4.58 (dd, J=11.3, 5.3 Hz, 1H), 4.52 (bt, 1H), 4.18 (d, J=2.5 Hz, 1H), 3.78-3.64 (m, 2H), 3.38 (s, 3H), 3.13 (s, 3H), 2.89 (s, 3H).

Example 4

4-Chloro-N,N-dimethyl-benzamide-2-yl 3-[4-(4-chloro-3,5-difluorophenyl)-1H-1,2,3-triazol-1-yl]-3-deoxy-2-O-methyl-1-thio-α-D-galactopyranoside

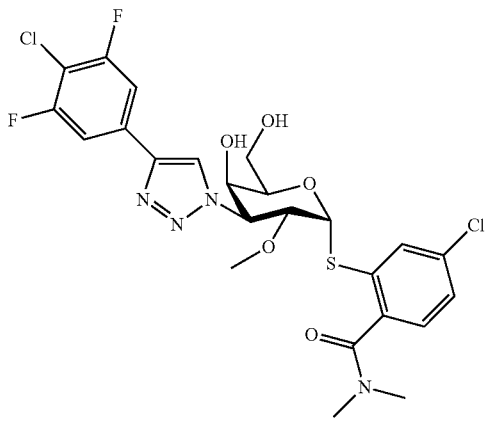

4-Chloro-N,N-dimethyl-benzamide-2-yl 3-[4-(4-chloro-3,5-difluorophenyl)-1H-1,2,3-triazol-1-yl]-3-deoxy-1-thio-α-D-galactopyranoside (34 mg, 0.059 mmol) was dissolved in MeCN (2.0 mL) and benzaldehyde dimethylacetal (36 µL, 0.24 mmol) followed by p-toluenesulfonic acid monohydrate (5 mg, 0.023 mmol) were added. The mixture was stirred 2 h at rt followed by evaporation of the solvent. The residue was dissolved in DMF (1.5 mL), iodomethane (15 µL, 0.24 mmol) followed by NaH (60% in oil, 5.0 mg, 0.12 mmol) were added. The mixture was stirred 2.5 h at rt, then poured onto ice and HCl (0.2 M). The precipitate was isolated by filtration and dried. This material was dissolved in 80% aq TFA (1.5 mL) and stirred 2 h at rt before being concentrated. The residue was purified by chromatography (SiO$_2$, PE/EtOAc) and further purified by preparative HPLC (Method B) afforded the title compound (6.0 mg, 17%). ESI-MS m/z calcd for [C$_{24}$H$_{24}$Cl$_2$F$_2$N$_4$O$_5$S] [M+H]$^+$: 589.1; found: 589.2. $^1$H NMR (400 MHz, Methanol-d$_4$) δ 8.63 (s, 1H), 7.87 (s, 1H), 7.67 (d, J=8.6 Hz, 2H), 7.47 (d, J=8.1 Hz, 1H), 7.30 (d, J=8.2 Hz, 1H), 6.20 (bs, 1H), 4.99 (dd, J=11.3, 2.6 Hz, 1H), 4.59 (dd, J=11.5, 5.1 Hz, 1H), 4.53 (bs, 1H), 4.18 (s, 1H), 3.79-3.64 (m, 2H), 3.39 (s, 3H), 3.14 (s, 3H), 2.90 (s, 3H).

Example 5

5-Bromopyridin-3-yl 3-deoxy-3-[4-(3,4,5-trifluorophenyl)-1H-1,2,3-triazol-1-yl]-2-O-(1,1,1-trifluoro-2-hydroxyprop-3-yl)-1-thio-α-D-galactopyranoside

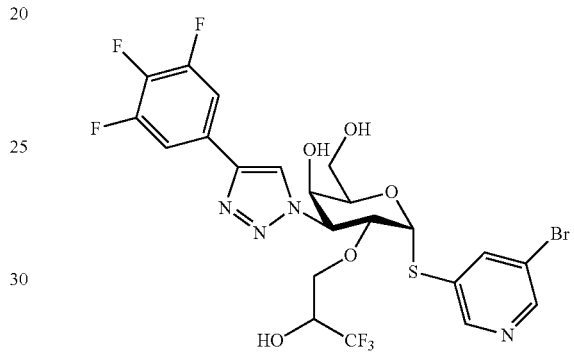

5-Bromopyridin-3-yl 4,6-O-benzylidene-3-deoxy-3-[4-(3,4,5-trifluorophenyl)-1H-1,2,3-triazol-1-yl]-1-thio-α-D-galactopyranoside (1.00 g, 1.6 mmol) and NaH (60% in oil, 77 mg, 1.92 mmol) were stirred 20 min in DMF (10 mL) before 1,2-epoxy-3,3,3-trifluoropropane (0.211 mL, 1.91 M solution in THF, 1.76 mmol) was added. The mixture was stirred 1 h at rt, then water (20 mL) was added. The solids were isolated by filtration and this material was heated in MeOH (10 mL) then cooled to rt. The solids were filtered off, the filtrate was concentrated and purified by chromatography (SiO$_2$, PE/EtOAc). The product was treated in 80% aqueous TFA (3.0 mL) for 2 h, then concentrated and purified by chromatography (SiO$_2$, PE/EtOAc). Further purification by preparative HPLC (Method B) yielded the title compound (30 mg, 3%). ESI-MS m/z calcd for [C$_{22}$H$_{19}$BrF$_6$N$_4$O$_5$S] [M+H]$^+$: 645.0; found: 645.1. $^1$H NMR (400 MHz, Methanol-d$_4$) δ 8.69 (s, 1H), 8.58 (s, 2H), 8.35 (d, J=1.8 Hz, 1H), 7.69-7.59 (m, 2H), 6.28 (d, J=5.1 Hz, 1H), 5.09 (d, J=11.3 Hz, 1H), 4.85 (m, 1H), 4.49 (t, J=5.8 Hz, 1H), 4.25 (s, 1H), 4.03 (d, J=10.5 Hz, 1H), 3.96 (m, 1H), 3.76-3.65 (m, 2H), 3.60 (m, 1H).

Example 6

2-(N-piperidinyl-carbonyl)-5-chlorophenyl 3-[4-(4-chloro-3,5-difluorophenyl)-1H-1,2,3-triazol-1-yl]-3-deoxy-2-O-methyl-1-thio-α-D-galactopyranoside

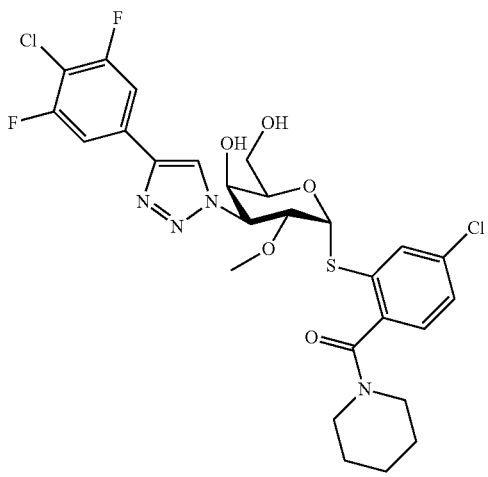

2-(N-piperidinyl-carbonyl)-5-chlorophenyl 3-[4-(4-chloro-3,5-difluorophenyl)-1H-1,2,3-triazol-1-yl]-3-deoxy-1-thio-α-D-galactopyranoside (25 mg, 0.04 mmol) was dissolved in MeCN (2.0 mL) and benzaldehyde dimethylacetal (24 μL, 0.16 mmol) followed by p-toluenesulfonic acid monohydrate (5 mg, 0.023 mmol) were added. The mixture was stirred 2.5 h at rt followed by evaporation of the solvent. The residue was dissolved in DMF (1.5 mL), iodomethane (10 μL, 0.16 mmol) followed by NaH (60% in oil, 5.0 mg, 0.12 mmol) were added. The mixture was stirred 1 h at rt, then poured onto ice and HCl (0.2 M). The precipitate was isolated by filtration and dried. This material was dissolved in 80% aq TFA (1.2 mL) and stirred 2 h at rt before being concentrated. The residue was purified by chromatography (SiO$_2$, PE/EtOAc) and further purified by preparative HPLC (Method B) to afford the title compound (16 mg, 78%). ESI-MS m/z calcd for [C$_{27}$H$_{28}$Cl$_2$F$_2$N$_4$O$_5$S] [M+H]$^+$: 629.1; found: 629.2. $^1$H NMR (400 MHz, Methanol-d$_4$) (two conformational isomers) δ 8.63 (s, 1H), 7.95-7.79 (m, 1H), 7.66 (m, 2H), 7.55-7.35 (m, 1H), 7.34-7.19 (m, 1H), 6.37-6.08 (m, 1H), 4.99 (d, J=11.0 Hz, 1H), 4.70-4.37 (m, 2H), 4.19 (s, 1H), 3.93-3.58 (m, 4H), 3.39 (s, 3H), 3.22 (bs, 2H), 1.82-1.57 (m, 5H), 1.52 (bs, 1H).

Example 7

4-Chloro-N,N-dimethyl-benzamide-2-yl 3-[4-(4-chloro-3,5-difluorophenyl)-1H-1,2,3-triazol-1-yl]-3-deoxy-2-O-trifluoromethyl-1-thio-α-D-galactopyranoside

Example 8

4-Chloro-N,N-dimethyl-benzamide-2-yl 3-deoxy-2-O-trifluoromethyl-3-[4-(3,4,5-trifluorophenyl)-1H-1,2,3-triazol-1-yl]-1-thio-α-D-galactopyranoside

Example 9

5-Chloro-2-(N,N-dimethylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside

Example 10

5-Chloro-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside

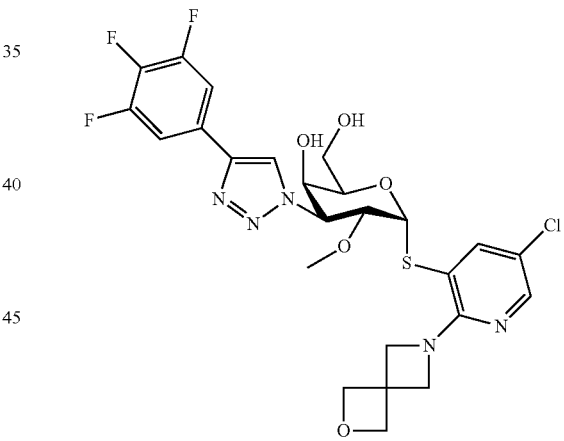

2-Bromo-5-chloropyridin-3-yl 3-deoxy-3-[4-(3,4,5-trifluorophenyl)-1H-1,2,3-triazol-1-yl]-2-O-methyl-1-thio-α-D-galactopyranoside (75 mg, 0.13 mmol), 2-oxa-6-azaspiro[3.3]heptane oxalic acid (149 mg, 0.52 mmol) and DIEA (0.33 mL, 1.93 mmol) dissolved in MeCN (2.5 mL) was sealed in a microwave vial and stirred 6 h at 130° C. in a microwave reactor. The mixture was concentrated and purified by preparative HPLC (Method B) to afford the title compound (24 mg, 31%). ESI-MS m/z calcd for [C$_{25}$H$_{25}$ClF$_3$N$_5$O$_5$S] [M+H]$^+$: 600.1; found: 600.2. $^1$H NMR (400 MHz, Methanol-d$_4$) δ 8.60 (s, 1H), 8.03 (d, J=2.3 Hz, 1H), 7.95 (d, J=2.4 Hz, 1H), 7.67 (dd, J=8.6, 6.7 Hz, 2H), 5.98 (d, J=5.2 Hz, 1H), 5.04 (dd, J=11.4, 2.8 Hz, 1H), 4.85-4.81 (m, 4H), 4.62 (dd, J=11.4, 5.3 Hz, 1H), 4.53 (d, J=9.4 Hz, 2H), 4.46-4.39 (m, 3H), 4.20 (d, J=2.5 Hz, 1H), 3.74-3.63 (m, 2H), 3.41 (s, 3H).

Example 11

5-Chloro-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside

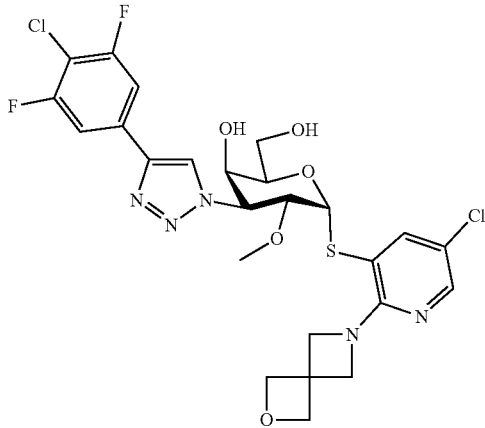

5-Chloro-2-{N-(2-oxa)-6-azaspiro[3.3]heptanyl}-pyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside (115 mg, 0.16 mmol) was dissolved in DCM/TFA (10 mL, 19:1) and stirred 1 h at rt. The mixture was neutralized with Et$_3$N and concentrated under reduced pressure. The residue was purified by preparative HPLC (Method A) to give the title compound (55.4 mg, 55%) as a white solid. ESI-MS m/z calcd for [C$_{25}$H$_{25}$Cl$_2$F$_2$N$_5$O$_5$S] [M+H]$^+$: 616.1; found: 616.0. $^1$H NMR (400 MHz, DMSO-d$_6$) δ 8.92 (s, 1H), 8.06 (d, J=2.4 Hz, 1H), 7.86-7.78 (m, 3H), 6.10 (d, J=5.2 Hz, 1H), 5.56 (d, J=6.0 Hz, 1H), 4.88 (dd, J=11.6, 2.8 Hz, 1H), 4.76 (t, J=5.2 Hz, 1H), 4.72-4.65 (m, 4H), 4.47 (dd, J=11.6, 5.2 Hz, 1H), 4.35 (d, J=9.2 Hz, 2H), 4.27 (d, J=9.2 Hz, 2H), 4.24 (d, J=6.4 Hz, 1H), 4.03 (dd, J=6.0, 2.8 Hz, 1H), 3.51 (dt, J=11.2, 5.6 Hz, 1H), 3.40 (dd, J=11.2, 6.0 Hz, 1H), 3.32 (s, 3H).

Example 12

5-Chloro-2-cyanopyridin-3-yl 3-deoxy-3-[4-(3,5-difluoro-4-methylphenyl)-1H-1,2,3-triazol-1-yl]-2-O-methyl-1-thio-α-D-galactopyranoside

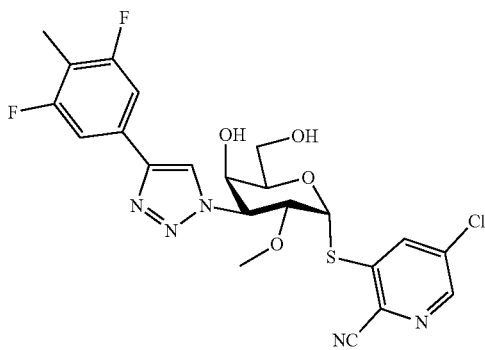

5-Chloro-2-cyanopyridin-3-yl 4,6-O-benzylidene-3-deoxy-3-[4-(3,5-difluoro-4-methylphenyl)-1H-1,2,3-triazol-1-yl]-2-O-methyl-1-thio-α-D-galactopyranoside (80.0 mg, 0.13 mmol) was dissolved in DCM/TFA (10 mL, 19:1) and stirred 1 h at rt. The mixture was neutralized with Et$_3$N and concentrated under reduced pressure. The residue was purified by preparative HPLC (Method A) to give the title compound (36.2 mg, 53%) as a white solid. ESI-MS m/z calcd for [C$_{22}$H$_{20}$ClF$_2$N$_5$O$_4$S] [M+H]$^+$: 524.1; found: 524.2. $^1$H NMR (400 MHz, CD$_3$OD) δ 8.60 (d, J=2.0 Hz, 1H), 8.57 (s, 1H), 8.47 (d, J=2.0 Hz, 1H), 7.44 (d, J=8.0 Hz, 2H), 6.51 (d, J=5.2 Hz, 1H), 5.07 (dd, J=11.6, 2.8 Hz, 1H), 4.72 (dd, J=11.6, 5.2 Hz, 1H), 4.39 (t, J=6.0 Hz, 1H), 4.18 (d, J=2.4 Hz, 1H), 3.67 (d, J=6.0 Hz, 2H), 3.46 (s, 3H), 2.21 (s, 3H).

Example 13

5-Chloro-2-cyanopyridin-3-yl 3-deoxy-3-[4-(3-fluoro-4-methylphenyl)-1H-1,2,3-triazol-1-yl]-2-O-methyl-1-thio-α-D-galactopyranoside

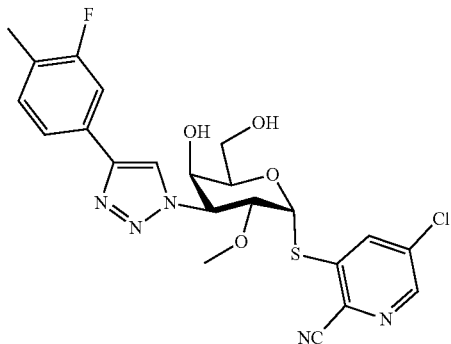

5-Chloro-2-cyanopyridin-3-yl 4,6-O-benzylidene-3-deoxy-3-[4-(3-fluoro-4-methylphenyl)-1H-1,2,3-triazol-1-yl]-2-O-methyl-1-thio-α-D-galactopyranoside (35.0 mg, 0.059 mmol) was dissolved in DCM/TFA (10 mL, 19:1). The mixture was stirred 1 h at rt and neutralized with Et$_3$N. Solvent was removed under reduced pressure and the residue was purified by preparative HPLC (Method A) to give the title compound (16.7 mg, 56%) as a white solid. ESI-MS m/z calcd for [C$_{22}$H$_{21}$ClFN$_5$O$_4$S] [M+H]$^+$: 506.1; found: 506.1. $^1$H NMR (400 MHz, CD$_3$OD) δ 8.50 (d, J=2.0 Hz, 1H), 8.41 (s, 1H), 8.38 (d, J=2.0 Hz, 1H), 7.52-7.38 (m, 2H), 7.21 (t, J=8.0 Hz, 1H), 6.42 (d, J=5.2 Hz, 1H), 4.97 (dd, J=11.6, 3.2 Hz, 1H), 4.63 (dd, J=11.6, 5.2 Hz, 1H), 4.30 (t, J=6.0 Hz, 1H), 4.10 (d, J=2.0 Hz, 1H), 3.59 (d, J=6.0 Hz, 2H), 3.37 (s, 3H), 2.20 (d, J=1.2 Hz, 3H).

Example 14

5-Chloro-2-cyanophenyl 3-deoxy-3-[4-(3,5-difluoro-4-methylphenyl)-1H-1,2,3-triazol-1-yl]-2-O-methyl-1-thio-α-D-galactopyranoside

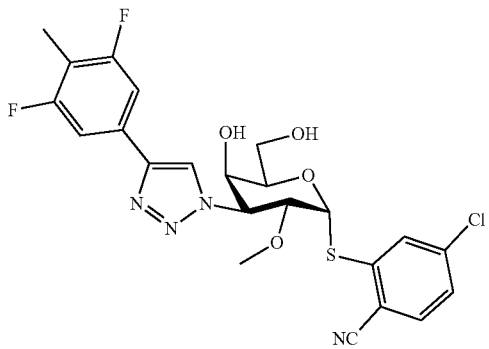

To a solution of 5-chloro-2-cyanophenyl 4,6-di-O-acetyl-3-deoxy-3-[4-(3,5-difluoro-4-methylphenyl)-1H-1,2,3-triazol-1-yl]-2-O-methyl-1-thio-α-D-galactopyranoside (56.0 mg, 0.092 mmol) in the MeOH (3 mL), Et$_3$N (2 mL) and water (1 mL) were added. The mixture was stirred 4 h at rt under nitrogen atmosphere. The solvent was removed under the reduced pressure the residue was purified by preparative HPLC (Method A) to give the title compound (31.0 mg, 64%) as a white solid. ESI-MS m/z calcd for [$C_{23}H_{21}ClF_2N_4O_4S$] [M+H]$^+$: 523.1; found: 523.0. $^1$H NMR (400 MHz, CD$_3$OD) δ 8.59 (s, 1H), 8.02 (d, J=2.0 Hz, 1H), 8.78 (d, J=8.4 Hz, 1H), 7.54 (dd, J=8.4, 2.0 Hz, 1H), 7.47 (d, J=7.6 Hz, 1H), 6.43 (d, J=5.2 Hz, 1H), 5.08 (dd, J=11.2, 2.8 Hz, 1H), 4.74-4.70 (m, 1H), 4.45 (t, J=6.4 Hz, 1H), 4.21 (d, J=2.4 Hz, 1H), 3.74-3.67 (m, 2H), 3.48 (s, 3H), 2.24 (s, 3H).

Example 15

5-Chloro-2-cyanopyridin-3-yl 3-deoxy-2-O-(2,2,2-trifluoroethyl)-3-[4-(3,4,5-trifluorophenyl)-1H-1,2,3-triazol-1-yl]-1-thio-α-D-galactopyranoside

Example 16

5-Chloro-2-cyanopyridin-3-yl 3-deoxy-2-O-ethyl-3-[4-(3,4,5-trifluorophenyl)-1H-1,2,3-triazol-1-yl]-1-thio-α-D-galactopyranoside

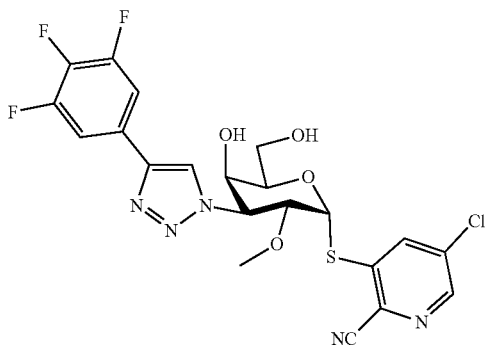

A nitrogen purged solution of 2-bromo-5-chloro-pyridin-3-yl 3-deoxy-2-O-ethyl-3-[4-(3,4,5-trifluorophenyl)-1H-1,2,3-triazol-1-yl]-1-thio-α-D-galactopyranoside (10 mg, 0.017 mmol) in N,N-dimethylacetamide (0.5 mL) was added to a nitrogen purged solution of Zn (0.5 mg, 0.0084 mmol), Zn(CN)$_2$ (2.0 mg, 0.017 mmol), Pd(dibenzylideneacetone)$_2$ (0.8 mg, 0.0013 mmol) and 1,1'-bis(diphenylphosphino)ferrocene (0.8 mg, 0.0013 mmol) in N,N-dimethylacetamide (0.5 mL) and the resulting mixture was stirred 23 h at 100° C. The mixture was purified by preparative HPLC (Method B) to afford the title compound (1.8 mg, 20%). ESI-MS m/z calcd for [$C_{22}H_{19}ClF_3N_5O_4S$] [M+H]$^+$: 542.1; found: 541.8. $^1$H NMR (400 MHz, Methanol-d$_4$) δ 8.60 (s, 2H), 8.47 (d, J=2.1 Hz, 1H), 7.67 (dd, J=8.6, 6.7 Hz, 2H), 6.48 (d, J=5.3 Hz, 1H), 5.08 (dd, J=11.3, 2.8 Hz, 1H), 4.80 (dd, J=11.3, 5.3 Hz, 1H), 4.39 (t, J=6.0 Hz, 1H), 4.20 (d, J=2.4 Hz, 1H), 3.92-3.83 (m, 1H), 3.68 (d, J=6.0 Hz, 2H), 3.53-3.44 (m, 1H), 1.05 (t, J=7.0 Hz, 3H).

Example 17

5-Bromopyridin-3-yl 3-deoxy-3-[4-(3,4,5-trifluorophenyl)-1H-1,2,3-triazol-1-yl]-2-O-ethyl-1-thio-α-D-galactopyranoside

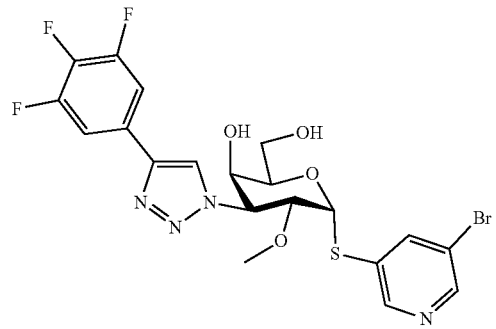

5-Bromopyridin-3-yl 4,6-O-benzylidene-3-deoxy-3-[4-(3,4,5-trifluorophenyl)-1H-1,2,3-triazol-1-yl]-1-thio-α-D-galactopyranoside (200 mg, 0.31 mmol) was stirred in DMF (3.0 mL) and NaH (60% in oil, 25 mg, 0.61 mmol) followed by ethyl iodide (52 µL, 0.61 mmol) were added. The mixture was stirred 2 h at rt, then partitioned between EtOAc and water and the organic phase was collected and evaporated. The residue was stirred 1 h in 80% aq TFA (3.0 mL). The mixture was concentrated to about 1 mL volume, then partitioned between water and EtOAc. NaOH (1 M) was added to pH approximately 10, the organic phase was collected and evaporated. The residue was purified by chromatography (SiO$_2$, PE/EtOAc) to afford the title compound (159 mg, 92%). ESI-MS m/z calcd for [$C_{21}H_{20}BrF_3N_4O_4S$] [M+H]$^+$: 561.0; found: 561.1. $^1$H NMR (400 MHz, Methanol-d$_4$) δ 8.67 (d, J=1.8 Hz, 1H), 8.59 (s, 1H), 8.56 (d, J=2.0 Hz, 1H), 8.33 (t, J=2.0 Hz, 1H), 7.71-7.61 (m, 2H), 6.24 (d, J=5.3 Hz, 1H), 5.05 (dd, J=11.3, 2.8 Hz, 1H), 4.74 (dd, J=11.3, 5.3 Hz, 1H), 4.45 (t, J=6.1 Hz, 1H), 4.20 (d, J=2.5 Hz, 1H), 3.85-3.76 (m, 1H), 3.75-3.64 (m, 2H), 3.49-3.40 (m, 1H), 1.03 (t, J=7.0 Hz, 3H).

Example 18

5-Bromopyridin-3-yl 3-deoxy-3-[4-(3,4,5-trifluorophenyl)-1H-1,2,3-triazol-1-yl]-2-O-isopropyl-1-thio-α-D-galactopyranoside

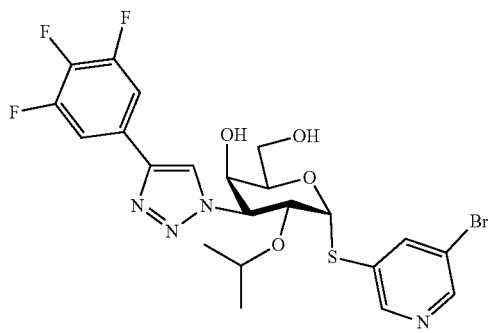

5-Bromopyridin-3-yl 4,6-O-benzylidene-3-deoxy-3-[4-(3,4,5-trifluorophenyl)-1H-1,2,3-triazol-1-yl]-1-thio-α-D-galactopyranoside (200 mg, 0.31 mmol), $Cs_2CO_3$ (200 mg, 0.6 mmol), and isopropyl iodide (91 μL, 0.9 mmol) were stirred in DMF (2.0 mL) 17 h at 90° C. The mixture was poured onto cold water and the precipitate was collected, then stirred 2 h at rt in 80% aq TFA (3.0 mL). The mixture was partitioned between EtOAc and NaOH (0.5 M), the organic phase was collected and evaporated. The residue was purified by preparative HPLC (Method B) to afford the title compound (15 mg, 8%). ESI-MS m/z calcd for $[C_{22}H_{22}BrF_3N_4O_4S]$ $[M+H]^+$: 575.1; found: 575.2. $^1H$ NMR (400 MHz, Methanol-$d_4$) δ 8.67 (d, J=1.7 Hz, 1H), 8.61 (s, 1H), 8.56 (d, J=2.0 Hz, 1H), 8.33 (t, J=1.9 Hz, 1H), 7.66 (dd, J=8.8, 6.7 Hz, 2H), 6.20 (d, J=5.3 Hz, 1H), 5.03 (dd, J=11.3, 2.8 Hz, 1H), 4.79 (dd, J=11.3, 5.3 Hz, 1H), 4.43 (t, J=6.0 Hz, 1H), 4.19 (d, J=2.1 Hz, 1H), 3.79 (p, J=6.1 Hz, 1H), 3.74-3.62 (m, 2H), 1.13 (d, J=6.1 Hz, 3H), 0.87 (d, J=6.0 Hz, 3H).

Example 19

5-Bromopyridin-3-yl 3-deoxy-3-[4-(3,4,5-trifluorophenyl)-1H-1,2,3-triazol-1-yl]-2-O-(2-fluoroethyl)-1-thio-α-D-galactopyranoside

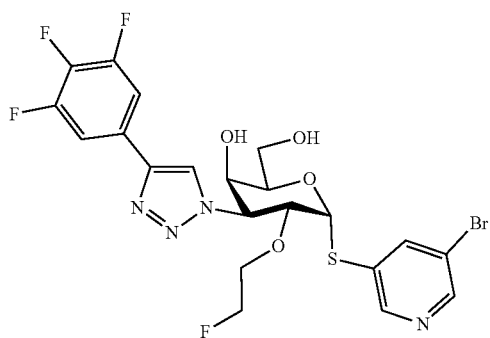

5-Bromopyridin-3-yl 4,6-O-benzylidene-3-deoxy-3-[4-(3,4,5-trifluorophenyl)-1H-1,2,3-triazol-1-yl]-1-thio-α-D-galactopyranoside (200 mg, 0.31 mmol) was stirred in DMF (3.0 mL) and 1-fluoro-2-iodo-ethane (82 μL, 0.92 mmol) followed by NaH (60% in oil, 50 mg, 1.23 mmol) were added. The mixture was stirred 3 h at rt, then poured onto ice cooled water (30 mL) and HCl (1 M, 5 mL). The solids were isolated by filtration and purified by chromatography ($SiO_2$, PE/EtOAc). The crude was stirred 1 h in 80% aq TFA (4.0 mL). The mixture was poured on ice and NaOH (1 M), the precipitate was collected by filtration and purified by preparative HPLC (Method B) to afford the title product (63 mg, 35%). ESI-MS m/z calcd for $[C_{21}H_{19}BrF_4N_4O_4S][M+H]^+$: 579.0; found: 579.1. $^1H$ NMR (400 MHz, Methanol-$d_4$) δ 8.69 (d, J=1.4 Hz, 1H), 8.58 (d, J=1.8 Hz, 1H), 8.57 (s, 1H), 8.35 (t, J=1.6 Hz, 1H), 7.68-7.58 (m, 2H), 6.24 (d, J=5.3 Hz, 1H), 5.08 (dd, J=11.3, 2.8 Hz, 1H), 4.81 (dd, J=11.4, 5.4 Hz, 1H), 4.48 (t, 1H), 4.45 (m, 1H), 4.33 (m, 1H), 4.24 (d, J=2.6 Hz, 1H), 3.96 (m, 1H), 3.73 (m, 1H), 3.73-3.67 (m, 2H).

Example 20

5-Bromopyridin-3-yl 3-deoxy-3-[4-(3,4,5-trifluorophenyl)-1H-1,2,3-triazol-1-yl]-2-O-[2-(methylamino)ethyl]-1-thio-α-D-galactopyranoside

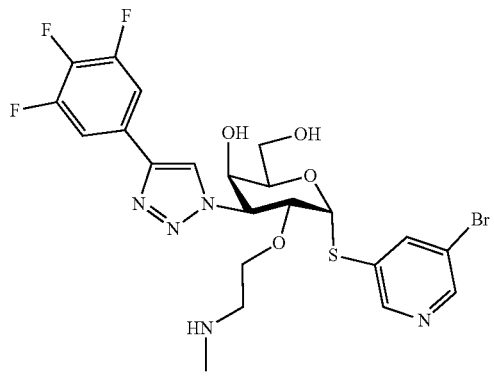

2-[(tert-Butoxycarbonyl)(methyl)amino]ethyl 4-methylbenzenesulfonate (238 mg, 0.72 mmol) and 5-bromopyridin-3-yl 4,6-O-benzylidene-3-deoxy-3-[4-(3,4,5-trifluorophenyl)-1H-1,2,3-triazol-1-yl]-1-thio-α-D-galactopyranoside (155 mg, 0.25 mmol) were stirred in DMF (3.0 mL) and NaH (60% in oil, 40 mg, 1.0 mmol) was added. The mixture was stirred 5 h at rt, then poured onto ice. The solids were isolated by filtration and purified by chromatography ($SiO_2$, PE/EtOAc). The crude was stirred 1 h in 80% aq TFA (3.0 mL). The mixture was concentrated, poured on ice and NaOH (1 M, pH>10). The precipitate was collected by filtration and purified by preparative HPLC (Method B) to afford the title product as the TFA salt (57 mg, 32%). ESI-MS m/z calcd for $[C_{22}H_{23}BrF_3N_5O_4S]$ $[M+H]^+$: 590.1; found: 589.8. $^1H$ NMR (400 MHz, Methanol-$d_4$) δ 8.71 (s, 1H), 8.63 (s, 1H), 8.61 (s, 1H), 8.39 (d, J=1.0 Hz, 1H), 7.72-7.60 (m, 2H), 6.30 (d, J=5.3 Hz, 1H), 5.14 (dd, J=11.3, 2.4 Hz, 1H), 4.90 (dd, J=11.2, 5.3 Hz, 1H), 4.50 (t, J=6.0 Hz, 1H), 4.23 (d, J=2.5 Hz, 1H), 4.10 (ddd, J=10.6, 7.5, 2.9 Hz, 1H), 3.79-3.65 (m, 3H), 3.22-3.13 (m, 1H), 3.13-3.04 (m, 1H), 2.61 (s, 3H).

Example 21

3,4-Dichlorophenyl 3-[4-(4-chloro-3,5-difluorophenyl)-1H-1,2,3-triazol-1-yl]-3-deoxy-2-O-(2-hydroxyethyl)-1-thio-α-D-galactopyranoside

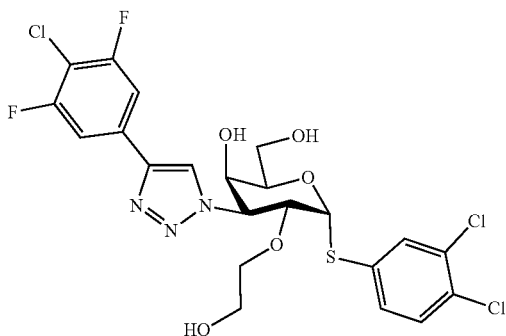

To a solution of 3,4-dichlorophenyl 4,6-O-benzylidene-3-[4-(4-chloro-3,5-difluorophenyl)-1H-1,2,3-triazol-1-yl]-3-deoxy-2-O-carboxymethyl-1-thio-α-D-galactopyranoside (50 mg, 0.081 mmol) in THF (0.5 mL) borane THF complex solution (0.5 mL, 1 M in THF, 0.5 mmol) was added. The mixture was stirred 40 min at rt and then quenched with cold HCl (1 M). The mixture was extracted with EtOAc, the solvents were removed, and the residue was purified preparative HPLC (Method B) to afford the title compound (33 mg, 67%). ESI-MS m/z calcd for $[C_{22}H_{20}Cl_3F_2N_3O_5S][M+H]^+$: 582.0; found: 582.1. $^1$H NMR (400 MHz, Methanol-$d_4$) δ 8.68 (s, 1H), 7.82 (d, J=1.4 Hz, 1H), 7.65 (m, 2H), 7.55 (dd, J=8.4, 1.3 Hz, 1H), 7.49 (d, J=8.4 Hz, 1H), 6.18 (d, J=5.3 Hz, 1H), 5.04 (dd, J=11.3, 2.8 Hz, 1H), 4.80 (dd, J=11.3, 5.3 Hz, 1H), 4.48 (t, J=6.1 Hz, 1H), 4.26 (d, J=2.5 Hz, 1H), 3.81 (m, 1H), 3.76-3.67 (m, 2H), 3.60-3.50 (m, 3H).

Example 22

5-Chloro-6-cyano-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside

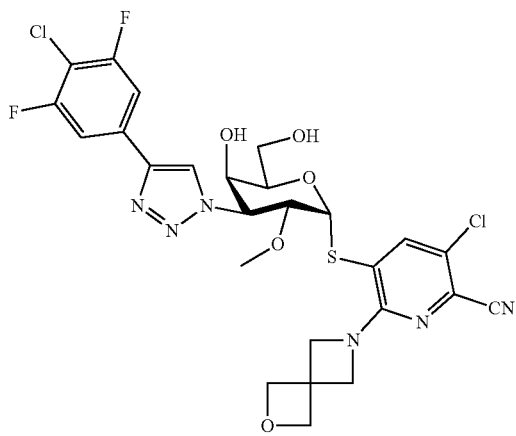

A solution of 5-chloro-6-cyano-2-{N-(2-oxa)-6-azaspiro[3.3]heptanyl}-pyridin-3-yl 4,6-di-O-acetyl-3-[4-(4-chloro-3,5-difluorophenyl)-1H-1,2,3-triazol-1-yl]-3-deoxy-2-O-methyl-1-thio-α-D-galactopyranoside (58.0 mg, 0.080 mmol) in MeOH (3 mL), Et$_3$N (2 mL) and water (1 mL) was stirred 4 h at rt under a nitrogen atmosphere. The solvent was removed under reduced preesure and the residue was purified by preparative HPLC (Method A) to give the title compound (17.6 mg, 34%). ESI-MS m/z calcd for $[C_{26}H_{24}Cl_2F_2N_6O_5S]$ $[M+H]^+$: 641.1; found: 641.0. $^1$H NMR (400 MHz, CD$_3$OD) δ 8.57 (s, 1H), 7.96 (s, 1H), 7.57 (d, J=7.6 Hz, 2H), 6.14 (d, J=5.2 Hz, 1H), 4.96 (dd, J=11.6, 2.8 Hz, 1H), 4.74 (s, 4H), 4.58-4.54 (m, 1H), 4.40-4.29 (m, 4H), 4.26-4.22 (m, 1H), 4.08 (d, J=2.4 Hz, 1H), 3.59-3.58 (m, 2H), 3.30 (s, 3H).

Example 23

5-Chloro-6-cyano-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside

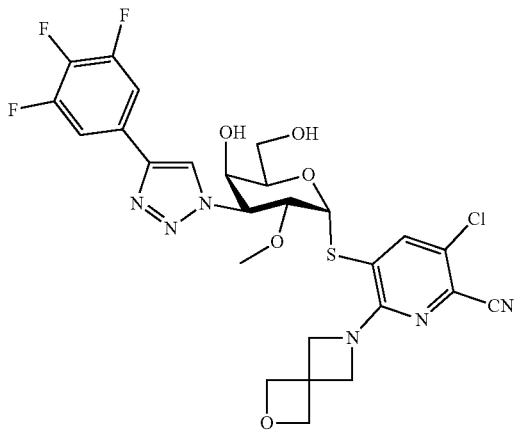

To a solution of 5-chloro-6-cyano-2-{N-(2-oxa)-6-azaspiro[3.3]heptanyl}-pyridin-3-yl 4,6-di-O-acetyl-3-[4-(3,4,5-trifluorophenyl)-1H-1,2,3-triazol-1-yl]-3-deoxy-2-O-methyl-1-thio-α-D-galactopyranoside (54.0 mg, 0.076 mmol) in MeOH (3 mL) Et$_3$N (2 mL) and water (1 mL) were added. The mixture was stirred 4 h at rt under a nitrogen atmosphere. The solvent was removed under reduced preesure and the residue was purified by preparative HPLC (Method A) to give the title compound (26.5 mg, 56%). ESI-MS m/z calcd for $[C_{26}H_{24}ClF_3N_6O_5S]$ $[M+H]^+$: 625.1; found: 625.1. $^1$H NMR (400 MHz, CD$_3$OD) δ 8.64 (s, 1H), 8.09 (s, 1H), 7.71-7.67 (m, 2H), 6.26 (d, J=5.2 Hz, 1H), 5.07 (dd, J=11.6, 2.8 Hz, 1H), 4.86 (s, 4H), 4.69-4.65 (m, 1H), 4.52-4.41 (m, 4H), 4.36-4.33 (m, 1H), 4.18 (d, J=2.4 Hz, 1H), 3.71-3.68 (m, 2H), 3.41 (s, 3H).

Example 24

5-Chloro-2-(pyrimidin-5-yl)pyridin-3-yl 3-deoxy-3-[4-(3,4,5-trifluorophenyl)-1H-1,2,3-triazol-1-yl]-2-O-methyl-1-thio-α-D-galactopyranoside

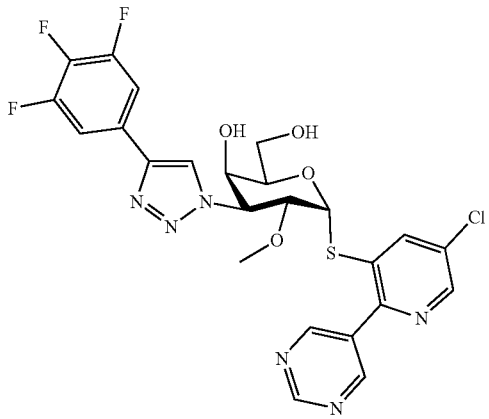

5-Chloro-2-(pyrimidin-5-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (90.0 mg, 0.14 mmol) was dissolved in DCM/TFA (10 mL, 19:1) and stirred 1 h at rt. The mixture was neutralized with Et₃N and then concentrated. The residue was purified by preparative HPLC (Method A) to give the title compound (52.5 mg, 67%) as a white solid. ESI-MS n/z calcd for $[C_{24}H_{20}ClF_3N_6O_4S]$ $[M+H]^+$: 581.1; found: 581.1. $^1$H NMR (400 MHz, CD₃OD) δ 9.13 (s, 1H), 9.06 (s, 2H), 8.54 (d, J=2.0 Hz, 1H), 8.44 (s, 1H), 8.36 (d, J=2.0 Hz, 1H), 7.53 (m, 2H), 6.00 (d, J=5.2 Hz, 1H), 4.79 (m, 1H), 4.46 (dd, J=11.2, 5.2 Hz, 1H), 4.13 (t, J=6.0 Hz, 1H), 4.01 (d, J=2.4 Hz, 1H), 3.56 (d, J=6.0 Hz, 2H), 3.07 (s, 3H).

Example 25

5-Chloro-2-(pyridin-2-yl)pyridin-3-yl 3-deoxy-3-[4-(3,4,5-trifluorophenyl)-1H-1,2,3-triazol-1-yl]-2-O-methyl-1-thio-α-D-galactopyranoside

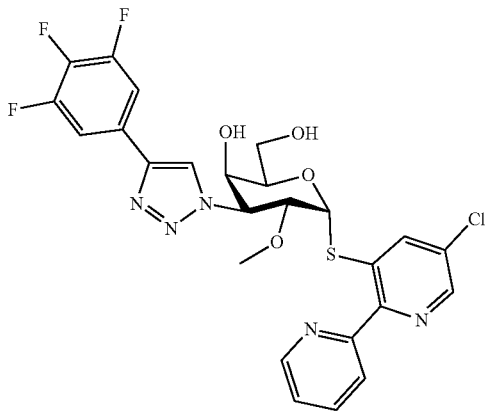

5-Chloro-2-(pyridin-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (30.0 mg, 0.045 mmol) was dissolved in DCM/TFA (10 mL, 19:1) and stirred 1 h at rt. The mixture was neutralized with Et₃N and then concentrated. The residue was purified by preparative HPLC (Method A) to give the title compound (16.3 mg, 63%) as a white solid. ESI-MS m/z calcd for $[C_{25}H_{21}ClF_3N_5O_4S]$ $[M+H]^+$: 580.1; found: 580.1. $^1$H NMR (400 MHz, CD₃OD) δ 8.59 (s, 1H), 8.44 (s, 1H), 8.42 (s, 1H), 8.36 (d, J=2.0 Hz, 1H), 7.89 (m, 1H), 7.75 (d, J=7.6 Hz, 1H), 7.60-7.50 (m, 2H), 7.46-7.37 (m, 1H), 6.10 (d, J=5.2 Hz, 1H), 4.83 (m, 1H), 4.47 (dd, J=11.2, 5.2 Hz, 1H), 4.19 (t, J=6.0 Hz, 1H), 4.01 (d, J=2.4 Hz, 1H), 3.64-3.52 (m, 2H), 3.09 (s, 3H).

Example 26

5-Chloro-2-(pyridin-3-yl)pyridin-3-yl 3-deoxy-3-[4-(3,4,5-trifluorophenyl)-1H-1,2,3-triazol-1-yl]-2-O-methyl-1-thio-α-D-galactopyranoside

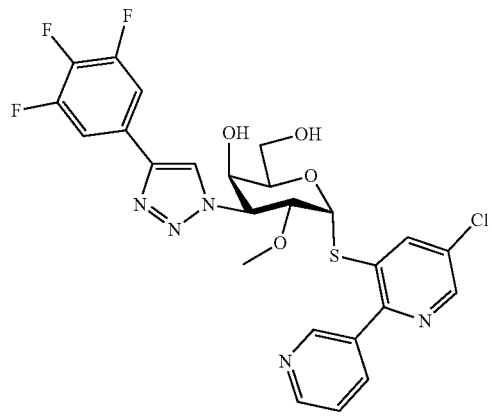

To a solution of 5-chloro-2-(pyridin-3-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (50 mg, 0.075 mmol) in DCM (3 mL) TFA (0.29 mL) and water (0.5 mL) were added and the mixture was stirred 12 h at rt. The mixture was neutralized with Et₃N and then concentrated. The residue was purified by preparative HPLC (Method A) to give the title compound (31 mg, 70%) as a white solid. ESI-MS m/z calcd for $[C_{25}H_{21}ClF_3N_5O_4S]$ $[M+H]^+$: 580.1, found: 580.2. $^1$H NMR (400 MHz, DMSO-d₆) δ 8.84 (s, 2H), 8.66 (d, J=2.0 Hz, 2H), 8.42 (d, J=2.0 Hz, 1H), 8.07 (d, J=8.0 Hz, 1H), 7.83 (dd, J=8.8, 7.2 Hz, 2H), 7.56 (dd, J=7.6, 4.8 Hz, 1H), 6.38 (d, J=5.2 Hz, 1H), 5.59 (s, 1H), 4.77 (dd, J=11.2, 2.4 Hz, 2H), 4.46 (dd, J=11.6, 5.2 Hz, 1H), 4.09 (t, J=6.0 Hz, 1H), 3.97 (s, 1H), 3.49-3.41 (m, 2H), 3.14 (s, 3H).

Example 27

5-Chloro-2-(pyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside

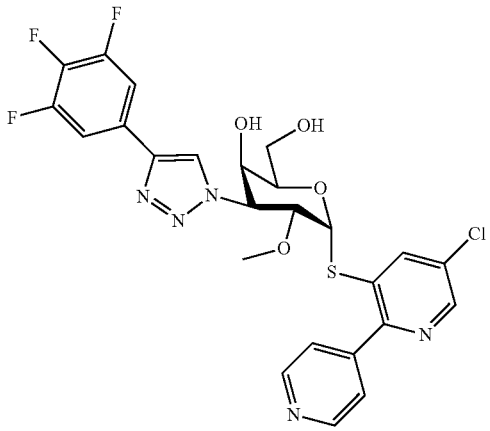

To a solution of 5-chloro-2-(pyridin-4-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (50 mg, 0.075 mmol) in DCM (5.0 mL) TFA (0.5 mL) was added and the mixture was stirred 2 h at rt. The mixture was neutralized with Et$_3$N (1 mL) and then concentrated. The residue was purified by preparative HPLC (Method A) to give the title compound (17 mg, 39%). ESI-MS m/z calcd for [C$_{25}$H$_{21}$ClF$_3$N$_5$O$_4$S] [M+H]$^+$: 580.1; found: 579.8. $^1$H NMR (400 MHz, CD$_3$OD) δ 8.70 (dd, J=4.8, 1.6 Hz, 2H), 8.60 (d, J=2.4 Hz, 1H), 8.55 (s, 1H), 8.45 (d, J=2.4 Hz, 1H), 7.76 (dd, J=4.8, 1.6 Hz, 2H), 7.65 (dd, J=8.8, 6.8 Hz, 2H), 6.11 (d, J=5.2 Hz, 1H), 4.89-4.83 (m, 1H), 4.57 (dd, J=11.2, 5.2 Hz, 1H), 4.26 (t, J=6.4 Hz, 1H), 4.16-4.09 (m, 1H), 3.73-3.61 (m, 2H), 3.17 (s, 3H).

Example 28

5-Chloro-2-(1,2,3,6-tetrahydropyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside

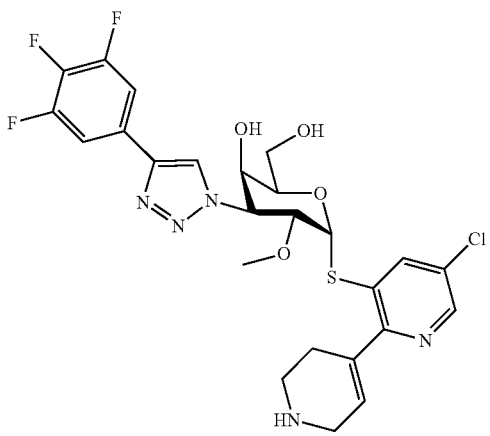

To a solution of 5-chloro-2-(1,2,3,6-tetrahydropyridin-4-yl)pyridin-3-yl 3-azido-3-deoxy-2-O-methyl-1-thio-α-D-galactopyranoside (60.0 mg, 0.12 mmol) in DMF (2 mL), trimethyl-[2-(3,4,5-trifluorophenyl)ethynyl]silane (23.5 mg, 0.10 mmol), (+)-sodium L-ascorbate (18.5 mg, 0.094 mmol), copper(II) sulfate pentahydrate (23.3 mg, 0.094 mmol) and CsF (21.3 mg, 0.14 mmol) were added. The mixture was stirred under a nitrogen atmosphere at rt overnight. The mixture was filtered, and the filtrate was purified by preparative HPLC (Method A) to give the product (7.8 mg, 14%). ESI-MS m/z calcd for [C$_{25}$H$_{25}$ClF$_3$N$_5$O$_4$S] [M+H]$^+$: 584.1; found: 583.9. $^1$H NMR (400 MHz, CD$_3$OD) δ 8.62 (s, 1H), 8.39 (d, J=2.0 Hz, 1H), 8.31 (d, J=2.0 Hz, 1H), 7.72-7.65 (m, 2H), 6.31 (d, J=5.2 Hz, 1H), 6.08-5.99 (m, 1H), 5.06 (dd, J=11.2, 2.8 Hz, 1H), 4.66 (dd, J=11.2, 5.2 Hz, 1H), 4.38-4.29 (m, 1H), 4.21-4.14 (m, 1H), 3.75-3.56 (m, 4H), 3.39 (s, 3H), 3.18-3.13 (m, 2H), 2.64-2.50 (m, 2H).

Example 29

5-Chloro-2-(3-pyrrolin-3-yl)pyridin-3-yl 3-deoxy-3-[4-(3,4,5-trifluorophenyl)-1H-1,2,3-triazol-1-yl]-2-O-methyl-1-thio-α-D-galactopyranoside

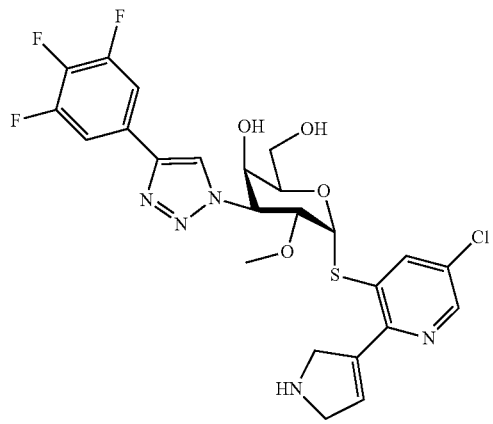

To a solution of 5-chloro-2-[1-(N-tert-butoxycarbonyl)-3-pyrrolin-3-yl]pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (50 mg, 0.066 mmol) in DCM (6 mL), TFA (0.49 mL, 6.59 mmol) was added. The mixture was stirred 2 h at rt and TEA (1 mL) was added. The mixture was concentrated, and the residue was purified by preparative HPLC (Method A) to give the product (13 mg, 37%). ESI-MS m/z calcd for [C$_{24}$H$_{23}$ClF$_3$N$_5$O$_4$S] [M+H]$^+$: 570.1; found: 569.8. $^1$H NMR (400 MHz, CD$_3$OD) δ 8.63 (s, 1H), 8.42 (d, J=2.4 Hz, 1H), 8.31 (d, J=2.4 Hz, 1H), 7.69 (dd, J=8.8, 6.4 Hz, 2H), 6.95-6.85 (m, 1H), 6.33 (d, J=5.2 Hz, 1H), 5.08 (dd, J=11.6, 2.8 Hz, 1H), 4.67 (dd, J=11.2, 5.2 Hz, 1H), 4.38-4.31 (m, 1H), 4.30-4.25 (m, 2H), 4.22-4.17 (m, 1H), 4.12-4.04 (m, 2H), 3.76-3.61 (m, 2H), 3.39 (s, 3H).

Example 30

5-Chloro-2-(oxazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside

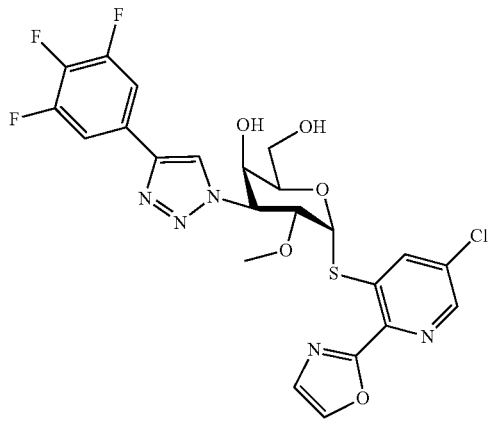

To a solution of 5-chloro-2-(oxazol-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (80 mg, 0.11 mmol) in DCM (5 mL) TFA (618 mg, 5.42 mmol) and H$_2$O (0.5 mL) were added. The mixture was stirred 12 h at rt before Et$_3$N (1.5 mL) was added dropwise at 0° C. The solvent was removed by evaporation and the residue was purified by preparative HPLC (Method A) to give the title compound (31 mg, 50%) as a white solid. ESI-MS m/z calcd for [C$_{23}$H$_{19}$ClF$_3$N$_5$O$_5$S] [M+H]$^+$:570.1; found: 570.1. $^1$H NMR (400 MHz, DMSO-d$_6$): δ 8.91 (s, 1H), 8.60 (d, J=2.4 Hz, 1H), 8.43 (d, J=2.0 Hz, 1H), 8.36 (d, J=0.8 Hz, 1H), 7.86-7.82 (m, 2H), 7.58 (d, J=0.8 Hz, 1H), 6.70 (d, J=5.2 Hz, 1H), 5.63 (d, J=6.0 Hz, 1H), 4.94 (dd, J=11.6, 2.8 Hz, 1H), 4.66 (d, J=11.2 Hz, 1H), 4.56 (dd, J=11.2, 5.2 Hz, 1H), 4.14-4.11 (m, 1H), 4.03-4.01 (m, 1H), 3.54-3.49 (m, 1H), 3.43-3.38 (m, 1H), 3.29 (s, 3H).

Example 31

5-Chloro-2-(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside

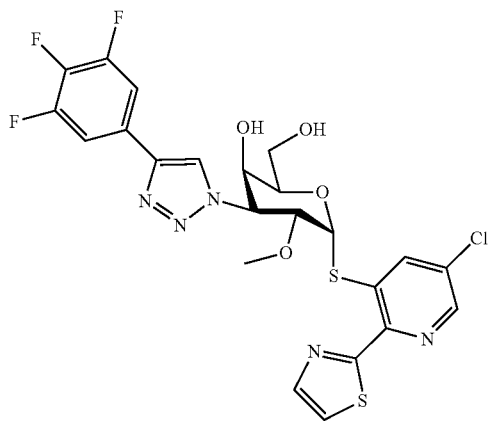

To a solution of 5-chloro-2-(thiazol-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (85 mg, 0.12 mmol) in DCM (6 mL) TFA (0.43 mL) and H$_2$O (0.5 mL) were added. The mixture was stirred 12 h at rt, Et$_3$N (1.5 mL) was added dropwise at 0° C. The solvent was removed by evaporation and the residue was purified by preparative HPLC (Method A) to give the title compound (11 mg, 16%). ESI-MS m/z calcd for [C$_{23}$H$_{19}$ClF$_3$N$_5$O$_4$S$_2$]$^+$ [M+H]$^+$: 586.0; found: 586.0. $^1$H NMR (400 MHz, CD$_3$OD) δ 8.60 (s, 1H), 8.43-8.40 (m, 2H), 8.00 (d, J=3.2 Hz, 1H), 7.70-7.65 (m, 3H), 6.51 (d, J=5.6 Hz, 1H), 5.14 (dd, J=11.2, 2.8 Hz, 1H), 4.70 (dd, J=11.2, 5.2 Hz, 1H), 4.36-4.33 (m, 1H), 4.16 (d, J=2.0 Hz, 1H), 3.72-3.62 (m, 2H), 3.38 (s, 3H).

Example 32

2,5-Bis(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside

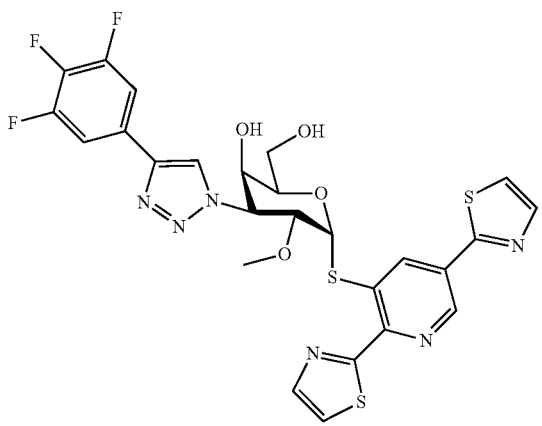

To a solution of 2,5-bis(thiazol-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (125 mg, 53%, 0.091 mmol) in DCM (5 mL) TFA (0.34 mL) and H$_2$O (0.5 mL) were added. The mixture was stirred 12 h at rt, Et$_3$N (1.5 mL) was added dropwise at 0° C. The solvent was removed by evaporation and the residue was purified by preparative HPLC (Method A) to give the title compound (23 mg, 40%) as a white solid. ESI-MS m/z calcd for [C$_{26}$H$_{21}$F$_3$N$_6$O$_4$S$_3$] [M+H]$^+$: 635.1; found: 635.0. $^1$H NMR (400 MHz, CD$_3$OD): δ 8.80 (d, J=2.0 Hz, 1H), 8.52 (s, 1H), 8.23 (d, J=2.0 Hz, 1H), 7.79 (d, J=3.2 Hz, 1H), 7.66 (d, J=3.2 Hz, 1H), 7.61-7.55 (m, 4H), 6.32 (d, J=5.6 Hz, 1H), 4.98 (dd, J=11.2, 2.8 Hz, 1H), 4.57 (dd, J=11.2, 5.2 Hz, 1H), 4.40-4.37 (m, 1H), 4.10 (d, J=2.8 Hz, 1H), 3.61-3.59 (m, 2H), 3.33 (s, 3H).

Examples 33 and 34

5-Chloropyridin-3-yl 3-[4-(4-chloro-3,5-difluoro-phenyl)-1H-1,2,3-triazol-1-yl]-3-deoxy-2-O-methyl-1-thio-α-D-galactopyranoside

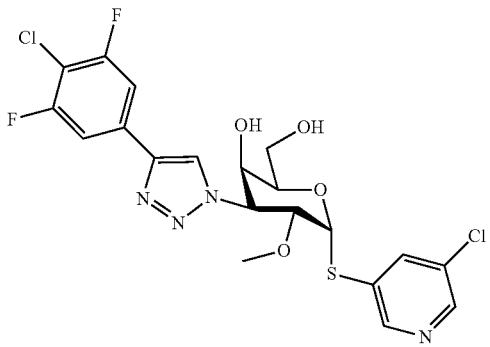

5-Bromopyridin-3-yl 3-[4-(4-chloro-3,5-difluoro-phenyl)-1H-1,2,3-triazol-1-yl]-3-deoxy-2-O-methyl-1-thio-α-D-galactopyranoside

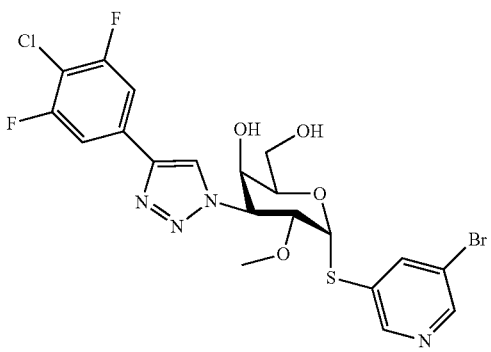

A mixture of 5-chloropyridin-3-yl 3-azido-3-deoxy-2-O-methyl-1-thio-α-D-galactopyranoside and 5-bromopyridin-3-yl 3-azido-3-deoxy-2-O-methyl-1-thio-α-D-galactopyranoside (115 mg), trimethyl-[2-(4-chloro-3,5-difluorophenyl)ethynyl]silane (101 mg, 0.42 mmol) and CuI (6.3 mg, 0.033 mmol) were dissolved in MeCN (3 mL). DIEA (0.11 mL, 0.66 mmol) was added and the mixture was stirred 16 h at 50° C. The mixture was diluted with EtOAc and washed with water. The organic phase was dried, evaporated and purified by preparative HPLC (Method B) to afford the two title compounds (65 mg of the chloro analog and 31 mg of the bromo analog).

5-Chloropyridin-3-yl 3-[4-(4-chloro-3,5-difluoro-phenyl)-1H-1,2,3-triazol-1-yl]-3-deoxy-2-O-methyl-1-thio-α-D-galactopyranoside ESI-MS m/z calcd for [$C_{20}H_{18}ClF_2N_4O_4S$] [M+H]$^+$: 519.1; found: 519.1. $^1$H NMR (400 MHz, Methanol-$d_4$) δ 8.67 (d, J=1.8 Hz, 1H), 8.64 (s, 1H), 8.49 (d, J=2.2 Hz, 1H), 8.24 (t, J=2.0 Hz, 1H), 7.67 (d, J=8.0 Hz, 2H), 6.29 (d, J=5.3 Hz, 1H), 5.05 (dd, J=11.4, 2.9 Hz, 1H), 4.65 (dd, J=11.3, 5.3 Hz, 1H), 4.46 (t, J=6.1 Hz, 1H), 4.19 (d, J=2.4 Hz, 1H), 3.75-3.65 (m, 2H), 3.41 (s, 3H).

5-Bromopyridin-3-yl 3-[4-(4-chloro-3,5-difluoro-phenyl)-1H-1,2,3-triazol-1-yl]-3-deoxy-2-O-methyl-1-thio-α-D-galactopyranoside ESI-MS m/z calcd for [$C_{20}H_{18}BrF_2N_4O_4S$] [M+H]$^+$: 563.0; found: 563.0. $^1$H NMR (400 MHz, Methanol-$d_4$) δ 8.71 (d, J=1.8 Hz, 1H), 8.64 (s, 1H), 8.59 (d, J=2.1 Hz, 1H), 8.39 (t, J=2.0 Hz, 1H), 7.67 (d, J=8.0 Hz, 2H), 6.29 (d, J=5.3 Hz, 1H), 5.05 (dd, J=11.4, 2.9 Hz, 1H), 4.65 (dd, J=11.3, 5.3 Hz, 1H), 4.46 (t, J=6.1 Hz, 1H), 4.19 (d, J=2.4 Hz, 1H), 3.76-3.66 (m, 2H), 3.41 (s, 3H).

Examples 35 and 36

5-Chloropyridin-3-yl 3-deoxy-3-[4-(3-fluoro-4-methylphenyl)-1H-1,2,3-triazol-1-yl]-2-O-methyl-1-thio-α-D-galactopyranoside

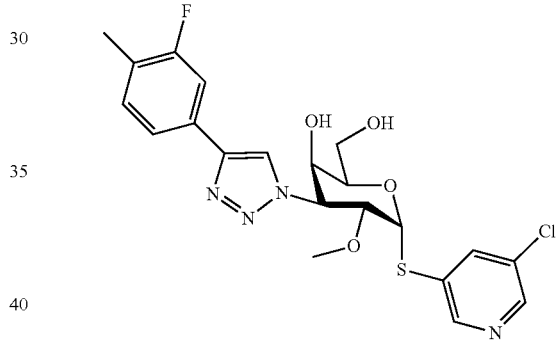

5-Bromopyridin-3-yl 3-deoxy-3-[4-(3-fluoro-4-methylphenyl)-1H-1,2,3-triazol-1-yl]-2-O-methyl-1-thio-α-D-galactopyranoside

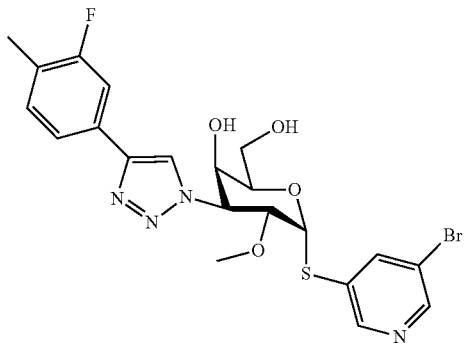

A mixture of 5-chloropyridin-3-yl 3-azido-3-deoxy-2-O-methyl-1-thio-α-D-galactopyranoside and 5-bromopyridin-3-yl 3-azido-3-deoxy-2-O-methyl-1-thio-α-D-galactopyranoside (115 mg), trimethyl-[2-(3-fluoro-4-methylphenyl)ethynyl]silane (86 mg, 0.42 mmol) and CuI (6.3 mg, 0.033 mmol) were dissolved in MeCN (3 mL). DIEA (0.11 mL, 0.66 mmol) was added and the mixture was stirred 26 h at 50° C. The mixture was diluted with EtOAc and washed with water. The organic phase was dried, evaporated and purified by chromatography (SiO$_2$, PE/EtOAc). Further purification by preparative HPLC (Method B) to afford the two title compounds (25 mg of the chloro analog and 12 mg of the bromo analog).

5-Chloropyridin-3-yl 3-deoxy-3-[4-(3-fluoro-4-methylphenyl)-1H-1,2,3-triazol-1-yl]-2-O-methyl-1-thio-α-D-galactopyranoside ESI-MS m/z calcd for [C$_{21}$H$_{22}$ClFN$_4$O$_4$S] [M+H]$^+$: 481.1; found: 481.1. $^1$H NMR (400 MHz, Methanol-d$_4$) δ 8.67 (d, J=1.6 Hz, 1H), 8.49 (s, 2H), 8.25 (t, J=2.0 Hz, 1H), 7.58-7.51 (m, 2H), 7.31 (t, J=8.0 Hz, 1H), 6.29 (d, J=5.3 Hz, 1H), 5.03 (dd, J=11.3, 2.8 Hz, 1H), 4.66 (dd, J=11.3, 5.3 Hz, 1H), 4.46 (t, J=6.0 Hz, 1H), 4.19 (d, J=2.5 Hz, 1H), 3.74-3.65 (m, 2H), 3.41 (s, 3H), 2.30 (s, 3H).

5-Bromopyridin-3-yl 3-deoxy-3-[4-(3-fluoro-4-methylphenyl)-1H-1,2,3-triazol-1-yl]-2-O-methyl-1-thio-α-D-galactopyranoside ESI-MS m/z calcd for [C$_{21}$H$_{22}$BrFN$_4$O$_4$S] [M+H]$^+$: 525.1; found: 525.1. $^1$H NMR (400 MHz, Methanol-d$_4$) δ 8.71 (d, J=1.8 Hz, 1H), 8.59 (d, J=2.1 Hz, 1H), 8.49 (s, 1H), 8.38 (t, J=2.0 Hz, 1H), 7.58-7.51 (m, 2H), 7.31 (t, J=8.0 Hz, 1H), 6.28 (d, J=5.3 Hz, 1H), 5.03 (dd, J=11.4, 2.8 Hz, 1H), 4.66 (dd, J=11.3, 5.3 Hz, 1H), 4.46 (t, J=6.1 Hz, 1H), 4.19 (d, J=2.4 Hz, 1H), 3.75-3.65 (m, 2H), 3.41 (s, 3H), 2.30 (s, 3H).

Examples 37 and 38

5-Chloropyridin-3-yl 3-[4-(4-chloro-3-fluorophenyl)-1H-1,2,3-triazol-1-yl]-3-deoxy-2-O-methyl-1-thio-α-D-galactopyranoside

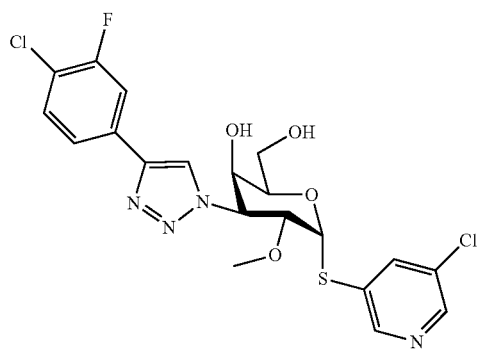

5-Bromopyridin-3-yl 3-[4-(4-chloro-3-fluorophenyl)-1H-1,2,3-triazol-1-yl]-3-deoxy-2-O-methyl-1-thio-α-D-galactopyranoside

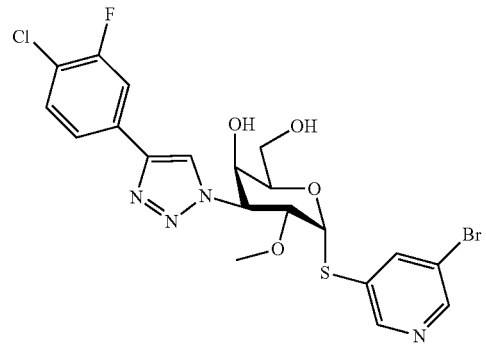

A mixture of 5-chloropyridin-3-yl 3-azido-3-deoxy-2-O-methyl-1-thio-α-D-galactopyranoside and 5-bromopyridin-3-yl 3-azido-3-deoxy-2-O-methyl-1-thio-α-D-galactopyranoside (115 mg), trimethyl-[2-(4-chloro-3-fluorophenyl)ethynyl]silane (94 mg, 0.42 mmol) and CuI (6.3 mg, 0.033 mmol) were dissolved in MeCN (3 mL). DIEA (0.11 mL, 0.66 mmol) was added and the mixture was stirred 26 h at 50° C. The mixture was diluted with EtOAc and washed with water. The organic phase was dried, evaporated and purified by chromatography (SiO$_2$, PE/EtOAc). Further purification by preparative HPLC (Method B) to afford the two title compounds (36 mg of the chloro analog and 14 mg of the bromo analog).

5-Chloropyridin-3-yl 3-[4-(4-chloro-3-fluorophenyl)-1H-1,2,3-triazol-1-yl]-3-deoxy-2-O-methyl-1-thio-α-D-galactopyranoside ESI-MS m/z calcd for [C$_{20}$H$_{19}$Cl$_2$FN$_4$O$_4$S] [M+H]$^+$: 501.1; found: 501.1. $^1$H NMR (400 MHz, Methanol-d$_4$) δ 8.67 (d, J=1.8 Hz, 1H), 8.58 (s, 1H), 8.50 (d, J=2.2 Hz, 1H), 8.25 (t, J=2.1 Hz, 1H), 7.77 (dd, J=10.4, 1.9 Hz, 1H), 7.69 (dd, J=8.4, 1.8 Hz, 1H), 7.55 (t, J=8.0 Hz, 1H), 6.29 (d, J=5.3 Hz, 1H), 5.05 (dd, J=11.3, 2.9 Hz, 1H), 4.66 (dd, J=11.4, 5.3 Hz, 1H), 4.46 (t, J=6.1 Hz, 1H), 4.19 (d, J=2.5 Hz, 1H), 3.74-3.65 (m, 2H), 3.41 (s, 3H).

5-Bromopyridin-3-yl 3-[4-(4-chloro-3-fluorophenyl)-1H-1,2,3-triazol-1-yl]-3-deoxy-2-O-methyl-1-thio-α-D-galactopyranoside ESI-MS m/z calcd for [C$_{20}$H$_{19}$BrClFN$_4$O$_4$S] [M+H]$^+$: 545.0; found: 545.0. $^1$H NMR (400 MHz, Methanol-d$_4$) δ 8.71 (d, J=1.8 Hz, 1H), 8.60-8.57 (m, 2H), 8.38 (t, J=2.0 Hz, 1H), 7.77 (dd, J=10.4, 1.9 Hz, 1H), 7.69 (dd, J=8.4, 1.3 Hz, 1H), 7.55 (t, J=8.0 Hz, 1H), 6.28 (d, J=5.3 Hz, 1H), 5.04 (dd, J=11.4, 2.9 Hz, 1H), 4.66 (dd, J=11.3, 5.3 Hz, 1H), 4.46 (t, J=6.0 Hz, 1H), 4.19 (d, J=2.2 Hz, 1H), 3.75-3.66 (m, 2H), 3.41 (s, 3H).

Example 39

6-Trifluoromethyl-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside

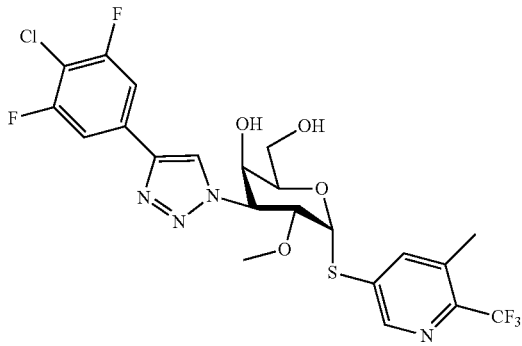

6-Trifluoromethyl-5-methylpyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside (190 mg, 0.27 mmol was dissolved in solution of DCM/TFA (20 mL, 19:1) and the mixture was stirred 6 h at rt. Et$_3$N was added to neutralize the TFA. The solvent was removed by evaporation and the residue was purified by preparative HPLC (Method A) to give the title compound (111 mg, 73%) as a white solid. ESI-MS m/z calcd for [C$_{22}$H$_{20}$ClF$_5$N$_4$O$_4$S] [M+H]$^+$: 567.1; found: 567.1. $^1$H NMR (400 MHz, CD$_3$OD) δ 8.65 (s, 1H), 8.62 (d, J=1.6 Hz, 1H), 8.13 (s, 1H), 7.69-7.64 (m, 2H), 6.35 (d, J=5.2 Hz, 1H), 5.06 (dd, J=11.2, 2.8 Hz, 1H), 4.65 (dd, J=11.2, 5.2 Hz, 1H), 4.46-4.43 (m, 1H), 4.17 (d, J=2.4 Hz, 1H), 3.70-3.68 (m, 2H), 3.41 (s, 3H), 2.51-2.48 (m, 3H).

Example 40

2-(N-azetidinyl-carbonyl)-5-chlorophenyl 3-[4-(4-chloro-3,5-difluorophenyl)-1H-1,2,3-triazol-1-yl]-3-deoxy-2-O-methyl-1-thio-α-D-galactopyranoside

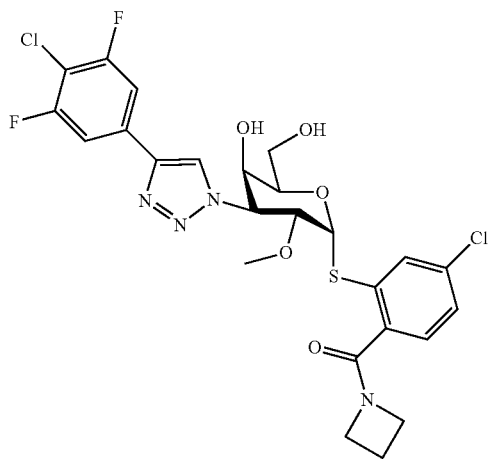

2-(N-azetidinyl-carbonyl)-5-chlorophenyl 3-[4-(4-chloro-3,5-difluorophenyl)-1H-1,2,3-triazol-1-yl]-3-deoxy-1-thio-α-D-galactopyranoside (100 mg, 0.17 mmol), benzaldehyde dimethylacetal (53 μL, 0.35 mmol) and p-toluenesulfonic acid monohydrate (catalytic amount) were stirred 20 h at rt in MeCN (1.5 mL). The mixture was neutralized with Et$_3$N, water was added, and the precipitate was collected by filtration. The precipitate was dissolved in DMF (2 mL), iodomethane (30 μL, 0.46 mmol) followed by NaH (60% in oil, 20 mg, 0.46 mmol) were added. The mixture was stirred 4 h at rt, then poured onto ice/water. The precipitate was isolated by filtration and dried. This material was dissolved in 80% aq TFA (2.0 mL) and stirred 1 h at rt and poured onto ice/water. The precipitate was collected and purified by preparative HPLC (Method B) to afford the title compound (40 mg, 39%). ESI-MS m/z calcd for [C$_{25}$H$_{24}$Cl$_2$F$_2$N$_4$O$_5$S] [M+H]$^+$: 601.1; found: 600.8. $^1$H NMR (400 MHz, Methanol-d$_4$) δ 8.64 (s, 1H), 7.87 (d, J=2.0 Hz, 1H), 7.67 (d, J=8.0 Hz, 2H), 7.44 (dd, J=8.2, 2.0 Hz, 1H), 7.35 (d, J=8.2 Hz, 1H), 6.23 (d, J=5.3 Hz, 1H), 5.03 (dd, J=11.4, 2.9 Hz, 1H), 4.61 (dd, J=11.4, 5.3 Hz, 1H), 4.51 (t, J=6.2 Hz, 1H), 4.26-4.15 (m, 3H), 4.01 (h, J=8.7 Hz, 2H), 3.77-3.62 (m, 2H), 3.42 (s, 3H), 2.36 (p, J=7.7 Hz, 2H).

Example 41

2-(N-azetidinyl-carbonyl)-5-chlorophenyl 3-deoxy-3-[4-(3-fluoro-4-methylphenyl)-1H-1,2,3-triazol-1-yl]-2-O-methyl-1-thio-α-D-galactopyranoside

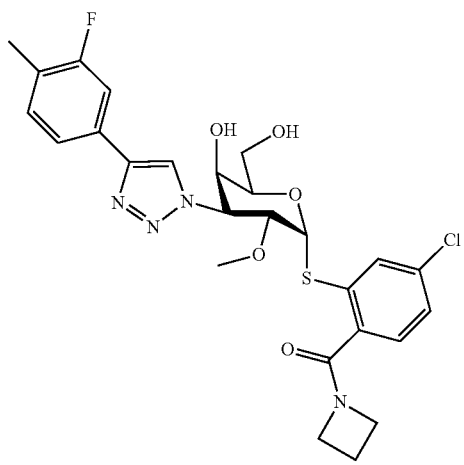

To a solution of 2-(N-azetidinyl-carbonyl)-5-chlorophenyl 4,6-O-benzylidene-3-deoxy-3-[4-(3-fluoro-4-methylphenyl)-1H-1,2,3-triazol-1-yl]-2-O-methyl-1-thio-α-D-galactopyranoside (125 mg, 0.19 mmol) in DCM (4 mL) TFA (0.70 mL, 9.60 mmol) was added. The mixture was stirred 24 h at rt before Et$_3$N (2 mL) was added at 0° C. The solvent was removed under reduced pressure and the residue was purified by preparative HPLC (Method A) to give the title compound (40.4 mg, 37%). ESI-MS m/z calcd for [C$_{26}$H$_{28}$ClFN$_4$O$_5$S] [M+H]$^+$: 563.1, found: 563.2. $^1$H NMR (400 MHz, CD$_3$OD) δ 8.48 (s, 1H), 7.86 (d, J=2.0 Hz, 1H), 7.56-7.51 (m, 2H), 7.44 (dd, J=8.0, 2.0 Hz, 1H), 7.34-7.27 (m, 2H), 6.22 (d, J=5.2 Hz, 1H), 5.02 (dd, J=11.6, 2.8 Hz, 1H), 4.64 (dd, J=11.6, 5.6 Hz, 1H), 4.51 (t, J=8.0 Hz, 1H), 4.21-4.17 (m, 3H), 4.03-3.97 (m, 2H), 4.73-3.64 (m, 2H), 3.41 (s, 3H), 2.38-2.31 (m, 2H), 2.29 (d, J=1.2 Hz, 3H).

Example 42

5-Chloropyridin-3-yl 3-deoxy-3-[4-(3,4,5-trifluorophenyl)-1H-1,2,3-triazol-1-yl]-2-O-methyl-1-thio-α-D-galactopyranoside

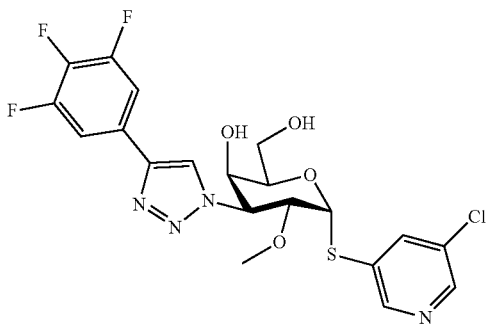

To a solution of 5-chloropyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (100 mg, 0.17 mmol) in DCM (10 mL) TFA (0.63 mL, 8.46 mmol) was added at 0° C. The mixture was stirred 2 h at rt, then Et$_3$N (2 mL) was added at 0° C. The solvent was removed under reduced pressure and the residue was purified by preparative HPLC (Method A) to give the title compound (47 mg, 55%). ESI-MS m/z calcd for [C$_{20}$H$_{18}$ClF$_3$N$_4$O$_4$S][M+H]$^+$: 503.1; found: 503.2. $^1$H NMR (400 MHz, CD$_3$OD) δ 8.66 (d, J=2.0 Hz, 1H), 8.60 (s, 1H), 8.48 (d, J=2.0 Hz, 1H), 8.22 (t, J=2.0 Hz, 1H), 7.72-7.62 (m, 2H), 6.28 (d, J=5.2 Hz, 1H), 5.04 (dd, J=11.2, 2.8 Hz, 1H), 4.64 (dd, J=11.2, 5.2 Hz, 1H), 4.46 (t, J=6.4 Hz, 1H), 4.18 (d, J=2.4 Hz, 1H), 3.75-3.66 (m, 2H), 3.41 (s, 3H).

Example 43

5-Chloropyridin-3-yl 3-deoxy-3-[4-(6-fluoro-5-methylpyridin-2-yl)-1H-1,2,3-triazol-1-yl]-2-O-methyl-1-thio-α-D-galactopyranoside

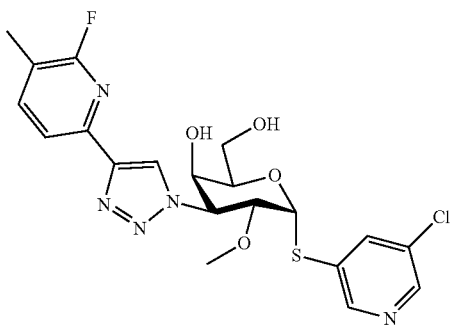

To a solution of 5-chloropyridin-3-yl 4,6-O-benzylidene-3-deoxy-3-[4-(6-fluoro-5-methylpyridin-2-yl)-1H-1,2,3-triazol-1-yl]-2-O-methyl-1-thio-α-D-galactopyranoside (100 mg, 0.18 mmol) in DCM (5 mL) TFA (0.70 mL, 9.60 mmol) was added. The mixture was stirred 24 h at rt before Et$_3$N was added at 0° C. The solvent was removed under reduced pressure and the residue was purified by preparative HPLC (Method A) to give the title compound (34.3 mg, 41%). ESI-MS m/z calcd for [C$_{20}$H$_{21}$ClFN$_5$O$_4$S][M+H]$^+$: 482.1, found: 482.0. $^1$H NMR (400 MHz, CD$_3$OD) δ 8.64 (d, J=1.6 Hz, 1H), 8.54 (s, 1H), 8.46 (d, J=2.4 Hz, 1H), 8.21 (t, J=2.0 Hz, 1H), 7.85 (s, 1H), 7.84 (d, J=4.4 Hz, 1H), 6.27 (d, J=5.2 Hz, 1H), 5.07 (dd, J=11.2, 2.8 Hz, 1H), 4.65 (dd, J=11.6, 5.6 Hz, 1H), 4.47 (t, J=6.0 Hz, 1H), 4.19 (d, J=2.4 Hz, 1H), 3.70-3.67 (m, 2H), 3.40 (s, 3H), 2.31 (s, 3H).

Example 44

5-Chloropyridin-3-yl 3-[4-(5-chloro-6-methylpyridin-2-yl)-1H-1,2,3-triazol-1-yl]-3-deoxy-2-O-methyl-1-thio-α-D-galactopyranoside TBAF (15 μL, 1 M in THF, 15 μmol) and DIEA (51.4 μL, 300 μmol) were added to 5-chloropyridin-3-yl 3-azido-3-deoxy-2-O-methyl-1-thio-α-D-galactopyranoside (52.0 mg, 150 μmol), 3-chloro-2-methyl-6-[2-(trimethylsilyl)ethynyl]pyridine (40.0 mg, 0.187 μmol) and CuI (2.9 mg, 15 μmol) in MeCN (2 mL). The mixture was stirred 1 h at rt and then heated to 50° C. After additionally 1 h the mixture was cooled to rt and more TBAF (150 μL, 1 M, in THF, 150 μmol) was added. The mixture was stirred for 1 h before it was concentrated. Water (10 mL) was added and the mixture was extracted twice with EtOAc (10 mL). The organic phases were dried and concentrated. Purification by preparative HPLC (Method B) yielded the title compound (36.0 mg, 48%) as a white solid. ESI-MS m/z calcd for [C$_{20}$H$_{22}$Cl$_2$N$_5$O$_4$S] [M+H]$^+$: 498.1; found: 498.1, $^1$H NMR (400 MHz, Methanol-d$_4$) δ 8.70-8.64 (m, 1H), 8.63 (s, 1H), 8.49 (d, J=1.8 Hz, 1H), 8.27-8.20 (m, 1H), 7.95-7.84 (m, 2H), 6.29 (d, J=5.3 Hz, 1H), 5.08 (dd, J=11.4, 2.6 Hz, 1H), 4.65 (dd, J=11.3, 5.4 Hz, 1H), 4.47 (t, J=5.8 Hz, 1H), 4.26-4.16 (m, 1H), 3.78-3.64 (m, 2H), 3.41 (s, 3H), 2.66 (s, 3H).

Example 45

3-Chloro-2-cyanopyridin-5-yl 3-deoxy-3-[4-(3,4,5-trifluorophenyl)-1H-1,2,3-triazol-1-yl]-2-O-methyl-1-thio-α-D-galactopyranoside

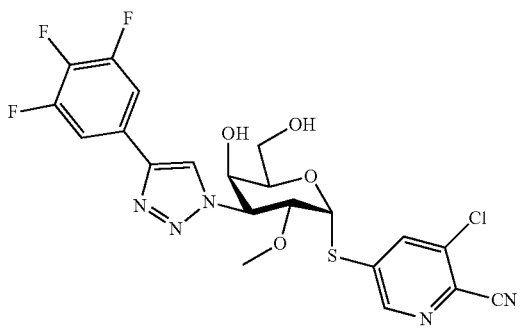

To a solution of 5-chloro-6-cyanopyridin-3-yl 4,6-di-O-acetyl-3-deoxy-3-[4-(3,4,5-trifluorophenyl)-1H-1,2,3-triazol-1-yl]-2-O-methyl-1-thio-α-D-galactopyranoside (25.0 mg, 0.041 mmol) in MeOH (3 mL) Et₃N (2 mL) and water (1 mL) were added. The mixture was stirred 3 h at rt. The solvent was removed under the reduced pressure and the residue was purified by preparative HPLC (method A) to give the title compound (10.5 mg, 49%) as a white solid. ESI-MS m/z calcd for [$C_{21}H_{17}ClF_3N_5O_4S$][M+H]⁺: 528.1; found: 528.0. ¹H NMR (400 MHz, CD₃OD) δ 8.76 (d, J=2.0 Hz, 1H), 8.63 (s, 1H), 8.40 (d, J=2.0 Hz, 1H), 7.71-7.66 (m, 2H), 6.60 (d, J=5.2 Hz, 1H), 5.09 (dd, J=11.6, 2.8 Hz, 1H), 4.74 (dd, J=11.2, 5.2 Hz, 1H), 4.35 (t, J=6.0 Hz, 1H), 4.18 (d, J=2.8 Hz, 1H), 3.72-3.70 (m, 2H), 3.42 (s, 3H).

Example 46

5-Chloro-2-cyanopyridin-3-yl 3-deoxy-3-[4-(3,4,5-trifluorophenyl)-1H-1,2,3-triazol-1-yl]-2-O-methyl-1-thio-α-D-galactopyranoside

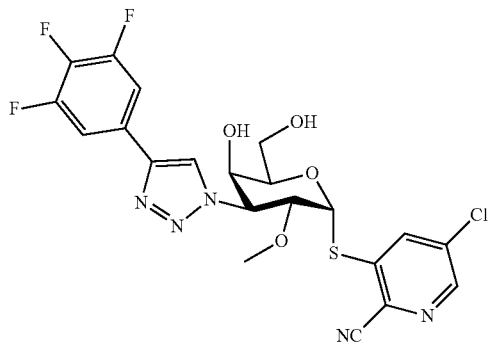

A nitrogen purged solution of 2-bromo-5-chloropyridin-3-yl 3-deoxy-3-[4-(3,4,5-trifluorophenyl)-1H-1,2,3-triazol-1-yl]-2-O-methyl-1-thio-α-D-galactopyranoside (75 mg, 0.13 mmol) in N,N-dimethylacetamide (1 mL) was added to a nitrogen purged solution of Zn (4.2 mg, 0.065 mmol), Zn(CN)₂ (15 mg, 0.13 mmol), Pd(dibenzylideneacetone)₂ (5.9 mg, 0.010 mmol) and 1,1'-bis(diphenylphosphino)ferrocene (5.8 mg, 0.010 mmol) in N,N-dimethylacetamide (0.5 mL) and the resulting mixture was stirred 3 h at 100° C. The mixture was purified by preparative HPLC (Method B) to afford the title compound (14 mg, 21%). ESI-MS m/z calcd for [$C_{21}H_{17}ClF_3N_5O_4S$] [M+H]⁺: 528.1; found: 528.1. ¹H NMR (400 MHz, Methanol-d₄) δ 8.61-8.58 (m, 2H), 8.48 (d, J=2.1 Hz, 1H), 7.66 (dd, J=8.7, 6.7 Hz, 2H), 6.52 (d, J=5.3 Hz, 1H), 5.08 (dd, J=11.3, 2.8 Hz, 1H), 4.72 (dd, J=11.3, 5.3 Hz, 1H), 4.40 (t, J=6.0 Hz, 1H), 4.20 (d, J=2.5 Hz, 1H), 3.69 (d, J=5.9 Hz, 2H), 3.46 (s, 3H).

Example 47

5-Chloro-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside

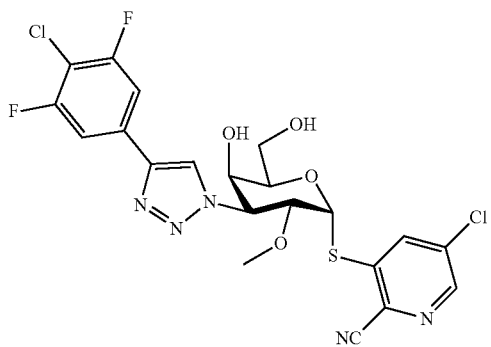

5-Chloro-2-cyanopyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside (100 mg, 0.16 mmol) was dissolved in DCM/TFA (10 mL, 19:1). The mixture was stirred 6 h at rt before Et₃N was added. The solvent was removed by evaporation, and the residue was purified by preparative HPLC (Method A) to give the title compound (71.0 mg, 83%). ESI-MS m/z calcd for [$C_{21}H_{17}Cl_2F_2N_5O_4S$] [M+H]⁺: 544.0; found: 544.2. ¹H NMR (400 MHz, CD₃OD) δ 8.65 (s, 1H), 8.60 (d, J=2.4 Hz, 1H), 8.47 (d, J=2.0 Hz, 1H), 7.66 (dd, J=10.4, 2.4 Hz, 2H), 6.51 (d, J=5.2 Hz, 1H), 5.08 (dd, J=11.2, 2.8 Hz, 1H), 4.71 (dd, J=11.2, 5.2 Hz, 1H), 4.41-4.38 (m, 1H), 4.18 (d, J=2.4 Hz, 1H), 3.67 (d, J=6.0 Hz, 2H), 3.46 (s, 3H).

Example 48

5-Chloro-2-cyanopyridin-3-yl 3-[4-(4-chloro-3-fluorophenyl)-1H-1,2,3-triazol-1-yl]-3-deoxy-2-O-methyl-1-thio-α-D-galactopyranoside

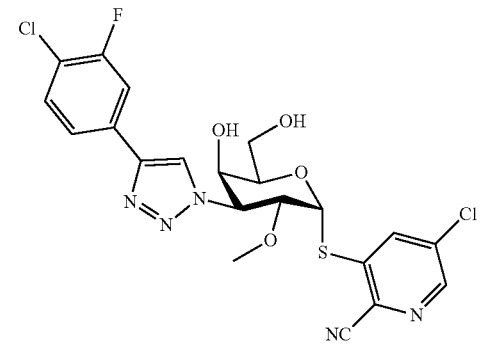

5-Chloro-2-cyanopyridin-3-yl 4,6-O-benzylidene-3-[4-(4-chloro-3-fluorophenyl)-1H-1,2,3-triazol-1-yl]-3-deoxy-2-O-methyl-1-thio-α-D-galactopyranoside (97.0 mg, 0.16 mmol) was dissolved in a mixed solution of DCM/TFA (10 mL, 19:1) and stirred 1 h at rt. The mixture was neutralized with Et₃N and the solvent was removed by evaporation. The residue was purified by preparative HPLC (Method A) to give the title compound (47.2 mg, 57%) as a white solid. ESI-MS m/z calcd for $[C_{21}H_{18}Cl_2FN_5O_4S][M+H]^+$: 526.0; found: 526.2. ¹H NMR (400 MHz, CD₃OD) δ 8.60 (d, J=2.4 Hz, 1H), 8.59 (s, 1H), 8.48 (d, J=2.4 Hz, 1H), 7.76 (dd, J=10.4, 2.0 Hz, 1H), 7.71-7.64 (m, 1H), 7.61-7.49 (m, 1H), 6.52 (d, J=5.2 Hz, 1H), 5.08 (dd, J=11.2, 2.4 Hz, 1H), 4.72 (dd, J=11.2, 5.2 Hz, 1H), 4.39 (t, J=6.0 Hz, 1H), 4.19 (d, J=2.0 Hz, 1H), 3.68 (d, J=6.0 Hz, 2H), 3.46 (s, 3H).

Example 49

2-Cyano-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside

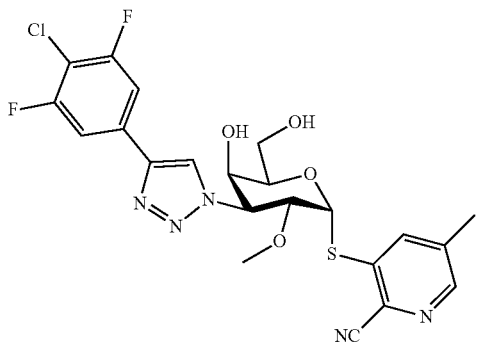

2-Cyano-5-methylpyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside (80 mg, 0.13 mmol) was dissolved in a mixed solution of DCM/TFA (10 mL, 19:1) and stirred 1 h at rt. The mixture was neutralized with Et₃N and then evaporated. The residue was purified by preparative HPLC (Method A) to give the title compound (31.6 mg, 46%) as a white solid. ESI-MS m/z calcd for $[C_{22}H_{20}ClF_2N_5O_4S]$ $[M+H]^+$: 524.1; found: 524.1. ¹H NMR (400 MHz, DMSO-d₆) δ 8.96 (s, 1H), 8.52 (s, 1H), 8.24 (s, 1H), 7.84 (d, J=8.4 Hz, 2H), 6.51 (d, J=4.4 Hz, 1H), 5.63 (d, J=5.6 Hz, 1H), 4.95 (d, J=10.8 Hz, 1H), 4.79 (s, 1H), 4.58 (dd, J=10.8, 4.8 Hz, 1H), 4.29 (s, 1H), 4.08 (s, 1H), 3.52 (m, 2H), 3.47 (s, 3H), 2.40 (s, 3H).

Example 50

5-Bromo-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside

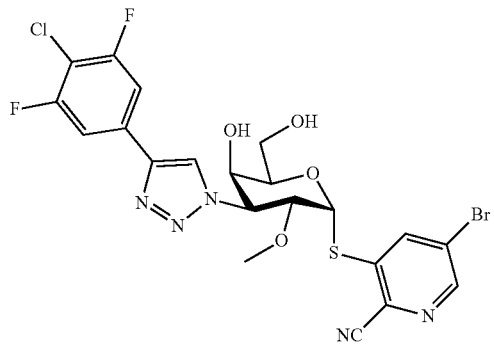

To a solution of 5-bromo-2-cyanopyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside (45.0 mg, 0.067 mmol) in DCM (5 mL) TFA (0.247 mL, 3.32 mmol) was added at 0° C. The mixture was stirred 2 h at rt before Et₃N (2 mL) was added at 0° C. The solvent was removed under reduced pressure and the residue was purified by preparative HPLC (Method A) to afford the title compound (15.0 mg, 38%) as a white solid. ESI-MS m/z calcd for $[C_{21}H_{17}BrClF_2N_5O_4S]$ $[M+H]^+$: 588.0; found: 588.0. ¹H NMR (400 MHz, CD₃OD) δ 8.70 (d, J=2.0 Hz, 1H), 8.65 (s, 1H), 8.62 (d, J=2.0 Hz, 1H), 7.66 (d, J=8.0 Hz, 2H), 6.50 (d, J=5.2 Hz, 1H), 5.08 (dd, J=11.2, 2.8 Hz, 1H), 4.71 (dd, J=11.2, 5.2 Hz, 1H), 4.40 (t, J=6.0 Hz, 1H), 4.19 (d, J=2.4 Hz, 1H), 3.68 (d, J=6.0 Hz, 2H), 3.46 (s, 3H).

Example 51

5-Bromo-2-cyanopyridin-3-yl 3-[4-(4-chloro-3-fluorophenyl)-1H-1,2,3-triazol-1-yl]-3-deoxy-2-O-methyl-1-thio-α-D-galactopyranoside

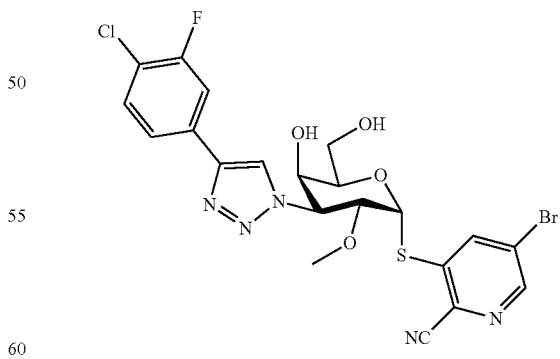

To a solution of 5-bromo-2-cyanopyridin-3-yl 4,6-O-benzylidene-3-[4-(4-chloro-3-fluorophenyl)-1H-1,2,3-triazol-1-yl]-3-deoxy-2-O-methyl-1-thio-α-D-galactopyranoside (45.0 mg, 0.068 mmol) in DCM (5 mL) TFA (0.203 mL, 2.73 mmol) was added. The mixture was stirred under a nitrogen atmosphere 2 h at rt. Et₃N (1 mL) was added at 0°

C. The solvent was removed under reduced pressure and the residue was purified by preparative HPLC (Method A) to afford the title compound (21.0 mg, 54%) as a white solid. ESI-MS m/z calcd for [$C_{21}H_{18}BrClFN_5O_4S$] [M+H]$^+$: 570.0; found: 570.0. $^1$H NMR (400 MHz, CD$_3$OD) δ 8.70 (d, J=2.0 Hz, 1H), 8.62 (d, J=2.0 Hz, 1H), 8.59 (s, 1H), 7.76 (dd, J=10.4, 2.0 Hz, 1H), 7.70-7.67 (m, 1H), 7.58-7.52 (m, 1H), 6.50 (d, J=5.2 Hz, 1H), 5.07 (dd, J=11.2, 2.8 Hz, 1H), 4.72 (dd, J=11.2, 5.2 Hz, 1H), 4.40 (t, J=6.0 Hz, 1H), 4.19 (d, J=2.4 Hz, 1H), 3.68 (d, J=6.0 Hz, 2H), 3.46 (s, 3H).

Example 52

5-Chloro-2-(N-azetidinylcarbamoyl)-3-pyridyl 3-[4-(4-chloro-3,5-difluorophenyl)-1H-1,2,3-triazol-1-yl]-3-deoxy-2-O-methyl-1-thio-α-D-galactopyranoside

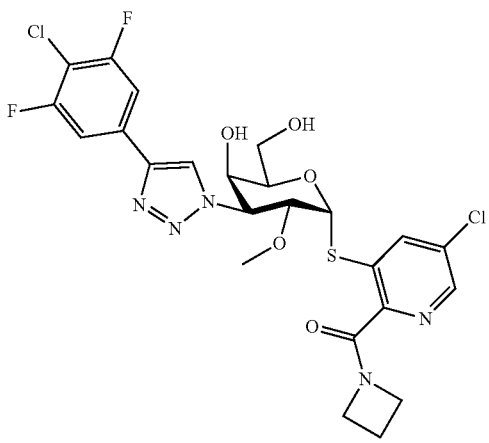

To a solution of 5-chloro-2-(N-azetidinylcarbamoyl)-3-pyridyl 3-azido-3-deoxy-2-O-methyl-1-thio-α-D-galactopyranoside (22.5 mg, 0.052 mmol), trimethyl-[2-(4-chloro-3,5-difluorophenyl)ethynyl]silane (19.2 mg, 0.079 mmol) and CuI (12.5 mg, 0.065 mmol) in MeCN (1.5 mL) DIEA (0.027 mL, 0.16 mmol) was added. The mixture was stirred 5 h at 50° C. The mixture was purified by preparative HPLC (Method B) to afford the title compound (8.0 mg, 25%). ESI-MS m/z calcd for [$C_{24}H_{23}Cl_2F_2N_5O_5S$] [M+H]$^+$: 602.1; found: 601.9. $^1$H NMR (400 MHz, Methanol-d$_4$) δ 8.64 (s, 1H), 8.49 (d, J=2.1 Hz, 1H), 8.38 (d, J=2.1 Hz, 1H), 7.67 (d, J=8.0 Hz, 2H), 6.36 (d, J=5.3 Hz, 1H), 5.07 (dd, J=11.4, 2.8 Hz, 1H), 4.65 (dd, J=11.3, 5.4 Hz, 1H), 4.44 (t, J=6.0 Hz, 1H), 4.27-4.16 (m, 5H), 3.73-3.65 (m, 2H), 3.41 (s, 3H), 2.39 (p, J=8.0 Hz, 2H).

Example 53

5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside

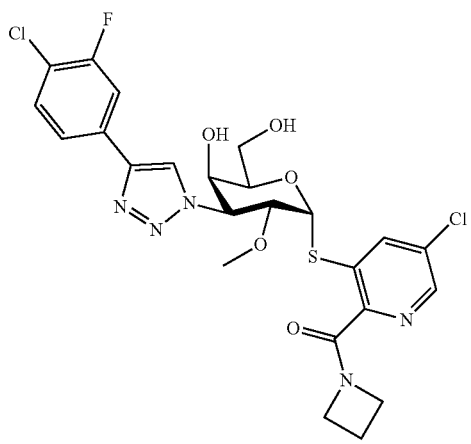

To a solution of 5-chloro-2-(N-azetidinylcarbamoyl)-3-pyridyl 3-azido-3-deoxy-2-O-methyl-1-thio-α-D-galactopyranoside (22.5 mg, 0.052 mmol), trimethyl-[2-(4-chloro-3-fluorophenyl)ethynyl]silane (19.2 mg, 0.079 mmol) and CuI (12.5 mg, 0.065 mmol) in MeCN (1.5 mL) DIEA (0.027 mL, 0.16 mmol) was added. The mixture was stirred 5 h at 50° C. The mixture was purified by preparative HPLC (Method B) to afford the title compound (6.6 mg, 22%). ESI-MS m/z calcd for [$C_{24}H_{24}Cl_2FN_5O_5S$] [M+H]$^+$: 584.1; found: 583.8. $^1$H NMR (400 MHz, Methanol-d$_4$) δ 8.58 (s, 1H), 8.49 (d, J=1.9 Hz, 1H), 8.38 (d, J=2.2 Hz, 1H), 7.77 (d, J=10.3 Hz, 1H), 7.69 (d, J=6.8 Hz, 1H), 7.55 (t, J=8.0 Hz, 1H), 6.36 (d, J=5.2 Hz, 1H), 5.06 (dd, J=11.1, 2.7 Hz, 1H), 4.66 (dd, J=11.4, 5.3 Hz, 1H), 4.44 (t, J=6.0 Hz, 1H), 4.27-4.16 (m, 5H), 3.73-3.64 (m, 2H), 3.41 (s, 3H), 2.39 (p, J=8.0 Hz, 3H).

Example 54

5-Ethynylpyridin-3-yl 3-[4-(4-chloro-3,5-difluorophenyl)-1H-1,2,3-triazol-1-yl]-3-deoxy-2-O-methyl-1-thio-α-D-galactopyranoside

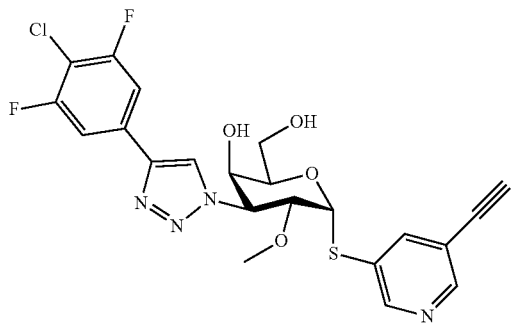

5-(2-Trimethylsilyl-1-ethynyl)-pyridin-3-yl 3-[4-(4-chloro-3,5-difluorophenyl)-1H-1,2,3-triazol-1-yl]-3-deoxy-2-O-methyl-1-thio-α-D-galactopyranoside (140 mg, 0.24 mmol) was stirred in THF (2.0 mL) and TBAF (1.0 mL, 1M in THF, 1.0 mmol) for 90 min. The mixture was partitioned between EtOAc, water, and NaOH (6 mL, 1 M). The organic phase was separated, dried, evaporated and the residue was purified by chromatography (SiO₂, PE/EtOAc) to give the title compound (108 mg, 88%). ESI-MS m/z calcd for [C$_{22}$H$_{19}$ClF$_2$N$_4$O$_4$S] [M+H]$^+$: 509.1; found: 508.8. $^1$H NMR (400 MHz, Methanol-d$_4$) δ 8.71 (d, J=2.1 Hz, 1H), 8.64 (s, 1H), 8.54 (d, J=1.7 Hz, 1H), 8.20 (t, J=2.0 Hz, 1H), 7.67 (d, J=8.0 Hz, 2H), 6.25 (d, J=5.3 Hz, 1H), 5.05 (dd, J=11.3, 2.9 Hz, 1H), 4.64 (dd, J=11.3, 5.3 Hz, 1H), 4.48 (t, J=6.1 Hz, 1H), 4.20 (d, J=2.4 Hz, 1H), 3.84 (s, 1H), 3.75-3.64 (m, 2H), 3.41 (s, 3H).

Example 55

5-Chloro-2-cyanopyridin-3-yl 3-[4-(5-chloro-6-fluoropyridin-2-yl)-1H-1,2,3-triazol-1-yl]-3-deoxy-2-O-methyl-1-thio-α-D-galactopyranoside

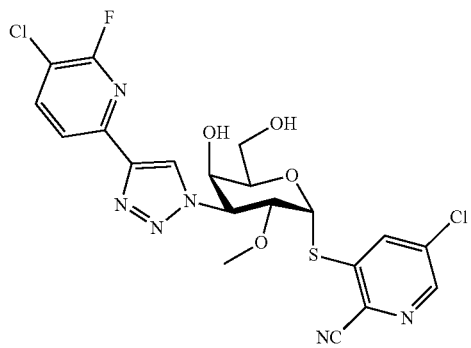

5-Chloro-2-cyanopyridin-3-yl 4,6-O-benzylidene-3-[4-(5-chloro-6-fluoropyridin-2-yl)-1H-1,2,3-triazol-1-yl]-3-deoxy-2-O-methyl-1-thio-α-D-galactopyranoside (125 mg, 0.20 mmol) was dissolved in a mixed solution of DCM/TFA (10 mL, 19:1) and stirred 1 h at rt. The mixture was neutralized with Et$_3$N and the solvent was removed by evaporation. The residue was purified by preparative HPLC (Method A) to give the title compound (48.3 mg, 45%) as a white solid. ESI-MS m/z calcd for [C$_{20}$H$_{17}$Cl$_2$FN$_6$O$_4$S] [M+H]$^+$: 527.0; found: 527.1. $^1$H NMR (400 MHz, DMSO-d$_6$) δ 8.86 (s, 1H), 8.72 (d, J=2.0 Hz, 1H), 8.57 (d, J=2.0 Hz, 1H), 8.23 (dd, J=8.8, 7.2 Hz, 1H), 7.26 (dd, J=8.8, 3.2 Hz, 1H), 6.70 (d, J=5.2 Hz, 1H), 5.01 (dd, J=11.6, 2.8 Hz, 1H), 4.79 (dd, J=11.6, 5.2 Hz, 1H), 4.25-4.15 (m, 1H), 4.08 (d, J=2.4 Hz, 1H), 3.51 (dd, J=11.2, 4.8 Hz, 1H), 3.46-3.42 (m, 3H), 3.36 (s, 3H).

Example 56

2-Cyano-5-ethynylpyridin-3-yl 3-[4-(4-chloro-3,5-difluorophenyl)-1H-1,2,3-triazol-1-yl]-3-deoxy-2-O-methyl-1-thio-α-D-galactopyranoside

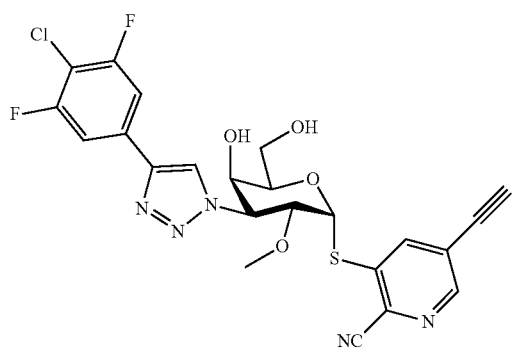

2-Cyano-5-(2-trimethylsilyl-1-ethynyl)-pyridin-3-yl 4,6-di-O-acetyl-3-[4-(4-chloro-3,5-difluorophenyl)-1H-1,2,3-triazol-1-yl]-3-deoxy-2-O-methyl-1-thio-α-D-galactopyranoside (85.0 mg, 123 μmol) was dissolved in MeOH (1.23 mL) and NaOMe (1M, 61.6 μL, 61.6 μmol) was added. After 10 min, the reaction was quenched with AcOH (30 μL) and concentrated. Purification by preparative HPLC (Method B) yielded the title compound as a white solid (29.0 mg, 44%). ESI-MS m/z calcd for [C$_{23}$H$_{19}$ClF$_2$N$_5$O$_4$S] [M+H]$^+$: 534.1; found: 534.1, $^1$H NMR (500 MHz, DMSO-d$_6$) δ 8.96 (s, 1H), 8.72 (d, J=1.8 Hz, 1H), 8.49 (d, J=1.8 Hz, 1H), 7.83 (d, J=8.2 Hz, 2H), 6.71 (d, J=5.2 Hz, 1H), 5.62 (d, J=5.6 Hz, 1H), 4.95 (dd, J=11.4, 2.9 Hz, 1H), 4.87 (s, 1H), 4.69 (s, 1H), 4.58 (dd, J=11.4, 5.3 Hz, 1H), 4.20 (t, J=6.1 Hz, 1H), 4.10-4.04 (m, 1H), 3.49 (dd, J=11.2, 5.2 Hz, 1H), 3.40 (dd, J=11.3, 7.2 Hz, 1H), 3.37 (s, 3H).

Example 57

2-Cyano-5-ethynylpyridin-3-yl 3-deoxy-3-[4-(3,5-difluoro-4-methylphenyl)-1H-1,2,3-triazol-1-yl]-2-O-methyl-1-thio-α-D-galactopyranoside

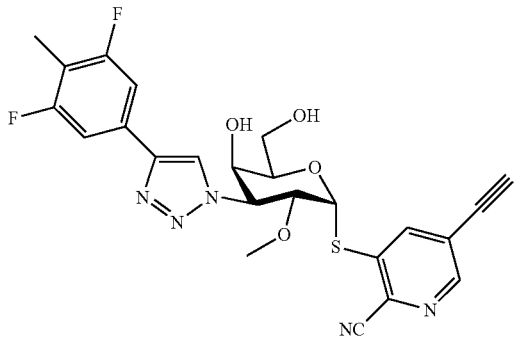

2-Cyano-5-(2-trimethylsilyl-1-ethynyl)-pyridin-3-yl 4,6-di-O-acetyl-3-deoxy-3-[4-(3,5-difluoro-4-methylphenyl)-1H-1,2,3-triazol-1-yl]-2-O-methyl-1-thio-α-D-galactopyranoside (92.0 mg, 137 μmol) was dissolved in MeOH (1.37 mL) and NaOMe (1M, 13.7 μL, 13.7 μmol) was added. After 10 min, the reaction was quenched with AcOH (20 μL) and concentrated. Purification by preparative HPLC (Method B) yielded the title compound as a white solid (41.0 mg, 58%). ESI-MS m/z calcd for [C$_{24}$H$_{22}$F$_2$N$_5$O$_4$S] [M+H]$^+$: 514.1; found: 514.0, $^1$H NMR (500 MHz, Methanol-d$_4$) δ 8.67 (d, J=1.8 Hz, 1H), 8.59 (s, 1H), 8.46 (d, J=1.8 Hz, 1H), 7.51-7.44 (m, 2H), 6.51 (d, J=5.3 Hz, 1H), 5.09 (dd, J=11.3, 2.9 Hz, 1H), 4.74 (dd, J=11.3, 5.3 Hz, 1H), 4.43 (t, J=6.1 Hz, 1H), 4.22 (d, J=2.4 Hz, 1H), 4.16 (s, 1H), 3.71 (dd, J=10.5, 4.2 Hz, 1H), 3.69-3.65 (m, 1H), 3.49 (s, 3H), 2.24 (s, 3H).

Example 58

5-Cyano-6-trifluoromethylpyridin-3-yl 3-[4-(4-chloro-3,5-difluorophenyl)-1H-1,2,3-triazol-1-yl]-3-deoxy-2-O-methyl-1-thio-α-D-galactopyranoside

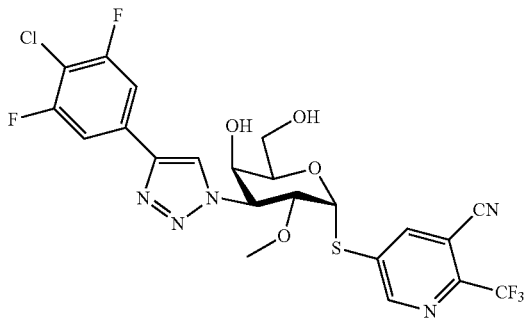

DIEA (44.8 μL, 262 μmol) was added to 5-cyano-6-trifluoromethylpyridin-3-yl 3-azido-3-deoxy-2-O-methyl-1-thio-α-D-galactopyranoside (53.0 mg, 131 μmol), trimethyl-[2-(4-chloro-3,5-difluorophenyl)ethynyl]silane (48.0 mg, 196 μmol) and CuI (2.5 mg, 13.1 mmol) in MeCN (4.64 mL). After 1 h at rt the mixture was heated to 50° C. and stirred 18 h before it cooled to rt and filtered through a plug of celite and concentrated. Purification by chromatography (SiO$_2$, PE/EtOAc) yielded the title compound as a white solid (25.9 mg, 34%). ESI-MS m/z calcd for [C$_{22}$H$_{18}$ClF$_5$N$_5$O$_4$S][M+H]$^+$: 578.1; found: 577.9, $^1$H NMR (400 MHz, Methanol-d$_4$) δ 9.03 (d, J=1.6 Hz, 1H), 8.69 (d, J=1.5 Hz, 1H), 8.66 (s, 1H), 7.67 (d, J=8.1 Hz, 2H), 6.59 (d, J=5.3 Hz, 1H), 5.09 (dd, J=11.3, 2.7 Hz, 1H), 4.70 (dd, J=11.3, 5.3 Hz, 1H), 4.41-4.32 (m, 1H), 4.17 (d, J=2.2 Hz, 1H), 3.78-3.63 (m, 2H), 3.42 (s, 3H).

Example 59

5-Cyanopyridin-3-yl 3-deoxy-3-[4-(3,4,5-trifluorophenyl)-1H-1,2,3-triazol-1-yl]-2-O-methyl-1-thio-α-D-galactopyranoside

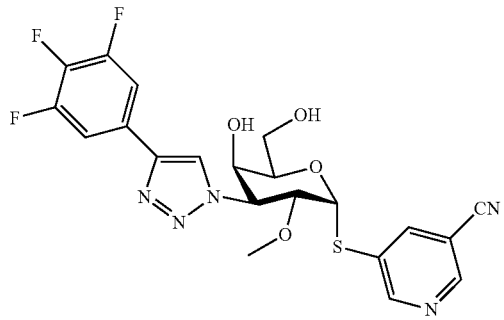

5-Cyanopyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (80.0 mg, 0.14 mmol) was dissolved in DCM (9.5 mL) and TFA (0.5 mL) and stirred 3 h at rt. The mixture was neutralized with Et$_3$N and then the solvent was removed by evaporation. The residue was purified by preparative HPLC (Method A) to give the title compound (33.7 mg, 50%) as a white solid. ESI-MS m/z calcd for [C$_{21}$H$_{18}$F$_3$N$_5$O$_4$S] [M+H]$^+$: 494.1; found: 494.1. $^1$H NMR (400 MHz, CD$_3$OD) δ 8.95 (d, J=2.4 Hz, 1H), 8.79 (d, J=1.6 Hz, 1H), 8.59 (s, 1H), 8.49 (t, J=2.0 Hz, 1H), 7.65 (dd, J=8.8, 6.8 Hz, 2H), 6.34 (d, J=5.2 Hz, 1H), 5.05 (dd, J=11.6, 3.2 Hz, 1H), 4.65 (dd, J=11.6, 5.2 Hz, 1H), 4.43 (t, J=6.0 Hz, 1H), 4.17 (d, J=2.0 Hz, 1H), 3.69 (d, J=6.0 Hz, 2H), 3.41 (s, 3H).

Example 60

5-Cyanopyridin-3-yl 3-[4-(4-chloro-3,5-difluorophenyl)-1H-1,2,3-triazol-1-yl]-3-deoxy-2-O-methyl-1-thio-α-D-galactopyranoside

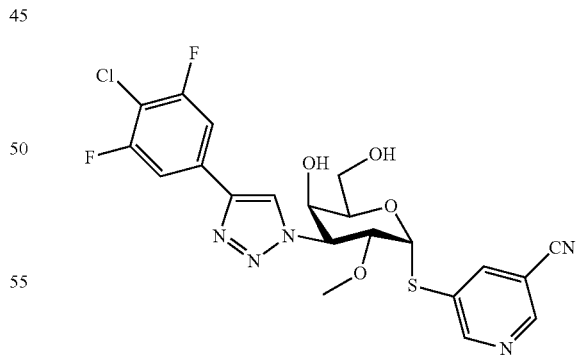

To a solution of 5-cyanopyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside (80.0 mg, 0.13 mmol) in DCM (6 mL) TFA (0.199 mL, 2.68 mmol) was added. The mixture was stirred under a nitrogen atmosphere at rt overnight. Then Et$_3$N (0.5 mL) was added at 0° C. The solvent was removed under reduced pressure and the residue was purified by preparative HPLC (Method A) to obtain the title compound (21.0 mg, 31%) as a white solid. ESI-MS m/z calcd for [C$_{21}$H$_{18}$ClF$_2$N$_5$O$_4$S][M+H]$^+$: 510.1; found: 510.2. $^1$H NMR (400 MHz, CD$_3$OD) δ 8.96 (d, J=2.0 Hz, 1H), 8.80 (d, J=2.0 Hz, 1H), 8.64 (s, 1H), 8.50 (t, J=2.0 Hz, 1H), 7.66 (d, J=8.0 Hz, 2H), 6.35 (d, J=5.2 Hz, 1H), 5.06 (dd, J=11.2, 2.8 Hz, 1H), 4.65 (dd, J=11.2, 5.2 Hz, 1H), 4.43 (t, J=6.0 Hz, 1H), 4.16 (d, J=2.0 Hz, 1H), 3.68 (d, J=6.0 Hz, 2H), 3.41 (s, 3H).

Example 61

5-Bromo-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside

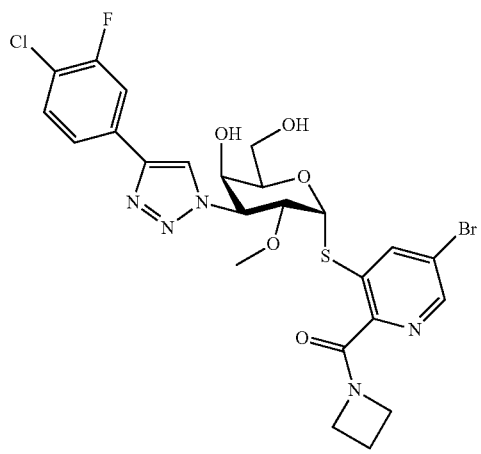

To a solution of 5-bromo-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-methyl-1-thio-α-D-galactopyranoside (60.0 mg, 0.084 mmol) in DCM (4 mL) TFA (0.205 mL, 2.76 mmol) was added. The mixture was stirred under a nitrogen atmosphere at rt overnight. The mixture was neutralized with Et$_3$N at 0° C. and then the solvent was removed by evaporation. The residue was purified by preparative HPLC (Method A) to afford the title compound (32.6 mg, 62%) as a white solid. ESI-MS m/z calcd for [C$_{24}$H$_{24}$BrClFN$_5$O$_5$S] [M+H]$^+$: 628.0; found: 628.0. $^1$H NMR (400 MHz, CD$_3$OD) δ 8.60-8.56 (m, 2H), 8.51 (d, J=2.0 Hz, 1H), 7.76 (dd, J=10.4, 2.0 Hz, 1H), 7.68 (dd, J=8.4, 1.6 Hz, 1H), 7.54 (t, J=8.0 Hz, 1H), 6.34 (d, J=5.2 Hz, 1H), 5.05 (dd, J=11.2, 2.8 Hz, 1H), 4.65 (dd, J=11.2, 5.2 Hz, 1H), 4.44 (t, J=6.0 Hz, 1H), 4.28-4.10 (m, 5H), 3.73-3.61 (m, 2H), 3.40 (s, 3H), 2.46-2.32 (m, 2H).

Example 62

5-Bromo-2-(N-azetidinylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside

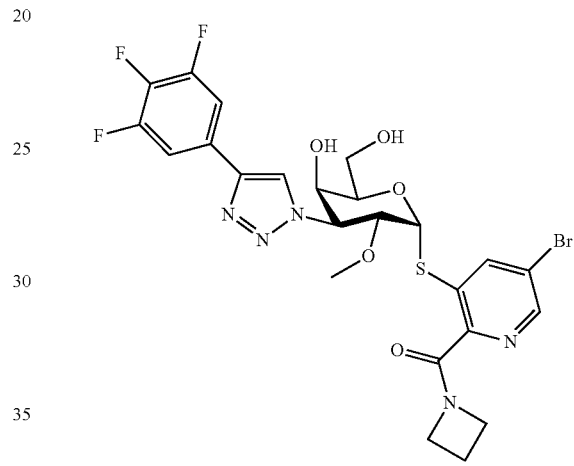

To a solution of 5-bromo-2-(N-azetidinylcarbamoyl)-3-pyridyl 4,6-O-benzylidene-3-deoxy-3-[4-(3,4,5-trifluorophenyl)-1H-1,2,3-triazol-1-yl]-2-O-methyl-1-thio-α-D-galactopyranoside (95.0 mg, 0.13 mmol) in DCM (5 mL) TFA (0.304 mL, 4.10 mmol) was added. The mixture was stirred under a nitrogen atmosphere at rt overnight. The mixture was neutralized with Et$_3$N at 0° C. and then the solvent was removed by evaporation. The residue was purified by preparative HPLC (Method A) to afford the title compound (37 mg, 44%) as a white solid. ESI-MS m/z calcd for [C$_{24}$H$_{23}$BrF$_3$N$_5$O$_5$S] [M+H]$^+$: 630.1; found: 630.1. $^1$H NMR (400 MHz, CD$_3$OD) δ 8.60-8.56 (m, 2H), 8.50 (d, J=2.0 Hz, 1H), 7.66 (d, J=8.8, 2.4 Hz, 2H), 6.34 (d, J=5.2 Hz, 1H), 5.04 (dd, J=11.2, 2.8 Hz, 1H), 4.63 (dd, J=11.2, 5.2 Hz, 1H), 4.43 (t, J=6.0 Hz, 1H), 4.28-4.10 (m, 5H), 3.73-3.61 (m, 2H), 3.40 (s, 3H), 2.45-2.31 (m, 2H).

Example 63

5-Bromo-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside

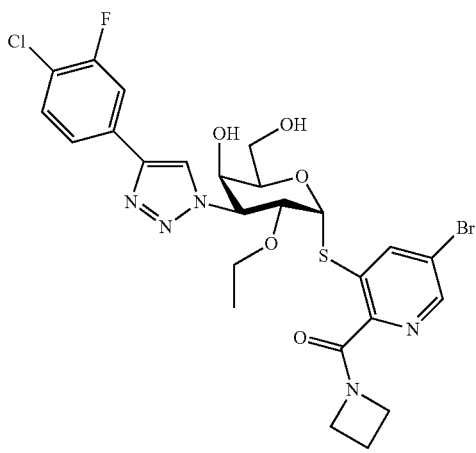

To a solution of 5-bromo-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-ethyl-1-thio-α-D-galactopyranoside (90.0 mg, 0.123 mmol) in DCM (5 mL) TFA (0.302 mL, 4.06 mmol) was added. The mixture was stirred under a nitrogen atmosphere at rt overnight. The mixture was neutralized with Et$_3$N at 0° C. and then the solvent was removed by evaporation. The residue was purified by preparative HPLC (Method A) to afford the title compound (32.9 mg, 42%) as a white solid. ESI-MS m/z calcd [C$_{25}$H$_{26}$BrClFN$_5$O$_5$S] [M+H]$^+$: 642.1; found: 642.0. $^1$H NMR (400 MHz, CD$_3$OD) δ 8.61-8.55 (m, 2H), 8.50 (d, J=2.0 Hz, 1H), 7.76 (dd, J=10.4, 1.8 Hz, 1H), 7.68 (dd, J=8.4, 1.7 Hz, 1H), 7.54 (t, J=8.0 Hz, 1H), 6.31 (d, J=5.2 Hz, 1H), 5.05 (dd, J=11.2, 2.8 Hz, 1H), 4.74 (dd, J=11.2, 5.2 Hz, 1H), 4.43 (t, J=6.0 Hz, 1H), 4.30-4.07 (m, 5H), 3.89-3.75 (m, 1H), 3.75-3.62 (m, 2H), 3.49-3.37 (m, 1H), 2.51-2.29 (m, 2H), 1.03 (t, J=6.8 Hz, 3H).

Example 64

2-(N-azetidinyl-carbonyl)-5-bromophenyl 3-deoxy-3-[4-(3,4,5-trifluorophenyl)-1H-1,2,3-triazol-1-yl]-2-O-methyl-1-thio-α-D-galactopyranoside

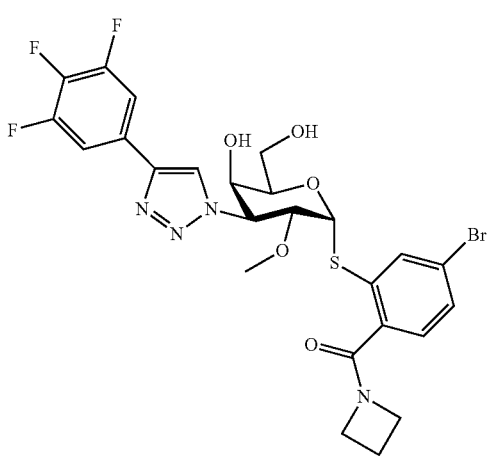

2-(N-azetidinyl-carbonyl)-5-bromophenyl 4,6-O-benzylidene-3-deoxy-3-[4-(3,4,5-trifluorophenyl)-1H-1,2,3-triazol-1-yl]-2-O-methyl-1-thio-α-D-galactopyranoside (120 mg, 0.17 mmol) was dissolved in a mixture of DCM/TFA (9.5 mL/0.5 mL) and stirred overnight at rt. The mixture was neutralized with Et$_3$N and then the solvent was removed by evaporation. The residue was purified by preparative HPLC (Method A) to give the title compound (60.3 mg, 57%) as a white solid. ESI-MS m/z calcd for [C$_{25}$H$_{24}$BrF$_3$N$_4$O$_5$S] [M+H]$^+$: 629.1; found: 629.2. $^1$H NMR (400 MHz, CD$_3$OD) δ 8.58 (s, 1H), 8.00 (d, J=2.0 Hz, 1H), 7.70-7.62 (m, 2H), 7.59 (dd, J=8.4, 2.0 Hz, 1H), 7.27 (d, J=8.0 Hz, 1H), 6.21 (d, J=5.6 Hz, 1H), 5.01 (dd, J=11.2, 2.8 Hz, 1H), 4.59 (dd, J=11.2, 5.2 Hz, 1H), 4.50 (t, J=6.4 Hz, 1H), 4.27-4.14 (m, 3H), 4.03-3.95 (m, 2H), 3.74-3.65 (m, 2H), 3.40 (s, 3H), 2.43-2.29 (m, 2H).

Example 65

2-(N-azetidinyl-carbonyl)-5-bromophenyl 3-deoxy-3-[4-(3,4,5-trifluorophenyl)-1H-1,2,3-triazol-1-yl]-2-O-ethyl-1-thio-α-D-galactopyranoside

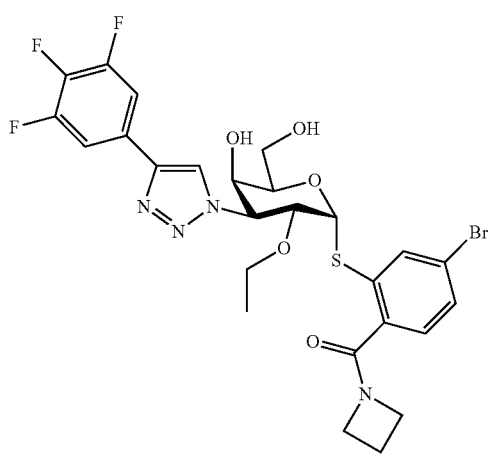

2-(N-azetidinyl-carbonyl)-5-bromophenyl 4,6-O-benzylidene-3-deoxy-3-[4-(3,4,5-trifluorophenyl)-1H-1,2,3-triazol-1-yl]-2-O-ethyl-1-thio-α-D-galactopyranoside (120 mg, 0.16 mmol) was dissolved in a mixture of DCM/TFA (9.5 mL/0.5 mL) and stirred overnight at rt. The mixture was neutralized with Et$_3$N and then the solvent was removed by evaporation. The residue was purified by preparative HPLC (Method A) to give the title compound (64.9 mg, 62%) as a white solid. ESI-MS m/z calcd for [C$_{26}$H$_{26}$BrF$_3$N$_4$O$_5$S] [M+H]$^+$: 643.1; found: 643.2. $^1$H NMR (400 MHz, CD$_3$OD) δ 8.60 (s, 1H), 8.01 (d, J=2.0 Hz, 1H), 7.72-7.63 (m, 2H), 7.60 (dd, J=8.4, 2.0 Hz, 1H), 7.28 (d, J=8.4 Hz, 1H), 6.19 (d, J=5.2 Hz, 1H), 5.03 (dd, J=11.6, 2.8 Hz, 1H), 4.70 (dd, J=11.6, 5.2 Hz, 1H), 4.51 (t, J=6.0 Hz, 1H), 4.27-4.13 (m, 3H), 4.07-3.96 (m, 2H), 3.88-3.80 (m, 1H), 3.76-3.66 (m, 2H), 3.48-3.40 (m, 1H), 2.41-2.33 (m, 2H), 1.05 (t, J=6.8 Hz, 3H).

Example 66

5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside

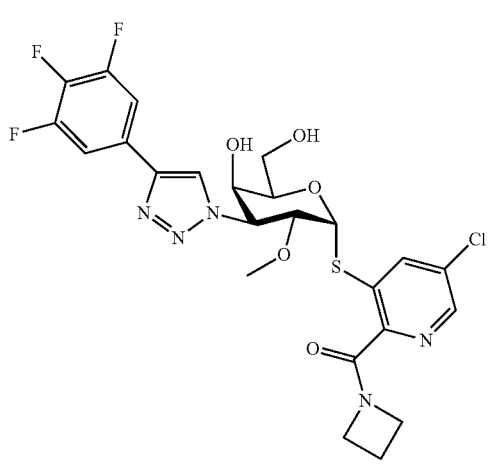

To a solution of 5-chloro-2-(N-azetidinylcarbamoyl)-3-pyridyl 4,6-O-benzylidene-3-deoxy-3-[4-(3,4,5-trifluorophenyl)-1H-1,2,3-triazol-1-yl]-2-O-methyl-1-thio-α-D-galactopyranoside (100 mg, 0.14 mmol) in DCM (10 mL) TFA (0.5 mL, 6.73 mmol) was added and the mixture was stirred overnight at rt. The mixture was neutralized with Et$_3$N at 0° C. and then the solvent was removed by evaporation. The residue was purified by preparative HPLC (Method A) to give the title compound (30.0 mg, 38%) as a white solid. ESI-MS m/z calcd for[C$_{24}$H$_{23}$ClF$_3$N$_5$O$_5$S] [M+H]$^+$: 586.1; found: 586.1. $^1$H NMR (400 MHz, CD$_3$OD) δ 8.58 (s, 1H), 8.48 (d, J=2.0 Hz, 1H), 8.37 (d, J=2.4 Hz, 1H), 7.69-7.63 (m, 2H), 6.36 (d, J=5.2 Hz, 1H), 5.05 (dd, J=11.6, 3.2 Hz, 1H), 4.64 (dd, J=11.2, 5.2 Hz, 1H), 4.43 (t, J=6.0 Hz, 1H), 4.25-4.14 (m, 5H), 3.76-3.64 (m, 2H), 3.40 (s, 3H), 2.42-2.34 (m, 2H).

Example 67

5-Chloro-2-(N-azetidinylcarbamoyl)-3-pyridyl 3-deoxy-3-[4-(3,4,5-trifluorophenyl)-1H-1,2,3-triazol-1-yl]-2-O-ethyl-1-thio-α-D-galactopyranoside

Example 68

5-Chloro-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside

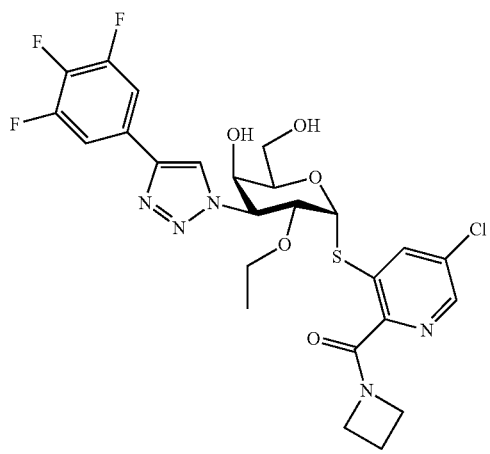

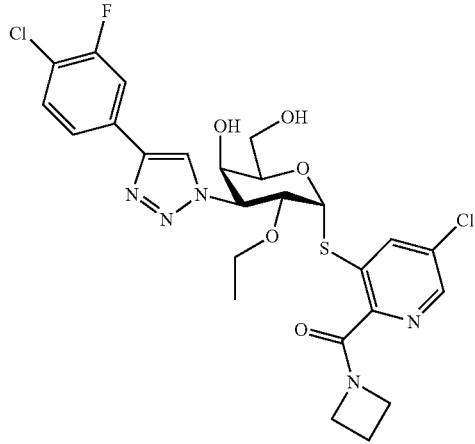

To a solution of 5-chloro-2-(N-azetidinylcarbamoyl)-3-pyridyl 4,6-O-benzylidene-3-deoxy-3-[4-(3,4,5-trifluorophenyl)-1H-1,2,3-triazol-1-yl]-2-O-ethyl-1-thio-α-D-galactopyranoside (160 mg, 0.22 mmol) in DCM (16 mL) TFA (0.82 mL, 11.0 mmol) was added and the mixture was stirred overnight at rt. The mixture was neutralized with Et$_3$N at 0° C. and then the solvent was removed by evaporation. The residue was purified by preparative HPLC (Method A) to give the title compound (83.0 mg, 63%) as a white solid. ESI-MS m/z calcd for[C$_{25}$H$_{25}$ClF$_3$N$_5$O$_5$S] [M+H]$^+$: 600.1; found: 600.2. $^1$H NMR (400 MHz, CD$_3$OD) δ 8.59 (s, 1H), 8.47 (d, J=2.0 Hz, 1H), 8.36 (d, J=2.0 Hz, 1H), 7.70-7.62 (m, 2H), 6.32 (d, J=5.2 Hz, 1H), 5.05 (dd, J=11.2, 2.8 Hz, 1H), 4.73 (dd, J=11.6, 5.6 Hz, 1H), 4.43 (t, J=6.0 Hz, 1H), 4.24-4.13 (m, 5H), 3.84-3.77 (m, 1H), 3.72-3.64 (m, 2H), 3.47-3.34 (m, 1H), 2.42-2.34 (m, 2H), 1.04-1.01 (m, 3H).

To a solution of 5-chloro-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-ethyl-1-thio-α-D-galactopyranoside (145 mg, 0.21 mmol) in DCM (15 mL) TFA (0.76 mL, 10.2 mmol) was added and the mixture was stirred overnight at rt. The mixture was neutralized with Et$_3$N at 0° C. and then the solvent was removed by evaporation. The residue was purified by preparative HPLC (Method A) to give the title compound (79.0 mg, 64%) as a white solid. ESI-MS m/z calcd for[C$_{25}$H$_{26}$Cl$_2$FN$_5$O$_5$S] [M+H]$^+$: 598.1; found: 598.2. $^1$H NMR (400 MHz, CD$_3$OD) δ 8.57 (s, 1H), 8.48 (d, J=2.0 Hz, 1H), 8.36 (d, J=2.0 Hz, 1H), 7.76 (dd, J=10.4, 1.6 Hz, 1H), 7.68 (dd, J=8.4, 1.6 Hz, 1H), 7.56-7.52 (m, 1H), 6.32 (d, J=5.2 Hz, 1H), 5.05 (dd, J=7.6, 3.2 Hz, 1H), 4.74 (dd, J=7.2, 1.6 Hz, 1H), 4.43 (t, J=6.0 Hz, 1H), 4.24-4.15 (m, 5H), 3.84-3.77 (m, 1H), 3.72-3.64 (m, 2H), 3.47-3.40 (m, 1H), 2.42-2.34 (m, 2H), 1.04-1.01 (m, 3H).

Example 69

5-Chloro-2-(N-azetidinylcarbamoyl)-3-pyridyl 3-[4-(4-chloro-3,5-difluorophenyl)-1H-1,2,3-triazol-1-yl]-3-deoxy-2-O-ethyl-1-thio-α-D-galactopyranoside

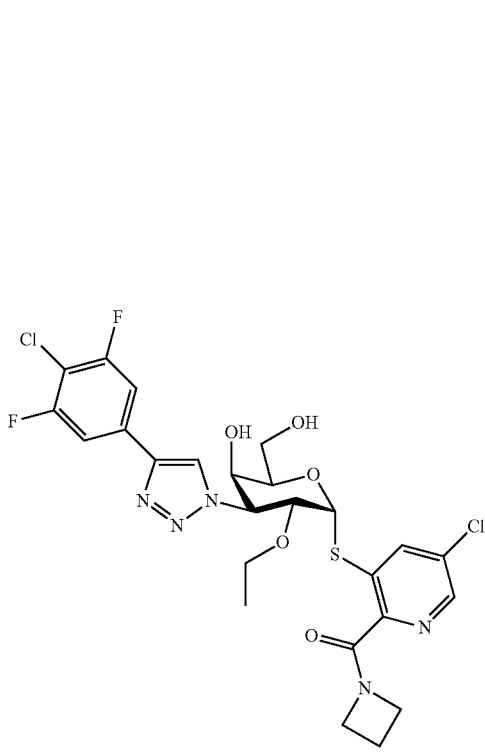

To a solution of 5-chloro-2-(N-azetidinylcarbamoyl)-3-pyridyl 4,6-O-benzylidene-3-[4-(4-chloro-3,5-difluorophenyl)-1H-1,2,3-triazol-1-yl]-3-deoxy-2-O-ethyl-1-thio-α-D-galactopyranoside (100 mg, 0.14 mmol) in DCM (10 mL) TFA (0.51 mL, 6.88 mmol) was added and the mixture was stirred overnight at rt. The mixture was neutralized with Et$_3$N at 0° C. and then the solvent was removed by evaporation. The residue was purified by preparative HPLC (Method A) to give the title compound (54.0 mg, 64%) as a white solid. ESI-MS m/z calcd for[C$_{25}$H$_{25}$Cl$_2$F$_2$N$_5$O$_5$S] [M+H]$^+$: 616.1; found: 616.2. $^1$H NMR (400 MHz, CD$_3$OD) δ 8.67 (s, 1H), 8.50 (d, J=2.0 Hz, 1H), 8.38 (d, J=2.4 Hz, 1H), 7.71-7.67 (m, 2H), 6.35 (d, J=5.2 Hz, 1H), 5.08 (dd, J=11.6, 2.8 Hz, 1H), 4.76 (dd, J=11.2, 5.2 Hz, 1H), 4.45 (t, J=6.0 Hz, 1H), 4.27-4.18 (m, 5H), 3.85-3.79 (m, 1H), 3.73-3.67 (m, 2H), 3.49-3.42 (m, 1H), 2.45-2.37 (m, 2H), 1.07-1.03 (m, 3H).

Example 70

2-(N-azetidinyl-carbonyl)-5-chlorophenyl 3-deoxy-3-[4-(3,4,5-trifluorophenyl)-1H-1,2,3-triazol-1-yl]-2-O-methyl-1-thio-α-D-galactopyranoside

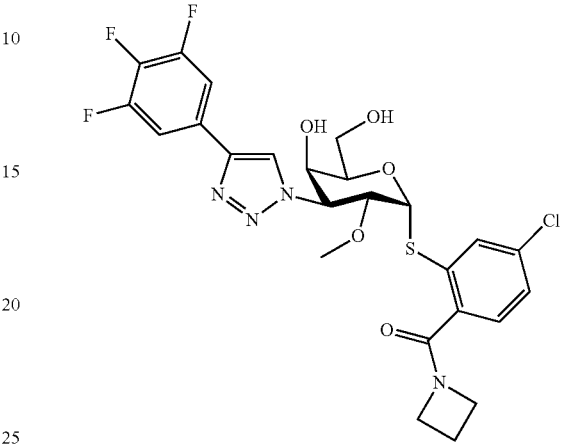

To a solution of 2-(N-azetidinyl-carbonyl)-5-chlorophenyl 4,6-O-benzylidene-3-deoxy-3-[4-(3,4,5-trifluorophenyl)-1H-1,2,3-triazol-1-yl]-2-O-methyl-1-thio-α-D-galactopyranoside (101 mg, 0.15 mmol) in DCM (8 mL) TFA (0.4 mL) was added and the mixture was stirred 16 h at rt. The mixture was neutralized with Et$_3$N and then the solvent was removed by evaporation. The residue was purified by preparative HPLC (Method A) to give the title compound (20 mg, 23%) as a white solid. ESI-MS m/z calcd for [C$_{25}$H$_{24}$ClF$_3$N$_4$O$_5$S] [M+H]$^+$: 585.1; found: 585.0. $^1$H NMR (400 MHz, CD$_3$OD) δ 8.59 (s, 1H), 7.87 (d, J=2.0 Hz, 1H), 7.68-7.65 (m, 2H), 7.43 (dd, J=8.0, 2.0 Hz, 1H), 7.34 (d, J=8.0 Hz, 1H), 6.24 (d, J=5.6 Hz, 1H), 5.03 (dd, J=11.2, 2.8 Hz, 1H), 4.62 (dd, J=11.2, 5.2 Hz, 1H), 4.51 (t, J=8.0 Hz, 1H), 4.23-4.17 (m, 3H), 4.03-3.97 (m, 2H), 3.72-3.68 (m, 2H), 3.41 (s, 3H), 2.38-2.31 (m, 2H).

Example 71

3,4-Dichlorophenyl 3-[4-(4-chloro-3,5-difluorophenyl)-1H-1,2,3-triazol-1-yl]-3-deoxy-2-O-methyl-1-thio-α-D-galactopyranoside

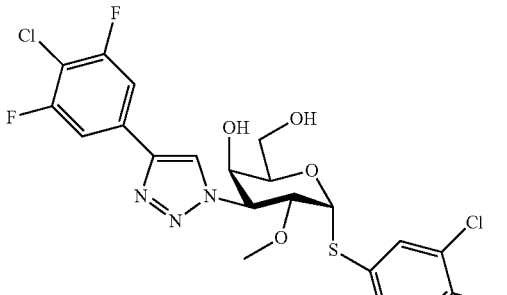

3,4-Dichlorophenyl 4,6-O-benzylidene-3-[4-(4-chloro-3,5-difluorophenyl)-1H-1,2,3-triazol-1-yl]-3-deoxy-2-O- methyl-1-thio-α-D-galactopyranoside (80.0 mg, 0.14 mmol) was dissolved in aq 80% AcOH (5 mL) and stirred 4 h at 85° C. The solvent was removed by evaporation and the residue was purified by preparative HPLC (Method A) to give the title compound (47.4 mg, 48%) as a white solid. ESI-MS m/z calcd for [$C_{21}H_{18}Cl_3F_2N_3O_4S$] [M+H]$^+$: 552.1; found: 552.0. $^1$H NMR (400 MHz, CD$_3$OD) δ 8.64 (s, 1H), 7.82 (d, J=1.2 Hz, 1H), 7.67 (d, J=8.4 Hz, 2H), 7.54-7.48 (m, 2H), 6.18 (d, J=5.2 Hz, 1H), 5.05 (dd, J=11.2, 2.4 Hz, 1H), 4.63 (dd, J=11.2, 5.2 Hz, 1H), 4.46 (t, J=6.0 Hz, 1H), 4.18-4.17 (m, 1H), 3.74-3.65 (m, 2H), 3.39 (s, 3H).

Intermediate 1

5-Bromopyridin-3-yl 4,6-O-benzylidene-3-deoxy-3-[4-(3,4,5-trifluorophenyl)-1H-1,2,3-triazol-1-yl]-1-thio-α-D-galactopyranoside

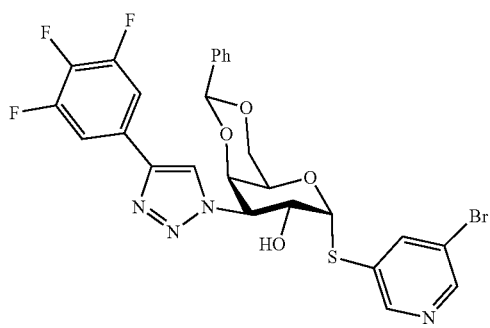

5-Bromopyridin-3-yl 3-deoxy-3-[4-(3,4,5-trifluorophenyl)-1H-1,2,3-triazol-1-yl]-1-thio-α-D-galactopyranoside (WO2016120403) (5.0 g, 9.37 mmol), MeCN (100 mL) and benzaldehyde dimethylacetal (2.88 mL, 19 mmol) were stirred at 40° C. and p-toluenesulfonic acid monohydrate (100 mg, 0.53 mmol) was added. The mixture was stirred 4 h at rt, then cooled to 0° C., the precipitate was collected by filtration, washed with cold MeCN and dried to afford the product (5.3 g, 91%). $^1$H NMR (400 MHz, DMSO-d$_6$) δ 8.85 (s, 1H), 8.67 (d, J=1.4 Hz, 1H), 8.62 (d, J=1.8 Hz, 1H), 8.27 (s, 1H), 7.83-7.74 (m, 2H), 7.40-7.29 (m, 5H), 6.24 (d, J=5.2 Hz, 1H), 6.16 (d, J=4.8 Hz, 1H), 5.57 (s, 1H), 5.12 (dd, J=11.3, 3.1 Hz, 1H), 4.91 (m, 1H), 4.57 (d, J=3.1 Hz, 1H), 4.29 (s, 1H), 4.12 (d, J=12.1 Hz, 1H), 3.92 (d, J=12.6 Hz, 1H).

Intermediate 3

4-Chloro-N,N-dimethyl-benzamide-2-yl 3-deoxy-3-[4-(3,4,5-trifluorophenyl)-1H-1,2,3-triazol-1-yl]-1-thio-α-D-galactopyranoside

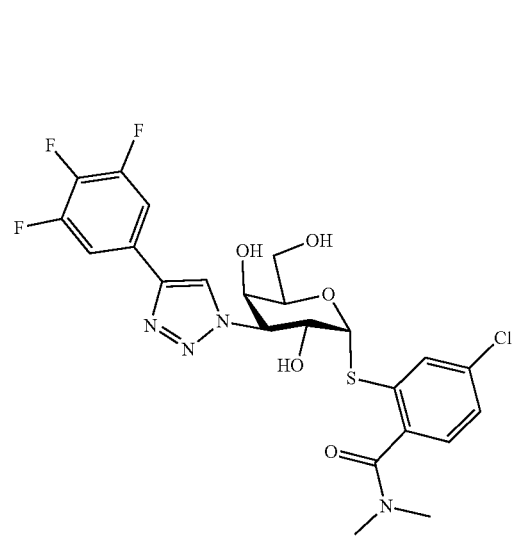

5-Chloro-2-cyanophenyl 2,4,6-tri-O-acetyl-3-azido-3-deoxy-1-thio-α-D-galactopyranoside

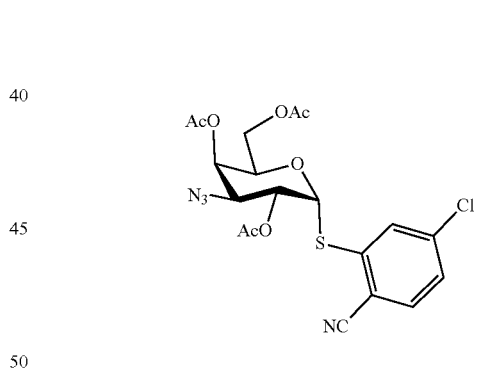

2,4,6-Tri-O-acetyl-3-azido-3-deoxy-β-D-galactopyranosyl chloride (9.6 g, 27.3 mmol), 4-chloro-2-sulfanylbenzonitrile (5.1 g, 30.1 mmol), Cs$_2$CO$_3$ (17.8 g, 54.7 mmol) and DMF (40 mL) were stirred 20 h at rt. The mixture was partitioned between ditheyl ether/EtOAc/aq HCl/water, the organic phase was separated, concentrated, and the residue was subjected to chromatography (SiO$_2$, PE/EtOAc) to afford the product (5.63 g, 42%). $^1$H NMR (400 MHz, Chloroform-d) δ 7.69 (d, J=1.7 Hz, 1H), 7.61 (d, J=8.3 Hz, 1H), 7.39 (dd, J=8.3, 1.9 Hz, 1H), 6.07 (d, J=5.5 Hz, 1H), 5.51 (d, J=2.2 Hz, 1H), 5.31 (dd, J=11.0, 5.5 Hz, 1H), 4.68-4.60 (m, 1H), 4.14 (dd, J=11.7, 5.1 Hz, 1H), 4.05 (dd, J=11.6, 7.6 Hz, 1H), 3.99 (dd, J=11.0, 3.2 Hz, 1H), 2.23 (s, 3H), 2.17 (s, 3H), 2.02 (s, 3H).

5-Chloro-2-cyanophenyl 3-deoxy-3-[4-(3,4,5-trifluorophenyl)-1H-1,2,3-triazol-1-yl]-1-thio-α-D-galactopyranoside

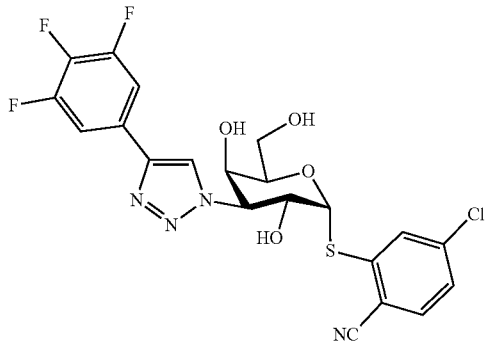

5-Chloro-2-cyanophenyl 2,4,6-tri-O-acetyl-3-azido-3-deoxy-1-thio-α-D-galactopyranoside (454 mg, 0.94 mmol), trimethyl-[2-(3,4,5-trifluorophenyl)ethynyl]silane (429 mg, 1.88 mmol) and $K_2CO_3$ (1.30 g, 9.41 mmol) were weighed into a glass flask and purged with nitrogen. MeOH (5.0 mL) and THF (5.0 mL) were added followed by a solution of copper(II) sulfate pentahydrate (40 mg, 0.16 mmol) and (+)-sodium L-ascorbate (70 mg, 0.35 mmol) in water (2.5 mL). The mixture was stirred 8 h at 60° C. and then copper(II) sulfate pentahydrate (40 mg, 0.16 mmol) and (+)-sodium L-ascorbate (70 mg, 0.35 mmol) were added. Stirring was continued for 4 h at 60° C. The mixture was filtered through a pad of silica eluted with EtOAc and concentrated. The residue was purified by chromatography ($SiO_2$, PE/EtOAc) to afford a residue that was recrystallized first from EtOAc/hexanes and then from EtOH and water to give the product (248 mg, 51%). ESI-MS m/z calcd for $[C_{21}H_{16}ClF_3N_4O_4S]$ $[M+H]^+$: 513.06; found: 513.1. $^1$H NMR (400 MHz, Methanol-$d_4$) δ 8.55 (s, 1H), 7.98 (d, J=1.8 Hz, 1H), 7.74 (d, J=8.4 Hz, 1H), 7.71-7.61 (m, 2H), 7.47 (dd, J=8.4, 1.9 Hz, 1H), 6.13 (d, J=5.1 Hz, 1H), 5.06 (dd, J=11.4, 2.6 Hz, 1H), 4.99 (dd, J=11.4, 5.2 Hz, 1H), 4.42 (t, J=6.1 Hz, 1H), 4.23 (d, J=2.4 Hz, 1H), 3.71 (dd, J=11.4, 5.6 Hz, 1H), 3.64 (dd, J=11.3, 6.6 Hz, 1H).

2-Carboxy-5-chlorophenyl 3-deoxy-3-[4-(3,4,5-trifluorophenyl)-1H-1,2,3-triazol-1-yl]-1-thio-α-D-galactopyranoside

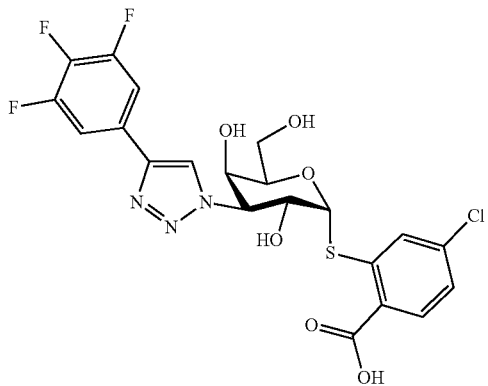

5-Chloro-2-cyanophenyl 3-deoxy-3-[4-(3,4,5-trifluorophenyl)-1H-1,2,3-triazol-1-yl]-1-thio-α-D-galactopyranoside (717 mg, 1.39 mmol) was stirred 5 h under nitrogen at 80° C. in a mixture of EtOH (36 mL) and NaOH (18 mL, 3 M). The mixture was concentrated to approximately 25 mL and acidified to approximately pH 1 with HCl (5 M). The precipitate was isolated by filtration and gave the product (702 mg, 95%). $^1$H NMR (400 MHz, Methanol-$d_4$) δ 8.55 (s, 1H), 7.96-7.88 (m, 2H), 7.70-7.59 (m, 2H), 7.29 (d, J=8.4 Hz, 1H), 6.00 (d, J=5.4 Hz, 1H), 5.09 (dd, J=11.5, 2.7 Hz, 1H), 4.99 (dd, J=11.4, 5.4 Hz, 1H), 4.42 (t, J=6.2 Hz, 1H), 4.22 (s, 1H), 3.76 (dd, J=11.3, 6.0 Hz, 1H), 3.67 (dd, J=11.2, 6.3 Hz, 1H).

4-Chloro-N,N-dimethyl-benzamide-2-yl 3-deoxy-3-[4-(3,4,5-trifluorophenyl)-1H-1,2,3-triazol-1-yl]-1-thio-α-D-galactopyranoside

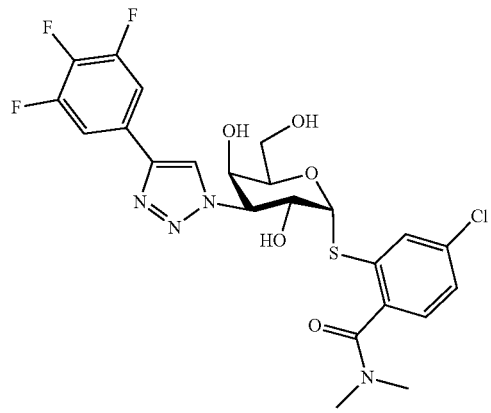

2-Carboxy-5-chlorophenyl 3-deoxy-3-[4-(3,4,5-trifluorophenyl)-1H-1,2,3-triazol-1-yl]-1-thio-α-D-galactopyranoside (473 mg, 0.82 mmol), 1-hydroxybenzotriazole hydrate (195 mg, 1.23 mmol) and N-(3-dimethylaminopropyl)-N'-ethylcarbodiimide hydrochloride (243 mg, 1.23 mmol) were stirred in DMF (3 mL) and dimethylamine (0.82 mL, 2M solution in THF, 1.64 mmol) was added followed by DIEA (0.14 mL, 0.82 mmol). The mixture was stirred 6 h at rt, then water (20 mL) was added and decanted. The residue was stirred in EtOH (5 mL) and NaOH (1.0 mL, 2 M) 1 h at rt, then poured onto ice/water and HCl. The precipitate was collected by filtration and purified by chromatography ($SiO_2$, PE/EtOAc) to afford the product (268 mg, 58%). ESI-MS m/z calcd for $[C_{23}H_{22}ClF_3N_4O_5S]$ $[M+H]^+$: 559.1; found: 558.7. $^1$H NMR (400 MHz, Methanol-$d_4$) δ 8.53 (s, 1H), 7.86 (s, 1H), 7.65 (m, 2H), 7.42 (d, J=8.2 Hz, 1H), 7.27 (d, J=8.2 Hz, 1H), 5.92 (d, J=5.0 Hz, 1H), 4.96 (dd, J=11.4, 2.5 Hz, 1H), 4.90 (dd, J=11.4, 5.0 Hz, 1H), 4.48 (t, J=6.1 Hz, 1H), 4.19 (s, 1H), 3.71 (m, 2H), 3.13 (s, 3H), 2.90 (s, 3H).

143

Intermediate 4

4-Chloro-N,N-dimethyl-benzamide-2-yl 3-[4-(4-chloro-3,5-difluorophenyl)-1H-1,2,3-triazol-1-yl]-3-deoxy-1-thio-α-D-galactopyranoside

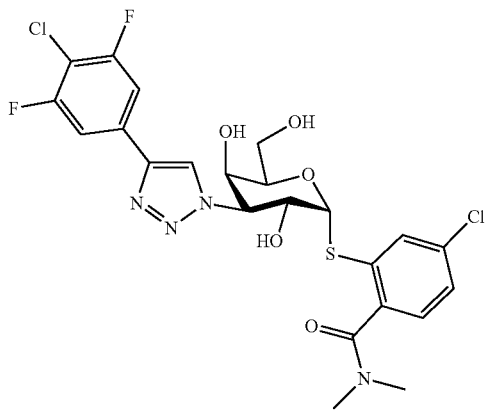

Trimethyl-[2-(4-Chloro-3,5-difluorophenyl)ethynyl]silane

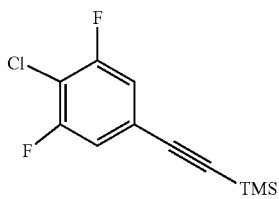 [SMILES: C[Si](C)(C)C#Cc1cc(F)c(Cl)c(F)c1]

Bis(triphenylphosphine)palladium(II) dichloride (1.54 g, 2.15 mmol) and CuI (836 mg, 4.39 mmol) were weighed into a glass flask and purged with nitrogen. THF (50 mL), 5-bromo-2-chloro-1,3-difluoro-benzene (10.0 g, 43.1 mmol), trimethylsilylacetylene (7.42 mL, 52.1 mmol), and DIEA (8.28 mL, 47.4 mmol) were added and the mixture was stirred 16 h at 50° C. The mixture was partitioned between HCl (0.5 M) and EtOAc. The organic phase was separated, evaporated, and the residue was purified by chromatography (SiO$_2$, PE/EtOAc) and gave the product (10.91 g, 100% yield) as a solid. $^1$H NMR (400 MHz, Chloroform-d) δ 7.11-7.04 (m, 2H), 0.26 (s, 9H).

144

5-Chloro-2-cyanophenyl 3-[4-(4-chloro-3,5-difluorophenyl)-1H-1,2,3-triazol-1-yl]-3-deoxy-1-thio-α-D-galactopyranoside

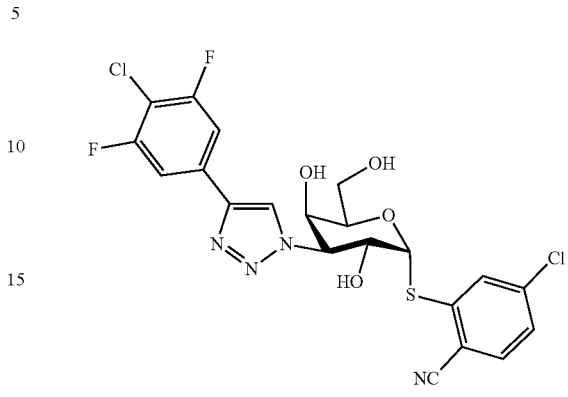

5-Chloro-2-cyanophenyl 2,4,6-tri-O-acetyl-3-azido-3-deoxy-1-thio-α-D-galactopyranoside (1.02 g, 2.1 mmol), trimethyl-[2-(4-chloro-3,5-difluorophenyl)ethynyl]silane (870 mg, 3.2 mmol) and K$_2$CO$_3$ (2.95 g, 21.4 mmol) were weighed into a glass flask and purged with nitrogen. MeOH (10.0 mL) and THF (5.0 mL) were added followed by a solution of copper(II) sulfate pentahydrate (53 mg, 0.21 mmol) and (+)-sodium L-ascorbate (83 mg, 0.42 mmol) in water (5.0 mL). The mixture was stirred 2 h at 60° C. and then copper(II) sulfate pentahydrate (53 mg, 0.21 mmol) and (+)-sodium L-ascorbate (83 mg, 0.42 mmol) were added. Stirring was continued for 4 h at 60° C. The mixture was partioned between water and EtOAc pH was adjusted to approximately 7 with HCl. The mixture was filtered through celite and the organic phase was evaporated. The residue was purified chromatography (SiO$_2$, EtOAc/MeOH) to afford a residue that was recrystallized from hot EtOH and water to give the product (992 mg, 89%). ESI-MS m/z calcd for [C$_{21}$H$_{16}$Cl$_2$F$_2$N$_4$O$_4$S] [M+H]$^+$: 529.0; found: 529.1. $^1$H NMR (400 MHz, Methanol-d$_4$) δ 8.61 (s, 1H), 7.98 (d, J=1.8 Hz, 1H), 7.74 (d, J=8.4 Hz, 1H), 7.66 (d, J=8.0 Hz, 2H), 7.47 (dd, J=8.3, 1.9 Hz, 1H), 6.13 (d, J=5.2 Hz, 1H), 5.07 (dd, J=11.4, 2.6 Hz, 1H), 5.00 (dd, J=11.4, 5.2 Hz, 1H), 4.42 (t, J=6.1 Hz, 1H), 4.27-4.20 (m, 1H), 3.71 (dd, J=11.4, 5.6 Hz, 1H), 3.65 (dd, J=11.4, 6.6 Hz, 1H).

2-Carboxy-5-chlorophenyl 3-[4-(4-chloro-3,5-difluorophenyl)-1H-1,2,3-triazol-1-yl]-3-deoxy-1-thio-α-D-galactopyranoside

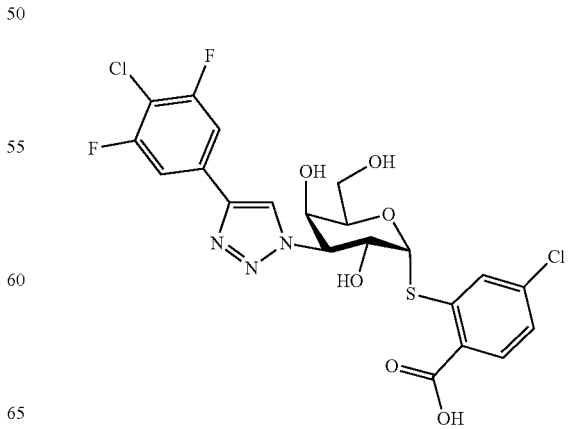

A solution of 5-chloro-2-cyanophenyl 3-[4-(4-chloro-3,5-difluorophenyl)-1H-1,2,3-triazol-1-yl]-3-deoxy-1-thio-α-D-galactopyranoside (3.53 g, 6.67 mmol) in EtOH (180 mL) and NaOH (90 mL, 3 M) was stirred 5 h at 80° C. under nitrogen. The mixture was cooled, concentrated to approximately 90 mL and acidified to approximately pH 1 with HCl (5 M). The precipitate was isolated by filtration, washed with 33% aq MeOH and dried to give the product (3.19 g, 87%). ESI-MS m/z calcd for $[C_{21}H_{17}Cl_2F_2N_3O_6S][M+H]^+$: 548.0; found: 548.1. $^1$H NMR (400 MHz, Methanol-$d_4$) δ 8.60 (s, 1H), 7.96-7.86 (m, 2H), 7.66 (d, J=8.0 Hz, 2H), 7.29 (dd, J=8.4, 1.9 Hz, 1H), 6.00 (d, J=5.4 Hz, 1H), 5.10 (dd, J=11.5, 2.7 Hz, 1H), 4.99 (dd, J=11.5, 5.4 Hz, 1H), 4.42 (t, J=6.2 Hz, 1H), 4.26-4.18 (m, 1H), 3.76 (dd, J=11.3, 6.1 Hz, 1H), 3.67 (dd, J=11.3, 6.3 Hz, 1H).

4-Chloro-N,N-dimethyl-benzamide-2-yl 3-[4-(4-chloro-3,5-difluorophenyl)-1H-1,2,3-triazol-1-yl]-3-deoxy-1-thio-α-D-galactopyranoside

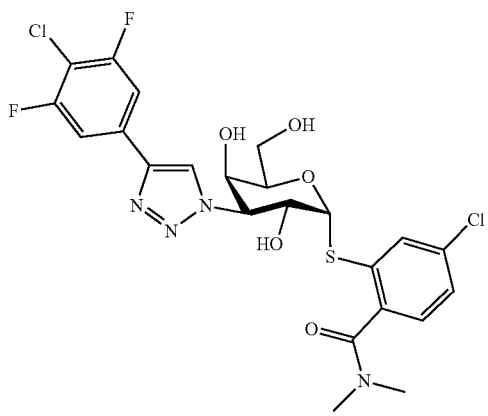

2-Carboxy-5-chlorophenyl 3-[4-(4-chloro-3,5-difluorophenyl)-1H-1,2,3-triazol-1-yl]-3-deoxy-1-thio-α-D-galactopyranoside (450 mg, 0.82 mmol), 1-hydroxybenzotriazole hydrate (195 mg, 1.23 mmol) and N-(3-dimethylaminopropyl)-N'-ethylcarbodiimide hydrochloride (243 mg, 1.23 mmol) were stirred in DMF (3 mL) and dimethylamine (0.82 mL, 2M solution in THF, 1.64 mmol) was added followed by DIEA (0.14 mL, 0.82 mmol). The mixture was stirred 18 h at rt, then water (8 mL) was added and decanted. The residue was stirred in EtOH (3 mL) and NaOH (0.5 mL, 2 M) 1 h at rt, then neutralized with HCl (0.5 mL, 2 M) and poured onto water. The precipitate was collected by filtration and purified by chromatography (SiO$_2$, PE/EtOAc) to afford the product (328 mg, 70%). ESI-MS m/z calcd for $[C_{23}H_{22}Cl_2F_2N_4O_5S]$ $[M+H]^+$: 575.1; found: 575.1. 1H NMR (400 MHz, Methanol-$d_4$) δ 8.59 (s, 1H), 7.86 (s, 1H), 7.69-7.60 (m, 2H), 7.42 (d, J=8.2 Hz, 1H), 7.27 (d, J=8.2 Hz, 1H), 5.92 (d, J=5.0 Hz, 1H), 4.97 (dd, J=11.5, 2.6 Hz, 1H), 4.91 (dd, J=11.4, 5.1 Hz, 1H), 4.48 (t, J=6.1 Hz, 1H), 4.20 (s, 1H), 3.77-3.66 (m, 2H), 3.13 (s, 3H), 2.90 (s, 3H).

Intermediate 6

2-(N-piperidinyl-carbonyl)-5-chlorophenyl 3-[4-(4-chloro-3,5-difluorophenyl)-1H-1,2,3-triazol-1-yl]-3-deoxy-1-thio-α-D-galactopyranoside

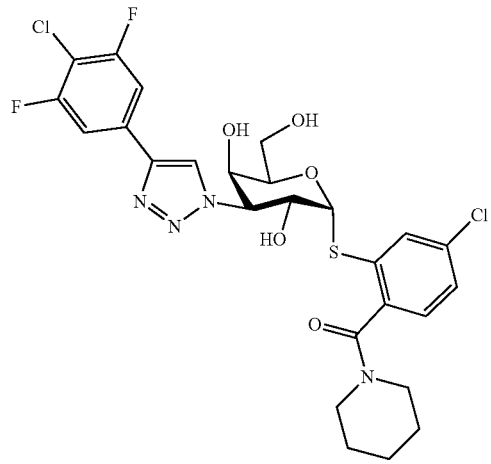

2-Carboxy-5-chlorophenyl 3-[4-(4-chloro-3,5-difluorophenyl)-1H-1,2,3-triazol-1-yl]-3-deoxy-1-thio-α-D-galactopyranoside (150 mg, 0.27 mmol), 1-hydroxybenzotriazole hydrate (62 mg, 0.39 mmol) and N-(3-dimethylaminopropyl)-N'-ethylcarbodiimide hydrochloride (77 mg, 0.39 mmol) were stirred in DMF (1 mL) and piperidine (39 μL, 0.39 mmol) was added followed by Et$_3$N (73 μL, 0.52 mmol). The mixture was stirred 3 h at rt, then water and HCl (1 M) were added. The precipitate was filtered off and recrystallized from EtOH/water. Further purification by chromatography (SiO$_2$, PE/EtOAc) afforded the product (106 mg, 66%). ESI-MS m/z calcd for $[C_{26}H_{26}Cl_2F_2N_4O_5S]$ $[M+H]^+$: 615.1; found: 615.2. $^1$H NMR (400 MHz, Methanol-$d_4$) (two conformational isomers) δ 8.59 (s, 1H), 7.92-7.81 (m, 1H), 7.66 (m, 2H), 7.48-7.35 (m, 1H), 7.30-7.20 (m, 1H), 5.96-5.88 (m, 1H), 5.01-4.86 (m, 2H), 4.54-4.44 (m, 1H), 4.19 (bs, 1H), 3.88-3.61 (m, 4H), 3.29-3.16 (m, 2H), 1.82-1.58 (m, 5H), 1.58-1.41 (m, 1H).

Intermediate 10

2-Bromo-5-chloropyridin-3-yl 3-deoxy-3-[4-(3,4,5-trifluorophenyl)-1H-1,2,3-triazol-1-yl]-2-O-methyl-1-thio-α-D-galactopyranoside

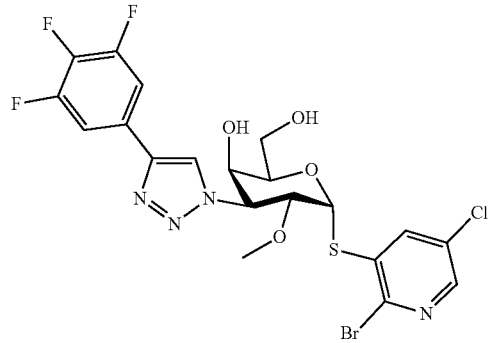

Intermediate 10

2,4,6-Tri-O-acetyl-3-azido-3-deoxy-β-D-galactopyranosyl chloride

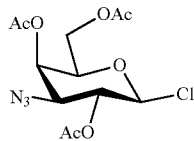

1,2,4,6-Tetra-O-acetyl-3-azido-3-deoxy-s-D-galactopyranoside (12.0 g, 32.1 mmol), PCl$_5$ (7.5 g, 36.0 mmol) and boron trifluoride diethyl etherate (50 μL, 0.41 mmol) were stirred in DCM (150 mL) for 1 h, then partitioned between saturated aq NaHCO$_3$ and DCM. The organic phase was dried, concentrated, and the residue was triturated in diethyl ether/PE to afford the product as a crystalline solid (10.2 g, 91%). 1H NMR (400 MHz, Chloroform-d) δ 5.48 (d, J=3.2 Hz, 1H), 5.34 (t, J=9.2 Hz, 1H), 5.24 (d, J=8.7 Hz, 1H), 4.18 (dd, J=11.5, 6.1 Hz, 1H), 4.10 (dd, J=11.6, 6.7 Hz, 1H), 3.98 (t, J=6.4 Hz, 1H), 3.60 (dd, J=10.3, 3.3 Hz, 1H), 2.20 (s, 3H), 2.17 (s, 3H), 2.07 (s, 3H).

Acetyl 2,4,6-tri-O-acetyl-3-azido-3-deoxy-1-thio-α-D-galactopyranoside

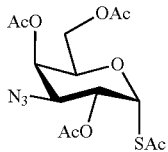

2,4,6-Tri-O-acetyl-3-azido-3-deoxy-s-D-galactopyranosyl chloride (4.0 g, 11.4 mmol) and potassium thioacetate (2.02 g, 17.1 mmol) were stirred in DMF (25 mL) 1 h at 40° C. The dark mixture was partitioned between EtOAc and saturated aq NaHCO$_3$, the organic phase was separated, dried and evaporated. The residue was purified by chromatography (SiO$_2$, PE/EtOAc) to afford the product (2.90 g, 52%). ESI-MS m/z calcd for [C$_{14}$H$_{19}$N$_3$O$_8$S] [M+Na]$^+$: 412.1; found: 411.9. $^1$H NMR (400 MHz, Chloroform-d) δ 6.25 (d, J=5.3 Hz, 1H), 5.43 (d, J=2.9 Hz, 1H), 5.40 (dd, J=11.0, 5.3 Hz, 1H), 4.16-3.97 (m, 3H), 3.71 (dd, J=10.9, 3.3 Hz, 1H), 2.43 (s, 3H), 2.16 (s, 3H), 2.08 (s, 3H), 2.04 (s, 3H).

2-Bromo-5-chloropyridin-3-yl 2,4,6-tri-O-acetyl-3-azido-3-deoxy-1-thio-α-D-galactopyranoside

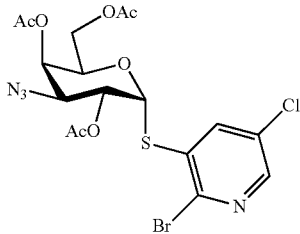

To a solution of acetyl 2,4,6-tri-O-acetyl-3-azido-3-deoxy-1-thio-α-D-galactopyranoside (WO2016120403) (2.46 g, 5.05 mmol) and 2-bromo-5-chloro-3-fluoropyridine (1.74 g, 8.0 mmol) in DMF (10 mL) diethylamine (1.60 mL, 15.5 mmol) was added. The mixture was stirred 1 h at rt, water and HCl (5.0 mL, 5 M, 25 mmol) was added, the solvents were decanted, the sticky residue was partitioned between DCM and water. The organic phase was evaporated, and the residue was purified by chromatography (SiO$_2$, PE/EtOAc) to afford the product (1.36 g, 50%). ESI-MS m/z calcd for [C$_{17}$H$_{18}$BrClN$_4$O$_7$S] [M+H]$^+$: 537.0; found: 537.0. $^1$H NMR (400 MHz, Chloroform-d) δ 8.20 (d, J=2.4 Hz, 1H), 7.83 (d, J=2.4 Hz, 1H), 6.13 (d, J=5.6 Hz, 1H), 5.50 (d, J=2.9 Hz, 1H), 5.35 (dd, J=11.0, 5.5 Hz, 1H), 4.54 (dd, J=7.7, 4.8 Hz, 1H), 4.17-3.99 (m, 3H), 2.21 (s, 3H), 2.18 (s, 3H), 1.97 (s, 3H).

2-Bromo-5-chloropyridin-3-yl 3-deoxy-3-[4-(3,4,5-trifluorophenyl)-1H-1,2,3-triazol-1-yl]-1-thio-α-D-galactopyranoside

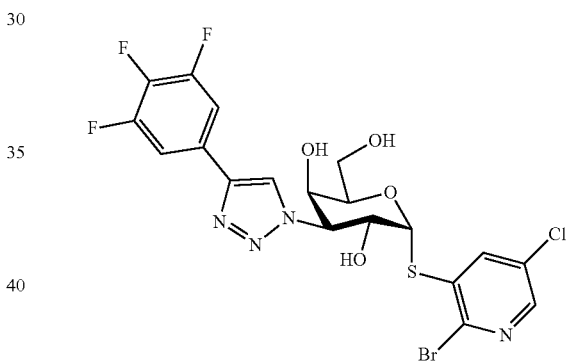

A solution of copper(II) sulfate pentahydrate (63 mg, 0.25 mmol) and (+)-sodium L-ascorbate (100 mg, 0.50 mmol) in water (5 mL) was added to a solution of 2-bromo-5-chloropyridin-3-yl 2,4,6-tri-O-acetyl-3-azido-3-deoxy-1-thio-α-D-galactopyranoside (1.35 g, 2.51 mmol), trimethyl-[2-(3,4,5-trifluorophenyl)ethynyl]silane (860 mg, 3.77 mmol) and K$_2$CO$_3$ (3.47 g, 25.1 mmol) in MeOH/THF (80 mL). The mixture was stirred 24 h at 50° C., concentrated and partitioned between EtOAc and water. The organic phase was dried, evaporated and purified by chromatography (SiO$_2$, PE/EtOAc) to afford the product (1.03 g, 72% yield). ESI-MS m/z calcd for [C$_{19}$H$_{15}$BrClF$_3$N$_4$O$_4$S][M+H]$^+$: 567.0; found: 567.0. $^1$H NMR (400 MHz, Methanol-d$_4$) δ 8.56 (s, 1H), 8.18 (d, J=2.5 Hz, 2H), 7.68-7.58 (m, 2H), 6.15 (d, J=5.1 Hz, 1H), 5.08 (dd, J=11.4, 2.5 Hz, 1H), 5.02 (dd, J=11.4, 5.1 Hz, 1H), 4.36 (t, J=6.1 Hz, 1H), 4.23 (d, J=2.1 Hz, 1H), 3.75-3.64 (m, 2H).

2-Bromo-5-chloropyridin-3-yl 4,6-O-benzylidene-3-deoxy-3-[4-(3,4,5-trifluorophenyl)-1H-1,2,3-triazol-1-yl]-1-thio-α-D-galactopyranoside

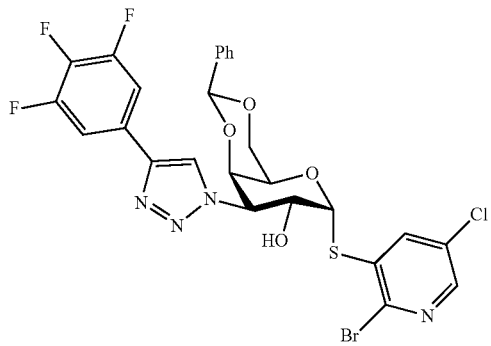

2-Bromo-5-chloropyridin-3-yl 3-deoxy-3-[4-(3,4,5-trifluorophenyl)-1H-1,2,3-triazol-1-yl]-1-thio-α-D-galactopyranoside (2.04 g, 3.59 mmol) was stirred in MeCN (25 mL) and benzaldehyde dimethylacetal (0.76 mL, 5.04 mmol) followed by p-toluenesulfonic acid monohydrate (5 mg, 0.023 mmol) were added. The mixture was stirred 18 h at rt and Et$_3$N (15 µL, 0.26 mmol) followed by water (15 mL) were added. The solids were filtered off and washed first with 33% aq MeOH then PE. The solids were dried to afford the product (1.99 g, 85%). ESI-MS m/z calcd for [C$_{26}$H$_{19}$BrClF$_3$N$_4$O$_4$S] [M+H]$^+$: 655.0; found: 654.7. $^1$H NMR (400 MHz, DMSO-d$_6$) δ 8.86 (s, 1H), 8.32 (d, J=2.3 Hz, 1H), 8.20 (d, J=2.4 Hz, 1H), 7.79 (m, 2H), 7.42-7.30 (m, 5H), 6.48 (d, J=5.3 Hz, 1H), 6.29 (d, J=4.9 Hz, 1H), 5.58 (s, 1H), 5.18 (dd, J=11.3, 3.2 Hz, 1H), 4.98 (m, 1H), 4.59 (d, J=3.0 Hz, 1H), 4.18 (s, 1H), 4.11 (d, J=11.7 Hz, 1H), 3.96 (d, J=12.6 Hz, 1H).

2-Bromo-5-chloropyridin-3-yl 3-deoxy-3-[4-(3,4,5-trifluorophenyl)-1H-1,2,3-triazol-1-yl]-2-O-methyl-1-thio-α-D-galactopyranoside

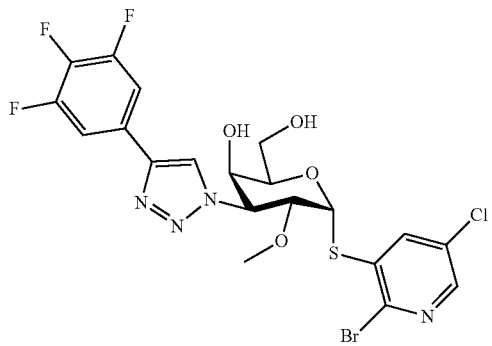

Iodomethane (133 µL, 2.13 mmol) was added to a solution of 2-bromo-5-chloropyridin-3-yl 4,6-O-benzylidene-3-deoxy-3-[4-(3,4,5-trifluorophenyl)-1H-1,2,3-triazol-1-yl]-1-thio-α-D-galactopyranoside (700 mg, 1.07 mmol) and Ag$_2$O (495 mg, 2.13 mmol) in DMF (8 mL). After stirring 48 h at rt the mixture was diluted with EtOAc, washed twice with water and the organic phase was dried and evaporated. The residue was dissolved in TFA/water (8 mL, 4:1), stirred 3 h at rt before partitioned between EtOAc and aq NaOH (1 M). The organic phase was dried, evaporated and purified by chromatography (SiO$_2$, PE/EtOAc) to afford the product (314 mg, 50%). ESI-MS m/z calcd for [C$_{20}$H$_{17}$BrClF$_3$N$_4$O$_4$S] [M+H]$^+$: 581.0; found: 581.0. $^1$H NMR (400 MHz, Methanol-d$_4$) δ 8.60 (s, 1H), 8.24-8.21 (m, 2H), 7.66 (dd, J=8.7, 6.7 Hz, 2H), 6.48 (d, J=5.3 Hz, 1H), 5.08 (dd, J=11.4, 2.9 Hz, 1H), 4.72 (dd, J=11.3, 2.9 Hz, 1H), 4.35 (t, J=6.1 Hz, 1H), 4.20 (d, J=2.6 Hz, 1H), 3.74-3.64 (m, 2H), 3.43 (s, 3H).

Intermediate 11

5-Chloro-2-{N-(2-oxa)-6-azaspiro[3.3]heptanyl}-pyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

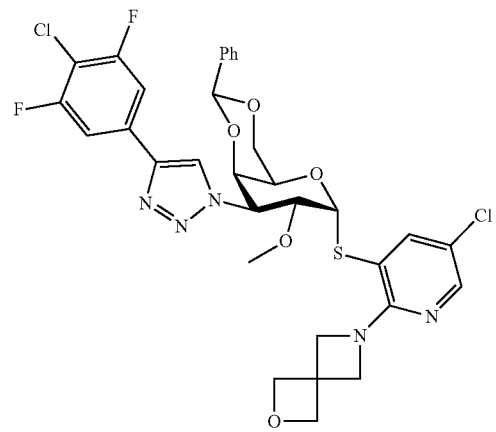

2-Bromo-5-chloropyridin-3-yl 3-azido-3-deoxy-1-thio-α-D-galactopyranoside

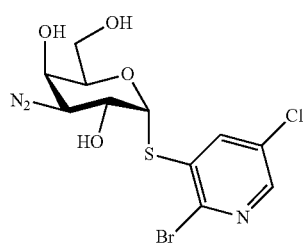

To a solution of 2-bromo-5-chloro-3-pyridine-3-yl 2,4,6-tri-O-acetyl-3-azido-3-deoxy-1-thio-α-D-galactopyranoside (770 mg, 1.43 mmol) in MeOH (5.0 mL) catalytical amount of sodium methanolate (pH=9-10) was added. The reaction was stirred 20 min and neutralized with acidic ion resin and filtered. The filtrate was concentrated to give the crude product (350 mg, 78%). ESI-MS m/z calcd for [C$_{11}$H$_{12}$BrClN$_4$O$_4$S] [M+H]$^+$: 411.0; found: 411.0.

2-Bromo-5-chloropyridin-3-yl 3-azido-4,6-O-benzylidene-3-deoxy-1-thio-α-D-galactopyranoside

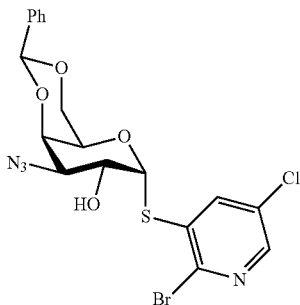

To a stirred solution of 2-bromo-5-chloropyridin-3-yl 3-azido-3-deoxy-1-thio-α-D-galactopyranoside (350 mg, 0.66 mmol) in DMF (5 mL) benzaldehyde dimethylacetal (404 mg, 2.65 mmol) was added followed by D(+)-10-camphorsulfonic acid (30.8 mg, 0.13 mmol). The mixture was stirred 4 h at 50° C. under vacuum using a water-pump.

After cooling to rt, the reaction was poured into water (15 mL) and extracted with EtOAc (2×10 mL). The combined organic layers were concentrated in vacuum and the residue was purified by column chromatography (PE/EtOAc=10/1~5/1, Silica-CS 12 g, 20 m/min, silica gel, UV 254) to give the product (300 mg, 91%) as a white solid. ESI-MS m/z calcd for [$C_{18}H_{16}BrClN_4O_4S$] [M+H]$^+$: 499.0, found: 499.0. $^1$H NMR (400 MHz, CDCl$_3$) δ 8.09 (d, J=2.3 Hz, 1H), 7.82 (d, J=2.3 Hz, 1H), 7.45 (dd, J=7.5, 1.9 Hz, 2H), 7.38-7.27 (m, 3H), 5.91 (d, J=5.3 Hz, 1H), 5.58 (s, 1H), 4.64 (dt, J=10.8, 5.4 Hz, 1H), 4.36 (d, J=3.0 Hz, 1H), 4.18 (dd, J=12.8, 1.4 Hz, 1H), 4.07-3.97 (m, 2H), 3.65 (dd, J=10.8, 3.3 Hz, 1H), 2.59 (d, J=5.7 Hz, 1H).

2-Bromo-5-chloropyridin-3-yl 3-azido-4,6-O-benzylidene-3-deoxy-2-O-methyl-1-thio-α-D-galactopyranoside

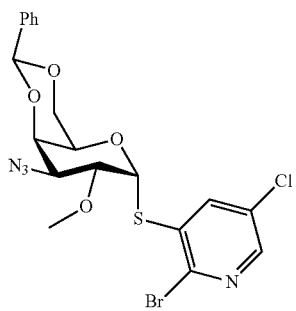

2-Bromo-5-chloro-3-pyridine-3-yl 3-azido-4,6-O-benzylidene-3-deoxy-1-thio-α-D-galactopyranoside (300 mg, 0.60 mmol) was dissolved in DMF (8.0 mL) and Ag$_2$O (696 mg, 3.00 mmol) was added followed by iodomethane (426 mg, 3.00 mmol). The reaction was stirred 48 h at rt and filtered. The filtrares was evaporated in vacuum and the residue was purified by column chromatography (PE/EtOAc=10/1~5/1, Silica-CS 12 g, 20 m/min, silica gel, UV 254) to give the product (240 mg, 78%) as a white solid. $^1$H NMR (400 MHz, CDCl$_3$) δ 8.08 (d, J=2.4 Hz, 1H), 7.81 (t, J=3.6 Hz, 1H), 7.46 (dd, J=7.5, 1.9 Hz, 2H), 7.31 (ddd, J=6.7, 5.1, 1.5 Hz, 3H), 6.09 (d, J=5.2 Hz, 1H), 5.56 (s, 1H), 4.28-4.21 (m, 2H), 4.13 (dd, J=12.7, 1.5 Hz, 1H), 4.07-4.04 (m, 1H), 3.96 (s, 1H), 3.76 (dd, J=10.6, 3.3 Hz, 1H), 3.50 (s, 3H).

5-Chloro-2-{N-(2-oxa)-6-azaspiro[3.3]heptanyl}-pyridin-3-yl 3-azido-4,6-O-benzylidene-3-deoxy-2-O-methyl-1-thio-α-D-galactopyranoside

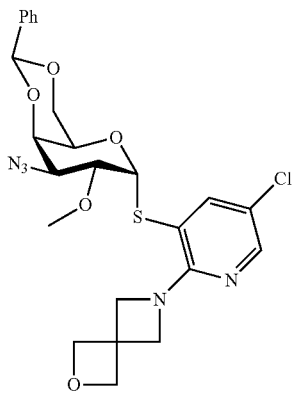

To a solution of 2-bromo-5-chloropyridin-3-yl 3-azido-4,6-O-benzylidene-3-deoxy-2-O-methyl-1-thio-α-D-galactopyranoside (400 mg, 0.78 mmol) and 2-oxa-6-azaspiro[3.3]heptane; oxalic acid (736 mg, 3.89 mmol) in DMF (5 mL) DIEA (1.33 mL, 7.79 mmol) was added. The mixture was stirred 4 h at 130° C. in a microwave reactor. The solvent was removed, and the residue was purified by column chromatography (PE/EtOAc=5/1~2/1, Silica-CS 20 g, 20 mL/min, silica gel, UV 254) to give the product (190 mg, 46%) as a white solid. ESI-MS m/z calcd for [$C_{24}H_{26}ClN_5O_5S$][M+H]$^+$: 532.1; found: 532.2. $^1$H NMR (400 MHz, CDCl$_3$) δ 8.01 (d, J=2.4 Hz, 1H), 7.59 (d, J=2.4 Hz, 1H), 7.54-7.45 (m, 2H), 7.40-7.32 (m, 3H), 5.84 (d, J=5.2 Hz, 1H), 5.60 (s, 1H), 4.90-4.76 (m, 4H), 4.40 (d, J=9.2 Hz, 2H), 4.32 (d, J=3.2 Hz, 1H), 4.27 (d, J=9.2 Hz, 2H), 4.23-4.06 (m, 4H), 3.72 (dd, J=10.4, 3.2 Hz, 1H), 3.54 (s, 3H).

5-Chloro-2-{N-(2-oxa)-6-azaspiro[3.3]heptanyl}-pyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

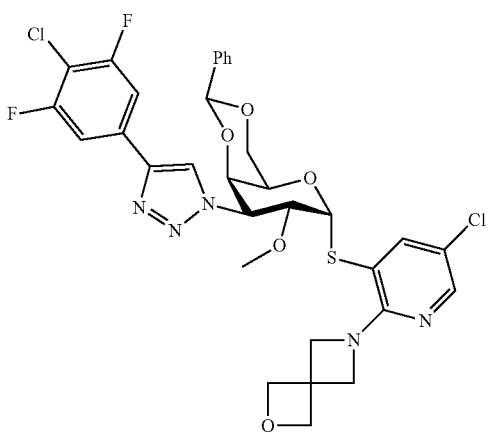

To a solution of 5-chloro-2-{N-(2-oxa)-6-azaspiro[3.3]heptanyl}-pyridin-3-yl 3-azido-4,6-O-benzylidene-3-deoxy-2-O-methyl-1-thio-α-D-galactopyranoside (130 mg, 0.244 mmol) and trimethyl-[2-(4-chloro-3,5-difluorophenyl)ethynyl]silane (60.0%, 120 mg, 0.29 mmol) in DMF (4 mL) (+)-sodium L-ascorbate (72.6 mg, 0.37 mmol) and copper(II) sulfate pentahydrate (30.5 mg, 0.12 mmol) were added. The mixture was stirred 4 h at rt under a nitrogen atmosphere. After diluting with water (20 mL), the mixture was extracted with EtOAc (3×10 mL). The combined organic layers were washed with brine, dried over anhydrous $Na_2SO_4$ and concentrated in vacuo. The residue was purified by preparative HPLC (Method A) to give the product (115 mg, 67%) as a white solid. ESI-MS m/z calcd for [$C_{32}H_{29}Cl_2F_2N_5O_5S$] [M+H]$^+$: 704.1; found: 704.2. $^1$H NMR (400 MHz, $CDCl_3$) δ 8.05 (d, J=2.4 Hz, 1H), 7.98 (s, 1H), 7.63 (d, J=2.4 Hz, 1H), 7.47-7.42 (m, 2H), 7.39 (s, 5H), 5.95 (d, J=5.2 Hz, 1H), 5.52 (s, 1H), 5.33 (dd, J=11.2, 2.8 Hz, 1H), 4.87-4.79 (m, 4H), 4.50 (d, J=2.8 Hz, 1H), 4.46 (dd, J=11.2, 5.2 Hz, 1H), 4.40 (d, J=9.2 Hz, 2H), 4.30 (d, J=9.2 Hz, 2H), 4.25 (s, 2H), 4.13 (dd, J=12.8, 2.0 Hz, 1H), 3.29 (s, 3H).

Intermediate 12

5-Chloro-2-cyanopyridin-3-yl 4,6-O-benzylidene-3-deoxy-3-[4-(3,5-difluoro-4-methylphenyl)-1H-1,2,3-triazol-1-yl]-2-O-methyl-1-thio-α-D-galactopyranoside

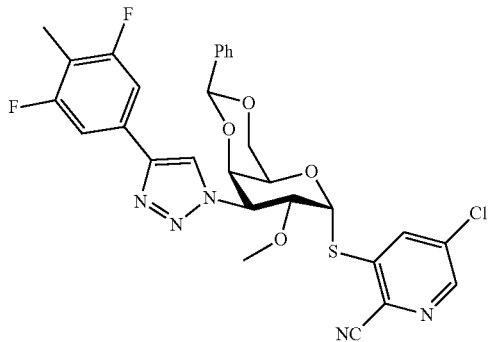

5-Chloro-2-cyanopyridin-3-yl 3-azido-4,6-O-benzylidene-3-deoxy-2-O-methyl-1-thio-α-D-galactopyranoside

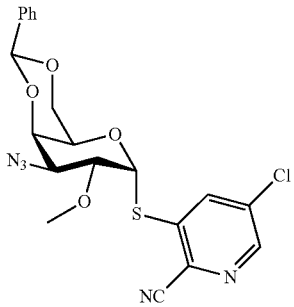

To a solution of 2-bromo-5-chloro-3-pyridine-3-yl 3-azido-4,6-O-benzylidene-3-deoxy-2-O-methyl-1-thio-α-D-galactopyranoside (230 mg, 0.45 mmol) in DMF (4.0 mL), Zn (14.6 mg, 0.22 mmol), $Zn(CN)_2$ (52.6 mg, 0.45 mmol), 1,1'-bis(diphenylphosphino)ferrocene (20.2 mg, 0.036 mmol) and $Pd_2$(dibenzylideneacetone)$_3$ (32.8 mg, 0.036 mmol) were added. The mixture was stirred 3 h at 100° C. under a nitrogen atmosphere. The solvent was removed under reduced pressure and the residue was purified by column chromatography (PE/EtOAc=10/1~5/1, Silica-CS 12 g, 20 mL/min, silica gel, UV 254) to give the product (105 mg, 51%). ESI-MS m/z calcd for [$C_{20}H_{18}ClN_5O_4S$] [M+H]$^+$: 460.0, found: 460.0. $^1$H NMR (400 MHz, $CDCl_3$) δ 8.52 (d, J=2.0 Hz, 1H), 8.06 (d, J=2.0 Hz, 1H), 7.53-7.51 (m, 2H), 7.41-7.37 (m, 3H), 6.15 (d, J=5.2 Hz, 1H), 5.64 (s, 1H), 4.37 (d, J=2.8 Hz, 1H), 4.30 (dd, J=10.8, 5.2 Hz, 1H), 4.18 (d, J=1.6 Hz, 1H), 4.15-4.12 (m, 2H), 3.79 (dd, J=10.8, 3.2 Hz, 1H), 3.61 (s, 3H).

5-Chloro-2-cyanopyridin-3-yl 4,6-O-benzylidene-3-deoxy-3-[4-(3,5-difluoro-4-methylphenyl)-1H-1,2,3-triazol-1-yl]-2-O-methyl-1-thio-α-D-galactopyranoside

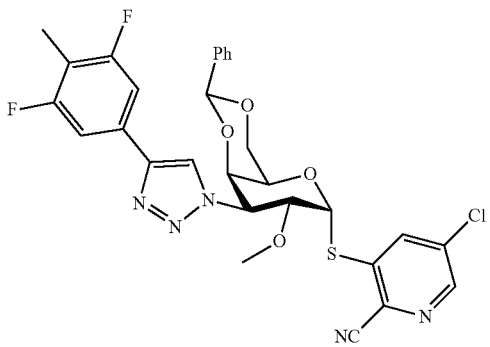

To a solution of 2-bromo-5-chloro-3-pyridine-3-yl 3-azido-4,6-O-benzylidene-3-deoxy-2-O-methyl-1-thio-α-D-galactopyranoside (100 mg, 0.22 mmol) and trimethyl-[2-(3,5-difluoro-4-methylphenyl)ethynyl]silane (70.0%, 58.5 mg, 0.18 mmol) in DMF (4 mL) (+)-sodium L-ascorbate (64.6 mg, 0.33 mmol) and copper(II) sulfate pentahydrate (27.1 mg, 0.11 mmol) were added. The mixture was stirred 4 h at rt under a nitrogen atmosphere. After diluting with water (20 mL), the mixture was extracted with EtOAc (3×10 mL). The combined organic layers were washed with brine, dried over anhydrous $Na_2SO_4$ and concentrated in vacuo. The residue was purified by preparative HPLC (Method A) to give the product (80.0 mg, 60%) as a white solid. ESI-MS m/z calcd for $[C_{29}H_{24}ClF_2N_5O_4S]$ $[M+H]^+$: 612.1; found: 612.1. $^1$H NMR (400 MHz, $CDCl_3$) δ 8.56 (d, J=2.0 Hz, 1H), 8.08 (d, J=2.0 Hz, 1H), 7.97 (s, 1H), 7.44-7.36 (m, 5H), 7.31 (m, 2H), 6.24 (d, J=4.8 Hz, 1H), 5.54 (s, 1H), 5.31 (dd, J=11.2, 2.8 Hz, 1H), 4.58 (dd, J=11.2, 5.2 Hz, 1H), 4.54 (d, J=2.8 Hz, 1H), 4.39 (s, 1H), 4.28 (dd, J=12.8, 1.2 Hz, 1H), 4.16 (dd, J=12.8, 1.2 Hz, 1H), 3.37 (s, 3H), 2.22 (s, 3H).

Intermediate 13

5-Chloro-2-cyanopyridin-3-yl 4,6-O-benzylidene-3-deoxy-3-[4-(3-fluoro-4-methylphenyl)-1H-1,2,3-triazol-1-yl]-2-O-methyl-1-thio-α-D-galactopyranoside

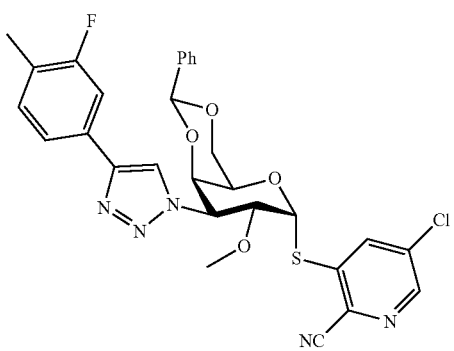

To a solution of 5-chloro-2-cyanopyridin-3-yl 3-azido-4,6-O-benzylidene-3-deoxy-2-O-methyl-1-thio-α-D-galactopyranoside (110 mg, 0.24 mmol) and trimethyl-[2-(3-fluoro-4-methylphenyl)ethynyl]silane (98.7 mg, 0.48 mmol) in DMF (5 mL) (+)-sodium L-ascorbate (94.8 mg, 0.48 mmol) and copper(II) sulfate pentahydrate (29.9 mg, 0.12 mmol) were added. The mixture was stirred overnight at rt under nitrogen atmosphere. The solvent was removed under reduced pressure and the residue was purified by preparative HPLC (Method A) to give the product (35 mg, 25%). ESI-MS m/z calcd for $[C_{29}H_{25}ClFN_5O_4S]$ $[M+H]^+$: 594.1; found: 594.1. $^1$H NMR (400 MHz, $CDCl_3$) δ 8.50 (d, J=1.2 Hz, 1H), 8.02 (s, 1H), 7.92 (s, 1H), 7.38-7.34 (m, 7H), 7.17-7.14 (m, 1H), 6.18 (d, J=4.8 Hz, 1H), 5.49 (s, 1H), 5.25 (d, J=10.8 Hz, 1H), 4.53 (m, 2H), 4.33 (s, 1H), 4.21 (d, J=12.4 Hz, 1H), 4.11 (d, J=12.4 Hz, 1H), 3.31 (s, 3H), 2.24 (d, J=1.2 Hz, 3H).

Intermediate 14

5-Chloro-2-cyanophenyl 4,6-di-O-acetyl-3-deoxy-3-[4-(3,5-difluoro-4-methylphenyl)-1H-1,2,3-triazol-1-yl]-2-O-methyl-1-thio-α-D-galactopyranoside

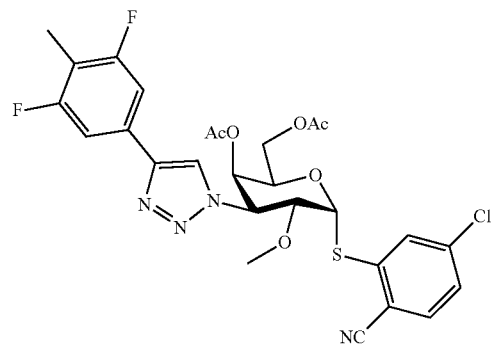

3-Azido-4,6-O-benzylidene-3-deoxy-D-galactopyranose

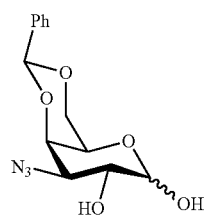

To a solution of 3-azido-3-deoxy-D-galactopyranose (Lowary, T. L.; Hindsgaul, O. Recognition of Synthetic O-Methyl, Epimeric, and Amino Analogues of the Acceptor A-L-Fucp-(1→2)-B-D-Galp- or Glycosyltransferases. *Carbohydrate Research* 1994, 251, 33-67.) (16.4 g, 79.9 mmol) in DMF (120 mL) benzaldehyde dimethylacetal (18.2 g, 120 mmol) was added followed by D(+)-10-Camphorsulfonic acid (3.71 g, 16.0 mmol). The mixture was stirred 4 h at 50° C. The mixture was added dropwise to saturated aq $NaHCO_3$ (200 mL). The mixture was filtered and the white solid was washed with water and dried in vacuum to afford the product (15.0 g, 64%, α/β=1:1).

3-Azido-4,6-O-benzylidene-3-deoxy-α-D-galactopyranose $^1$H NMR (400 MHz, CD$_3$OD) δ 7.51-7.53 (m, 2H), 7.35-7.39 (m, 3H), 5.65 (s, 1H), 5.25 (d, J=3.2 Hz, 1H, H-1α), 3.35-3.45 (m, 6H).

3-Azido-4,6-O-benzylidene-3-deoxy-beta-D-galactopyranose $^1$H NMR (400 MHz, CD$_3$OD) δ 7.51-7.53 (m, 2H), 7.35-7.39 (m, 3H), 5.65 (s, 1H), 4.58 (d, J=7.6 Hz, 1H, H-1β), 3.35-3.45 (m, 6H).

Methyl 3-azido-4,6-O-benzylidene-3-deoxy-2-O-methyl-D-galactopyranoside

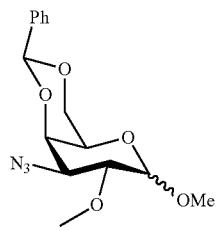

To a solution of 3-azido-4,6-O-benzylidene-3-deoxy-D-galactopyranose (5.00 g, 17.0 mmol) in DMF (40 mL) NaH (60% in oil, 1.96 g, 51.1 mmol) was added at 0° C. under a nitrogen atmosphere and the mixture was stirred 20 min. Iodomethane (3.18 mL, 51.1 mmol) was added and the mixture was stirred 1 h at rt. After diluting with water (50 mL), the mixture was extracted with EtOAc (3×50 mL). The combined organic layers were washed with brine, dried over Na$_2$SO$_4$ and concentrated in vacuo. The residue was purified by column chromatography (PE/EtOAc=10/1~1/1, Silica-CS 20 g, 25 mL/min, silica gel, UV 254) to give the product (5.10 g, 93%, α/β=0.5:1).

Methyl 3-azido-4,6-O-benzylidene-3-deoxy-2-O-methyl-α-D-galactopyranoside $^1$H NMR (400 MHz, CD$_3$OD) δ 7.42-7.44 (m, 2H), 7.27-7.29 (m, 3H), 5.56 (s, 1H), 4.99 (d, J=3.2 Hz, 1H, H-1α), 3.62-4.27 (m, 4H), 3.44 (s, 3H), 3.39 (s, 3H), 3.32-3.40 (m, 1H), 3.23-3.25 (m, 1H).

Methyl 3-azido-4,6-O-benzylidene-3-deoxy-2-O-methyl-β-D-galactopyranoside $^1$H NMR (400 MHz, CD$_3$OD) δ 7.42-7.44 (m, 2H), 7.27-7.29 (m, 3H), 5.55 (s, 1H), 4.31 (d, J=7.6 Hz, 1H, H-1β), 3.62-4.27 (m, 4H), 3.51 (s, 3H), 3.49 (s, 3H), 3.32-3.40 (m, 1H), 3.23-3.25 (m, 1H).

Acetyl 4,6-di-O-acetyl-3-azido-3-deoxy-2-O-methyl-D-galactopyranoside

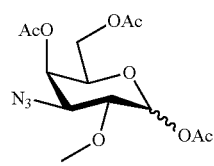

To a solution of methyl 3-azido-4,6-O-benzylidene-3-deoxy-2-O-methyl-D-galactopyranoside (5.10 g, 15.9 mmol) in acetic anhydride (40.0 mL) and acetic acid (20 mL), drops of concentrated H$_2$SO$_4$ was added at 0° C. The mixture was stirred 4 h at 0° C., followed by dropwise addition to a saturated aq NaHCO$_3$ solution. The mixture was extracted with DCM (3×100 mL). The combined organic layers were washed with brine, dried over Na$_2$SO$_4$ and concentrated in vacuo. The residue was purified by column chromatography (PE/EtOAc=10/1~1/1, Silica-CS 4 g, 12 mL/min, silica gel, UV 254). The obtained material was suspended in EtOAc (4.00 mL). The mixture was heated to 60° C., then cooled to 25° C. and n-heptane (20.0 mL) was added while stirring. The mixture was cooled to 0° C. and stirred for 1 h, filtered, washed with n-heptane/EtOAc (4:1, 10 mL), to give the product (1.2 g) as a white solid used as is in the next step. $^1$H NMR (400 MHz, CDCl$_3$) δ 6.38 (d, J=3.6 Hz, 1H), 5.33 (dd, J=3.2, 1.2 Hz, 1H), 4.14-4.17 (m, 1H), 3.91-4.03 (m, 2H), 3.80 (dd, J=6.4, 3.2 Hz, 1H), 3.62 (dd, J=10.4, 3.6 Hz, 1H), 3.43 (s, 3H), 2.11 (s, 3H), 2.10 (s, 3H), 1.98 (s, 3H).

Acetyl 4,6-di-O-acetyl-3-azido-3-deoxy-2-O-methyl-1-thio-D-galactopyranoside

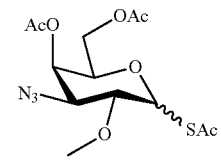

To a solution of acetyl 4,6-di-O-acetyl-3-azido-3-deoxy-2-O-methyl-D-galactopyranoside (1.17 g, 3.39 mmol) in DCM (15 mL) PCl$_5$ (1.06 g, 5.08 mmol) was added followed by boron trifluoride diethyl etherate (0.209 mL, 1.69 mmol) at 30° C. under a nitrogen atmosphere. The mixture was stirred 30 min at 30° C. followed by dropwise addition to a saturated aq NaHCO$_3$ solution. The mixture was extracted with DCM (3×100 mL). The combined organic layers were washed with brine, dried over Na$_2$SO$_4$ and concentrated in vacuum. The residue was dissolved in DMF (4.0 mL) and potassium thioacetate (731 mg, 6.4 mmol) was added. The mixture was stirred overnight at rt under a nitrogen atmosphere. After diluting with water (50 mL), the mixture was extracted with EtOAc (3×30 mL). The combined organic layers were washed with brine, dried over Na$_2$SO$_4$ and concentrated in vacuum. The residue was purified by column chromatography (PE/EtOAc=10/1~3/1, Silica-CS 20 g, 18 mL/min, silica gel, UV 254) to give the product (1.15 g, 75%, α/β=0.23:1).

Acetyl 4,6-di-O-acetyl-3-azido-2-O-methyl-3-deoxy-1-thio-α-D-galactopyranoside $^1$H NMR (400 MHz, CDCl$_3$) δ 6.25 (d, J=5.2 Hz, 1H, H-1α), 5.27-5.29 (m, 1H), 3.85-4.08 (m, 4H), 3.42-3.45 (m, 1H), 3.39 (s, 3H), 2.39 (s, 3H), 2.09 (s, 3H), 1.97 (s, 3H).

Acetyl 4,6-di-O-acetyl-3-azido-2-O-methyl-3-deoxy-1-thio-β-D-galactopyranoside $^1$H NMR (400 MHz, CDCl$_3$) δ 5.32-5.33 (m, 1H), 5.04 (d, J=10.0 Hz, 1H, H-1β), 3.85-4.08 (m, 3H), 3.57 (dd, J=9.2, 3.2 Hz, 1H), 3.52 (s, 3H), 3.33 (t, J=9.6 Hz, 1H), 2.36 (s, 3H), 2.08 (s, 3H), 1.97 (s, 3H).

5-Chloro-2-cyanophenyl 4,6-di-O-acetyl-3-azido-3-deoxy-2-O-methyl-1-thio-D-galactopyranoside

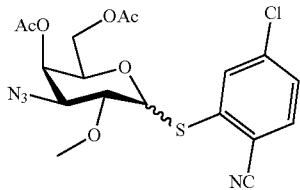

To a solution of acetyl 4,6-di-O-acetyl-3-azido-3-deoxy-2-O-methyl-1-thio-D-galactopyranoside (300 mg, 0.83 mmol) and 4-chloro-2-fluoro-benzonitrile (250 mg, 1.61 mmol) in DMF (5.0 mL) diethylamine (121 mg, 1.66 mmol) was added. The mixture was stirred overnight at rt under nitrogen atmosphere. After diluting with water (20 mL), the mixture was extracted with EtOAc (3×10 mL). The combined organic layers were washed with brine, dried over anhydrous $Na_2SO_4$ and concentrated in vacuo. The residue was purified by column chromatography (PE/EtOAc=10/1~3/1, Silica-CS 4 g, 12 mL/min, silica gel, UV 254) to give the product (180 mg, 62%, α/β=0.44/1). ESI-MS m/z calcd for $[C_{18}H_{19}ClN_4O_6S]$ $[M+H]^+$: 455.1; found: 455.0.

5-Chloro-2-cyanophenyl 4,6-di-O-acetyl-3-azido-3-deoxy-2-O-methyl-1-thio-α-D-galactopyranoside $^1$H NMR (400 MHz, $CDCl_3$): δ 7.64 (d, J=2.0 Hz, 1H), 7.57-7.53 (m, 1H), 7.33-7.27 (m, 1H), 6.04 (d, J=5.2 Hz, 1H, H-1α), 5.34 (d, J=3.2 Hz, 1H), 4.47-4.46 (m, 1H), 4.08-3.78 (m, 3H), 3.54 (s, 3H), 3.44-3.34 (m, 1H), 2.09 (s, 3H), 1.98 (s, 3H).

5-Chloro-2-cyanophenyl 4,6-di-O-acetyl-3-azido-3-deoxy-2-O-methyl-1-thio-α-D-galactopyranoside $^1$H NMR (400 MHz, $CDCl_3$): δ 7.69 (d, J=2.0 Hz, 1H), 7.57-7.53 (m, 1H), 7.33-7.27 (m, 1H), 5.33 (d, J=3.2 Hz, 1H), 4.66 (d, J=9.2 Hz, 1H, H-1β), 4.08-3.78 (m, 3H), 3.61 (s, 3H), 3.57-3.55 (m, 1H), 3.43-3.33 (m, 1H), 2.12 (s, 3H), 2.01 (s, 3H).

5-Chloro-2-cyanophenyl 4,6-di-O-acetyl-3-deoxy-3-[4-(3,5-difluoro-4-methylphenyl)-1H-1,2,3-triazol-1-yl]-2-O-methyl-1-thio-α-D-galactopyranoside

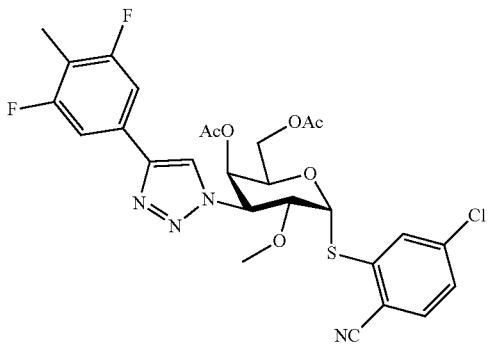

To a solution of 5-chloro-2-cyanophenyl 4,6-di-O-acetyl-3-azido-3-deoxy-2-O-methyl-1-thio-D-galactopyranoside (260 mg, 0.57 mmol) and trimethyl-[2-(3,5-difluoro-4-methylphenyl)ethynyl]silane (247 mg, 1.10 mmol) in DMF (6 mL) copper(II) sulfate pentahydrate (71.4 mg, 0.29 mmol) and (+)-sodium L-ascorbate (113 mg, 0.57 mmol) were added. The mixture was stirred 3 h at rt under nitrogen atmosphere. After diluting with water (20 mL), the mixture was extracted with EtOAc (3×10 mL). The combined organic layers were washed with brine, dried over anhydrous $Na_2SO_4$ and concentrated in vacuo. The residue was purified by column chromatography (PE/EtOAc=10/1~1/1, Silica-CS 4 g, 12 mL/min, silica gel, UV 254) to give an anomeric mixture of the product. The mixture was purified by preparative —SFC to give the product (56.0 mg, 16%) as a white solid. ESI-MS m/z calcd for $[C_{27}H_{25}ClF_2N_4O_6S][M+H]^+$: 607.1; found: 607.0. $^1$H NMR (400 MHz, $CDCl_3$) δ 7.74 (s, 1H), 7.69 (d, J=2.4 Hz, 1H), 7.59 (d, J=8.4 Hz, 1H), 7.36 (dd, J=8.4, 2.0 Hz, 1H), 7.23 (d, J=8.0 Hz, 1H), 6.25 (d, J=5.2 Hz, 1H), 5.53 (d, J=2.0 Hz, 1H), 4.90-4.78 (m, 2H), 4.68 (d, J=6.4 Hz, 1H), 4.02-3.99 (m, 2H), 3.39 (s, 3H), 2.15 (s, 3H), 2.00 (s, 3H), 1.90 (s, 3H).

Intermediate 16

2-Bromo-5-chloropyridin-3-yl 3-deoxy-2-O-ethyl-3-[4-(3,4,5-trifluorophenyl)-1H-1,2,3-triazol-1-yl]-1-thio-α-D-galactopyranoside

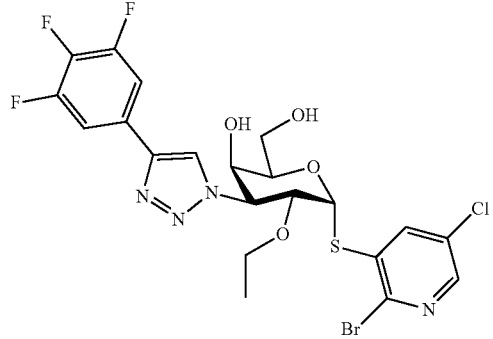

2-Bromo-5-chloropyridin-3-yl 4,6-O-benzylidene-3-deoxy-3-[4-(3,4,5-trifluorophenyl)-1H-1,2,3-triazol-1-yl]-1-thio-α-D-galactopyranoside (202 mg, 0.31 mmol) and NaH (60% in oil, 24 mg, 0.62 mmol) were dissolved in DMF (3 mL) and stirred 10 min before the addition of iodoethane (37 μL, 0.46 mmol). After stirring 3 h at rt the mixture was diluted with EtOAc, washed twice with water and the organic phase was dried and evaporated. Another batch was made in parallel. 2-Bromo-5-chloropyridin-3-yl 4,6-O-benzylidene-3-deoxy-3-[4-(3,4,5-trifluorophenyl)-1H-1,2,3-triazol-1-yl]-1-thio-α-D-galactopyranoside (202 mg, 0.31 mmol) and $Ag_2O$ (143 mg, 0.62 mmol) were dissolved in DMF (3 mL) and stirred 5 min before the addition of iodoethane (49 μL, 0.62 mmol). After stirring 20 h at 50° C. the mixture was diluted with EtOAc, washed twice with water and the organic phase was dried and evaporated. The crude from the two batches were pooled and dissolved in TFA/water (4 mL, 4:1). The mixture was stirred 3 h at rt before being partitioned between EtOAc and aq NaOH (1 M). The organic phase was dried, evaporated and purified by preparative HPLC (Method B) to afford the product (10 mg, 3%) as a white powder. ESI-MS m/z calcd for

[C₂₁H₁₉BrClF₃N₄O₄S] [M+H]⁺: 595.0; found: 594.7. ¹H NMR (400 MHz, Methanol-d₄) δ 8.60 (s, 1H), 8.22 (s, 2H), 7.69-7.63 (m, 2H), 6.44 (d, J=5.4 Hz, 1H), 5.09 (dd, J=11.3, 2.8 Hz, 1H), 4.80 (dd, J=11.3, 5.4 Hz, 1H), 4.34 (t, J=6.0 Hz, 1H), 4.20 (d, J=2.6 Hz, 1H), 3.85-3.78 (m, 1H), 3.73-3.63 (m, 2H), 3.51-3.42 (m, 1H), 1.03 (t, J=7.0 Hz, 3H).

Intermediate 21

3,4-Dichlorophenyl 4,6-O-benzylidene-3-[4-(4-chloro-3,5-difluorophenyl)-1H-1,2,3-triazol-1-yl]-3-deoxy-2-O-carboxymethyl-1-thio-α-D-galactopyranoside

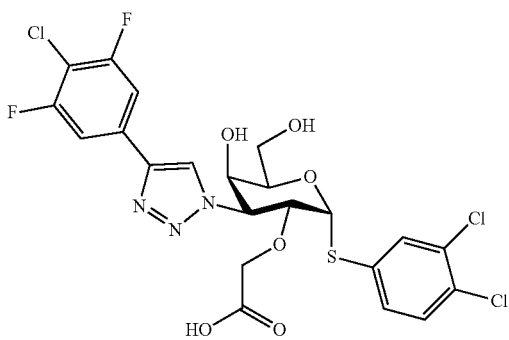

3,4-Dichlorophenyl 3-[4-(4-chloro-3,5-difluorophenyl)-1H-1,2,3-triazol-1-yl]-3-deoxy-1-thio-α-D-galactopyranoside

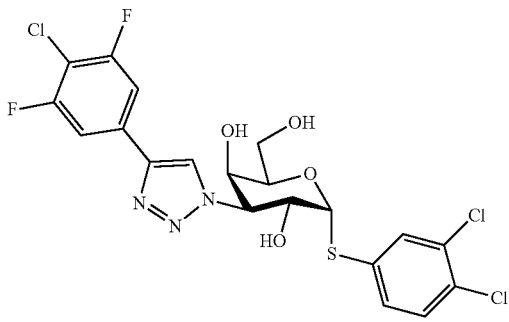

Copper(II) sulfate pentahydrate (127 mg, 0.5 mmol) was dissolved in hot water (5.0 mL) and added to (+)-sodium L-ascorbate (198 mg, 1.0 mmol). The resulting brownish dispersion was added to a mixture of 3,4-dichlorophenyl 3-azido-3-deoxy-1-thio-α-D-galactopyranoside (2.33 g, 4.7 mmol), K₂CO₃ (6.5 g, 47 mmol), and trimethyl-[2-(4-chloro-3,5-difluorophenyl)ethynyl]silane (1.40 g, 5.68 mmol) in MeOH (20 mL) and THF (20 mL). The resulting mixture was stirred 20 h at 50° C., celite was added, the mixture was filtered, and the filter cake was washed with EtOAc/MeOH. The filtrate was partitioned between EtOAc and aqueous HCl (0.5 M), the organic phase was concentrated. The residue was purified by chromatography (SiO₂, PE/EtOAc) and the crude was triturated in MeCN (30 mL) to give the product (1.73 g, 68%). ESI-MS m/z calcd for [C₂₀H₁₆Cl₃F₂N₃O₄S] [M+H]⁺: 538.0; found: 538.0. ¹H NMR (400 MHz, Methanol-d₄) δ 8.60 (s, 1H), 7.80 (d, J=2.0 Hz, 1H), 7.67 (d, J=8.0 Hz, 2H), 7.54 (dd, J=8.4, 2.0 Hz, 1H), 7.48 (d, J=8.4 Hz, 1H), 5.85 (d, J=5.2 Hz, 1H), 4.99 (dd, J=11.4, 2.7 Hz, 1H), 4.96-4.90 (m, 1H), 4.49 (t, J=6.0 Hz, 1H), 4.20 (d, J=1.9 Hz, 1H), 3.77-3.66 (m, 2H).

3,4-Dichlorophenyl 4,6-O-benzylidene-3-[4-(4-chloro-3,5-difluorophenyl)-1H-1,2,3-triazol-1-yl]-3-deoxy-1-thio-α-D-galactopyranoside

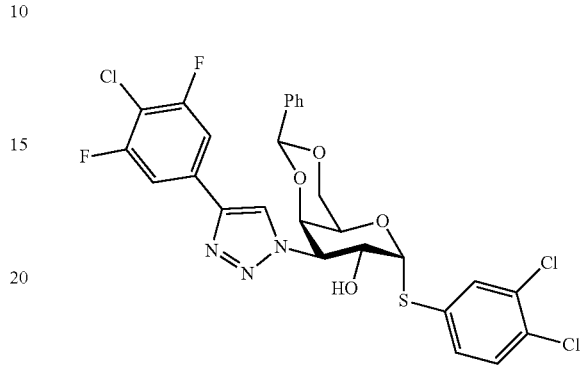

To a solution of 3,4-dichlorophenyl 3-[4-(4-chloro-3,5-difluorophenyl)-1H-1,2,3-triazol-1-yl]-3-deoxy-1-thio-α-D-galactopyranoside (1.73 g, 3.2 mmol) in MeCN (40 mL) benzaldehyde dimethylacetal (0.974 mL, 6.46 mmol) followed by p-toluenesulfonic acid monohydrate (50 mg, 0.26 mmol) were added. The suspension was stirred 72 h at rt, then cooled to 0° C. and filtered to give the product (1.876 g, 93%). ¹H NMR (400 MHz, DMSO-d₆) δ 8.92 (s, 1H), 7.86-7.75 (m, 3H), 7.63 (d, J=8.5 Hz, 1H), 7.52 (dd, J=8.5, 2.0 Hz, 1H), 7.35 (dt, J=11.3, 3.9 Hz, 5H), 6.18 (d, J=5.2 Hz, 1H), 6.13 (d, J=4.7 Hz, 1H), 5.57 (s, 1H), 5.10 (dd, J=11.3, 3.2 Hz, 1H), 4.91 (dt, J=10.9, 5.0 Hz, 1H), 4.56 (d, J=3.0 Hz, 1H), 4.29 (s, 1H), 4.13 (d, J=12.1 Hz, 1H), 3.96 (d, J=12.4 Hz, 1H).

3,4-Dichlorophenyl 4,6-O-benzylidene-3-[4-(4-chloro-3,5-difluorophenyl)-1H-1,2,3-triazol-1-yl]-3-deoxy-2-O-(methoxycarbonyl)methyl-1-thio-α-D-galactopyranoside

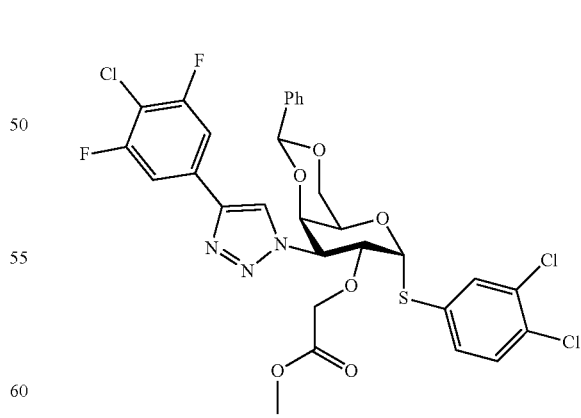

3,4-Dichlorophenyl 4,6-O-benzylidene-3-[4-(4-chloro-3,5-difluorophenyl)-1H-1,2,3-triazol-1-yl]-3-deoxy-1-thio-α-D-galactopyranoside (800 mg, 1.28 mmol) and NaH (60% in oil, 77 mg, 1.91 mmol) were stirred 5 min in DMF (3.0 mL) before methyl 2-bromoacetate (0.16 mL, 1.66 mmol) was added. The mixture was stirred 2 h at rt and was then poured onto ice cooled water (30 mL) and HCl (4 mL, 1 M). The solids were isolated by filtration and recrystallized from EtOAc/PE to give the product (746 mg, 84%). ¹H NMR (400 MHz, DMSO-$d_6$) δ 8.97 (s, 1H), 7.86 (d, J=1.9 Hz, 1H), 7.73 (d, J=8.5 Hz, 2H), 7.66 (d, J=8.4 Hz, 1H), 7.54 (dd, J=8.3, 1.8 Hz, 1H), 7.34 (s, 5H), 6.61 (d, J=5.2 Hz, 1H), 5.59 (s, 1H), 5.23 (dd, J=11.5, 3.2 Hz, 1H), 4.87 (dd, J=11.4, 5.1 Hz, 1H), 4.61 (d, J=3.1 Hz, 1H), 4.34 (s, 1H), 4.31 (s, 2H), 4.14 (d, J=12.6 Hz, 1H), 3.99 (d, J=12.5 Hz, 1H), 3.54 (s, 3H).

3,4-Dichlorophenyl 4,6-O-benzylidene-3-[4-(4-chloro-3,5-difluorophenyl)-1H-1,2,3-triazol-1-yl]-3-deoxy-2-O-carboxymethyl-1-thio-α-D-galactopyranoside

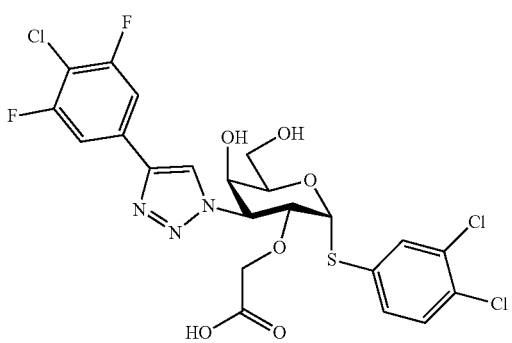

3,4-Dichlorophenyl 4,6-O-benzylidene-3-[4-(4-chloro-3,5-difluorophenyl)-1H-1,2,3-triazol-1-yl]-3-deoxy-2-O-(methoxycarbonyl)methyl-1-thio-α-D-galactopyranoside (721 mg, 1.103 mmol) was stirred 30 min in 80% aq TFA (10 mL), the mixture was concentrated and water was added, which resulted in precipitation. The precipitate was collected by filtration and then stirred 2 h in EtOH (5.0 mL) and NaOH (3.0 mL, 2 M). The mixture was neutralized with HCl (1 M), concentrated, water was added, and pH was adjusted to approximately 1 with HCl (1 M). The precipitate was collected and then triturated in MeOH/water, the solids were collected and to the crude MeOH (3.0 mL) and 28% ammonia (0.20 mL) were added. The mixture was concentrated to dryness, then triturated in Et₂O, the precipitate was collected, and the product was obtained as the ammonium salt (381 mg, 60%). ESI-MS m/z calcd for [$C_{22}H_{18}Cl_3F_2N_3O_6S$] [M+H]⁺: 596.0; found: 596.1. ¹H NMR (400 MHz, Methanol-$d_4$) δ 9.18 (s, 1H), 7.83 (d, J=1.9 Hz, 1H), 7.67 (d, J=8.1 Hz, 2H), 7.57 (dd, J=8.4, 1.8 Hz, 1H), 7.48 (d, J=8.4 Hz, 1H), 6.24 (d, J=3.9 Hz, 1H), 5.05 (m, 2H), 4.48 (t, J=6.1 Hz, 1H), 4.29 (s, 1H), 4.04 (d, J=15.7 Hz, 1H), 3.96 (d, J=15.7 Hz, 1H), 3.76-3.63 (m, 2H).

Intermediate 22

5-Chloro-6-cyano-2-{N-(2-oxa)-6-azaspiro[3.3]heptanyl}-pyridin-3-yl 4,6-di-O-acetyl-3-[4-(4-chloro-3,5-difluorophenyl)-1H-1,2,3-triazol-1-yl]-3-deoxy-2-O-methyl-1-thio-α-D-galactopyranoside

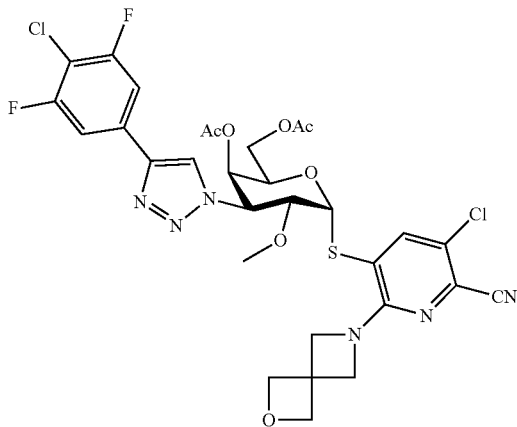

5-Bromo-3-chloro-2-cyano-pyridine-N-oxide

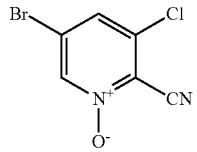 [SMILES: N#Cc1c(Cl)cc(Br)c[n+]1[O-]]

To a solution of 5-bromo-3-chloro-2-cyano-pyridine (1.50 g, 6.90 mmol) in TFA (10 mL) H₂O₂ (35.0%, 1.01 g, 10.3 mmol) was slowly added. The mixture was heated to 70° C. and was kept stirring 3 h. The solvent was carefully removed under reduced pressure. The residue was dissolved in EtOAc and washed with water, brine, dried over Na₂SO₄ and filtered. The filtrate was concentrated to give the product (1.30 g, 81%) as a light yellow solid. ESI-MS m/z calcd for [$C_6H_2BrClN_2O$] [M+H]⁺: 232.9; found: 232.9.

5-Bromo-3,6-dichloro-2-cyano-pyridine

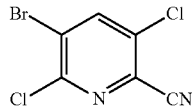

To a stirred solution of 5-bromo-3-chloro-2-cyano-pyridine-N-oxide (700 mg, 3.00 mmol) in toluene (7 mL) POCl₃ (0.823 mL, 9.00 mmol) was added. The mixture was stirred 3 h at 100° C. The mixture was cooled to rt and was poured into ice-water under vigorous stirring. The solution was extracted with EtOAc and the organic layer was washed with water, saturated aq NaHCO₃, brine, dried over Na₂SO₄ and concentrated. The residue by was purified by column chromatography (PE/EtOAc=10/1~3/1, Silica-CS 4 g, 12 mL/min, silica gel, UV 254) to give the product (400 mg, 53%) as a light yellow solid. ¹H NMR (400 MHz, CDCl₃) δ 8.34 (s, 1H).

5-Bromo-3-chloro-2-cyano-6-{N-(2-oxa)-6-azaspiro[3.3]heptanyl}-pyridine

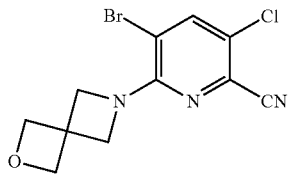 [SMILES: N#Cc1nc(N2CC3(COC3)C2)c(Br)cc1Cl]

To a solution of 5-bromo-3,6-dichloro-2-cyano-pyridine (50.0 mg, 0.20 mmol) and 2-oxa-6-azaspiro[3.3]heptane (21.6 mg, 0.22 mmol) in MeCN (2 mL) K₂CO₃ (41.1 mg, 0.30 mmol) was added. The mixture was stirred overnight at 60° C. The solvent was removed under reduced pressure and the residue was dissolved in EtOAc and washed with water, brine, dried over Na₂SO₄, filtered and concentrated. The residue was purified by column chromatography (PE/EtOAc=10/1~3/1, Silica-CS 4 g, 12 mL/min, silica gel, UV 254) to give the product (33.0 mg, 53%) as a light yellow solid. ESI-MS m/z calcd for [C₁₁H₉BrClN₃O] [M+H]⁺: 314.0; found: 314.2. ¹H NMR (400 MHz, DMSO-d₆) δ 8.31 (s, 1H), 4.70 (s, 4H), 4.40 (s, 4H).

5-Chloro-6-cyano-2-{N-(2-oxa)-6-azaspiro[3.3]heptanyl}-pyridin-3-yl 4,6-di-O-acetyl-3-azido-3-deoxy-2-O-methyl-1-thio-D-galactopyranoside

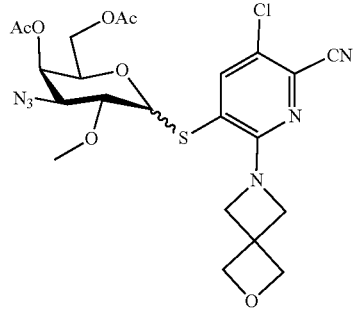

To a solution of 4,6-di-O-acetyl-3-azido-3-deoxy-2-O-methyl-1-thio-D-galactopyranoside (950 mg, 2.63 mmol) and 5-bromo-3-chloro-2-cyano-6-{N-(2-oxa)-6-azaspiro[3.3]heptanyl}-pyridine (992 mg, 3.15 mmol) in DMF (10 mL) diethylamine (385 mg, 5.26 mmol) was added. The mixture was stirred overnight at rt under nitrogen atmosphere. After diluting with water (20 mL), the mixture was extracted with EtOAc (3×10 mL). The combined organic layers were washed with brine, dried over anhydrous Na₂SO₄ and concentrated in vacuo. The residue was purified by column chromatography (PE/EtOAc=10/1~3/1, Silica-CS 4 g, 12 mL/min, silica gel, UV 254) to give the product (280 mg, 74%, a/0=0.44:1). ESI-MS m/z calcd for [C₂₂H₂₅ClN₆O₇S] [M+H]⁺: 553.1; found: 553.0.

5-Chloro-6-cyano-2-{N-(2-oxa)-6-azaspiro[3.3]heptanyl}-pyridin-3-yl 4,6-di-O-acetyl-3-azido-3-deoxy-2-O-methyl-1-thio-α-D-galactopyranoside ¹H NMR (400 MHz, CDCl₃) δ 7.68 (s, 1H), 5.82 (d, J=5.2 Hz, 1H, 1-Hu), 5.33 (d, J=3.6 Hz, 1H), 4.78 (s, 4H), 4.38-4.26 (m, 5H), 4.08-3.72 (m, 3H), 3.49 (s, 3H), 3.33-3.32 (m, 1H), 2.09 (s, 3H), 1.92 (s, 3H).

5-Chloro-6-cyano-2-{N-(2-oxa)-6-azaspiro[3.3]heptanyl}-pyridin-3-yl 4,6-di-O-acetyl-3-azido-3-deoxy-2-O-methyl-1-thio-β-D-galactopyranoside ¹H NMR (400 MHz, CDCl₃): δ 7.70 (s, 1H), 5.31 (d, J=2.8 Hz, 1H), 4.77 (s, 4H), 4.49 (d, J=9.2 Hz, 1H, 1-HO), 4.38-4.26 (m, 4H), 4.08-3.72 (m, 3H), 3.57-3.55 (m, 1H), 3.33-3.32 (m, 1H), 2.12 (s, 3H), 1.97 (s, 3H).

5-Chloro-6-cyano-2-{N-(2-oxa)-6-azaspiro[3.3]heptanyl}-pyridin-3-yl 4,6-di-O-acetyl-3-[4-(4-chloro-3,5-difluorophenyl)-1H-1,2,3-triazol-1-yl]-3-deoxy-2-O-methyl-1-thio-α-D-galactopyranoside

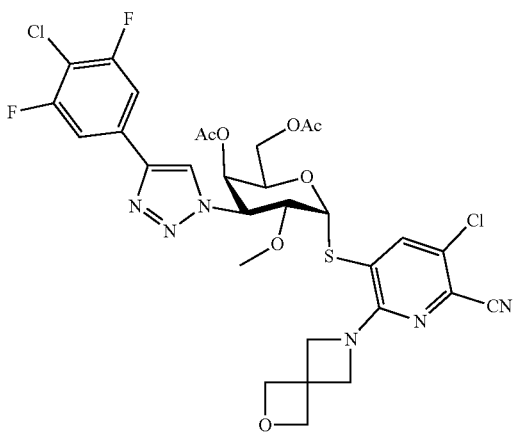

To a solution of 5-chloro-6-cyano-2-{N-(2-oxa)-6-azaspiro[3.3]heptanyl}-pyridin-3-yl 4,6-di-O-acetyl-3-azido-3-deoxy-2-O-methyl-1-thio-D-galactopyranoside (400 mg, 0.72 mmol) and trimethyl-[2-(4-chloro-3,5-difluorophenyl)ethynyl]silane (215 mg, 0.94 mmol) in DMF (6 mL) copper(II) sulfate pentahydrate (90.3 mg, 0.362 mmol) and (+)-sodium L-ascorbate (143 mg, 0.72 mmol) were added. The mixture was stirred 3 h at rt under nitrogen atmosphere. After diluting with water (20 mL), the mixture was extracted three times with EtOAc (10 mL). The combined organic layers were washed with brine, dried over anhydrous Na₂SO₄ and concentrated in vacuo. The residue was purified by column chromatography (PE/EtOAc=10/1~1/1, Silica-CS 4 g, 12 mL/min, silica gel, UV 254) to give an anomeric mixture of the product. The mixture was separated by preparative —SFC to give the product (58.0 mg, 11%). ESI-MS m/z calcd for [C₃₀H₂₈Cl₂F₂N₆O₇S] [M+H]⁺: 725.1; found: 725.0. ¹H NMR (400 MHz, CDCl₃) δ 7.81 (s, 1H), 7.74 (s, 1H), 7.38 (d, J=7.6 Hz, 2H), 6.02 (d, J=4.8 Hz, 1H), 5.50 (d, J=1.6 Hz, 1H), 4.86-4.75 (m, 6H), 4.59-4.56 (m, 1H), 4.40-4.29 (m, 4H), 4.07-3.96 (m, 2H), 3.34 (s, 3H), 2.00 (s, 3H), 1.93 (s, 3H).

Intermediate 23

5-Chloro-6-cyano-2-{N-(2-oxa)-6-azaspiro[3.3]heptanyl}-pyridin-3-yl 4,6-di-O-acetyl-3-deoxy-3-[4-(3,4,5-trifluorophenyl)-1H-1,2,3-triazol-1-yl]-2-O-methyl-1-thio-α-D-galactopyranoside

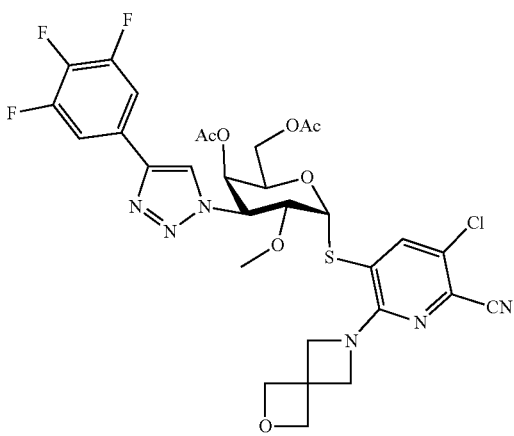

To a solution of 5-chloro-6-cyano-2-{N-(2-oxa)-6-azaspiro[3.3]heptanyl}-pyridin-3-yl 4,6-di-O-acetyl-3-azido-3-deoxy-2-O-methyl-1-thio-D-galactopyranoside (400 mg, 0.72 mmol) and trimethyl-[2-(3,4,5-trifluorophenyl)ethynyl]silane (215 mg, 0.94 mmol) in DMF (6 mL) copper(II) sulfate pentahydrate (90.3 mg, 0.362 mmol) and (+)-sodium L-ascorbate (143 mg, 0.72 mmol) were added. The mixture was stirred 3 h at rt under nitrogen atmosphere. After diluting with water (20 mL), the mixture was extracted three times with EtOAc (10 mL). The combined organic layers were washed with brine, dried over anhydrous $Na_2SO_4$ and concentrated in vacuo. The residue was purified by column chromatography (PE/EtOAc=10/1~1/1, Silica-CS 4 g, 12 mL/min, silica gel, UV 254) to give an anomeric mixture of the product. The mixture was separated by preparative —SFC to give the product (54.0 mg, 11%). ESI-MS m/z calcd for $[C_{30}H_{28}ClF_3N_6O_7S][M+H]^+$: 709.1; found: 709.0. $^1$H NMR (400 MHz, $CDCl_3$) δ 7.80 (s, 1H), 7.75 (s, 1H), 7.41-7.36 (m, 2H), 6.03 (d, J=5.2 Hz, 1H), 5.50 (s, 1H), 4.85-4.76 (m, 6H), 4.59-4.56 (m, 1H), 4.40-4.28 (m, 4H), 4.07-3.96 (m, 2H), 3.33 (s, 3H), 2.00 (s, 3H), 1.93 (s, 3H).

Intermediate 24

5-Chloro-2-(pyrimidin-5-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

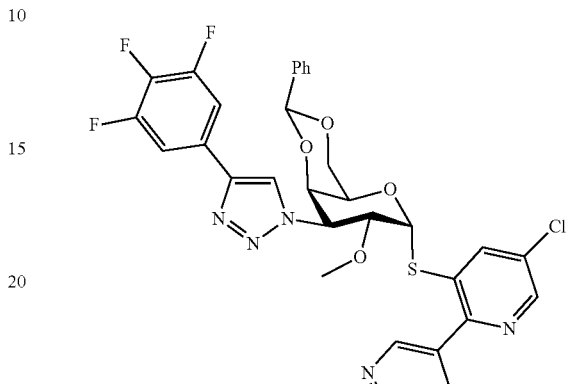

5-Chloro-2-(pyrimidin-5-yl)pyridin-3-yl 3-azido-4,6-O-benzylidene-3-deoxy-2-O-methyl-1-thio-α-D-galactopyranoside

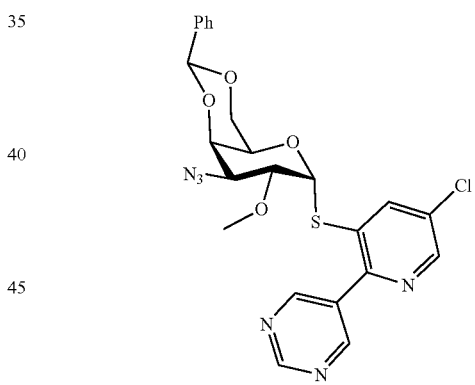

To a solution of 2-bromo-5-chloropyridin-3-yl 3-azido-4,6-O-benzylidene-3-deoxy-2-O-methyl-1-thio-α-D-galactopyranoside (350 mg, 0.68 mmol) and 5-(4,4,5,5-tetramethyl-1,3,2-dioxaborolan-2-yl)pyrimidine (281 mg, 1.36 mmol) in 1,4-dioxane/water (3.3 mL, 10:1) in a microwave tube, bis(triphenylphosphine)palladium(II) chloride (47.8 mg, 0.068 mmol) and $K_2CO_3$ (282 mg, 2.04 mmol) were added. The mixture was degassed by bubbling argon through the solution and it was then stirred 1 h at 100° C. in a microwave reactor. The solvent was removed, and the residue was purified by column chromatography (PE/EtOAc=5/1~1/1, Silica-CS 20 g, 30 mL/min, silica gel, UV 254) to give the product (260 mg, 74%). ESI-MS m/z calcd for $[C_{23}H_{21}ClN_6O_4S] [M+H]^+$: 513.1; found: 513.1. $^1$H NMR (400 MHz, $CDCl_3$) δ 9.22 (s, 1H), 9.01 (s, 2H), 8.49 (d, J=2.4 Hz, 1H), 8.03 (d, J=2.4 Hz, 1H), 7.42 (m, 2H), 7.35-7.26 (m, 3H), 5.86 (d, J=5.2 Hz, 1H), 5.52 (s, 1H), 4.19

(d, J=2.4 Hz, 1H), 4.12 (dd, J=10.4, 5.2 Hz, 1H), 4.07-3.93 (m, 2H), 3.72 (s, 1H), 3.54 (dd, J=10.4, 2.8 Hz, 1H), 3.37 (s, 3H).

5-Chloro-2-(pyrimidin-5-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

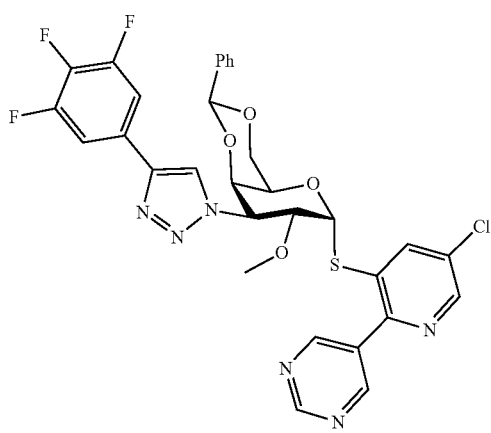

Intermediate 25

5-Chloro-2-(pyridin-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

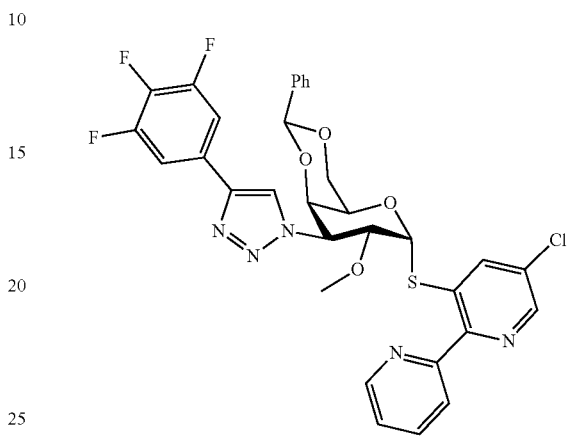

5-Chloro-2-(pyridin-2-yl)pyridin-3-yl 3-azido-4,6-O-benzylidene-3-deoxy-2-O-methyl-1-thio-α-D-galactopyranoside

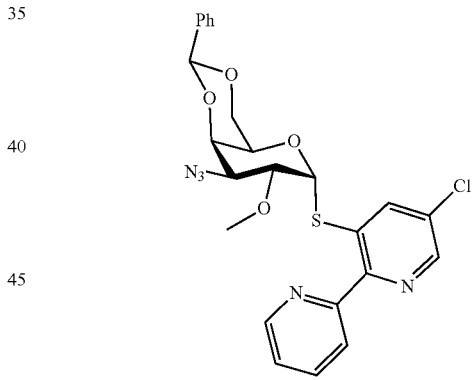

To a solution of 5-chloro-2-(pyrimidin-5-yl)pyridin-3-yl 3-azido-4,6-O-benzylidene-3-deoxy-2-O-methyl-1-thio-α-D-galactopyranoside (130 mg, 0.25 mmol) and trimethyl-[2-(3,4,5-trifluorophenyl)ethynyl]silane (69.4 mg, 0.30 mmol) in DMF (3 mL), (+)-sodium L-ascorbate (100 mg, 0.51 mmol) and copper(II) sulfate pentahydrate (31.6 mg, 0.13 mmol) were added. The mixture was stirred overnight at rt under nitrogen atmosphere and was then concentrated under reduced pressure. The residue was purified by preparative HPLC (Method A) to give the product (90.0 mg, 53%). ESI-MS m/z calcd for [C$_{31}$H$_{24}$ClF$_3$N$_6$O$_4$S] [M+H]$^+$: 669.1; found: 669.1. $^1$H NMR (400 MHz, CDCl$_3$) δ 8.56 (s, 1H), 8.07 (s, 1H), 7.84 (s, 1H), 7.34-7.30 (m, 10H), 5.92 (d, J=5.2 Hz, 1H), 5.45 (s, 1H), 5.12 (s, 1H), 4.44-4.40 (m, 2H), 4.04-4.02 (m, 3H), 3.13 (s, 3H).

To a solution of 2-bromo-5-chloropyridin-3-yl 3-azido-4,6-O-benzylidene-3-deoxy-2-O-methyl-1-thio-α-D-galactopyranoside (200 mg, 0.39 mmol) and tributyl(2-pyridyl)stannane (143 mg, 0.39 mmol) in DMF (3 mL) bis(triphenylphosphine)palladium(II) chloride (27.3 mg, 0.039 mmol) was added. The mixture was stirred 6 h at 110° C. under a nitrogen atmosphere. After cooling to rt, the mixture was purified by preparative HPLC (Method A) to give the product (25.0 mg, 13%). ESI-MS m/z calcd for [C$_{24}$H$_{22}$ClN$_5$O$_4$S] [M+H]$^+$: 512.1; found: 512.1. $^1$H NMR (400 MHz, CDCl$_3$) δ 8.65 (s, 1H), 8.39 (s, 1H), 8.15 (m, 1H), 7.93 (m, 1H), 7.83-7.69 (m, 1H), 7.54-7.40 (m, 2H), 7.37-7.26 (m, 4H), 5.91 (d, J=5.6 Hz, 1H), 5.55 (s, 1H), 4.29-4.12 (m, 3H), 4.09-3.99 (m, 2H), 3.72 (dd, J=10.8, 3.2 Hz, 1H), 3.39 (s, 3H).

171

5-Chloro-2-(pyridin-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

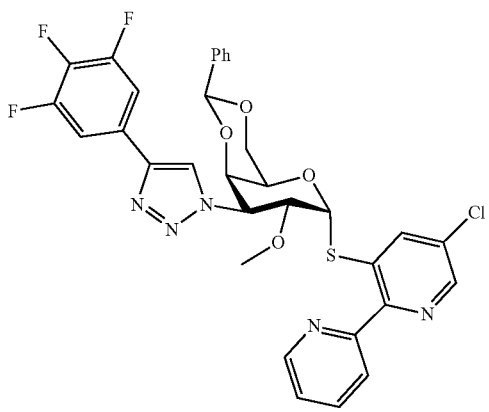

To a solution of 5-chloro-2-(pyridin-2-yl)pyridin-3-yl 3-azido-4,6-O-benzylidene-3-deoxy-2-O-methyl-1-thio-α-D-galactopyranoside (50.0 mg, 0.098 mmol) and trimethyl-[2-(3,4,5-trifluorophenyl)ethynyl]silane (24.5 mg, 0.11 mmol) in DMF (3 mL), (+)-sodium L-ascorbate (38.7 mg, 0.20 mmol) and copper(II) sulfate pentahydrate (12.2 mg, 0.049 mmol) were added. The mixture was stirred overnight at rt under nitrogen atmosphere and was then purified by preparative HPLC (Method A) to give the product (30.0 mg, 46%). ESI-MS m/z calcd for [$C_{32}H_{25}ClF_3N_5O_4S$] [M+H]$^+$: 668.1; found: 668.1. $^1$H NMR (400 MHz, CDCl$_3$) δ 8.15 (s, 1H), 7.92 (s, 2H), 7.47-7.26 (m, 11H), 6.11 (s, 1H), 5.45 (s, 1H), 5.32 (d, J=10.0 Hz, 1H), 4.57 (s, 1H), 4.43 (s, 1H), 4.27 (m, 2H), 4.08 (d, J=11.8 Hz, 1H), 3.17 (s, 3H).

Intermediate 26

5-Chloro-2-(pyridin-3-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

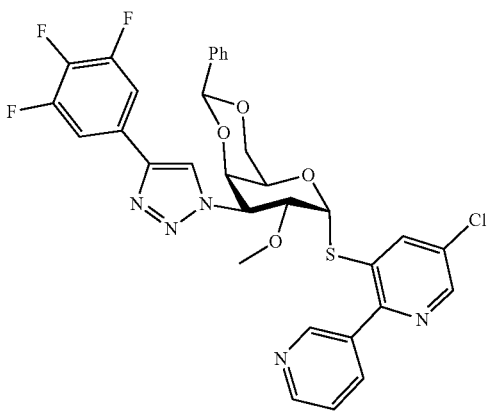

172

5-Chloro-2-(pyridin-3-yl)pyridin-3-yl 3-azido-4,6-O-benzylidene-3-deoxy-2-O-methyl-1-thio-α-D-galactopyranoside

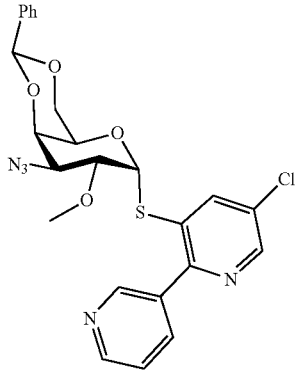

To a solution of 2-bromo-5-chloropyridin-3-yl 3-azido-4,6-O-benzylidene-3-deoxy-2-O-methyl-1-thio-α-D-galactopyranoside (320 mg, 0.62 mmol) in DMF (5 mL) 3-pyridylboronic acid (153 mg, 1.25 mmol), bis(triphenylphosphine)palladium(II) chloride (91 mg, 0.013 mmol) and K$_2$CO$_3$ (172 mg, 1.25 mmol) were added. The mixture was stirred 6 h at rt. The mixture was concentrated and purified by column chromatography (DCM/MeOH=10/1, Silica-CS 12 g, 20 mL/min, silica gel, UV 254) to give the product (150 mg, 47%). ESI-MS m/z calcd for [$C_{24}H_{22}ClN_5O_4S$] [M+H]$^+$: 512.1, found: 512.0. $^1$H NMR (400 MHz, DMSO-d$_6$) δ 8.90 (s, 1H), 8.65 (d, J=3.6 Hz, 1H), 8.47 (d, J=2.0 Hz, 1H), 8.12 (d, J=8.0 Hz, 1H), 8.02 (d, J=2.4 Hz, 1H), 7.52-7.49 (m, 1H), 7.43-7.39 (m, 2H), 7.33-7.28 (m, 3H), 5.87 (d, J=4.8 Hz, 1H), 5.52 (s, 1H), 4.19 (d, J=2.8 Hz, 1H), 4.13-4.04 (m, 2H), 3.99 (d, J=12.8 Hz, 1H), 3.72 (d, J=4.4 Hz, 1H), 3.57 (dd, J=10.8, 3.2 Hz, 1H), 3.36 (s, 3H).

5-Chloro-2-(pyridin-3-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

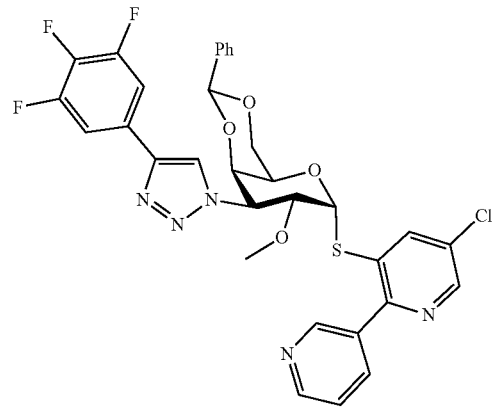

To a solution of 5-chloro-2-(pyridin-3-yl)pyridin-3-yl 3-azido-4,6-O-benzylidene-3-deoxy-2-O-methyl-1-thio-α-D-galactopyranoside (72 mg, 0.14 mmol) in DMF (3 mL), trimethyl-[2-(3,4,5-trifluorophenyl)ethynyl]silane (48 mg, 0.21 mmol), (+)-sodium L-ascorbate (28 mg, 0.14 mmol) and copper(II) sulfate pentahydrate (35 mg, 0.14 mmol) were added. The mixture was stirred 6 h at rt. The mixture was concentrated and was then purified by column chromatography (DCM/MeOH=10/1, Silica-CS 12 g, 20 mL/min, silica gel, UV 254) to give the product (59.0 mg, 63%). ESI-MS m/z calcd for [$C_{32}H_{25}ClF_3N_5O_4S$] [M+H]$^+$: 668.1, found: 668.2.

Intermediate 27

5-Chloro-2-(pyridin-4-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

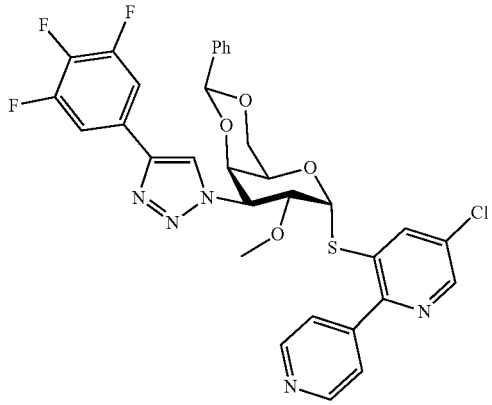

5-Chloro-2-(pyridin-4-yl)pyridin-3-yl 3-azido-4,6-O-benzylidene-3-deoxy-2-O-methyl-1-thio-α-D-galactopyranoside

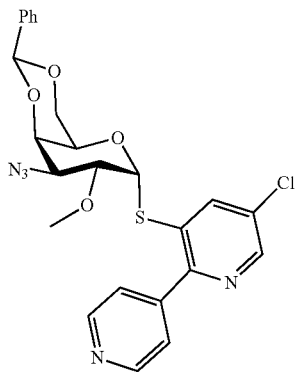

To a solution of 2-bromo-5-chloro-3-pyridine-3-yl 3-azido-4,6-O-benzylidene-3-deoxy-2-O-methyl-1-thio-α-D-galactopyranoside (180 mg, 0.35 mmol) in 1,4-dioxane (4.0 mL), 4-(4,4,5,5-tetramethyl-1,3,2-dioxaborolan-2-yl)pyridine (144 mg, 0.70 mmol), K$_2$CO$_3$ (145 mg, 1.05 mmol), bis(triphenylphosphine)palladium(II) chloride (12.3 mg, 0.018 mmol) and H$_2$O (0.5 mL) were added. The mixture was stirred 1 h at 100° C. in a microwave reactor. The solvent was concentrated under reduced pressure. The residue was dissolved in EtOAc (100 mL), washed with water (80 mL), brine (80 mL), dried over Na$_2$SO$_4$ and filtered. The filtrate was concentrated under reduced pressure and the residue was purified by column chromatography (PE/EtOAc=10/1~2/1, Silica-CS 12 g, 20 m/min, silica gel, UV 254) to afford the the product (130 mg, 73%). ESI-MS m/z calcd for [$C_{24}H_{22}ClN_5O_4S$] [M+H]$^+$: 512.1; found: 511.9.

5-Chloro-2-(pyridin-4-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

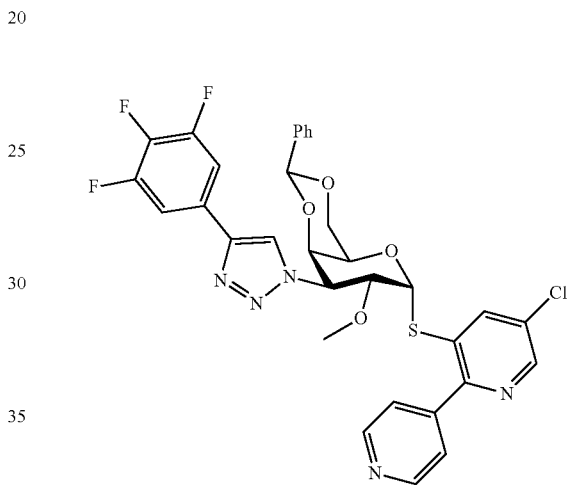

To a solution of 5-chloro-2-(pyridin-4-yl)pyridin-3-yl 3-azido-4,6-O-benzylidene-3-deoxy-2-O-methyl-1-thio-α-D-galactopyranoside (60.0 mg, 0.12 mmol) in DMF (5 mL), trimethyl-[2-(3,4,5-trifluorophenyl)ethynyl]silane (53.5 mg, 0.23 mmol), (+)-sodium L-ascorbate (23.2 mg, 0.12 mmol), copper(II) sulfate pentahydrate (29.3 mg, 0.12 mmol) and CsF (17.8 mg, 0.12 mmol) were added. The mixture was stirred at rt overnight. The mixture was poured into water (20 mL) and extracted with EtOAc (2×10 mL). the organic layers were washed with water (25 mL), dried with Na$_2$SO$_4$ and concentrated. The residue was purified by column chromatography (PE/EtOAc=10/1~1/1, Silica-CS 4 g, 10 mL/min, silica gel, UV 254) to give the product (50.0 mg, 64%). ESI-MS m/z calcd for [$C_{32}H_{25}ClF_3N_5O_4S$] [M+H]$^+$: 668.1; found: 668.1. $^1$H NMR (400 MHz, CDCl$_3$) δ 8.60 (d, J=2.0 Hz, 1H), 8.19-8.14 (m, 2H), 7.98-7.94 (m, 1H), 7.74-7.62 (m, 2H), 7.54-7.41 (m, 8H), 6.12 (d, J=5.2 Hz, 1H), 5.54 (s, 1H), 5.34 (d, J=10.0 Hz, 1H), 4.59-4.54 (m, 1H), 4.50 (dd, J=11.2, 5.2 Hz, 1H), 4.27-4.18 (m, 1H), 4.16-4.11 (m, 2H), 3.19 (s, 3H).

Intermediate 28

5-Chloro-2-(1,2,3,6-tetrahydropyridin-4-yl)pyridin-3-yl 3-azido-3-deoxy-2-O-methyl-1-thio-α-D-galactopyranoside

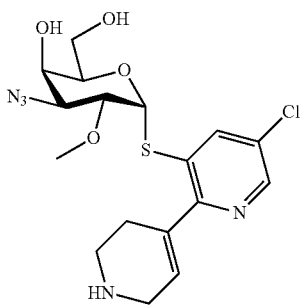

5-Chloro-2-[1-(N-tert-butoxycarbonyl)-1,2,3,6-tetrahydropyridin-4-yl]pyridin-3-yl 3-azido-4,6-O-benzylidene-3-deoxy-2-O-methyl-1-thio-α-D-galactopyranoside

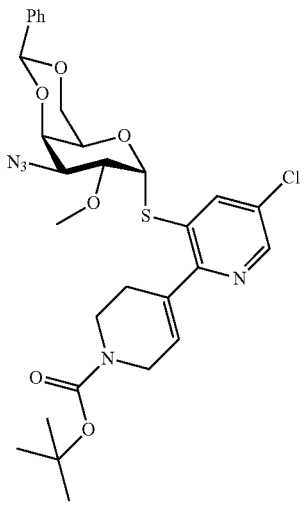

To a solution of 2-bromo-5-chloro-3-pyridine-3-yl 3-azido-4,6-O-benzylidene-3-deoxy-2-O-methyl-1-thio-α-D-galactopyranoside (400 mg, 0.78 mmol) in 1,4-dioxane (10 mL), tert-butyl 4-(4,4,5,5-tetramethyl-1,3,2-dioxaborolan-2-yl)-3,6-dihydro-2H-pyridine-1-carboxylate (361 mg, 1.17 mmol), K$_2$CO$_3$ (215 mg, 1.56 mmol), bis(triphenylphosphine)palladium(II) chloride (546 mg, 0.78 mmol) and H$_2$O (1 mL) were added. The mixture was stirred 1 h at 100° C. in a microwave reactor. The solvent was concentrated under reduced pressure. The residue was dissolved in EtOAc (100 mL), washed with water (80 mL), brine (80 mL), dried over anhydrous Na$_2$SO$_4$, filtered and concentrated. The residue was purified by column chromatography (PE/EtOAc=10/1~3/1, Silica-CS 12 g, 20 mL/min, silica gel, UV 254) to give the product (220 mg, 46%). ESI-MS m/z calcd for [C$_{29}$H$_{34}$ClN$_5$O$_6$S] [M+Na]$^+$: 638.2; found: 637.9. $^1$H NMR (400 MHz, CDCl$_3$) δ 8.29 (d, J=2.0 Hz, 1H), 7.89 (d, J=2.0 Hz, 1H), 7.48-7.45 (m, 1H), 7.35-7.27 (m, 4H), 5.99-5.82 (m, 2H), 5.56 (s, 1H), 4.26 (d, J=3.2 Hz, 1H), 4.20 (dd, J=10.4, 5.2 Hz, 1H), 4.16-4.11 (m, 1H), 4.09-4.03 (m, 2H), 3.92 (d, J=11.6 Hz, 1H), 3.71-3.57 (m, 4H), 3.45 (s, 3H), 2.57-2.41 (m, 2H), 1.44 (s, 9H).

5-Chloro-2-(1,2,3,6-tetrahydropyridin-4-yl)pyridin-3-yl 3-azido-3-deoxy-2-O-methyl-1-thio-α-D-galactopyranoside

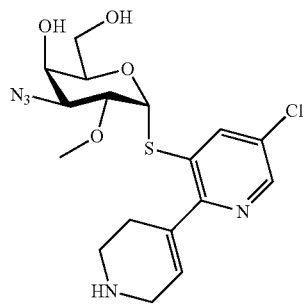

To a solution of 5-chloro-2-[1-(N-tert-butoxycarbonyl)-1,2,3,6-tetrahydropyridin-4-yl]pyridin-3-yl 3-azido-4,6-O-benzylidene-3-deoxy-2-O-methyl-1-thio-α-D-galactopyranoside (400 mg, 0.65 mmol) in DCM (15 mL) TFA (2.41 mL, 32.5 mmol) was added. The mixture was stirred 2 h at rt and Et$_3$N (4 mL) was added at 0° C. followed by concentration of the mixture. The residue was purified by preparative HPLC (Method A) to give the product (97 mg, 35%) as a white solid. ESI-MS m/z calcd for [C$_{17}$H$_{22}$ClN$_5$O$_4$S] [M+H]$^+$: 428.1; found: 428.0. $^1$H NMR (400 MHz, CD$_3$OD) δ 8.35 (d, J=2.0 Hz, 1H), 8.25 (d, J=2.0 Hz, 1H), 6.09 (d, J=5.2 Hz, 1H), 6.05-5.95 (m, 1H), 4.16-4.04 (m, 2H), 4.00 (d, J=2.4 Hz, 1H), 3.73-3.55 (m, 5H), 3.51 (s, 3H), 3.18-3.13 (m, 2H), 2.61-2.48 (m, 2H).

Intermediate 29

5-Chloro-2-[1-(N-tert-butoxycarbonyl)-3-pyrrolin-3-yl]pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

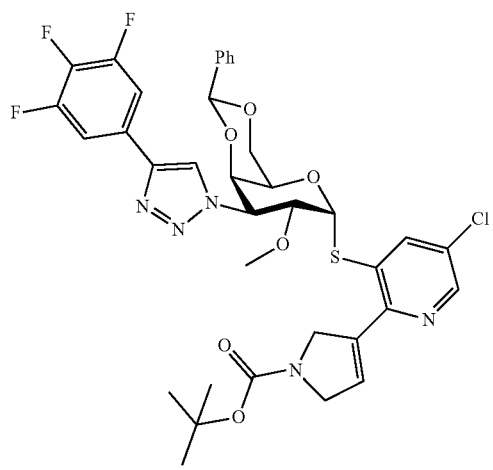

177

5-Chloro-2-[1-(N-tert-butoxycarbonyl)-3-pyrrolin-3-yl]pyridin-3-yl 3-azido-4,6-O-benzylidene-3-deoxy-2-O-methyl-1-thio-α-D-galactopyranoside

178

5-Chloro-2-[1-(N-tert-butoxycarbonyl)-3-pyrrolin-3-yl]pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

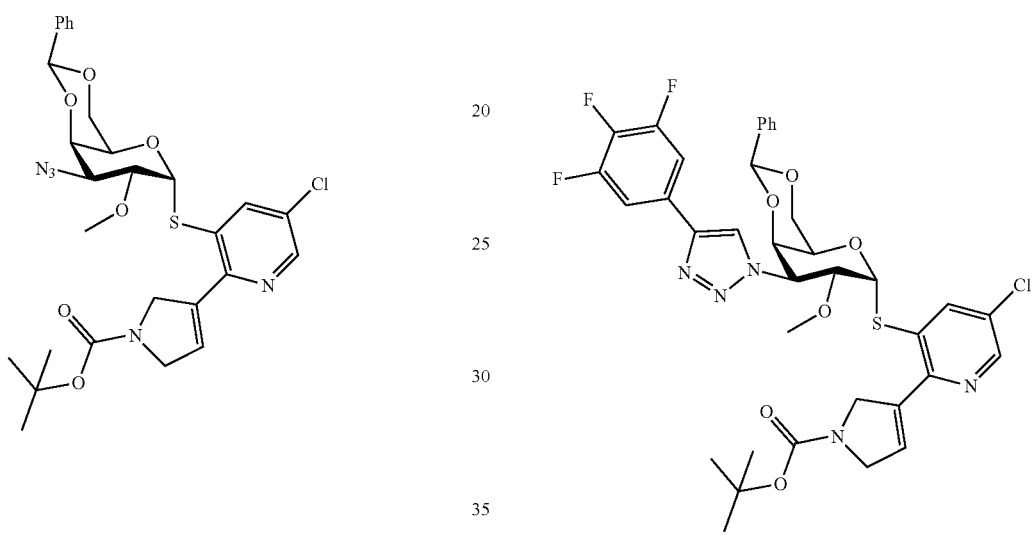

To a solution of 2-bromo-5-chloropyridin-3-yl 3-azido-4,6-O-benzylidene-3-deoxy-2-O-methyl-1-thio-α-D-galactopyranoside (100 mg, 0.20 mmol) in 1,4-dioxane (10 mL) a solution of tert-butyl 3-(4,4,5,5-tetramethyl-1,3,2-dioxaborolan-2-yl)-2,5-dihydropyrrole-1-carboxylate (91.9 mg, 0.31 mmol), $K_2CO_3$ (53.8 mg, 0.39 mmol), bis(triphenylphosphine)palladium(II) chloride (10.9 mg, 0.016 mmol) in water (1 mL) was added. The mixture was stirred 1 h at 100° C. in a microwave reactor. The mixture was concentrated, and the residue was dissolved in EtOAc (100 mL) and washed with water and brine. The organic layer was dried with $Na_2SO_4$ and concentrated. The residue was purified by column chromatography (PE/EtOAc=10/1~3/1, Silica-CS 12 g, 20 mL/min, silica gel, UV 254) to give the product (90 mg, 77%). ESI-MS m/z calcd for $[C_{28}H_{32}ClN_5O_6S]$ $[M+Na]^+$: 624.2; found: 623.8. $^1$H NMR (400 MHz, $CDCl_3$) δ 8.35 (d, J=2.0 Hz, 1H), 8.00-7.94 (m, 1H), 7.54-7.51 (m, 2H), 7.40-7.36 (m, 3H), 6.08 (d, J=5.2 Hz, 1H), 5.63 (s, 1H), 4.67-4.53 (m, 2H), 4.44-4.00 (m, 6H), 3.95-3.92 (m, 1H), 3.79-3.66 (m, 2H), 3.54 (s, 3H), 1.48 (s, 9H).

To a solution of 5-chloro-2-[1-(N-tert-butoxycarbonyl)-3-pyrrolin-3-yl]pyridin-3-yl 3-azido-4,6-O-benzylidene-3-deoxy-2-O-methyl-1-thio-α-D-galactopyranoside (90 mg, 0.15 mmol) in DMF (2 mL), trimethyl-[2-(3,4,5-trifluorophenyl)ethynyl]silane (37.5 mg, 0.16 mmol), (+)-sodium L-ascorbate (29.6 mg, 0.15 mmol), copper(II) sulfate pentahydrate (37.3 mg, 0.15 mmol) and CsF (34.1 mg, 0.22 mmol) were added. The mixture was stirred under a nitrogen atmosphere at rt overnight. The mixture was filtered and the filtrate was purified by reverse-phase column [$CH_3CN$/water (0.01% TFA)=0~65%, C18 40 g, 50 mL/min, UV 254] to give the product (50 mg, 44%). ESI-MS m/z calcd for $[C_{36}H_{35}ClF_3N_5O_6S]$ $[M+H]^+$: 758.2; found: 758.1. $^1$H NMR (400 MHz, $CDCl_3$) δ 8.40 (s, 1H), 8.04-7.99 (m, 1H), 7.98-7.94 (m, 1H), 7.46-7.41 (m, 7H), 6.80-6.44 (m, 1H), 6.22-6.15 (m, 1H), 5.55 (s, 1H), 5.45-5.27 (m, 1H), 4.71-4.38 (m, 5H), 4.31 (d, J=12.8 Hz, 1H), 4.30-4.10 (m, 2H), 3.30 (s, 3H), 1.51 (s, 9H).

Intermediate 30

5-Chloro-2-(oxazol-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

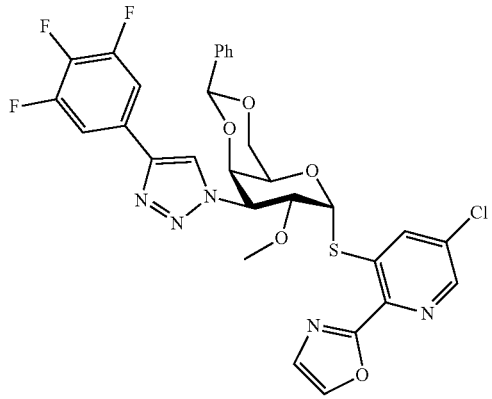

2-Bromo-5-chloropyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

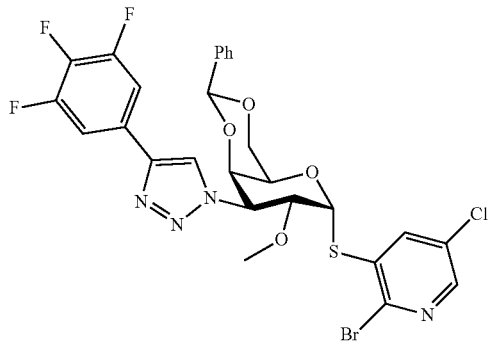

To a solution of 2-bromo-5-chloro-3-pyridine-3-yl 3-azido-4,6-O-benzylidene-3-deoxy-2-O-methyl-1-thio-α-D-galactopyranoside (185 mg, 0.36 mmol) in DMF (3 mL) trimethyl-[2-(3,4,5-trifluorophenyl)ethynyl]silane (123 mg, 0.54 mmol), copper(II) sulfate pentahydrate (45.0 mg, 0.18 mmol) and (+)-sodium L-ascorbate (36 mg, 0.18 mmol) were added. The mixture was stirred 3 h at rt, water (50 mL) and DCM (50 mL) were added, and the aqueous phase was extracted with DCM (2×50 mL). The combined organic phases were washed with water (50 mL) and brine (50 mL) and dried over anhydrous $Na_2SO_4$. The solvent was removed under reduced pressure, and the residue was purified by column chromatography (PE/EtOAc=10/1~1/1, Silica-CS 20 g, 20 m/min, silica gel, UV 254) to afford the product (210 mg, 85%). ESI-MS m/z calcd for $[C_{27}H_{21}BrClF_3N_4O_4S]$ $[M+H]^+$: 669.0; found: 669.0. $^1H$ NMR (400 MHz, DMSO-$d_6$) δ 8.97 (s, 1H), 8.36 (d, J=2.4 Hz, 1H), 8.19 (d, J=2.4 Hz, 1H), 7.80-7.75 (m, 2H), 7.39-7.35 (m, 5H), 6.93 (d, J=5.2 Hz, 1H), 5.60 (s, 1H), 5.23 (dd, J=11.2, 3.2 Hz, 1H), 4.73 (dd, J=11.6, 5.2 Hz, 1H), 4.60 (d, J=3.2 Hz, 1H), 4.23 (s, 1H), 4.12-3.98 (m, 2H), 3.37 (s, 3H).

5-Chloro-2-(oxazol-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

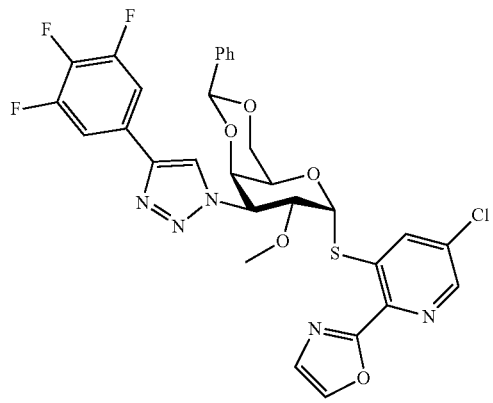

To a solution of 2-bromo-5-chloropyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (180 mg, 0.26 mmol) in DMF (5 mL) tributyl(oxazol-2-yl)stannane (283 mg, 0.79 mmol), tetrakis(triphenylphosphine)palladium(0) (37 mg, 0.053 mmol) and CsF (80 mg, 0.53 mmol) were added. The mixture was stirred 16 h at 60° C. under a nitrogen atmosphere. The solvent was removed by evaporation and the residue was purified by column chromatography (PE/EtOAc=10/1~5/7, Silica-CS 20 g, 20 mL/min, silica gel, UV 254) to afford the product (72 mg, 37%). ESI-MS m/z calcd for $[C_{30}H_{23}ClF_3N_5O_5S]$ $[M+H]^+$: 658.1; found: 658.1. $^1H$ NMR (400 MHz, DMSO-$d_6$) δ 8.97 (s, 1H), 8.62 (d, J=2.0 Hz, 1H), 8.39-8.38 (m, 2H), 7.80-7.76 (m, 2H), 7.60 (s, 1H), 7.40-7.35 (m, 5H), 6.91 (d, J=5.2 Hz, 1H), 5.58 (s, 1H), 5.22 (dd, J=11.6, 3.2 Hz, 1H), 4.72 (dd, J=7.6, 4.2 Hz, 1H), 4.56 (d, J=2.8, 1H), 4.18 (s, 1H), 4.09-3.96 (m, 2H), 3.37 (s, 3H).

Intermediate 31

5-Chloro-2-(thiazol-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

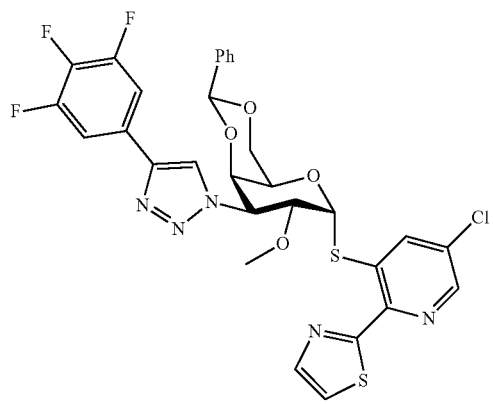

To a solution of 2-bromo-5-chloropyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (200 mg, 0.30 mmol) in DMF (5 mL) tributyl(thiazol-2-yl)stannane (223 mg, 0.6 mmol), tetrakis(triphenylphosphine)palladium(0) (63 mg, 0.09 mmol) and CsF (91 mg, 0.9 mmol) were added. The mixture was stirred 3 h at 100° C. under a nitrogen atmosphere before the solvent was removed by evaporation. The residue was purified by column chromatography (PE/EtOAc=10/1~1/1, Silica-CS 20 g, 20 mL/min, silica gel, UV 254) to afford the product (85 mg, 39%). ESI-MS m/z calcd for [$C_{30}H_{23}ClF_3N_5O_4S_2$] [M+H]$^+$: 674.1; found: 674.0. $^1$H NMR (400 MHz, DMSO-$d_6$) δ 8.98 (s, 1H), 8.56 (d, J=2.0 Hz, 1H), 8.35 (d, J=2.0 Hz, 1H), 8.14 (d, J=3.2 Hz, 1H), 7.94 (d, J=3.6 Hz, 1H), 7.81-7.77 (m, 2H), 7.41-7.35 (m, 5H), 6.92 (d, J=5.60 Hz, 1H), 5.58 (s, 1H), 5.27 (dd, J=11.6, 3.6 Hz, 1H), 4.74 (dd, J=7.6, 5.2 Hz, 1H), 4.57 (d, J=3.6 Hz, 1H), 4.22 (s, 1H), 4.10-3.98 (m, 2H), 3.35 (s, 3H).

Intermediate 32

2,5-Bis(thiazol-2-yl)pyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

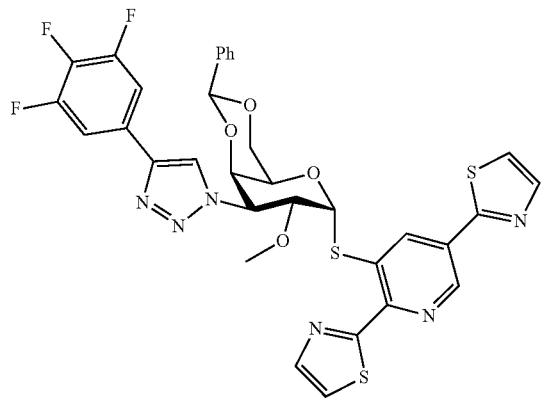

To a solution of 2-bromo-5-chloropyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside (180 mg, 0.27 mmol) in DMF (5 mL) tributyl(thiazol-2-yl)stannane (302 mg, 0.81 mmol), tetrakis(triphenylphosphine)palladium(0) (57 mg, 0.08 mmol) and CsF (122 mg, 0.81 mmol) were added. The mixture was stirred 3 h at 100° C. under a nitrogen atmosphere before the solvent was removed by evaporation. The residue was purified by column chromatography (PE/EtOAc=10/1~1/1, Silica-CS 20 g, 20 mL/min, silica gel, UV 254) to afford the product (125 mg, 34%). ESI-MS m/z calcd for [$C_{33}H_{25}F_3N_6O_4S_3$] [M+H]$^+$: 722.8; found: 723.1. $^1$H NMR (400 MHz, DMSO-$d_6$) δ 8.97 (s, 1H), 8.88 (d, J=2.4 Hz, 1H), 8.33 (d, J=2.4 Hz, 1H), 7.95-7.94 (m, 2H), 7.92-7.89 (m, 2H), 7.79 (d, J=3.2 Hz, 2H), 7.38-7.35 (m, 5H), 6.82 (d, J=5.2 Hz, 1H), 5.76 (s, 1H), 5.22 (dd, J=11.2, 4.8 Hz, 1H), 4.69 (dd, J=11.2, 4.8 Hz, 1H), 4.60 (d, J=3.2 Hz, 1H), 4.38 (s, 1H), 4.16-3.97 (m, 2H), 3.34 (s, 3H).

Intermediates 33 and 34

5-Chloropyridin-3-yl 3-azido-3-deoxy-2-O-methyl-1-thio-α-D-galactopyranoside and 5-Bromopyridin-3-yl 3-azido-3-deoxy-2-O-methyl-1-thio-α-D-galactopyranoside (mixture)

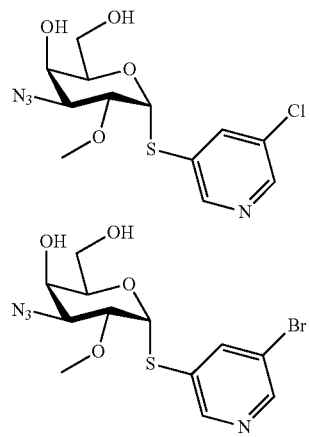

5-Chloropyridine-3-thiol and 5-Bromopyridine-3-thiol (mixture)

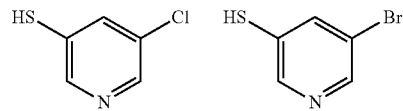

To a solution of 3-bromo-5-chloropyridine (4.52 g, 23.5 mmol) and NaH (60% in oil, 0.90 g, 23.5 mmol) in DMF (40 mL) benzyl mercaptan (2.51 mL, 21.3 mmol) was added dropwise and the mixture was stirred 2 h at rt. The mixture was concentrated, diluted with EtOAc, washed twice with water and the organic phase was dried and evaporated. The residue was dissolved in toluene (15 mL) and cooled to 0° C. To the formed suspension, a solution of AlCl$_3$ (4.83 g, 36.2 mmol) in toluene (55 mL) was added and the mixture reached rt in 30 min, it was then stirred 2 h at rt. The mixture was cooled to 0° C. and quenched by addition of water. The phases were separated, and the organic phase was washed with water, dried and concentrated. The residue was purified by chromatography (SiO$_2$, PE/EtOAc) to afford the mixture of products (3.05 g).

5-Chloropyridine-3-thiol

ESI-MS m/z calcd for [$C_5H_4ClNS$] [M+H]$^+$: 146.0; found: 145.9.

5-Bromopyridine-3-thiol

ESI-MS m/z calcd for [$C_5H_4BrNS$] [M+H]$^+$: 189.9; found: 189.9.

5-Chloropyridin-3-yl 2,4,6-tri-O-acetyl-3-azido-3-deoxy-1-thio-α-D-galactopyranoside and 5-Bromopyridin-3-yl 2,4,6-tri-O-acetyl-3-azido-3-deoxy-1-thio-α-D-galactopyranoside (mixture)

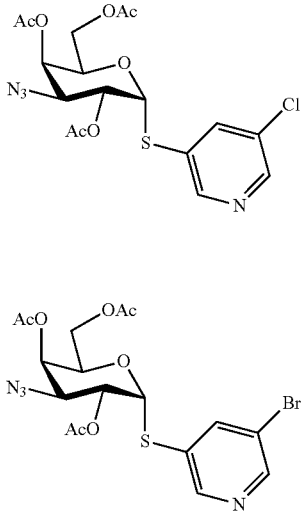

To a mixture of 5-chloropyridine-3-thiol and 5-bromopyridine-3-thiol (650 mg) was dissolved together with 2,4,6-tri-O-acetyl-3-azido-3-deoxy-β-D-galactopyranosyl chloride (1.72 g, 4.91 mmol) in DMF (20 mL) NaH (60% in oil, 428 mg, 11.2 mmol) was added. The mixture was stirred 3 h at rt before being diluted with EtOAc and washed twice with water and once with brine. The organic phase was dried, concentrated and purified by chromatography (SiO$_2$, PE/EtOAc) to afford the mixture of products (1.17 g).

5-Chloropyridin-3-yl 2,4,6-tri-O-acetyl-3-azido-3-deoxy-1-thio-α-D-galactopyranoside ESI-MS m/z calcd for [C$_{17}$H$_{19}$ClN$_4$O$_7$S] [M+H]$^+$: 459.0; found: 459.1. $^1$H NMR (400 MHz, Chloroform-d) δ 8.53 (d, J=1.8 Hz, 1H), 8.50 (d, J=2.2 Hz, 1H), 7.84 (t, J=2.1 Hz, 1H), 5.99 (d, J=5.5 Hz, 1H), 5.50 (d, J=3.3 Hz, 1H), 5.30 (dd, J=10.9, 5.5 Hz, 1H), 4.68-4.60 (m, 1H), 4.14 (dd, J=11.7, 4.6 Hz, 1H), 4.03 (dd, J=11.6, 7.9 Hz, 1H), 3.96 (dd, J=10.9, 3.4 Hz, 1H), 2.21 (s, 3H), 2.18 (s, 3H), 2.04 (s, 3H).

5-Bromopyridin-3-yl 2,4,6-tri-O-acetyl-3-azido-3-deoxy-1-thio-α-D-galactopyranoside ESI-MS m/z calcd for [C$_{17}$H$_{19}$BrN$_4$O$_7$S] [M+H]$^+$: 503.0; found: 503.1. $^1$H NMR (400 MHz, Chloroform-d) δ 8.60 (d, J=2.0 Hz, 1H), 8.57 (d, J=1.8 Hz, 1H), 7.98 (t, J=2.1 Hz, 1H), 5.99 (d, J=5.5 Hz, 1H), 5.50 (d, J=3.3 Hz, 1H), 5.30 (dd, J=10.9, 5.5 Hz, 1H), 4.68-4.60 (m, 1H), 4.14 (dd, J=11.7, 4.6 Hz, 1H), 4.03 (dd, J=11.6, 7.9 Hz, 1H), 3.96 (dd, J=10.9, 3.4 Hz, 1H), 2.21 (s, 3H), 2.18 (s, 3H), 2.04 (s, 3H).

5-Chloropyridin-3-yl 3-azido-3-deoxy-2-O-methyl-1-thio-α-D-galactopyranoside and 5-Bromopyridin-3-yl 3-azido-3-deoxy-2-O-methyl-1-thio-α-D-galactopyranoside (mixture)

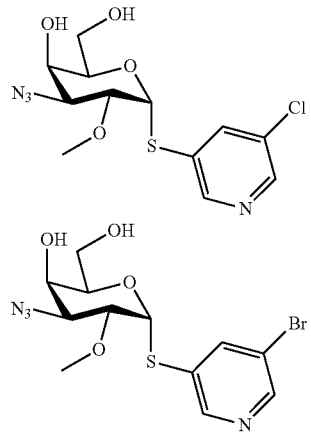

A mixture of 5-chloropyridin-3-yl 2,4,6-tri-O-acetyl-3-azido-3-deoxy-1-thio-α-D-galactopyranoside and 5-bromopyridin-3-yl 2,4,6-tri-O-acetyl-3-azido-3-deoxy-1-thio-α-D-galactopyranoside (1.17 g) was dissolved in MeOH (20 mL) and NaOMe (1 mL, 1 M) and stirred 2 h at rt. AcOH (0.2 mL) was added and the mixture was concentrated and the residue was partitioned between EtOAc and NaOH (aq, 1M). The organic phase was dried, evaporated and the residue was dissolved together with p-toluenesulfonic acid monohydrate (146 mg, 0.77 mmol) in MeCN (100 mL). Benzaldehyde dimethyl acetal (0.77 mL, 5.10 mmol) was added and the mixture was stirred 2 h at rt, precipitation was observed. The solids were filtered off and the filtrate was evaporated, diluted with EtOAc and washed with saturated aq NaHCO$_3$. The organic phase was dried and evaporated. The residue and the solid material were dissolved together with NaH (60% in oil, 164 mg, 4.28 mmol) in DMF (10 mL). The mixture was stirred 5 min before the addition of iodomethane (0.2 mL, 3.21 mmol). After stirring 2 h at rt the mixture was diluted with EtOAc, washed twice with water and the organic phase was dried and evaporated. The residue was stirred 30 min at rt in TFA/water (7.5 mL, 4:1). The mixture was concentrated to a third of its volume and partitioned between EtOAc and NaOH (aq, 1M). The organic phase was dried, evaporated and purified by chromatography (SiO$_2$, PE/EtOAc) to afford the mixture of products (380 mg).

5-Chloropyridin-3-yl 3-azido-3-deoxy-2-O-methyl-1-thio-α-D-galactopyranoside ESI-MS m/z calcd for [C$_{12}$H$_{15}$ClN$_4$O$_4$S] [M+H]$^+$: 347.1; found: 347.1. $^1$H NMR (400 MHz, Methanol-d$_4$) δ 8.59 (d, J=1.9 Hz, 1H), 8.44 (d, J=2.2 Hz, 1H), 8.15 (t, J=2.1 Hz, 1H), 6.07 (d, J=5.2 Hz, 1H), 4.23 (t, J=6.0 Hz, 1H), 4.06 (dd, J=10.6, 5.3 Hz, 1H), 4.00 (d, J=2.5 Hz, 1H), 3.70-3.60 (m, 3H), 3.53 (s, 3H).

5-Bromopyridin-3-yl 3-azido-3-deoxy-2-O-methyl-1-thio-α-D-galactopyranoside

ESI-MS m/z calcd for [C$_{12}$H$_{15}$BrN$_4$O$_4$S] [M+H]$^+$: 391.0; found: 391.0. $^1$H NMR (400 MHz, Methanol-d$_4$) δ 8.63 (d, J=1.8 Hz, 1H), 8.54 (d, J=2.2 Hz, 1H), 8.29 (t, J=1.9 Hz, 1H), 6.07 (d, J=5.2 Hz, 1H), 4.23 (t, J=6.0 Hz, 1H), 4.06 (dd, J=10.6, 5.3 Hz, 1H), 4.00 (d, J=2.5 Hz, 1H), 3.70-3.60 (m, 3H), 3.53 (s, 3H).

Intermediate 39

6-Trifluoromethyl-5-methylpyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

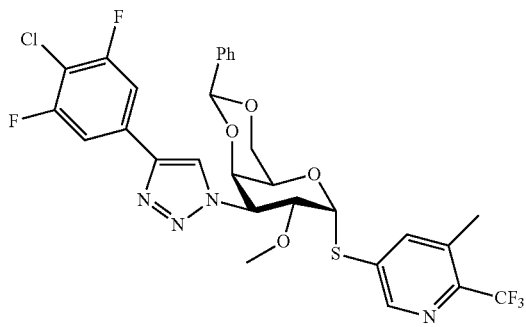

5-Fluoro-3-methyl-2-(trifluoromethyl)pyridine

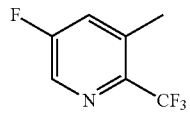

To a solution of 2-bromo-5-fluoro-3-methylpyridine (3.8 g, 20 mmol) in DMF (20 mL) CuI (6.0 g, 31.5 mmol) and methyl 2,2-difluoro-2-fluorosulfonyl-acetate (11.5 g, 60 mmol) were added. The mixture was stirred 5 h at 100° C. in a microwave reactor. Water (100 mL) was added, then extracted with diethyl ether (3×100 mL). The combined organic layers were washed with brine (3×100 mL), dried over anhydrous Na$_2$SO$_4$ and concentrated to afford the product. (2.5 g, 63%). GC-MS calcd for [C$_7$H$_5$F$_4$N] [M]: 179.0; found: 179.0.

5-Methyl-6-(trifluoromethyl)pyridine-3-thiol

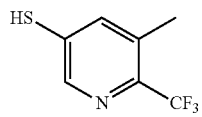

To a solution of 5-fluoro-3-methyl-2-(trifluoromethyl) pyridine (2.5 g, 12.6 mmol) in DMF (20 mL) Na$_2$S (1.96 g, 25.1 mmol) was added. The mixture was stirred overnight at rt. The solvent was removed to afford the product (2.0 g, 82%). ESI-MS m/z calcd for [C$_7$H$_6$F$_3$NS] [M−H]$^-$: 192.0; found: 192.0.

6-Trifluoromethyl-5-methylpyridin-3-yl 2,4,6-tri-O-acetyl-3-azido-3-deoxy-1-thio-α-D-galactopyranoside

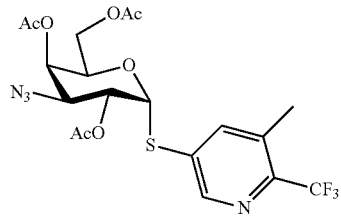

To a solution of 2,4,6-tri-O-acetyl-3-azido-3-deoxy-β-D-galactopyranosyl chloride (3.50 g, 10.0 mmol) and 5-methyl-6-(trifluoromethyl)pyridine-3-thiol (2.0 g, 10.4 mmol) in DMF (50 mL) Cs$_2$CO$_3$ (6.52 g, 20.0 mmol) was added. The mixture was stirred 6 h at rt before water (200 mL) was added. The mixture was extracted with EtOAc (3×100 mL). The combined organic layers were washed with brine (3×100 mL), dried over anhydrous Na$_2$SO$_4$ and concentrated. The residue was purified by column chromatography (PE/EtOAc=10/1~1/1, Silica-CS 40 g, 40 m/min, silica gel, UV 254) to give the product (2.6 g, 51%). ESI-MS m/z calcd for [C$_{19}$H$_{21}$F$_3$N$_4$O$_7$S][M+H]$^+$: 507.1; found: 507.1. $^1$H NMR (400 MHz, CDCl$_3$) δ 8.50 (d, J=1.6 Hz, 1H), 7.71 (s, 1H), 6.07 (d, J=5.6 Hz, 1H), 5.48 (d, J=2.8 Hz, 1H), 5.29 (dd, J=11.2, 5.6 Hz, 1H), 4.60-4.57 (m, 1H), 4.12-3.96 (m, 3H), 2.51-2.48 (m, 3H), 2.18 (s, 3H), 2.16 (s, 3H), 1.94 (s, 3H).

6-Trifluoromethyl-5-methylpyridin-3-yl 3-azido-3-deoxy-1-thio-α-D-galactopyranoside

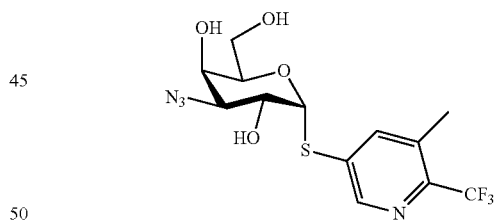

To a solution of 6-trifluoromethyl-5-methylpyridin-3-yl 2,4,6-tri-O-acetyl-3-azido-3-deoxy-1-thio-α-D-galactopyranoside (2.6 g, 5.13 mmol) in MeOH (50 mL) NaOMe (0.03 g, 0.51 mmol) was added. The mixture was stirred 6 h at rt before the solvent was removed by evaporation. The residue was purified by preparative HPLC (Method A) to give the product (1.90 g, 93%). ESI-MS m/z calcd for [C$_{13}$H$_{15}$F$_3$N$_4$O$_4$S] [M+H]$^+$: 381.1; found: 381.1. $^1$H NMR (400 MHz, CDCl$_3$) δ 8.53 (d, J=1.6 Hz, 1H), 8.04 (d, J=0.4 Hz, 1H), 5.82 (d, J=5.2 Hz, 1H), 4.40 (dd, J=10.8, 5.6 Hz, 1H), 4.24-4.20 (m, 1H), 4.03 (d, J=2.0 Hz, 1H), 3.70-3.62 (m, 2H), 3.54 (dd, J=10.8, 2.8 Hz, 1H), 2.51-2.48 (m, 3H).

6-Trifluoromethyl-5-methylpyridin-3-yl 3-azido-4,6-O-benzylidene-3-deoxy-1-thio-α-D-galactopyranoside

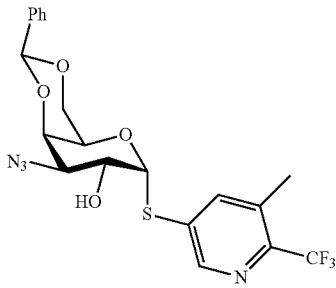

To a stirred solution of 6-trifluoromethyl-5-methylpyridin-3-yl 3-azido-3-deoxy-1-thio-α-D-galactopyranoside (1.90 g, 4.8 mmol) in DMF (15 mL) benzaldehyde dimethyl acetal (2.19 g, 14.4 mmol) was added followed by D(+)-10-camphorsulfonic acid (334 mg, 1.44 mmol). The mixture was stirred 2 h at 50° C. The mixture was added dropwise to aq NaHCO$_3$ (200 mL) then filtered. The white solid was collected and dried in vacuum to afford the product (1.10 g, 47%). ESI-MS m/z calcd for [C$_{20}$H$_{19}$F$_3$N$_4$O$_4$S][M+H]$^+$: 469.1; found: 469.1. $^1$H NMR (400 MHz, CDCl$_3$) δ 8.52 (d, J=1.6 Hz, 1H), 7.78 (s, 1H), 7.52-7.35 (m, 5H), 5.94 (d, J=5.6 Hz, 1H), 5.64 (s, 1H), 4.68-4.63 (m, 1H), 4.42 (d, J=3.2 Hz, 1H), 4.27-4.14 (m, 3H), 3.61 (dd, J=10.8, 3.2 Hz, 1H), 2.51-2.48 (m, 3H).

6-Trifluoromethyl-5-methylpyridin-3-yl 3-azido-4,6-O-benzylidene-3-deoxy-2-O-methyl-1-thio-α-D-galactopyranoside

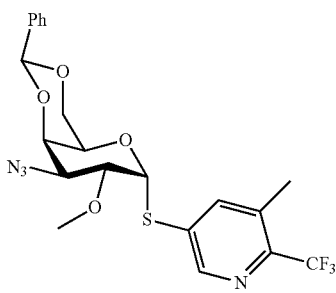

To a solution of 6-trifluoromethyl-5-methylpyridin-3-yl 3-azido-4,6-O-benzylidene-3-deoxy-1-thio-α-D-galactopyranoside (400 mg, 0.82 mmol) in DMF (8 mL) Cs$_2$CO$_3$ (0.534 g, 1.64 mmol) and iodomethane (0.349 g, 2.46 mmol) were added. The mixture was stirred 6 h at rt. Water (100 mL) was added, and the mixture was extracted with EtOAc (3×50 mL). The organic layers were washed with brine (3×50 mL), dried over anhydrous Na$_2$SO$_4$ and concentrated. The residue was purified by column chromatography (PE/EtOAc=10/1~1/1, Silica-CS 20 g, 20 m/min, silica gel, UV 254) to afford the product (350 mg, 82%) as a white solid. ESI-MS m/z calcd for [C$_{21}$H$_{21}$F$_3$N$_4$O$_4$S] [M+H]$^+$: 483.1; found: 483.1. $^1$H NMR (400 MHz, CDCl$_3$) δ 8.53 (d, J=2.0 Hz, 1H), 7.78 (d, J=0.8 Hz, 1H), 7.55-7.38 (m, 5H), 6.14 (d, J=5.2 Hz, 1H), 5.64 (s, 1H), 4.35 (d, J=2.8 Hz, 1H), 4.28 (dd, J=10.8, 5.2 Hz, 1H), 4.24-4.01 (m, 3H), 3.77-3.73 (m, 1H), 3.57 (s, 3H), 2.51-2.48 (m, 3H).

6-Trifluoromethyl-5-methylpyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

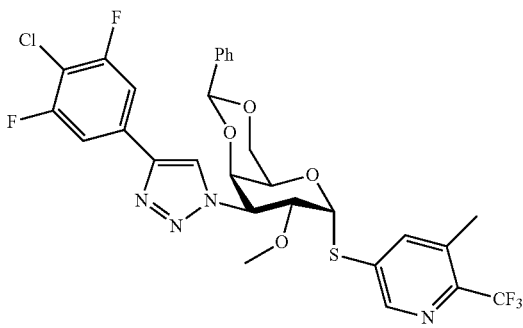

To a solution of 6-trifluoromethyl-5-methylpyridin-3-yl 3-azido-4,6-O-benzylidene-3-deoxy-2-O-methyl-1-thio-α-D-galactopyranoside (200 mg, 0.39 mmol) in DMF (6 mL) trimethyl-[2-(4-chloro-3,5-difluorophenyl)ethynyl]silane (236 mg, 60%, 0.58 mol), copper(II) sulfate pentahydrate (48.2 mg, 0.19 mmol) and (+)-sodium L-ascorbate (38.2 mg, 0.19 mmol) were added. The mixture was stirred 3 h at rt under nitrogen atmosphere. Water (50 mL) and DCM (50 mL) were added. The aqueous phase was extracted with DCM (2×50 mL). The combined organic phases were washed with water (50 mL) and brine (3×50 mL), dried over anhydrous Na$_2$SO$_4$ and concentrated. The residue was purified by column chromatography (PE/EtOAc=10/1~1/1, Silica-CS 20 g, 20 mL/min, silica gel, UV 254) to afford the product (200 mg, 73%). ESI-MS m/z calcd for [C$_{29}$H$_{24}$ClF$_5$N$_4$O$_4$S] [M+H]$^+$: 655.1; found: 655.0. $^1$H NMR (400 MHz, CDCl$_3$) δ 8.57 (d, J=1.6 Hz, 1H), 8.00 (s, 1H), 7.79 (s, 1H), 7.45 (d, J=7.6 Hz, 2H), 7.39 (s, 5H), 6.24 (d, J=4.8 Hz, 1H), 5.52 (s, 1H), 5.32 (dd, J=11.2, 3.2 Hz, 1H), 4.56-4.51 (m, 2H), 4.32-4.13 (m, 3H), 3.33 (s, 3H), 2.51-2.48 (m, 3H).

Intermediate 40

2-(N-azetidinyl-carbonyl)-5-chlorophenyl 3-[4-(4-chloro-3,5-difluorophenyl)-1H-1,2,3-triazol-1-yl]-3-deoxy-1-thio-α-D-galactopyranoside

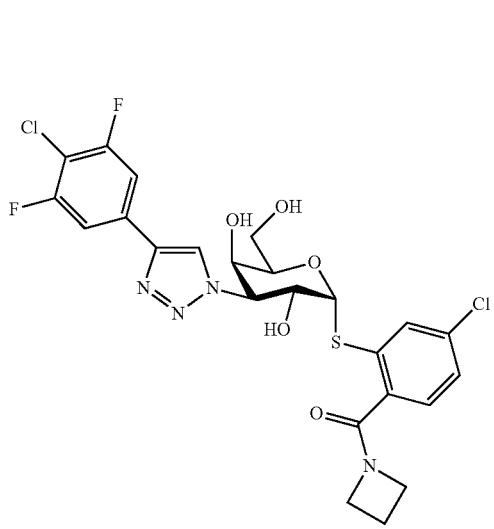

2-Carboxy-5-chlorophenyl 3-[4-(4-chloro-3,5-difluorophenyl)-1H-1,2,3-triazol-1-yl]-3-deoxy-1-thio-α-D-galactopyranoside (150 mg, 0.27 mmol), 1-hydroxybenzotriazole hydrate (65 mg, 0.41 mmol) and N-(3-dimethylaminopropyl)-N'-ethylcarbodiimide hydrochloride (81 mg, 0.41 mmol) were stirred in DMF (2.0 mL) and azetidine (39 μL, 0.55 mmol) was added followed by Et$_3$N (39 μL, 0.27 mmol). The mixture was stirred 5 h at rt, then water (8.0 mL) was added and decanted. The residue was stirred in EtOH (3 mL) and NaOH (0.5 mL, 2 M) 1 h at rt, then neutralized with HCl (0.5 mL, 2 M) and poured onto water. The precipitate was collected by filtration and further purification by chromatography (SiO$_2$, PE/EtOAc) afforded the product (93 mg, 58%). ESI-MS m/z calcd for [C$_{24}$H$_{22}$Cl$_2$F$_2$N$_4$O$_5$S] [M+H]$^+$: 587.1; found: 587.1. $^1$H NMR (400 MHz, Methanol-d$_4$) δ 8.60 (s, 1H), 7.87 (d, J=1.8 Hz, 1H), 7.66 (d, J=8.0 Hz, 2H), 7.40 (dd, J=8.2, 1.9 Hz, 1H), 7.32 (d, J=8.2 Hz, 1H), 5.93 (d, J=5.2 Hz, 1H), 5.01 (dd, J=11.5, 2.7 Hz, 1H), 4.93 (dd, J=11.5, 5.2 Hz, 1H), 4.48 (t, J=6.1 Hz, 1H), 4.26-4.15 (m, 3H), 4.03 (m, 2H), 3.72 (m, 2H), 2.34 (m, 2H).

Intermediate 41

2-(N-azetidinyl-carbonyl)-5-chlorophenyl 4,6-O-benzylidene-3-deoxy-3-[4-(3-fluoro-4-methylphenyl)-1H-1,2,3-triazol-1-yl]-2-O-methyl-1-thio-α-D-galactopyranoside

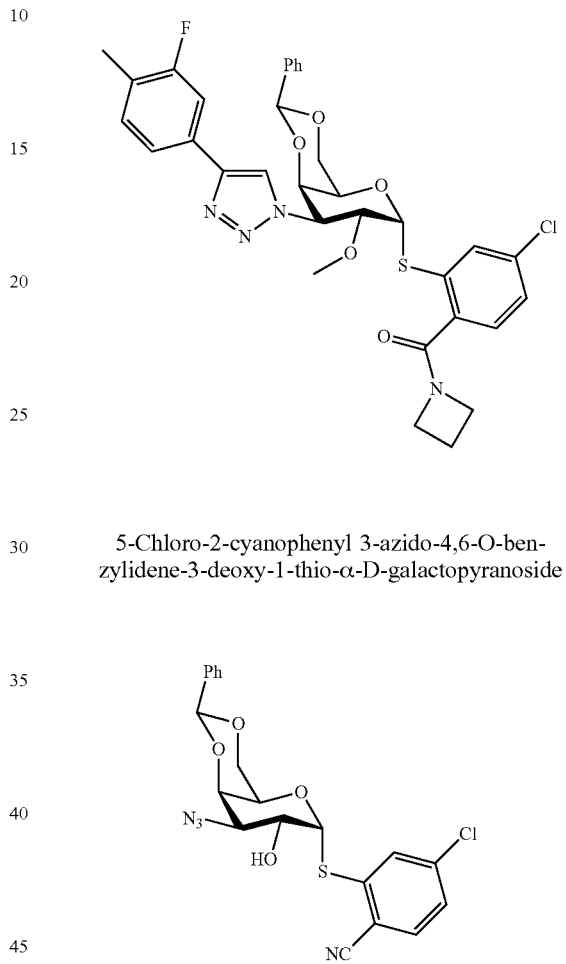

5-Chloro-2-cyanophenyl 3-azido-4,6-O-benzylidene-3-deoxy-1-thio-α-D-galactopyranoside To a solution of 5-chloro-2-cyanophenyl 2,4,6-tri-O-acetyl-3-azido-3-deoxy-1-thio-α-D-galactopyranoside (1.33 g, 2.75 mmol) in MeOH (5.0 mL) was added catalytical amount of NaOMe (pH=9-10). The mixture was stirred for 20 min before being neutralized with acid ion resin and filtrated. The filtrate was concentrated, and the residue was dissolved in DMF (10 mL). To the solution D(+)-10-camphorsulfonic acid (195 mg, 0.84 mmol) and benzaldehyde dimethyl acetal (1.28 g, 8.41 mmol) were added and the mixture was stirred 2 h at 60° C. The mixture was concentrated and the residue was purified by column chromatography (PE/EtOAc=2/1~1/1, Silica-CS 12 g, 12 mL/min, silica gel, UV 254) to give the product (768 mg, 62%). ESI-MS m/z calcd for [C$_{20}$H$_{17}$ClN$_4$O$_4$S] [M+H]$^+$: 445.1; found: 445.2. $^1$H NMR (400 MHz, CDCl$_3$) δ 7.76 (d, J=2.0 Hz, 1H), 7.60 (d, J=8.4 Hz, 1H), 7.51-7.49 (m, 2H), 7.38-7.34 (m, 4H), 5.89 (d, J=5.2 Hz, 1H), 5.63 (s, 1H), 4.67-4.62 (m, 1H), 4.42 (d, J=2.8 Hz, 1H), 4.29-4.25 (m, 2H), 4.17-4.14 (m, 1H), 3.64 (dd, J=10.8, 3.2 Hz, 1H), 2.48 (d, J=6.4 Hz, 1H).

2-Cyano-5-chlorophenyl 3-azido-4,6-O-benzylidene-3-deoxy-2-O-methyl-1-thio-α-D-galactopyranoside

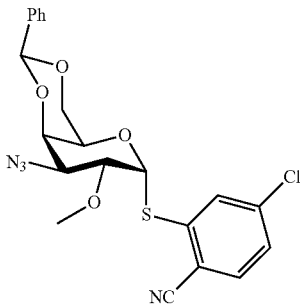

To a solution of 5-chloro-2-cyanophenyl 3-azido-4,6-O-benzylidene-3-deoxy-1-thio-α-D-galactopyranoside (768 mg, 1.73 mmol) in DMF (2 mL) iodomethane (490 mg, 3.45 mmol) and Cs$_2$CO$_3$ (1.69 g, 5.18 mmol) were added. The mixture was stirred 16 h at rt under nitrogen atmosphere. The mixture was concentrated, and the residue was purified by column chromatography (PE/EtOAc=25/1~6/1, Silica-CS 12 g, 12 mL/min, silica gel, UV 254) to give the product (407 mg, 51%). ESI-MS m/z calcd for [C$_{21}$H$_{19}$ClN$_4$O$_4$S][M+H]$^+$: 459.1; found: 459.0. $^1$H NMR (400 MHz, CDCl$_3$) δ 7.72 (d, J=2.0 Hz, 1H), 7.60 (d, J=8.4 Hz, 1H), 7.51-7.49 (m, 2H), 7.36-7.34 (m, 4H), 6.11 (d, J=5.2 Hz, 1H), 5.61 (s, 1H), 4.34 (d, J=3.2 Hz, 1H), 4.27 (dd, J=10.8, 5.2 Hz, 1H), 4.20-4.17 (m, 2H), 4.13-4.09 (m, 1H), 3.78 (dd, J=10.8, 3.2 Hz, 1H), 3.60 (s, 3H).

2-Cyano-5-chlorophenyl 4,6-O-benzylidene-3-deoxy-3-[4-(3-fluoro-4-methylphenyl)-1H-1,2,3-triazol-1-yl]-2-O-methyl-1-thio-α-D-galactopyranoside

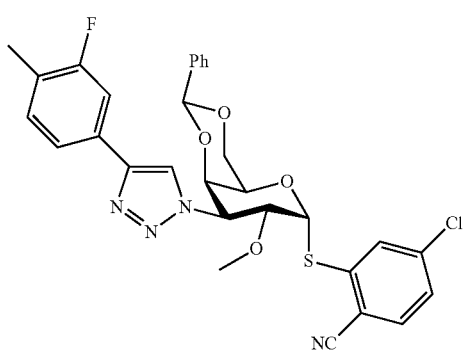

To a solution of 2-cyano-5-chlorophenyl 3-azido-4,6-O-benzylidene-3-deoxy-2-O-methyl-1-thio-α-D-galactopyranoside (338 mg, 0.74 mmol) and trimethyl-[2-(3-fluoro-4-methylphenyl)ethynyl]silane (0.304 g, 1.47 mmol) in DMF (5 mL) (+)-sodium L-ascorbate (72.9 mg, 0.37 mmol) and copper(II) sulfate pentahydrate (92.1 mg, 0.37 mmol) were added. The mixture was stirred 3 h at rt under nitrogen atmosphere. The solvent was removed under reduced pressure and the residue was purified by column chromatography (PE/EtOAc=10/1~4/1, Silica-CS 12 g, 20 mL/min, silica gel, UV 254) to afford the product (260 mg, 60%). ESI-MS m/z calcd for [C$_{30}$H$_{26}$ClFN$_4$O$_4$S][M+H]$^+$: 593.1, found: 593.1. $^1$H NMR (400 MHz, CDCl$_3$) δ 7.95 (s, 1H), 7.74 (d, J=2.0 Hz, 1H), 7.65 (d, J=8.4 Hz, 1H) 7.49-7.36 (m, 8H), 7.25 (s, 1H), 6.21 (d, J=4.8 Hz, 1H), 5.52 (s, 1H), 5.32 (dd, J=12.0, 3.2 Hz, 1H), 4.57-4.41 (m, 2H), 4.35 (s, 1H), 4.29 (dd, J=12.8, 1.6 Hz, 1H), 4.16 (dd, J=12.8, 1.6 Hz, 1H), 3.38 (s, 3H), 2.30 (d, J=1.2 Hz, 3H).

2-Carboxy-5-chlorophenyl 4,6-O-benzylidene-3-deoxy-3-[4-(3-fluoro-4-methylphenyl)-1H-1,2,3-triazol-1-yl]-2-O-methyl-1-thio-α-D-galactopyranoside

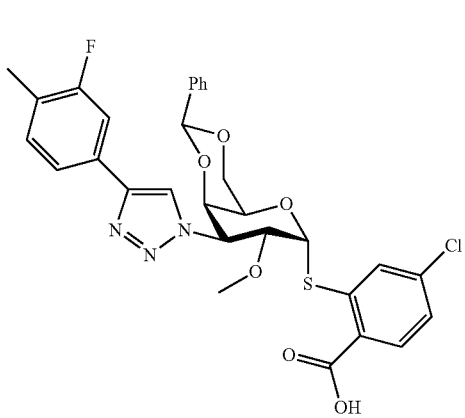

A mixture of 2-cyano-5-chlorophenyl 4,6-O-benzylidene-3-deoxy-3-[4-(3-fluoro-4-methylphenyl)-1H-1,2,3-triazol-1-yl]-2-O-methyl-1-thio-α-D-galactopyranoside (250 mg, 0.42 mmol) in ethanol (20 mL) and NaOH (11.4 mL, 3 M) was stirred 5 h at 80° C. After cooling to rt, the mixture was concentrated to a volume of approx. 12 mL, and then acidified with HCl (5 M) to pH approximately 1. The precipitation was collected by filtration, washed with 33% aq MeOH, and dried to afford the product (200 mg, 78%). ESI-MS m/z calcd for [C$_{30}$H$_{27}$ClFN$_3$O$_6$S] [M+H]$^+$: 612.1, found: 612.0. $^1$H NMR (400 MHz, DMSO-d$_6$) δ 13.36 (s, 1H), 8.81 (s, 1H), 7.89-7.87 (m, 2H), 7.58-7.56 (m, 2H) 7.39-7.32 (m, 7H), 6.68 (d, J=5.2 Hz, 1H), 5.56 (s, 1H), 5.18 (dd, J=11.6, 3.6 Hz, 1H), 4.75 (dd, J=12.0, 5.6 Hz, 1H), 4.53 (d, J=3.2 Hz, 1H) 4.21 (s, 1H), 4.11-4.08 (m, 1H), 3.97-3.94 (m, 1H), 3.30 (s, 3H), 2.23 (s, 3H).

2-(N-azetidinyl-carbonyl)-5-chlorophenyl 4,6-O-benzylidene-3-deoxy-3-[4-(3-fluoro-4-methylphenyl)-1H-1,2,3-triazol-1-yl]-2-O-methyl-1-thio-α-D-galactopyrandoside

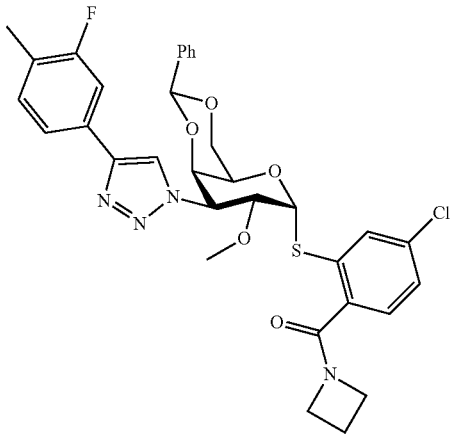

To a stirred mixture of 2-carboxy-5-chlorophenyl 4,6-O-benzylidene-3-deoxy-3-[4-(3-fluoro-4-methylphenyl)-1H-1,2,3-triazol-1-yl]-2-O-methyl-1-thio-α-D-galactopyranoside (200 mg, 0.33 mmol), azetidine hydrochloride (0.122 g, 1.31 mmol) and Et$_3$N (0.198 g, 1.96 mmol) in DMF (3 mL) 1-[bis(dimethylamino)methylene]-1H-1,2,3-triazolo[4,5-b]pyridinium 3-oxid hexafluorophosphate (0.373 g, 0.98 mol) was added in portions. The mixture was stirred overnight at rt, and was then concentrated under reduced pressure. The residue was purified by column chromatography (PE/EtOAc=½, Silica-CS 12 g, 20 mL/min, silica gel, UV 254) to give the product (127 mg, 60%). ESI-MS m/z calcd for [C$_{33}$H$_{32}$ClFN$_4$O$_5$S] [M+H]$^+$: 651.2, found: 651.1. $^1$H NMR (400 MHz, CDCl$_3$) δ 7.95 (s, 1H), 7.62 (d, J=2.0 Hz, 1H), 7.48-7.45 (m, 2H), 7.41-7.35 (m, 5H) 7.33-7.30 (m, 2H), 7.27 (s, 1H), 6.24 (d, J=4.8 Hz, 1H), 5.50 (s, 1H), 5.34 (dd, J=11.2, 3.2 Hz, 1H), 4.50-4.46 (m, 2H), 4.41 (s, 1H), 4.26-4.10 (m, 4H), 3.95 (t, J=8.0 Hz, 2H), 3.34 (s, 3H), 2.95 (s, 1H), 2.87 (s, 1H), 2.29 (s, 3H).

Intermediate 42

5-Chloropyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

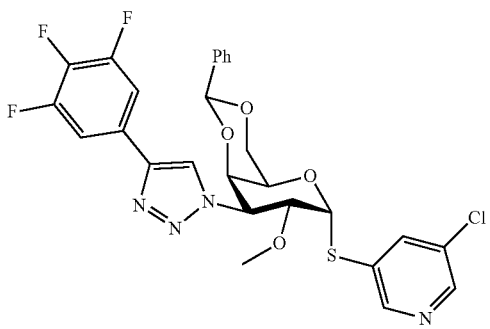

5-Chloropyridin-3-yl 3-azido-3-deoxy-1-thio-α-D-galactopyranoside

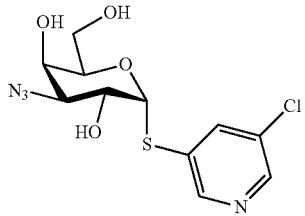

To a solution of 5-chloropyridin-3-yl 2,4,6-tri-O-acetyl-3-azido-3-deoxy-1-thio-α-D-galactopyranoside (WO2016120403) (2.80 g, 6.10 mmol) in MeOH (30 mL) NaOMe (330 mg, 6.10 mmol) was added. The mixture was stirred 2 h at rt, then AcOH was added to adjust pH to 7. The solvent was removed under reduced pressure and the residue was purified by column chromatography (PE/EtOAc=1/1~0/1, Silica-CS 20 g, 25 mL/min, silica gel, UV 254) to afford the product (1.50 g, 74%) as a white solid. ESI-MS m/z calcd for [C$_{11}$H$_{13}$ClN$_4$O$_4$S] [M+H]$^+$: 333.0; found: 333.2. $^1$H NMR (400 MHz, DMSO-d$_6$) δ 8.55 (d, J=2.0 Hz, 1H), 8.48 (d, J=2.0 Hz, 1H), 8.09 (t, J=2.0 Hz, 1H), 6.01 (d, J=5.2 Hz, 1H), 5.77 (d, J=5.2 Hz, 1H), 5.31 (d, J=6.4 Hz, 1H), 4.68 (t, J=5.6 Hz, 1H), 4.24 (dt, J=10.4, 5.2 Hz, 1H), 3.98 (t, J=6.0 Hz, 1H), 3.94-3.88 (m, 1H), 3.54-3.45 (m, 1H), 3.43-3.34 (m, 1H), 3.34-3.18 (m, 1H).

5-Chloropyridin-3-yl 3-azido-4,6-O-benzylidene-3-deoxy-1-thio-α-D-galactopyranoside

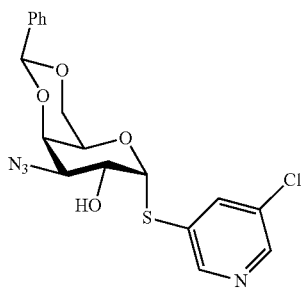

To a solution of 5-chloropyridin-3-yl 3-azido-3-deoxy-1-thio-α-D-galactopyranoside (1.50 g, 4.51 mmol) in DMF (10 mL) benzaldehyde dimethyl acetal (2.06 g, 13.5 mmol) and D(+)-10-camphorsulfonic acid (314 mg, 1.35 mmol) were added. The mixture was stirred 2 h at 60° C., then it was cooled to rt and Et$_3$N (1 mL) was added. The solvent was removed under reduced pressure and the residue was purified by column chromatography (PE/EtOAc=1/1~1/3, Silica-CS 20 g, 25 mL/min, silica gel, UV 254) to afford the product (1.00 g, 53%). ESI-MS m/z calcd for [C$_{18}$H$_{17}$ClN$_4$O$_4$S] [M+H]$^+$: 421.1; found: 421.2. $^1$H NMR (400 MHz, DMSO-d$_6$): δ 8.57 (d, J=2.0 Hz, 1H), 8.51 (d, J=2.0 Hz, 1H), 8.08 (t, J=2.0 Hz, 1H), 7.48-7.33 (m, 5H), 6.23 (d, J=5.2 Hz, 1H), 6.05 (d, J=5.2 Hz, 1H), 5.68 (s, 1H), 4.43 (d, J=3.2 Hz, 1H), 4.40-4.24 (m, 1H), 4.12-4.06 (m, 1H), 4.02 (s, 1H), 3.92-3.85 (m, 1H), 3.69 (dd, J=10.8, 3.2 Hz, 1H).

5-Chloropyridin-3-yl 3-azido-4,6-O-benzylidene-3-deoxy-2-O-methyl-1-thio-α-D-galactopyranoside

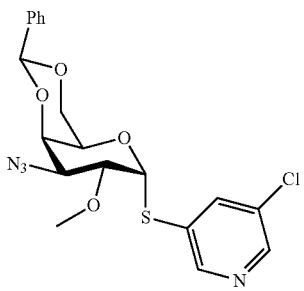

To a solution of 5-chloropyridin-3-yl 3-azido-4,6-O-benzylidene-3-deoxy-1-thio-α-D-galactopyranoside (1.00 g, 2.38 mmol) in DMF (10 mL) NaH (60% in oil, 190 mg, 4.75 mmol) was added at 0° C. After 2 min, iodomethane (0.296 mL, 4.75 mmol) was added and the mixture was stirred under nitrogen atmosphere 30 min at rt. The mixture was poured into water (20 mL) and extracted with EtOAc (2×50 mL). The organic layers were washed with brine (50 mL), dried over anhydrous Na$_2$SO$_4$, filtered and concentrated. The residue was purified by column chromatography (PE/EtOAc=2/1~1/2, Silica-CS 20 g, 25 mL/min, silica gel, UV 254) to afford the product (420 mg, 41%). ESI-MS m/z calcd for [C$_{19}$H$_{19}$ClN$_4$O$_4$S] [M+H]$^+$: 435.1; found: 435.0. $^1$H NMR (400 MHz, CDCl$_3$) δ 8.53 (s, 1H), 8.44 (s, 1H), 7.84 (t, J=2.0 Hz, 1H), 7.57-7.49 (m, 2H), 7.42-7.35 (m, 3H), 6.04 (d, J=5.2 Hz, 1H), 5.62 (s, 1H), 4.34 (d, J=3.2 Hz, 1H), 4.30-4.20 (m, 2H), 4.17-4.09 (m, 2H), 3.72 (dd, J=10.8, 3.2 Hz, 1H), 3.56 (s, 3H).

5-Chloropyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

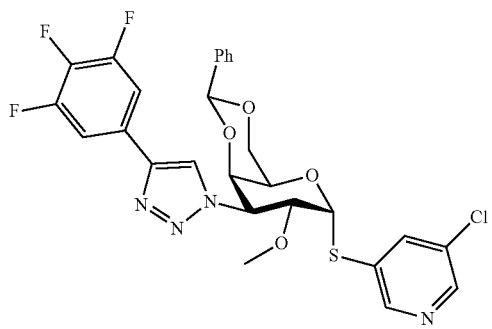

To a solution of 5-chloropyridin-3-yl 3-azido-4,6-O-benzylidene-3-deoxy-2-O-methyl-1-thio-α-D-galactopyranoside (100 mg, 0.230 mmol) in DMF (5 mL) trimethyl-[2-(3,4,5-trifluorophenyl)ethynyl]silane (78.7 mg, 0.35 mmol), (+)-sodium L-ascorbate (45.6 mg, 0.23 mmol), copper(II) sulfate pentahydrate (57.4 mg, 0.23 mmol) and CsF (34.9 mg, 0.23 mmol) were added. The mixture was stirred under nitrogen atmosphere at rt overnight. The mixture was poured into water (20 mL) and extracted twice with EtOAc (50 mL). The organic layers were washed with brine (50 mL), dried over Na$_2$SO$_4$, filtered and concentrated. The residue was purified by column chromatography (PE/EtOAc=10/1~1/1, Silica-CS 4 g, 10 mL/min, silica gel, UV 254) to afford the product (100 mg, 74%). ESI-MS m/z calcd for [C$_{27}$H$_{22}$ClF$_3$N$_4$O$_4$S][M+H]$^+$: 591.1; found: 591.2. $^1$H NMR (400 MHz, CDCl$_3$) δ 8.71-8.33 (m, 2H), 7.96-7.93 (m, 1H), 7.90-7.86 (m, 1H), 7.47-7.37 (m, 7H), 6.15 (d, J=5.2 Hz, 1H), 5.54 (s, 1H), 5.31 (dd, J=10.8, 3.6 Hz, 1H), 4.55-4.48 (m, 2H), 4.36-4.28 (m, 2H), 4.20-4.14 (m, 1H), 3.34 (s, 3H).

Intermediate 43

5-Chloropyridin-3-yl 4,6-O-benzylidene-3-deoxy-3-[4-(6-fluoro-5-methylpyridin-2-yl)-1H-1,2,3-triazol-1-yl]-2-O-methyl-1-thio-α-D-galactopyranoside

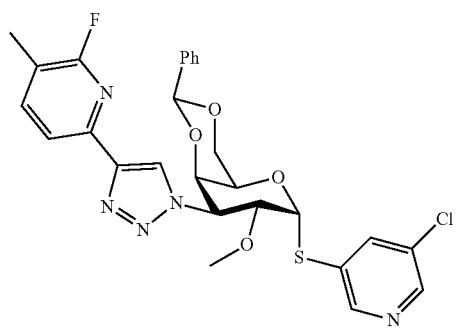

6-Bromo-2-fluoro-3-methylpyridine

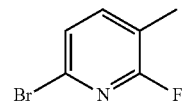

A solution of lithium diisopropylamide (6.25 mL, 2 M in THF, 12.5 mmol) was added dropwise to 2-bromo-6-fluoropyridine (2.0 g, 11.4 mmol) in THF (6 mL) at −78° C., and then stirred 30 min. Iodomethane (1.77 g, 12.5 mmol) was added slowly, and then continued to stir 3 h at −78° C. The mixture slowly reached rt and was then stirred 1 h. The reaction was quenched with EtOAc/water (50 mL/100 mL) and kept for 1 h. The layers were separated, and the organic layer was concentrated. The residue was purified by column chromatography (PE/EtOAc=20/1~10/1, Silica-CS 20 g, 20 mL/min, silica gel, UV 254) to give the product (1.00 g, 46%). $^1$H NMR (400 MHz, CDCl$_3$) δ 7.47 (t, J=8.8 Hz, 1H), 7.28 (d, J=8.0 Hz, 1H) 2.23 (s, 3H).

2-Fluoro-3-methyl-6-[2-(trimethylsilyl)ethynyl]pyridine

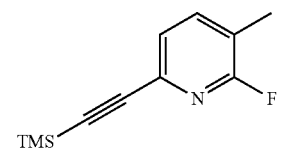

To a solution of 6-bromo-2-fluoro-3-methylpyridine (1.00 g, 5.26 mmol) and trimethylsilylacetylene (1.03 g, 10.5 mmol) in DMF (5 mL) CuI (50.1 mg, 0.26 mmol), bis(triphenylphosphine)palladium(II) dichloride (185 mg, 0.26 mol) and Et$_3$N (1.47 mL, 10.5 mmol) were added. The mixture was stirred 2 h at 50° C. under nitrogen atmosphere. The solvent was removed to afford the product (300 mg, 28%). ESI-MS m/z calcd for [C$_{11}$H$_{14}$FNSi] [M+H]$^+$: 208.1, found: 208.2.

5-Chloropyridin-3-yl 4,6-O-benzylidene-3-deoxy-3-[4-(6-fluoro-5-methylpyridin-2-yl)-1H-1,2,3-triazol-1-yl]-2-O-methyl-1-thio-α-D-galactopyranoside

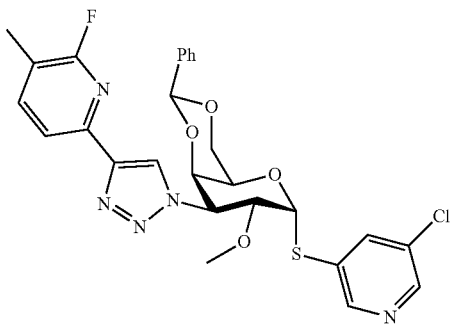

To a solution of 5-chloropyridin-3-yl 3-azido-4,6-O-benzylidene-3-deoxy-2-O-methyl-1-thio-α-D-galactopyranoside (114 mg, 0.26 mmol) and 2-fluoro-3-methyl-6-[2-(trimethylsilyl)ethynyl]pyridine (81.6 mg, 0.39 mmol) in DMF (2 mL) (+)-sodium L-ascorbate (25.0 mg, 0.13 mmol) and copper(II) sulfate pentahydrate (33.0 mg, 0.13 mmol) were added. The mixture was stirred 3 h at rt under a nitrogen atmosphere. The solvent was removed, and the residue was purified by column chromatography (PE/EtOAc=10/1~4/1, Silica-CS 12 g, 20 mL/min, silica gel, UV 254) to give the product (100 mg, 67%). ESI-MS m/z calcd for [C$_{27}$H$_{25}$ClFN$_5$O$_4$S] [M+H]$^+$: 570.1, found: 570.2. $^1$H NMR (400 MHz, CDCl$_3$) δ 7.74 (d, J=2.0 Hz, 1H), 8.47 (d, J=2.4 Hz, 1H), 8.33 (s, 1H), 7.97 (dd, J=7.6, 1.2 Hz, 1H), 7.87 (t, J=2.0 Hz, 1H), 7.69 (dd, J=9.6, 8.0 Hz, 1H), 7.43-7.35 (m, 5H), 6.17 (d, J=4.8 Hz, 1H), 5.51 (s, 1H), 5.32 (dd, J=11.2, 3.2 Hz, 1H), 4.60 (dd, J=11.6, 5.2 Hz, 1H), 4.52 (d, J=2.8 Hz, 1H), 4.32-4.27 (m, 2H), 4.16 (dd, J=12.8, 1.2 Hz, 1H), 3.34 (s, 3H), 2.21 (s, 3H).

Intermediate 44

3-Chloro-2-methyl-6-[2-(trimethylsilyl)ethynyl]pyridine

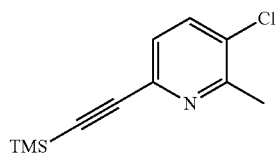

6-Bromo-3-chloro-2-methyl-pyridine (413 mg, 2 mmol) and trimethylsilylacetylene (416 μl, 3 mmol) were added to a solution of bis(triphenylphosphine)palladium(II) dichloride (73.0 mg, 0.10 mmol), CuI (38.1 mg, 0.20 mmol) and Et$_3$N (1.36 mL, 10 mmol) in THF (4 mL, degassed). The mixture was stirred 1 h at rt before it was diluted with PE (7 mL) and cooled to −20° C. The suspension was filtered through a plug of celite and concentrated. Purification by chromatography (SiO$_2$, PE/EtOAc) yielded the product (400 mg, 89%). ESI-MS m/z calcd for [C$_{11}$H$_{15}$ClNSi] [M+H]$^+$: 224.1; found: 224.1, $^1$H NMR (400 MHz, Chloroform-d) δ 7.58 (d, J=8.2 Hz, 1H), 7.27 (d, J=8.1 Hz, 1H), 2.63 (s, 3H), 0.27 (s, 9H).

5-Chloropyridin-3-yl 3-azido-3-deoxy-2-O-methyl-1-thio-α-D-galactopyranoside

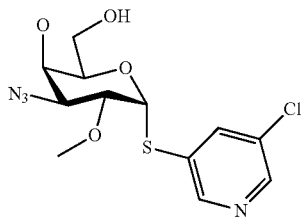

NaOMe (2.18 mL, 1M, 2.18 mmol) was added to 5-chloropyridin-3-yl 2,4,6-tri-O-acetyl-3-azido-3-deoxy-1-thio-α-D-galactopyranoside (2.00 g, 4.36 mmol) in MeOH (40 mL). After 20 minutes the reaction was quenched with AcOH (200 μL) and concentrated. NaOH (100 mL, 1 M) was added and the mixture was extracted with EtOAc (2×100 mL). The organic phases were dried and concentrated. The crude was suspended in MeCN (200 mL). Benzaldehyde dimethyl acetal (1.31 mL, 8.72 mmol) and p-toluenesulfonic acid monohydrate (249 mg, 1.31 mmol) were added. After 2 h additional benzaldehyde dimethyl acetal (1.31 mL, 8.72 mmol) was added and the mixture was stirred 45 min before it was concentrated. The crude was suspended in MeCN (200 mL) and benzaldehyde dimethyl acetal (1.31 ml, 8.72 mmol) was added. The mixture was stirred overnight and then concentrated. EtOAc (200 mL) was added and the mixture was washed with saturated aq NaHCO$_3$ (100 mL) and water (100 ml). The organic phase was concentrated. Toluene was added and the mixture was concentrated once more. The crude was dissolved in DMF (20 mL) and NaH (60% in oil, 334 mg, 8.72 mmol) was added. After 5 minutes iodomethane (0.407 mL, 6.54 mmol) was added and the mixture was stirred for additionally 45 min. The mixture was diluted with EtOAc (200 mL), washed with water (5×200 mL) and concentrated. Water/TFA (15 mL, 1:4) was added. After 30 min the mixture was diluted with water (25 mL) and TFA was removed under reduced pressure. NaOH (50 mL, 1 M) was added and the mixture was made basic using NaOH (50%). The mixture was extracted with EtOAc (2×50 mL). The organic phases were dried and concentrated. Recrystallization from EtOAc:PE yielded the product (1.10 g). The mother liquor was concentrated and purified by chromatography (SiO$_2$, PE/EtOAc) to yield the product (501 mg). ESI-MS m/z calcd for [C$_{12}$H$_{16}$ClN$_4$O$_4$S] [M+H]$^+$: 347.1; found: 347.1, $^1$H NMR (400 MHz, Methanol-d$_4$) δ 8.59 (d, J=1.8 Hz, 1H), 8.44 (d, J=2.2 Hz, 1H), 8.15 (t, J=2.0 Hz, 1H), 6.07 (d, J=5.3 Hz, 1H), 4.23 (t, J=6.0 Hz, 1H), 4.06 (dd, J=10.5, 5.3 Hz, 1H), 4.00 (d, J=2.4 Hz, 1H), 3.71-3.59 (m, 3H), 3.53 (s, 3H).

Intermediate 45

3-Chloro-2-cyanopyridin-5-yl 4,6-di-O-acetyl-3-deoxy-3-[4-(3,4,5-trifluorophenyl)-1H-1,2,3-triazol-1-yl]-2-O-methyl-1-thio-α-D-galactopyranoside

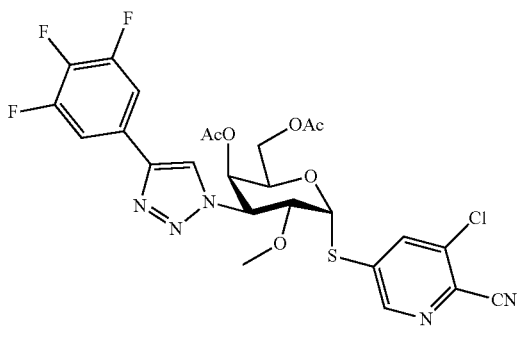

3-Chloro-2-cyanopyridin-5-yl 4,6-di-O-acetyl-3-azido-3-deoxy-2-O-methyl-1-thio-D-galactopyranoside

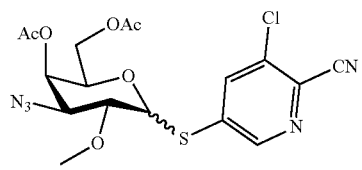

To a solution of acetyl 4,6-di-O-acetyl-3-azido-2-methyl-3-deoxy-1-thio-D-galactopyranoside (280 mg, 0.78 mmol) and 3-chloro-5-fluoro-pyridine-2-carbonitrile (146 mg, 0.93 mmol) in DMF (5.00 mL) diethylamine (113 mg, 1.55 mmol) was added at 0° C. The mixture was stirred at 0° C. under a nitrogen atmosphere for 8 h. After diluting with water (20 mL), the mixture was extracted with EtOAc (3×10 mL). The combined organic layers were washed with brine, dried over $Na_2SO_4$ and concentrated in vacuo. The residue was purified by column chromatography (PE/EtOAc=10/1~3/1, Silica-CS 4 g, 12 mL/min, silica gel, UV 254) to give the product (260 mg, 74%, α/0=0.25:1). ESI-MS m/z calcd for $[C_{17}H_{18}ClN_5O_6S]$ $[M+H]^+$: 456.1; found: 456.1

3-Chloro-2-cyano-pyridine-5-yl 4,6-di-O-acetyl-3-azido-3-deoxy-2-O-methyl-1-thio-α-D-galactopyranoside $^1$H NMR (400 MHz, $CDCl_3$) δ 8.55 (d, J=2.0 Hz, 1H), 8.08 (d, J=1.6 Hz, 1H), 6.02 (d, J=5.6 Hz, 1H), 5.34 (d, J=2.8 Hz, 1H), 4.37-4.39 (m, 1H), 3.91-4.01 (m, 2H), 3.74 (dd, J=10.4, 3.2 Hz, 1H), 3.49 (s, 3H), 3.32-3.38 (m, 1H), 2.11 (s, 3H), 1.91 (s, 3H).

3-Chloro-2-cyano-pyridine-5-yl 4,6-di-O-acetyl-3-azido-3-deoxy-2-O-methyl-1-thio-β-D-galactopyranoside $^1$H NMR (400 MHz, $CDCl_3$) δ 8.57 (d, J=2.0 Hz, 1H), 7.30 (d, J=1.6 Hz, 1H), 5.34 (d, J=2.8 Hz, 1H), 4.68 (d, J=9.6 Hz, 1H), 3.91-4.01 (m, 2H), 3.86-3.88 (m, 1H), 3.57 (s, 3H), 3.55-3.36 (m, 1H), 3.32-3.38 (m, 1H), 2.12 (s, 3H), 2.03 (s, 3H).

3-Chloro-2-cyanopyridin-5-yl 4,6-di-O-acetyl-3-deoxy-3-[4-(3,4,5-trifluorophenyl)-1H-1,2,3-triazol-1-yl]-2-O-methyl-1-thio-α-D-galactopyranoside

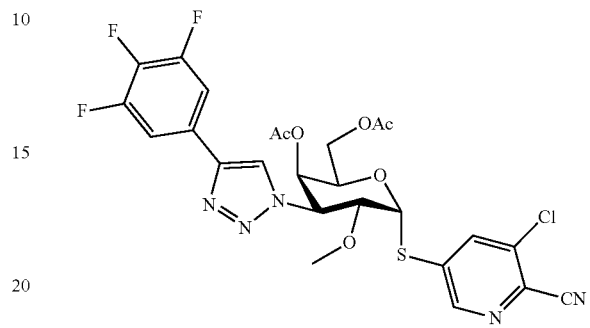

To a solution of 3-chloro-2-cyanopyridin-5-yl 4,6-di-O-acetyl-3-azido-3-deoxy-2-O-methyl-1-thio-D-galactopyranoside (180 mg, 0.40 mmol) and trimethyl-[2-(3,4,5-trifluorophenyl)ethynyl]silane (135 mg, 0.59 mmol) in DMF (3.00 mL) copper(II) sulfate pentahydrate (49.3 mg, 0.20 mmol) and (+)-sodium L-ascorbate (78.2 mg, 0.40 mmol) were added. The mixture was stirred 3 h at rt under nitrogen atmosphere. After diluting with water (20 mL), the mixture was extracted with EtOAc (3×10 mL). The combined organic layers were washed with brine, dried over anhydrous $Na_2SO_4$ and concentrated in vacuo. The residue was purified by column chromatography (PE/EtOAc=10/1~1/1, Silica-CS 4 g, 12 m/min, silica gel, UV 254) to give an anomeric mixture of the product. The mixture was separated by preparative-TLC (PE/EtOAc=1/1) to afford the product (25.0 mg, 10%) as a white solid. ESI-MS m/z calcd for $[C_{25}H_{21}ClF_3N_5O_6S][M+H]^+$: 612.1; found: 612.1. $^1$H NMR (400 MHz, $CDCl_3$) δ 8.60 (d, J=2.0 Hz, 1H), 7.98 (d, J=2.0 Hz, 1H), 7.72 (s, 1H), 7.40-7.36 (m, 2H), 6.24 (d, J=4.8 Hz, 1H), 5.51 (s, 1H), 4.84-4.81 (m, 2H), 4.61-4.57 (m, 1H), 3.99-4.10 (m, 2H), 3.34 (s, 3H), 2.02 (s, 3H), 1.92 (s, 3H).

Intermediate 47

5-Chloro-2-cyanopyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

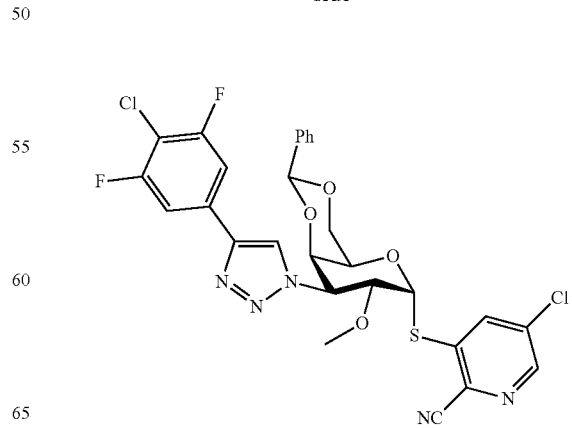

To a solution of 5-chloro-2-cyanopyridin-3-yl 3-azido-4,6-O-benzylidene-3-deoxy-2-O-methyl-1-thio-α-D-galactopyranoside (100 mg, 0.20 mmol) in DMF (5 mL) trimethyl-[2-(4-chloro-3,5-difluorophenyl)ethynyl]silane (122 mg, 60%, 0.3 mmol), (+)-sodium L-ascorbate (40 mg, 0.20 mmol) and copper(II) sulfate pentahydrate (50 mg, 0.20 mmol) were added. The mixture was stirred 3 h at rt under nitrogen atmosphere. Water (50 mL) and DCM (50 mL) were added. The aqueous phase was extracted with DCM (2×50 mL). The combined organic phases were washed with water (50 mL) and brine (3×50 mL), dried over anhydrous Na$_2$SO$_4$ and concentrated. The residue was purified by column chromatography (PE/EtOAc=10/1~1/1, Silica-CS 20 g, 20 m/min, silica gel, UV 254) to give the product (100 mg, 79%). ESI-MS m/z calcd for [C$_{28}$H$_{21}$Cl$_2$F$_2$N$_5$O$_4$S] [M+H]$^+$: 632.1; found: 632.0. $^1$H NMR (400 MHz, CDCl$_3$) δ 8.57 (d, J=2.4 Hz, 1H), 8.07 (d, J=2.0 Hz, 1H), 7.99 (s, 1H), 7.47-7.42 (m, 2H), 7.39 (s, 5H), 6.25 (d, J=5.2 Hz, 1H), 5.54 (s, 1H), 5.31 (dd, J=11.2, 3.2 Hz, 1H), 4.59-4.54 (m, 2H), 4.39 (s, 1H), 4.30-4.14 (m, 2H), 3.38 (s, 3H).

Intermediate 48

5-Chloro-2-cyanopyridin-3-yl 4,6-O-benzylidene-3-[4-(4-chloro-3-fluorophenyl)-1H-1,2,3-triazol-1-yl]-3-deoxy-2-O-methyl-1-thio-α-D-galactopyranoside

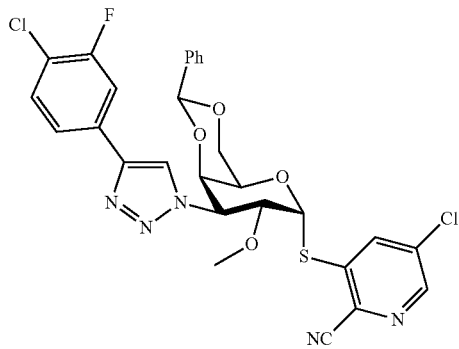

To a solution of 5-chloro-2-cyanopyridin-3-yl 3-azido-4,6-O-benzylidene-3-deoxy-2-O-methyl-1-thio-α-D-galactopyranoside (120 mg, 0.26 mmol) and trimethyl-[2-(4-chloro-3-fluorophenyl)ethynyl]silane (101 mg, 70%, 0.31 mmol) in DMF (4 mL) (+)-sodium L-ascorbate (77.5 mg, 0.39 mmol) and copper(II) sulfatepentahydrate (32.6 mg, 0.13 mmol) were added. The mixture was stirred 4 h at rt under a nitrogen atmosphere. After diluting with water (20 mL), the mixture was extracted with EtOAc (3×10 mL). The combined organic layers were washed with brine, dried over anhydrous Na$_2$SO$_4$, and concentrated. The residue was purified by preparative HPLC (Method A) to give the product (97.0 mg, 61%) as a white solid. ESI-MS m/z calcd for [C$_{28}$H$_{22}$Cl$_2$FN$_5$O$_4$S][M+H]$^+$: 614.1; found: 614.0. $^1$H NMR (400 MHz, DMSO-d$_6$) δ 8.95 (s, 1H), 8.76 (d, J=2.4 Hz, 1H), 8.52 (d, J=2.4 Hz, 1H), 7.88-7.81 (m, 1H), 7.75-7.67 (m, 2H), 7.44-7.30 (m, 5H), 6.92 (d, J=5.2 Hz, 1H), 5.60 (s, 1H), 5.22 (dd, J=11.6, 3.2 Hz, 1H), 4.77 (dd, J=11.6, 5.2 Hz, 1H), 4.62 (d, J=3.2 Hz, 1H), 4.30 (s, 1H), 4.12 (d, J=11.6 Hz, 1H), 3.99 (d, J=11.6 Hz, 1H), 3.40 (s, 3H).

Intermediate 49

2-Cyano-5-methylpyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

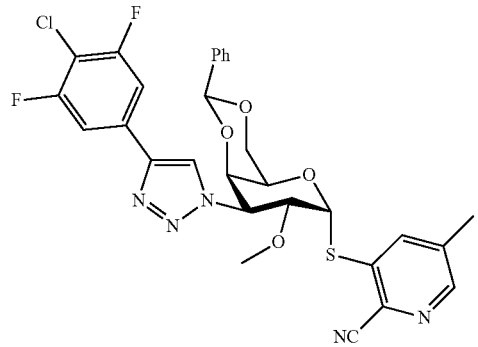

2-Bromo-5-methylpyridin-3-yl 2,4,6-tri-O-acetyl-3-azido-3-deoxy-1-thio-α-D-galactopyranoside

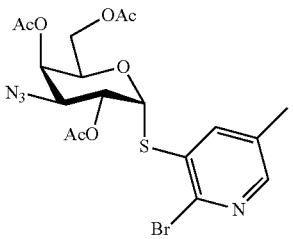

To a solution of 2-bromo-3-fluoro-5-methylpyridine (300 mg, 1.58 mmol) in DMF (10 mL) Na$_2$S (246 mg, 3.16 mmol) was added. The mixture was stirred 1 h at 100° C. in a microwave reactor. The mixture cooled to rt and 2,4,6-tri-O-acetyl-3-azido-3-deoxy-α-D-galactopyranosyl chloride (300 mg, 0.858 mmol) and Cs$_2$CO$_3$ (559 mg, 1.72 mmol) were added. The mixture was stirred overnight at rt. The mixture was extracted with EtOAc (30 mL) and washed with brine. The solvent was removed under reduced pressure, and the residue was purified by column chromatography (PE/EA=10/1~5/1, Silica-CS 20 g, 20 m/min, silica gel, UV 254) to afford the crude product. ESI-MS m/z calcd for [C$_{18}$H$_{21}$BrN$_4$O$_7$S] [M+H]$^+$: 517.0; found: 517.0.

2-Bromo-5-methylpyridin-3-yl 3-azido-3-deoxy-1-thio-α-D-galactopyranoside

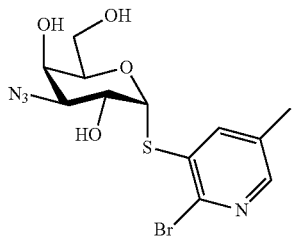

2-Bromo-5-methylpyridin-3-yl 2,4,6-tri-O-acetyl-3-azido-3-deoxy-1-thio-α-D-galactopyranoside (300 mg, 56%, 0.325 mmol) was dissolved in a mixed solution of MeOH/Et$_3$N/H$_2$O (9 mL, 5:3:1). The mixture was stirred overnight at rt. The solvent was removed under reduced pressure, and the residue was purified by preparative HPLC (Method A) to afford the product (65.0 mg) as a white solid. ESI-MS m/z calcd for [C$_{12}$H$_{15}$BrN$_4$O$_4$S] [M+H]$^+$: 391.0; found: 391.0. $^1$H NMR (400 MHz, DMSO-d$_6$) δ 8.00 (d, J=1.2 Hz, 1H), 7.86 (d, J=2.0 Hz, 1H), 6.03 (d, J=4.8 Hz, 1H), 5.85 (d, J=5.2 Hz, 1H), 5.30 (d, J=6.0 Hz, 1H), 4.60 (t, J=6.0 Hz, 1H), 4.28 (dt, J=10.8, 5.2 Hz, 1H), 3.89 (m, 2H), 3.47 (m 2H), 3.34 (m, 1H), 2.22 (s, 3H).

2-Bromo-5-methylpyridin-3-yl 3-azido-4,6-O-benzylidene-3-deoxy-1-thio-α-D-galactopyranoside

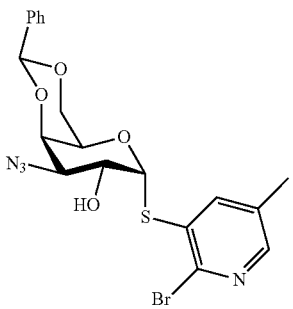

To a stirred solution of 2-bromo-5-methylpyridin-3-yl 3-azido-3-deoxy-1-thio-α-D-galactopyranoside (300 mg, 0.77 mmol) in DMF (6 mL) benzaldehyde dimethylacetal (350 mg, 2.30 mmol) was added followed by D(+)-10-camphorsulfonic acid (35.6 mg, 0.15 mmol). The mixture was stirred 3 h at 50° C. under nitrogen atmosphere. The mixture was neutralized with Et$_3$N and concentrated in vacuo. The residue was purified by column chromatography (PE/EtOAc=5/1~3/1, Silica-CS 12 g, 20 mL/min, silica gel, UV 254) to give the product (250 mg, 68%) as a white solid. ESI-MS m/z calcd for [C$_{19}$H$_{19}$BrN$_4$O$_4$S] [M+H]$^+$: 479.0; found: 479.0. $^1$H NMR (400 MHz, CDCl$_3$) δ 8.04 (d, J=2.0 Hz, 1H), 7.71 (d, J=2.0 Hz, 1H), 7.51-7.49 (m, 2H), 7.42-7.34 (m, 3H), 5.94 (d, J=5.2 Hz, 1H), 5.64 (s, 1H), 4.72-4.62 (m, 1H), 4.41 (d, J=3.2 Hz, 1H), 4.24 (dd, J=13.2, 2.0 Hz, 1H), 4.12-4.10 (m, 2H), 3.68 (dd, J=10.8, 3.2 Hz, 1H), 2.46 (d, J=7.2 Hz, 1H), 2.28 (s, 3H).

2-Bromo-5-methylpyridin-3-yl 3-azido-4,6-O-benzylidene-3-deoxy-2-O-methyl-1-thio-α-D-galactopyranoside

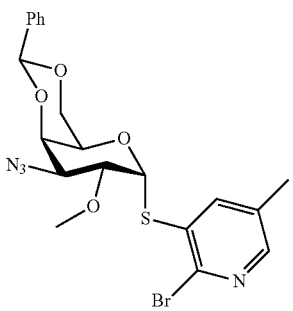

To a solution of 2-bromo-5-methylpyridin-3-yl 3-azido-4,6-O-benzylidene-3-deoxy-1-thio-α-D-galactopyranoside (250 mg, 0.52 mmol) and iodomethane (370 mg, 2.61 mmol) in DMF (5 mL) Cs$_2$CO$_3$ (510 mg, 1.56 mmol) was added. The mixture was stirred 4 h at rt and then extracted with EtOAc (30 mL). The solvent was removed, and the residue was purified by column chromatography (PE/EtOAc=5/1~2/1, Silica-CS 20 g, 20 mL/min, silica gel, UV 254) to give the product (180 mg, 70%) as a white solid. ESI-MS m/z calcd for [C$_{20}$H$_{21}$BrN$_4$O$_4$S] [M+H]$^+$: 493.0; found: 493.0. $^1$H NMR (400 MHz, CDCl$_3$) δ 8.02 (d, J=1.6 Hz, 1H), 7.68 (d, J=1.6 Hz, 1H), 7.55-7.48 (m, 2H), 7.41-7.33 (m, 3H), 6.14 (d, J=5.2 Hz, 1H), 5.62 (s, 1H), 4.33 (d, J=3.2 Hz, 1H), 4.28 (dd, J=10.4, 5.2 Hz, 1H), 4.18-4.05 (m, 3H), 3.83 (dd, J=10.4, 3.2 Hz, 1H), 3.57 (s, 3H), 2.27 (s, 3H).

2-Cyano-5-methylpyridin-3-yl 3-azido-4,6-O-benzylidene-3-deoxy-2-O-methyl-1-thio-α-D-galactopyranoside

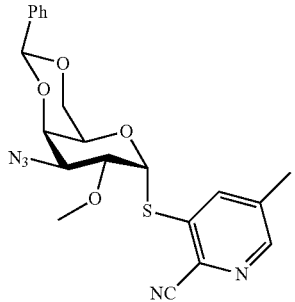

To a solution of 2-bromo-5-methylpyridin-3-yl 3-azido-4,6-O-benzylidene-3-deoxy-2-O-methyl-1-thio-α-D-galactopyranoside (180 mg, 0.37 mmol) in DMF (10.0 mL) Zn (23.9 mg, 0.37 mmol), Pd$_2$(dibenzylideneacetone)$_3$, (26.7 mg, 0.029 mmol) Zn(CN)$_2$ (129 mg, 1.09 mmol) and 1,1'-bis(diphenylphosphino)ferrocene (16.5 mg, 0.029 mmol) were added. The mixture was stirred 2.5 h at 100° C. under nitrogen atmosphere. The solvent was removed, and the residue was purified by column chromatography (PE/EtOAc=10/1~3/1, Silica-CS 12 g, 20 mL/min, silica gel, UV 254) to give the product (100 mg, 62%). ESI-MS m/z calcd for [C$_{21}$H$_{21}$N$_5$O$_4$S] [M+H]$^+$: 440.1; found: 440.1. $^1$H NMR (400 MHz, CDCl$_3$) δ 8.42 (d, J=1.2 Hz, 1H), 7.83 (d, J=0.8 Hz, 1H), 7.49 (m, 2H), 7.40-7.31 (m, 3H), 6.04 (d, J=5.2 Hz, 1H), 5.60 (s, 1H), 4.34 (d, J=2.8 Hz, 1H), 4.25 (dd, J=10.6, 5.2 Hz, 1H), 4.21 (s, 1H), 4.16 (dd, J=12.8, 1.6 Hz, 1H), 4.11 (dd, J=12.8, 1.6 Hz, 1H), 3.78 (dd, J=10.6, 3.2 Hz, 1H), 3.60 (s, 3H), 2.41 (s, 3H).

2-Cyano-5-methylpyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

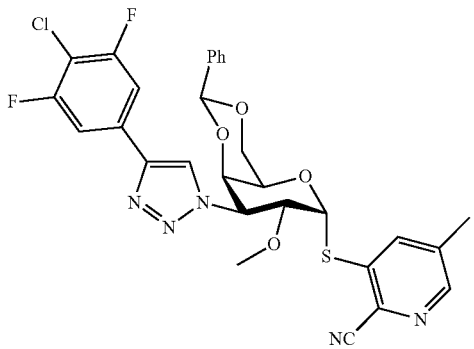

To a solution 2-cyano-5-methylpyridin-3-yl 3-azido-4,6-O-benzylidene-3-deoxy-2-O-methyl-1-thio-α-D-galactopyranoside (100 mg, 0.23 mmol) and trimethyl-[2-(4-chloro-3,5-difluorophenyl)ethynyl]silane (60.0%, 111 mg, 0.27 mmol) in DMF (4 mL) (+)-sodium L-ascorbate (67.6 mg, 0.34 mmol) and copper(II) sulfate pentahydrate (28.4 mg, 0.11 mmol) were added. The mixture was stirred 4 h at rt under nitrogen atmosphere before being purified by preparative HPLC (Method A) to give the product (80 mg, 57%) as a white solid. ESI-MS m/z calcd for [C$_{29}$H$_{24}$ClF$_2$N$_5$O$_4$S] [M+H]$^+$: 612.1; found: 612.1. $^1$H NMR (400 MHz, DMSO-d$_6$) δ 8.99 (s, 1H), 8.52 (d, J=1.2 Hz, 1H), 8.18 (d, J=0.8 Hz, 1H), 7.75 (d, J=8.0 Hz, 2H), 7.33 (s, 5H), 6.68 (d, J=5.2 Hz, 1H), 5.58 (s, 1H), 5.20 (dd, J=11.2, 3.2 Hz, 1H), 4.69 (dd, J=11.2, 5.2 Hz, 1H), 4.61 (d, J=3.2 Hz, 1H), 4.34 (s, 1H), 4.13 (d, J=12.0 Hz, 1H), 3.99 (d, J=12.0 Hz, 1H), 3.39 (s, 3H), 2.42 (s, 3H).

Intermediate 50

5-Bromo-2-cyanopyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

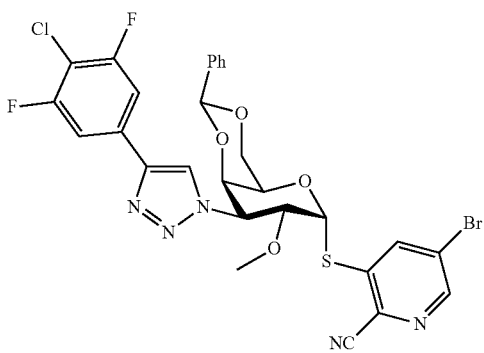

2,5-Dibromopyridin-3-yl 2,4,6-tri-O-acetyl-3-azido-3-deoxy-1-thio-α-D-galactopyranoside

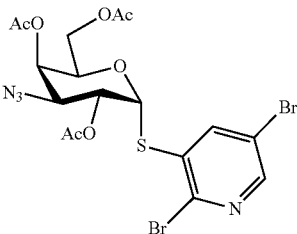

To a solution of acetyl 2,4,6-tri-O-acetyl-3-azido-3-deoxy-1-thio-α-D-galactopyranoside (3 g, 7.70 mmol) in DMF (30 mL) 2,5-dibromo-3-fluoropyridine (2.16 g, 8.47 mmol) and diethylamine (1.13 g, 15.4 mmol) were added at 0° C. The mixture was stirred under a nitrogen atmosphere overnight at rt. The mixture was poured into water (100 mL) and extracted with EtOAc (2×100 mL). The organic layers were washed with brine (100 mL), dried over anhydrous Na$_2$SO$_4$, filtered and concentrated. The residue was purified by column chromatography (PE/EtOAc=10/1~1/1, Silica-CS 40 g, 50 mL/min, silica gel, UV 254) to afford the product (2.6 g, 58%). ESI-MS m/z calcd for [C$_{17}$H$_{18}$Br$_2$N$_4$O$_7$S] [M+H]$^+$: 580.9; found: 581.0. $^1$H NMR (400 MHz, CDCl$_3$) δ 8.28 (d, J=2.4 Hz, 1H), 7.94 (d, J=2.4 Hz, 1H), 6.12 (d, J=5.6 Hz, 1H), 5.49 (d, J=2.8 Hz, 1H), 5.34 (dd, J=11.2, 5.6 Hz, 1H), 4.53 (dd, J=7.6, 4.8 Hz, 1H), 4.15-4.11 (m, 1H), 4.04-3.98 (m, 2H), 2.20 (s, 3H), 2.17 (s, 3H), 1.97 (s, 3H).

2,5-Dibromopyridin-3-yl 3-azido-3-deoxy-1-thio-α-D-galactopyranoside

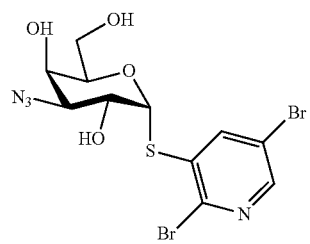

To a solution of 2,5-dibromopyridin-3-yl 2,4,6-tri-O-acetyl-3-azido-3-deoxy-1-thio-α-D-galactopyranoside (2.60 g, 4.47 mmol) in MeOH (30 mL) Et$_3$N (2 mL) and H$_2$O (1 mL) were added. The mixture was stirred under a nitrogen atmosphere overnight at rt. The solvent was removed under reduced pressure and the residue was suspended in DCM (50 mL). The solid was collected and washed by DCM and Et$_2$O. The product (1.10 g, 54%) was obtained as a white solid. ESI-MS m/z calcd for [C$_{11}$H$_{12}$Br$_2$N$_4$O$_4$S][M+H]$^+$: 454.9; found: 455.0. $^1$H NMR (400 MHz, DMSO-d$_6$) δ 8.31 (d, J=2.4 Hz, 1H), 8.20 (d, J=2.4 Hz, 1H), 6.13 (d, J=5.2 Hz, 1H), 6.02 (d, J=5.2 Hz, 1H), 5.33 (d, J=6.0 Hz, 1H), 4.60 (t, J=5.6 Hz, 1H), 4.28 (dt, J=10.4, 5.2 Hz, 1H), 3.90 (dd, J=6.0, 2.4 Hz, 1H), 3.83 (t, J=6.4 Hz, 1H), 3.55-3.44 (m, 2H), 3.35-3.32 (m, 1H).

2,5-Dibromopyridin-3-yl 3-azido-4,6-O-benzylidene-3-deoxy-1-thio-α-D-galactopyranoside

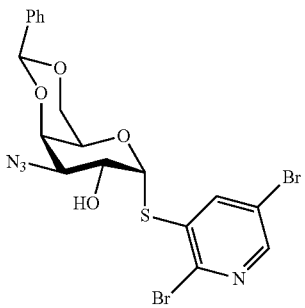

To a solution of 2,5-dibromopyridin-3-yl 3-azido-3-deoxy-1-thio-α-D-galactopyranoside (1.10 g, 2.41 mmol) in DMF (10 mL) benzaldehyde dimethyl acetal (1.1 g, 7.24 mmol) and D(+)-10-camphorsulfonic acid (112 mg, 0.48 mmol) were added. The mixture was stirred under a nitrogen atmosphere 2 h at 50° C. The mixture was cooled to rt and Et$_3$N (1 mL) was added. The solvent was removed under reduced pressure and the residue was purified by column chromatography (PE/EtOAc=1/1~1/3, Silica-CS 20 g, 25 mL/min, silica gel, UV 254) to afford the product (1.05 g, 80%) as a white solid. ESI-MS m/z calcd for [C$_{18}$H$_6$Br$_2$N$_4$O$_4$S] [M+H]$^+$: 542.9; found: 543.0. $^1$H NMR (400 MHz, CDCl$_3$) δ 8.19 (d, J=2.4 Hz, 1H), 7.94 (d, J=2.4 Hz, 1H), 7.48-7.42 (m, 2H), 7.36-7.28 (m, 3H), 5.92 (d, J=5.2 Hz, 1H), 5.59 (s, 1H), 4.64 (dt, J=10.4, 5.2 Hz, 1H), 4.37 (d, J=2.8 Hz, 1H), 4.19 (dd, J=12.8, 1.6 Hz, 1H), 4.08 (dd, J=12.8, 1.6 Hz, 1H), 4.05-4.02 (m, 1H), 3.65 (dd, J=10.8, 3.2 Hz, 1H), 2.42 (d, J=5.6 Hz, 1H).

2,5-Dibromopyridin-3-yl 3-azido-4,6-O-benzylidene-3-deoxy-2-O-methyl-1-thio-α-D-galactopyranoside

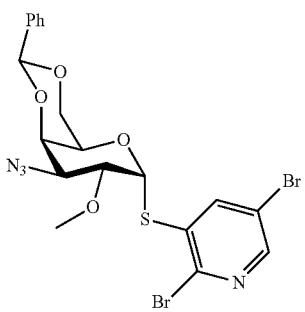

To a solution of 2,5-dibromopyridin-3-yl 3-azido-4,6-O-benzylidene-3-deoxy-1-thio-α-D-galactopyranoside (1.05 g, 1.93 mmol) in DMF (10 mL) Cs$_2$CO$_3$ (1.86 g, 5.79 mmol) and iodomethane (0.601 mL, 9.65 mmol) were added. The mixture was stirred under a nitrogen atmosphere overnight at rt. The mixture was poured into water (100 mL), the precipitate was collected, and dried in vacuo to afford the product (900 mg, 84%). ESI-MS m/z calcd for [C$_{19}$H$_{18}$Br$_2$N$_4$O$_4$S] [M+H]$^+$: 556.9; found: 556.8. $^1$H NMR (400 MHz, CDCl$_3$) δ 8.24 (d, J=2.4 Hz, 1H), 7.99 (d, J=2.4 Hz, 1H), 7.55-7.47 (m, 2H), 7.40-7.35 (m, 3H), 6.15 (d, J=5.2 Hz, 1H), 5.63 (s, 1H), 4.36-4.27 (m, 2H), 4.19 (dd, J=12.8, 1.6 Hz, 1H), 4.11-4.05 (m, 1H), 4.05-4.00 (m, 1H), 3.82 (dd, J=10.8, 3.2 Hz, 1H), 3.57 (s, 3H).

5-Bromo-2-cyanopyridin-3-yl 3-azido-4,6-O-benzylidene-3-deoxy-2-O-methyl-1-thio-α-D-galactopyranoside

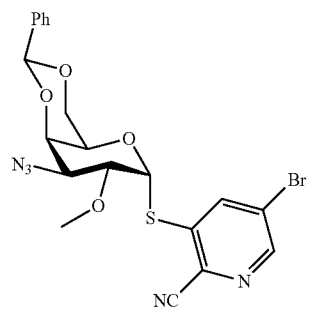

To a solution of 2,5-dibromopyridin-3-yl 3-azido-4,6-O-benzylidene-3-deoxy-2-O-methyl-1-thio-α-D-galactopyranoside (400 mg, 0.72 mmol) in DMSO (15 mL) copper(I) cyanide (77.0 mg, 0.86 mmol) was added. The mixture was stirred under a nitrogen atmosphere 2 h at 120° C. in a microwave reactor. The mixture was poured into water (50 mL) and extracted with EtOAc (2×50 mL). The organic layers were washed with brine, dried over anhydrous Na$_2$SO$_4$, filtered and concentrated. The residue was purified by column chromatography (PE/EtOAc=10/1~1/1, Silica-CS 4 g, 10 mL/min, silica gel, UV 254) to afford the product (140 mg, 39%) as a white solid. ESI-MS m/z calcd for [C$_{20}$H$_{18}$BrN$_5$O$_4$S] [M+H]$^+$: 504.0; found: 504.0. $^1$H NMR (400 MHz, CDCl$_3$) δ 8.61 (d, J=2.0 Hz, 1H), 8.20 (d, J=2.0 Hz, 1H), 7.53-7.49 (m, 2H), 7.39-7.34 (m, 3H), 6.13 (d, J=5.2 Hz, 1H), 5.62 (s, 1H), 4.35 (d, J=3.2 Hz, 1H), 4.29-4.25 (m, 1H), 4.18-4.08 (m, 3H), 3.77 (dd, J=10.4, 3.2 Hz, 1H), 3.59 (s, 3H).

5-Bromo-2-cyanopyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

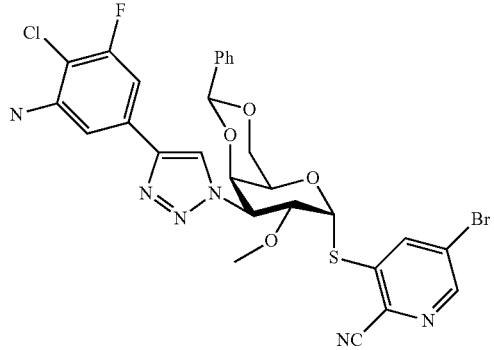

To a solution of 5-bromo-2-cyanopyridin-3-yl 3-azido-4,6-O-benzylidene-3-deoxy-2-O-methyl-1-thio-α-D-galactopyranoside (60.0 mg, 0.12 mmol) in DMF (5 mL) trimethyl-

[2-(4-chloro-3,5-difluorophenyl)ethynyl]silane (58.2 mg, 0.24 mmol), (+)-sodium L-ascorbate (23.6 mg, 0.12 mmol), copper(II) sulfate pentahydrate (29.7 mg, 0.12 mmol) and CsF (18.1 mg, 0.12 mmol) were added. The mixture was stirred under a nitrogen atmosphere overnight at rt. The mixture was poured into water (50 mL) and extracted with EtOAc (2×80 mL). The organic layers were washed with brine (50 mL), dried over $Na_2SO_4$, filtered and concentrated. The residue was purified by column chromatography (PE/EtOAc=10/1~1/1, Silica-CS 4 g, 10 mL/min, silica gel, UV 254) to afford the product (40.0 mg, 50%). ESI-MS m/z calcd for $[C_{28}H_{21}BrClF_2N_5O_4S][M+H]^+$: 676.0; found: 675.9. $^1$H NMR (400 MHz, $CDCl_3$) δ 8.68 (d, J=2.0 Hz, 1H), 8.24 (d, J=2.0 Hz, 1H), 8.00-7.98 (m, 1H), 7.47-7.43 (m, 2H), 7.43-7.37 (m, 5H), 6.25 (d, J=5.2 Hz, 1H), 5.55 (s, 1H), 5.32 (dd, J=11.2, 3.2 Hz, 1H), 4.61-4.55 (m, 2H), 4.42-4.37 (m, 1H), 4.32-4.27 (m, 1H), 4.20-4.14 (m, 1H), 3.39 (s, 3H).

Intermediate 51

5-Bromo-2-cyanopyridin-3-yl 4,6-O-benzylidene-3-[4-(4-chloro-3-fluorophenyl)-1H-1,2,3-triazol-1-yl]-3-deoxy-2-O-methyl-1-thio-α-D-galactopyranoside

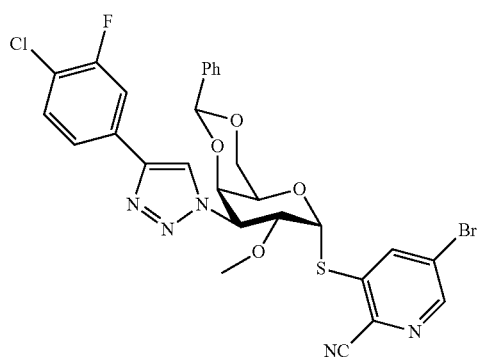

To a solution of 5-bromo-2-cyanopyridin-3-yl 3-azido-4,6-O-benzylidene-3-deoxy-2-O-methyl-1-thio-α-D-galactopyranoside (60.0 mg, 0.12 mmol) in DMF (5 mL) trimethyl-[2-(4-chloro-3-fluorophenyl)ethynyl]silane (40.5 mg, 0.18 mmol), (+)-sodium L-ascorbate (23.6 mg, 0.12 mmol), copper(II) sulfate pentahydrate (29.7 mg, 0.12 mmol) and CsF (18.1 mg, 0.12 mmol) were added. The mixture was stirred under a nitrogen atmosphere overnight at rt. The mixture was poured into water (50 mL) and extracted with EtOAc (2×80 mL). The combined organic layers were washed with brine (50 mL), dried over anhydrous $Na_2SO_4$, filtered and concentrated. The residue was purified by column chromatography (PE/EtOAc=10/1~1/1, Silica-CS 4 g, 10 m/min, silica gel, UV 254) to afford the product (40 mg, 51%). ESI-MS m/z calcd for $[C_{28}H_{22}BrClFN_5O_4S]$ $[M+H]^+$: 658.0; found: 658.0. $^1$H NMR (400 MHz, $CDCl_3$) δ 8.67 (d, J=2.0 Hz, 1H), 8.23 (d, J=2.0 Hz, 1H), 7.98 (s, 1H), 7.43-7.36 (m, 8H), 6.24 (d, J=5.2 Hz, 1H), 5.55 (s, 1H), 5.31 (dd, J=11.2, 3.2 Hz, 1H), 4.61-4.53 (m, 2H), 4.40 (s, 1H), 4.31-4.14 (m, 2H), 3.38 (s, 3H).

Intermediate 52

5-Chloro-2-(N-azetidinylcarbamoyl)-3-pyridyl 3-azido-3-deoxy-2-O-methyl-1-thio-α-D-galactopyranoside

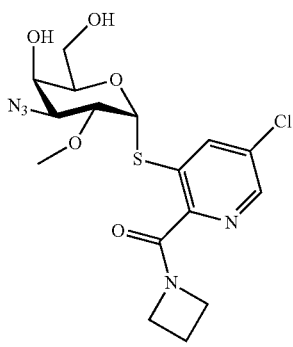

2-(Azetidin-1-ylcarbonyl)-3-bromo-5-chloropyridine

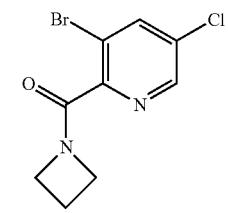 [SMILES: O=C(c1ncc(Cl)cc1Br)N1CCC1]

Azetidine (171 μL, 2.54 mmol) was added to a solution of 3-bromo-5-chloropyridine-2-carboxylic acid (500 mg, 2.11 mmol), 1-hydroxybenzotriazole hydrate (389 mg, 2.54 mmol) and N-(3-dimethylaminopropyl)-N'-ethylcarbodiimide hydrochloride (486 mg, 2.54 mmol) in DMF (8 ml) and $Et_3N$ (0.35 mL, 2.54 mmol). After stirring 26 h at rt the mixture was diluted with EtOAc and washed with water. The aqueous phase was extracted with EtOAc and the combined organic phases were dried and evaporated. Purification of the residue by chromatography ($SiO_2$, PE/EtOAc) yielded the product (264 mg, 45% yield). ESI-MS m/z calcd for $[C_9H_8BrClN_2O]$ $[M+H]^+$: 275.0; found: 274.6. $^1$H NMR (400 MHz, Chloroform-d) δ 8.49-8.46 (m, 1H), 7.97-7.94 (m, 1H), 4.29-4.21 (m, 2H), 4.14-4.07 (m, 2H), 2.40-2.29 (m, 2H).

211

2-(Azetidin-1-ylcarbonyl)-3-[(2,4-dimethoxyphenyl)methylsulfanyl]-5-chloropyridine

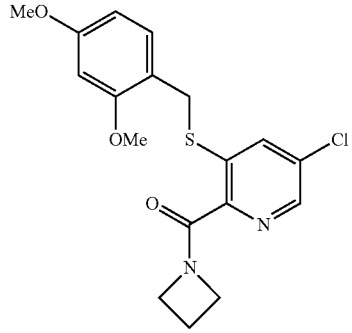 [SMILES: COc1ccc(CSc2cc(Cl)cnc2C(=O)N2CCC2)c(OC)c1]

To a nitrogen purged solution of 2-(azetidin-1-ylcarbonyl)-3-bromo-5-chloropyridine (277 mg, 1.01 mmol), Pd(dibenzylideneacetone)$_2$ (35 mg, 0.060 mmol) and 4,5-bis(diphenylphosphino)-9,9-dimethylxanthene (29 mg, 0.050 mmol) in 1,4-dioxane (1 mL) a solution of 2,4-dimethoxybenzyl thiol (278 mg, 1.51 mmol) and DIEA (0.34 mL, 2.00 mmol) in 1,4-dioxane (2 mL) was added and the mixture was stirred 4 h at 100° C. The mixture was purified by chromatography (SiO$_2$, PE/EtOAc) to yield the product (359 mg, 94%). ESI-MS m/z calcd for [C$_{18}$H$_{19}$ClN$_2$O$_3$S] [M+H]$^+$: 379.1; found: 379.1. $^1$H NMR (400 MHz, Chloroform-d) δ 8.49 (d, J=2.0 Hz, 1H), 7.71 (d, J=2.0 Hz, 1H), 7.27 (s, 1H), 6.47-6.42 (m, 2H), 4.28 (s, 4H), 4.09 (s, 2H), 3.86 (s, 2H), 3.80 (s, 3H), 2.30 (p, J=7.8 Hz, 2H).

2-(Azetidin-1-ylcarbonyl)-5-chloropyridine-3-thiol

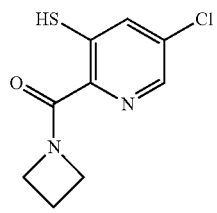

TFA (1.5 mL) was added to a solution of 2-(azetidin-1-ylcarbonyl)-3-[(2,4-dimethoxyphenyl)methylsulfanyl]-5-chloropyridine (359 mg, 0.95 mmol) in DCM (2 mL) and triethylsilane (1.5 mL) and the mixture was stirred 20 h at rt. The mixture was concentrated and purified by chromatography (SiO$_2$, PE/EtOAc) to afford the product (199 mg, 92%). ESI-MS m/z calcd for [C$_9$H$_9$ClN$_2$OS] [M+H]$^+$: 229.0; found: 228.7. $^1$H NMR (400 MHz, Chloroform-d) δ 8.23 (d, J=2.2 Hz, 1H), 7.63 (d, J=2.2 Hz, 1H), 4.41 (br s, 5H), 2.34 (p, J=7.8 Hz, 2H).

212

5-Chloro-2-(N-azetidinylcarbamoyl)-3-pyridyl 2,4,6-tri-O-acetyl-3-azido-3-deoxy-1-thio-α-D-galactopyranoside

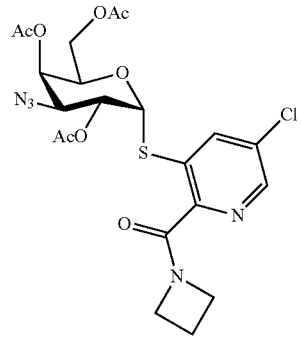

NaH (60% in oil, 70 mg, 1.81 mmol) was added to a solution of 2-(azetidin-1-ylcarbonyl)-5-chloropyridine-3-thiol (166 mg, 0.73 mmol) and 2,4,6-tri-O-acetyl-3-azido-3-deoxy-β-D-galactopyranosyl chloride (317 mg, 0.91 mmol) in DMF (6 mL) and the mixture was stirred 6 h at rt. The mixture was diluted with EtOAc and washed twice with water and once with brine. The organic phase was dried, concentrated and purified by chromatography (SiO$_2$, PE/EtOAc) to afford the product (315 mg, 67% yield). ESI-MS m/z calcd for [C$_{21}$H$_{24}$ClN$_5$O$_8$S] [M+H]$^+$: 542.1; found: 541.9. $^1$H NMR (400 MHz, Chloroform-d) δ 8.31 (d, J=2.0 Hz, 1H), 8.01 (d, J=2.1 Hz, 1H), 6.06 (d, J=5.6 Hz, 1H), 5.45 (d, J=2.8 Hz, 1H), 5.33 (dd, J=11.0, 5.6 Hz, 1H), 4.62-4.49 (m, 2H), 4.45-4.36 (m, 1H), 4.24 (t, J=7.7 Hz, 2H), 4.15-4.00 (m, 4H), 2.35 (p, J=7.7 Hz, 2H), 2.16 (s, 6H), 1.91 (s, 3H).

5-Chloro-2-(N-azetidinylcarbamoyl)-3-pyridyl 3-azido-3-deoxy-1-thio-α-D-galactopyranoside

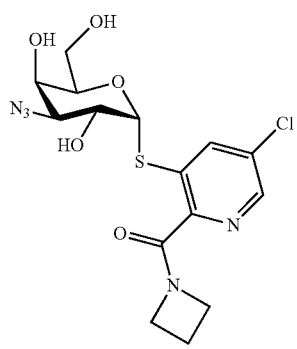

5-Chloro-2-(N-azetidinylcarbamoyl)-3-pyridyl 2,4,6-tri-O-acetyl-3-azido-3-deoxy-1-thio-α-D-galactopyranoside (275 mg, 0.51 mmol) was dissolved in MeOH (10 mL), Et$_3$N (1.5 mL) and water (0.5 mL) and stirred 24 h at rt. The mixture was concentrated and purified by preparative HPLC (Method B) to afford the product (206 mg, 98%). ESI-MS m/z calcd for [C$_{15}$H$_{18}$ClN$_5$O$_5$S] [M+H]$^+$: 416.1; found: 415.8. $^1$H NMR (400 MHz, Methanol-d$_4$) δ 8.41 (d, J=2.1 Hz, 1H), 8.30 (d, J=2.1 Hz, 1H), 5.83 (d, J=5.5 Hz, 1H), 4.41

(dd, J=10.8, 5.4 Hz, 1H), 4.26-4.14 (m, 5H), 4.04 (d, J=2.2 Hz, 1H), 3.72-3.61 (m, 2H), 3.56 (dd, J=10.8, 3.0 Hz, 1H), 2.38 (p, J=7.8 Hz, 2H).

5-Chloro-2-(N-azetidinylcarbamoyl)-3-pyridyl 3-azido-3-deoxy-2-O-methyl-1-thio-α-D-galactopyranoside

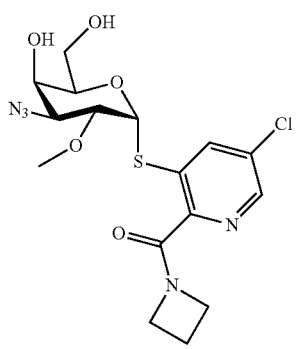

5-Chloro-2-(N-azetidinylcarbamoyl)-3-pyridyl 3-azido-3-deoxy-1-thio-α-D-galactopyranoside (200 mg, 0.48 mmol) was dissolved in MeCN (20 mL), p-toluenesulfonic acid monohydrate (92 mg, 0.48 mmol) followed by benzaldehyde dimethyl acetal (0.15 mL, 0.96 mmol) were added and the mixture was stirred 2 h at rt. Et$_3$N (0.1 mL, 0.72 mmol) was added and the mixture was concentrated. The residue was partitioned between EtOAc and saturated aq NaHCO$_3$. The organic phase was washed with brine, dried and evaporated. The residue and NaH (60% in oil, 37 mg, 0.96 mmol) were dissolved in DMF (3 mL) and stirred 5 min before the addition of iodomethane (45 μL, 0.72 mmol). After stirring 2 h at rt the mixture was diluted with EtOAc, washed twice with water and the organic phase was dried and evaporated. The residue was stirred 1 h at rt in TFA/water (2.5 mL, 4:1). The mixture was purified by preparative HPLC (Method B) to afford the product (45 mg, 22%). ESI-MS m/z calcd for [C$_{16}$H$_{20}$ClN$_5$O$_5$S] [M+H]$^+$: 430.1; found: 429.9. $^1$H NMR (400 MHz, Methanol-d$_4$) δ 8.44 (d, J=2.1 Hz, 1H), 8.31 (d, J=2.1 Hz, 1H), 6.15 (d, J=5.4 Hz, 1H), 4.26-4.14 (m, 5H), 4.06 (dd, J=10.6, 5.4 Hz, 1H), 3.99 (d, J=2.6 Hz, 1H), 3.69-3.59 (m, 3H), 3.52 (s, 3H), 2.39 (p, J=7.8 Hz, 2H).

Intermediate 54

5-(2-Trimethylsilyl-1-ethynyl)-pyridin-3-yl 3-[4-(4-chloro-3,5-difluorophenyl)-1H-1,2,3-triazol-1-yl]-3-deoxy-2-O-methyl-1-thio-α-D-galactopyranoside

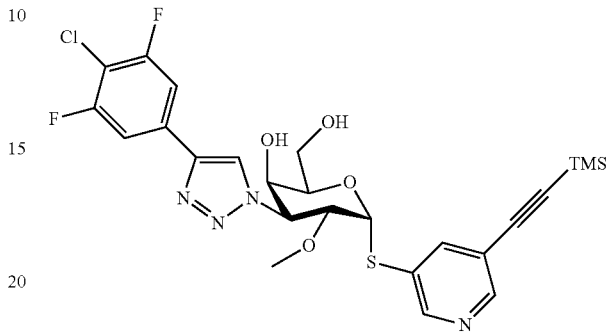

5-Bromopyridin-3-yl 3-[4-(4-chloro-3,5-difluorophenyl)-1H-1,2,3-triazol-1-yl]-3-deoxy-2-O-methyl-1-thio-α-D-galactopyranoside (174 mg, 0.30 mmol), bis(triphenylphosphine)palladium(II) chloride (22 mg, 0.03 mmol) and CuI (6.0 mg, 0.03 mmol) were evacuated and purged with nitrogen. THF (3.0 mL) followed by trimethylsilylacetylene (65 μL, 0.45 mmol) and DIEA (79 μL, 0.45 mmol) were added and the mixture was stirred 18 h at 50° C. Concentration and purification by chromatography (SiO$_2$, PE/EtOAc) gave the product (150 mg, 86%). ESI-MS m/z calcd for [C$_{25}$H$_{27}$ClF$_2$N$_4$O$_4$SSi] [M+H]$^+$: 581.1; found: 580.9. $^1$H NMR (400 MHz, Methanol-d$_4$) δ 8.68 (s, 1H), 8.64 (s, 1H), 8.51 (s, 1H), 8.14 (s, 1H), 7.66 (d, J=8.2 Hz, 2H), 6.25 (d, J=5.3 Hz, 1H), 5.05 (dd, J=11.3, 2.4 Hz, 1H), 4.64 (dd, J=11.3, 5.2 Hz, 1H), 4.47 (t, J=6.0 Hz, 1H), 4.19 (s, 1H), 3.75-3.63 (m, 2H), 3.41 (s, 3H), 0.27 (s, 9H).

Intermediate 55

5-Chloro-2-cyanopyridin-3-yl 4,6-O-benzylidene-3-[4-(5-chloro-6-fluoropyridin-2-yl)-1H-1,2,3-triazol-1-yl]-3-deoxy-2-O-methyl-1-thio-α-D-galactopyranoside

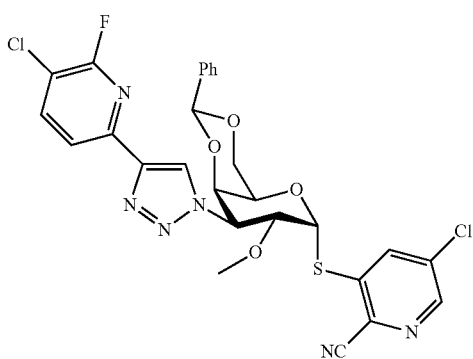

3-Chloro-2-fluoro-6-[2-(trimethylsilyl)ethynyl]pyridine

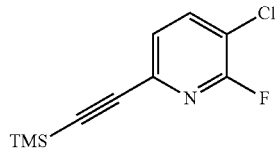 [SMILES: C[Si](C)(C)C#Cc1ccc(Cl)c(F)n1]

To a solution of 6-bromo-3-chloro-2-fluoro-pyridine (200 mg, 0.95 mmol) and trimethylsilylacetylene (140 mg, 1.43 mmol) in DMF (4 mL) CuI (9.05 mg, 0.048 mmol), bis(triphenylphosphine)palladium(II) dichloride (33.4 mg, 0.048 mmol) and DIEA (0.325 mL, 1.90 mmol) were added. The mixture was stirred overnight at rt under a nitrogen atmosphere. The solvent was removed, and the residue was purified by column chromatography (PE/EtOAc=20/1) to afford the product (165 mg, 76%). GC-MS calcd for [$C_{10}H_{11}ClFNSi$] [M]: 227.0; found: 227.0. $^1$H NMR (400 MHz, CDCl$_3$) δ 7.77 (dd, J=8.8, 6.8 Hz, 1H), 6.86 (dd, J=8.8, 3.6 Hz, 1H), 0.28 (s, 9H).

5-Chloro-2-cyanopyridin-3-yl 4,6-O-benzylidene-3-[4-(5-chloro-6-fluoropyridin-2-yl)-1H-1,2,3-triazol-1-yl]-3-deoxy-2-O-methyl-1-thio-α-D-galactopyranoside

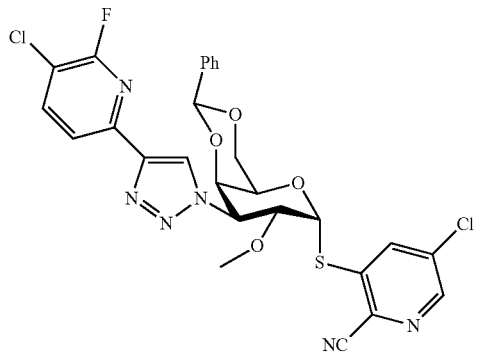

To a solution of 5-chloro-2-cyanopyridin-3-yl 3-azido-4,6-O-benzylidene-3-deoxy-2-O-methyl-1-thio-α-D-galactopyranoside (120 mg, 0.26 mmol) 3-chloro-2-fluoro-6-[2-(trimethylsilyl)ethynyl]pyridine (71.3 mg, 0.31 mmol) in DMF (4 mL) (+)-sodium L-ascorbate (77.5 mg, 0.39 mmol) and copper(II) sulfatepentahydrate (32.6 mg, 0.13 mmol) were added. The mixture was stirred 4 h at rt under a nitrogen atmosphere. After diluting with water (20 mL), the mixture was extracted with EtOAc (3×10 mL). The combined organic layers were washed with brine, dried over anhydrous Na$_2$SO$_4$, and concentrated. The residue was purified by preparative HPLC (Method A) to give the product (125 mg, 78%) as a white solid. ESI-MS m/z calcd for [$C_{27}H_{21}Cl_2FN_6O_4S$][M+H]$^+$: 615.1; found: 615.2. $^1$H NMR (400 MHz, DMSO-d$_6$) δ 8.93 (s, 1H), 8.75 (d, J=2.0 Hz, 1H), 8.53 (d, J=2.0 Hz, 1H), 8.22 (dd, J=8.8, 7.2 Hz, 1H), 7.47-7.40 (m, 2H), 7.40-7.33 (m, 3H), 7.27 (dd, J=8.8, 3.6 Hz, 1H), 6.89 (d, J=5.2 Hz, 1H), 5.64 (s, 1H), 5.29 (dd, J=11.6, 3.2 Hz, 1H), 4.92 (dd, J=11.6, 5.2 Hz, 1H), 4.66 (d, J=3.2 Hz, 1H), 4.29 (s, 1H), 4.12 (d, J=11.6 Hz, 1H), 3.99 (d, J=11.6 Hz, 1H), 3.36 (s, 3H).

Intermediate 56

2-Cyano-5-(2-trimethylsilyl-1-ethynyl)-pyridin-3-yl 4,6-di-O-acetyl-3-[4-(4-chloro-3,5-difluorophenyl)-1H-1,2,3-triazol-1-yl]-3-deoxy-2-O-methyl-1-thio-α-D-galactopyranoside

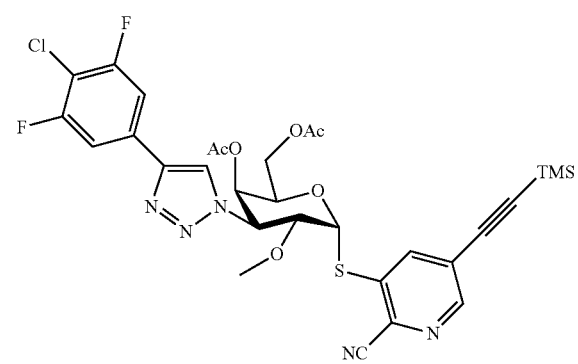

4,6-Di-O-acetyl-3-azido-3-deoxy-2-O-methyl-1-thio-α-D-galactopyranose

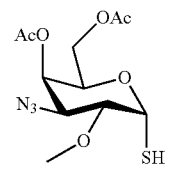

Boron trifluoride diethyl etherate (0.96 mL, 7.78 mmol) was added to acetyl 4,6-di-O-acetyl-3-azido-3-deoxy-2-O-methyl-D-galactopyranoside (895 mg, 2.59 mmol) in DCM (18 mL) and the mixture was subjected to H$_2$S (1 atm). The mixture was stirred vigorously for 21 h. Water (100 mL) was added and the mixture was extracted with DCM (3×100 mL). The combined organic phases were dried and concentrated. Purification by chromatography (SiO$_2$, PE/EtOAc) yielded the product (324 mg, 39%). ESI-MS m/z calcd for [$C_{11}H_{21}NO_6S$] [M+NH$_4$]$^+$: 337.0; found: 337.1, $^1$H NMR (400 MHz, Chloroform-d) δ 5.96 (t, J=3.9 Hz, 1H), 5.40-5.34 (m, 1H), 4.55 (t, J=6.3 Hz, 1H), 4.13 (dd, J=12.0, 6.7 Hz, 1H), 4.01 (dd, J=12.0, 7.4 Hz, 1H), 3.84 (dd, J=10.4, 4.8 Hz, 1H), 3.78 (dd, J=10.3, 2.8 Hz, 1H), 3.51 (s, 3H), 2.16 (s, 3H), 2.07 (s, 3H), 1.85 (d, J=3.8 Hz, 1H).

5-Bromo-2-cyanopyridin-3-yl 4,6-di-O-acetyl-3-azido-3-deoxy-2-O-methyl-1-thio-α-D-galactopyranoside

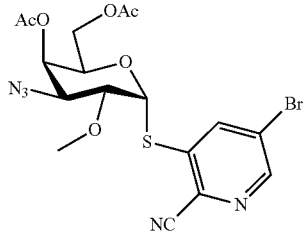

DIEA (261 µL, 1.52 mmol) was added to 5-bromo-3-fluoropyridine-2-carbonitrile (245 mg, 1.22 mmol) and 4,6-di-O-acetyl-3-azido-3-deoxy-2-O-methyl-1-thio-α-D-galactopyranose (324 mg, 1.01 mmol) in DMF (4 mL). The mixture was stirred 30 min at rt before it was diluted with EtOAc (40 mL) and washed with HCl (1 M, 40 mL), water (3×40 mL) and brine (40 mL). The organic phase was dried and concentrated. Purification by chromatography (SiO$_2$, PE/EtOAc) yielded the product (465 mg, 92%). ESI-MS m/z calcd for [C$_{17}$H$_{18}$BrN$_4$O$_6$S] [M+H]$^+$: 500.0; found: 499.8, $^1$H NMR (500 MHz, Chloroform-d) δ 8.67-8.62 (m, 1H), 8.22-8.18 (m, 1H), 6.11 (d, J=5.3 Hz, 1H), 5.42 (d, J=3.1 Hz, 1H), 4.49 (dd, J=7.3, 5.0 Hz, 1H), 4.05 (dd, J=11.7, 4.7 Hz, 1H), 4.00 (dd, J=9.8, 4.8 Hz, 1H), 3.97 (dd, J=10.9, 6.9 Hz, 1H), 3.86 (dd, J=10.4, 3.2 Hz, 1H), 3.61 (s, 3H), 2.16 (s, 3H), 1.97 (s, 3H).

5-Bromo-2-cyanopyridin-3-yl 4,6-di-O-acetyl-3-[4-(4-chloro-3,5-difluorophenyl)-1H-1,2,3-triazol-1-yl]-3-deoxy-2-O-methyl-1-thio-α-D-galactopyranoside

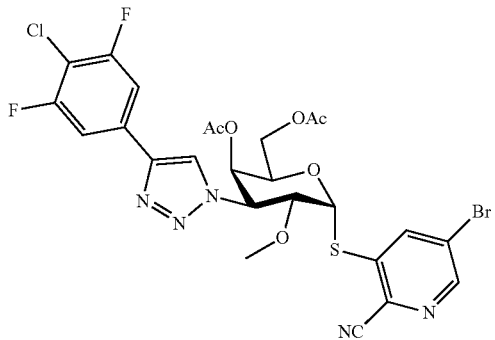

DIEA (79.4 µL, 464 µmol) was added to 5-bromo-2-cyanopyridin-3-yl 4,6-di-O-acetyl-3-azido-3-deoxy-2-O-methyl-1-thio-α-D-galactopyranoside (232 mg, 464 µmol), trimethyl-[2-(4-chloro-3,5-difluorophenyl)ethynyl]silane (96.0 mg, 556 µmol) and CuI (8.8 mg, 46.4 mmol) in MeCN (4.64 mL). After 19 h at 40° C., the mixture was filtered through a plug of celite and concentrated. Purification by chromatography (SiO$_2$, PE/EtOAc) yielded the product (277 mg, 89%). ESI-MS m/z calcd for [C$_{26}$H$_{22}$BrClF$_2$N$_5$O$_6$S] [M+H]$^+$: 672.0; found: 672.0, $^1$H NMR (400 MHz, Chloroform-d) δ 8.70 (d, J=2.0 Hz, 1H), 8.27 (d, J=2.0 Hz, 1H), 7.87 (s, 1H), 7.50-7.43 (m, 2H), 6.34 (d, J=3.9 Hz, 1H), 5.60 (s, 1H), 4.97-4.91 (m, 2H), 4.71 (t, J=6.4 Hz, 1H), 4.12-4.01 (m, 2H), 3.47 (s, 3H), 2.05 (s, 3H), 1.99 (s, 3H).

2-Cyano-5-(2-trimethylsilyl-1-ethynyl)-pyridin-3-yl 4,6-di-O-acetyl-3-[4-(4-chloro-3,5-difluorophenyl)-1H-1,2,3-triazol-1-yl]-3-deoxy-2-O-methyl-1-thio-α-D-galactopyranoside

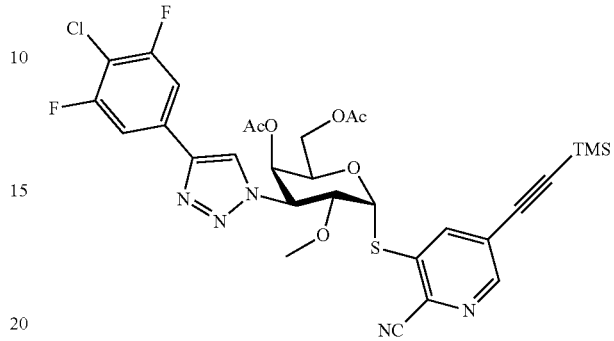

5-Bromo-2-cyanopyridin-3-yl 4,6-di-O-acetyl-3-[4-(4-chloro-3,5-difluorophenyl)-1H-1,2,3-triazol-1-yl]-3-deoxy-2-O-methyl-1-thio-α-D-galactopyranoside (85 mg, 126 µmol) and trimethylsilylacetylene (52.5 µL, 379 µmol) were added to bis(triphenylphosphine)palladium(II) chloride (4.6 mg, 6.3 µmol) and CuI (2.4 mg, 12.6 µmol) in THF (0.50 mL) and Et$_3$N (83.1 µL, 632 µmol). After 1.5 h the mixture was concentrated. Purification by chromatography (SiO$_2$, PE/EtOAc) yielded the product (72.0 mg, 83%). ESI-MS m/z calcd for [C$_{30}$H$_{31}$ClF$_2$N$_5$O$_6$SSi] [M+H]$^+$: 690.1; found: 690.0, $^1$H NMR (500 MHz, Chloroform-d) δ 8.66 (d, J=1.8 Hz, 1H), 8.10 (d, J=1.8 Hz, 1H), 7.88 (s, 1H), 7.52-7.43 (m, 2H), 6.35 (d, J=5.1 Hz, 1H), 5.62 (d, J=2.0 Hz, 1H), 4.98 (dd, J=11.0, 2.8 Hz, 1H), 4.92 (dd, J=11.0, 5.2 Hz, 1H), 4.75 (dd, J=7.0, 5.3 Hz, 1H), 4.11 (dd, J=11.7, 5.0 Hz, 1H), 4.06 (dd, J=11.7, 7.5 Hz, 1H), 3.49 (s, 3H), 2.10 (s, 3H), 1.99 (s, 3H), 0.31 (s, 9H).

Intermediate 57

2-Cyano-5-(2-trimethylsilyl-1-ethynyl)-pyridin-3-yl 4,6-di-O-acetyl-3-deoxy-3-[4-(3,5-difluoro-4-methylphenyl)-1H-1,2,3-triazol-1-yl]-2-O-methyl-1-thio-α-D-galactopyranoside

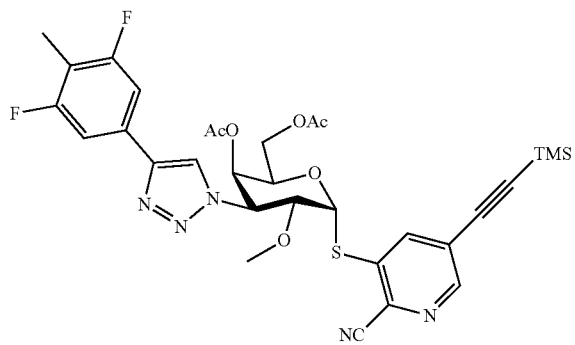

5-Bromo-2-cyanopyridin-3-yl 4,6-di-O-acetyl-3-deoxy-3-[4-(3,5-difluoro-4-methylphenyl)-1H-1,2,3-triazol-1-yl]-2-O-methyl-1-thio-α-D-galactopyranoside

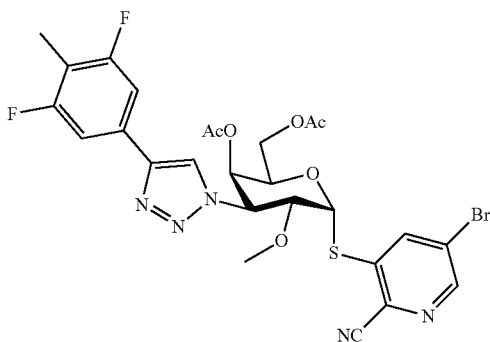

DIEA (79.4 µL, 464 µmol) was added to 5-bromo-2-cyanopyridin-3-yl 4,6-di-O-acetyl-3-azido-3-deoxy-2-O-methyl-1-thio-α-D-galactopyranoside (232 mg, 464 µmol), trimethyl-[2-(3,5-difluoro-4-methylphenyl)ethynyl]silane (84.7 mg, 556 µmol) and CuI (8.8 mg, 46.4 mmol) in MeCN (4.64 mL). After 25 h at rt, the mixture was filtered through a plug of celite and concentrated. Purification by chromatography (SiO$_2$, PE/EtOAc) yielded the product (259 mg, 86%). ESI-MS m/z calcd for [C$_{26}$H$_{25}$BrF$_2$N$_5$O$_6$S] [M+H]$^+$: 652.1; found: 652.0, $^1$H NMR (400 MHz, Chloroform-d) δ 8.69 (d, J=2.0 Hz, 1H), 8.27 (d, J=2.0 Hz, 1H), 7.82 (s, 1H), 7.33 (d, J=7.7 Hz, 2H), 6.34 (d, J=3.6 Hz, 1H), 5.61 (s, 1H), 4.95-4.91 (m, 2H), 4.70 (t, J=6.2 Hz, 1H), 4.12-4.08 (m, 1H), 4.04 (dd, J=11.7, 7.3 Hz, 1H), 3.46 (s, 3H), 2.23 (s, 3H), 2.09 (s, 3H), 1.98 (s, 3H).

2-Cyano-5-(2-trimethylsilyl-1-ethynyl)-pyridin-3-yl 4,6-di-O-acetyl-3-deoxy-3-[4-(3,5-difluoro-4-methylphenyl)-1H-1,2,3-triazol-1-yl]-2-O-methyl-1-thio-α-D-galactopyranoside

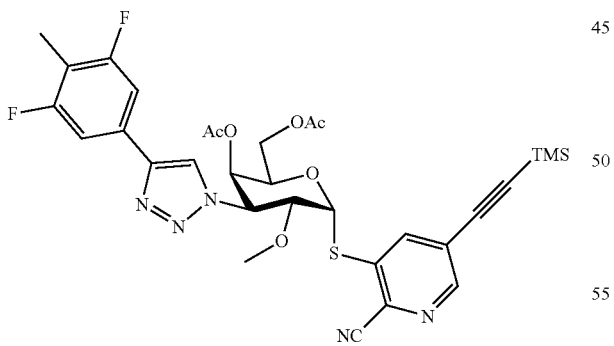

5-Bromo-2-cyanopyridin-3-yl 4,6-di-O-acetyl-3-[4-(3,5-difluoro-4-methylphenyl)-1H-1,2,3-triazol-1-yl]-3-deoxy-2-O-methyl-1-thio-α-D-galactopyranoside (100 mg, 153 µmol) and trimethylsilylacetylene (63.7 µL, 460 µmol) were added to bis(triphenylphosphine)palladium(II) chloride (5.6 mg, 7.7 µmol) and CuI (2.9 mg, 15.3 µmol) in THF (0.50 mL) and Et$_3$N (105 µL, 766 µmol). After 1 h the mixture was concentrated. Purification by chromatography (SiO$_2$, PE/EtOAc) yielded the product (93.0 mg, 91%). ESI-MS m/z calcd for [C$_{31}$H$_{34}$F$_2$N$_5$O$_6$SSi] [M+H]$^+$: 670.2; found: 670.2, $^1$H NMR (500 MHz, Chloroform-d) δ 8.64 (s, 1H), 8.08 (d, J=1.4 Hz, 1H), 7.82 (s, 1H), 7.32 (d, J=5.4 Hz, 2H), 6.33 (d, J=5.1 Hz, 1H), 5.65-5.55 (m, 1H), 4.95 (s, 1H), 4.89 (dd, J=10.9, 5.2 Hz, 1H), 4.77-4.66 (m, 1H), 4.09-4.06 (m, 1H), 4.04 (dd, J=11.7, 7.5 Hz, 1H), 3.46 (s, 3H), 2.22 (s, 3H), 2.07 (s, 3H), 1.97 (s, 3H), 0.29 (s, 9H).

Intermediate 58

5-Cyano-6-trifluoromethylpyridin-3-yl 3-azido3-deoxy-2-O-methyl-1-thio-α-D-galactopyranoside

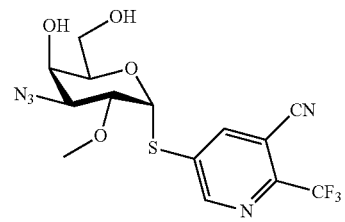

5-Fluoro-2-(trifluoromethyl)pyridine-3-carbonitrile

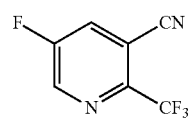

CuCN (91.8 mg, 1.02 mmol) was added to 3-bromo-5-fluoro-2-(trifluoromethyl)pyridine (200 mg, 0.82 mmol) in DMSO (0.80 mL) and the mixture was heated to 150° C. After 2 h, the mixture was cooled to rt. EtOAc (20 mL) and water (20 mL) were added and the resulting suspension was filtered. The organic phase was dried and concentrated to afford the product (147 mg, 94%). $^1$H NMR (400 MHz, Chloroform-d) δ 8.78 (d, J=2.6 Hz, 1H), 7.92 (dd, J=7.1, 2.5 Hz, 1H).

5-Cyano-6-trifluoromethylpyridin-3-yl 2,4,6-tri-O-acetyl-3-azido3-deoxy-2-O-methyl-1-thio-α-D-galactopyranoside

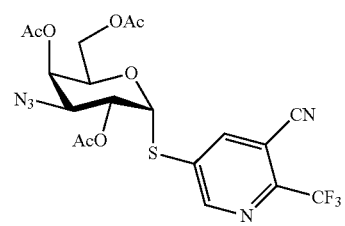

Et$_2$NH (198 µL, 191 mmol) was added to a solution of acetyl 2,4,6-tri-O-acetyl-3-azido-3-deoxy-1-thio-α-D-galactopyranoside (350 mg, 0.76 mmol) and 5-fluoro-2-(trifluoromethyl)pyridine-3-carbonitrile (145 mg, 0.76 mmol) in DMF (3 mL) at 0° C. The mixture was allowed to reach rt and then stirred for 30 min before it was diluted with EtOAc (30 mL) and washed with HCl (0.2 M, 30 mL), water (3×30 mL) and brine (30 mL). The organic phase was dried and concentrated. Purification by chromatography (SiO₂, PE/EtOAc) yielded the product (241 mg, 61%). ESI-MS m/z calcd for [C₁₉H₁₉F₃N₅O₇S] [M+H]⁺: 518.1; found: 517.9, ¹H NMR (400 MHz, Chloroform-d) δ 8.88 (d, J=2.1 Hz, 1H), 8.25 (d, J=2.0 Hz, 1H), 6.18 (d, J=5.5 Hz, 1H), 5.51 (d, J=2.9 Hz, 1H), 5.34 (dd, J=10.9, 5.5 Hz, 1H), 4.54 (dd, J=8.0, 4.1 Hz, 1H), 4.16 (dd, J=11.8, 4.4 Hz, 1H), 4.03 (dd, J=11.8, 8.0 Hz, 1H), 3.98 (dd, J=10.9, 3.3 Hz, 1H), 2.21 (s, 3H), 2.20 (s, 3H), 2.00 (s, 3H).

5-Cyano-6-trifluoromethylpyridin-3-yl 3-azido3-deoxy-2-O-methyl-1-thio-α-D-galactopyranoside

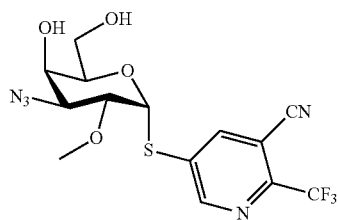

5-Cyano-6-trifluoromethylpyridin-3-yl 2,4,6-tri-O-acetyl-3-azido3-deoxy-2-O-methyl-1-thio-α-D-galactopyranoside (242 mg, 0.47 mmol) was dissolved in MeOH (20 mL) and NaOMe (1M, 234 μL) was added. After 45 min the reaction was quenched with AcOH (50 μL) and concentrated. Water (10 mL) was added and the mixture was extracted with EtOAc (3×10 mL). The combined organic phases were dried and concentrated. The crude was dissolved in MeCN (25 mL). Benzaldehyde dimethyl acetal (140 μL, 0.94 mmol) and p-toluenesulfonic acid monohydrate (26.7 mg, 0.14 mmol) were added. After 1.5 h the reaction was quenched with Et₃N (50 μL) and concentrated. The material was dissolved in EtOAc (25 mL) and washed with saturated aq NaHCO₃ (25 mL) and brine (25 mL). The organic phase was dried, concentrated and the residue was purified by chromatography (SiO₂, PE/EtOAc). The obtained material was dissolved in DCM (3 mL). Proton sponge (301 mg, 1.40 mmol) and trimethyloxonium tetrafluoroborate (138 mg, 0.94 mmol) were added. The reaction was stirred 18 h at rt before it was quenched with MeOH and concentrated. HCl (1 M, 20 mL) was added and the mixture was extracted with EtOAc (2×20 mL). The combined organic phases were dried and concentrated. TFA (3.35 mL) and water (0.75 mL) were added. After 1 h the mixture was concentrated to ~⅓ of its volume and NaOH (1 M, 10 mL) was added. The mixture was basified using NaOH (5 M) and extracted with EtOAc (2×10 mL). The combined organic phases were dried and concentrated. Purification by chromatography (SiO₂, PE/EtOAc) yielded the product (107 mg, 56%). ESI-MS m/z calcd for [C₁₄H₁₅F₃N₅O₄S] [M+H]⁺: 406.1; found: 405.9, ¹H NMR (400 MHz, Methanol-d₄) δ 8.97 (s, 1H), 8.61 (s, 1H), 6.37 (d, J=5.3 Hz, 1H), 4.15-4.09 (m, 2H), 3.98 (d, J=2.2 Hz, 1H), 3.72-3.60 (m, 3H), 3.54 (s, 3H).

Intermediate 59

5-Cyanopyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

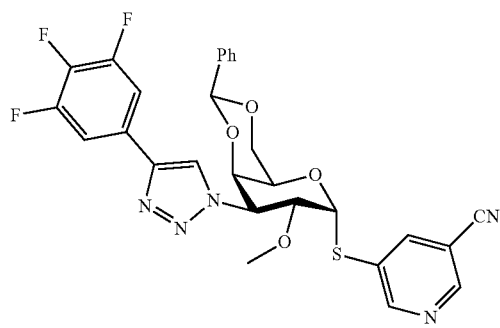

5-Bromopyridin-3-yl 3-azido-3-deoxy-1-thio-α-D-galactopyranoside

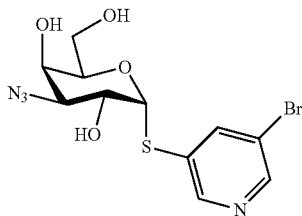

To a solution of 5-bromopyridin-3-yl 2,4,6-tri-O-acetyl-3-azido-3-deoxy-1-thio-α-D-galactopyranoside (1.2 g, 2.38 mmol) in MeOH (20 mL) Et₃N (1.99 mL, 14.3 mmol) and water (1 mL) were added. The solvent was removed under reduced pressure, and the residue was washed by DCM (20 mL) to give the product (700 mg, 78%). ESI-MS m/z calcd for [C₁₁H₁₃BrN₄O₄S] [M+H]⁺: 377.0; found: 377.2. ¹H NMR (400 MHz, CD₃OD) δ 8.61 (d, J=2.0 Hz, 1H), 8.51 (d, J=2.0 Hz, 1H), 8.25 (t, J=2.0 Hz, 1H), 5.72 (d, J=5.2 Hz, 1H), 4.38 (dd, J=10.8, 5.2 Hz, 1H), 4.30-4.20 (m, 1H), 4.06-4.00 (m, 1H), 3.70-3.58 (m, 2H), 3.52 (dd, J=10.8, 3.2 Hz, 1H).

5-Bromopyridin-3-yl 3-azido-4,6-O-benzylidene-3-deoxy-1-thio-α-D-galactopyranoside

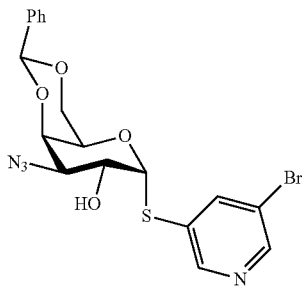

To a solution of 5-bromopyridin-3-yl 3-azido-3-deoxy-1-thio-α-D-galactopyranoside (0.700 g, 1.86 mmol) in DMF (10 mL) benzaldehyde dimethyl acetal (847 mg, 5.57 mmol) and D(+)-10-camphorsulfonic acid (129 mg, 0.557 mmol) were added. The mixture was stirred 2 h under a nitrogen atmosphere at 50° C. The mixture was cooled to rt and poured into water. The solid was collected and dried in vacuum to the product (650 mg, 75%). ESI-MS m/z calcd for [$C_{18}H_{17}BrN_4O_4S$] [M+H]$^+$: 465.0; found: 465.0. $^1$H NMR (400 MHz, DMSO-$d_6$) δ 8.59-8.54 (m, 2H), 8.18 (t, J=2.0 Hz, 1H), 7.42-7.33 (m, 5H), 6.20 (d, J=5.2 Hz, 1H), 6.02 (d, J=5.2 Hz, 1H), 5.66 (s, 1H), 4.41 (d, J=3.2 Hz, 1H), 4.33-4.25 (m, 1H), 4.10-4.05 (m, 1H), 4.00 (s, 1H), 3.89-3.82 (m, 1H), 3.67 (dd, J=10.8, 3.2 Hz, 1H).

5-Bromopyridin-3-yl 3-azido-4,6-O-benzylidene-3-deoxy-2-O-methyl-1-thio-α-D-galactopyranoside

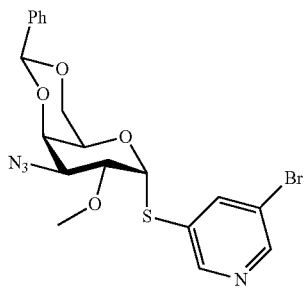

To a solution of 5-bromopyridin-3-yl 3-azido-4,6-O-benzylidene-3-deoxy-1-thio-α-D-galactopyranoside (400 mg, 0.86 mmol) in DMF (10 mL) sodium hydride (60% in oil, 68.8 mg, 1.72 mmol) was added at 0° C. After 20 min, iodomethane (0.214 mL, 3.44 mmol) was added. The mixture was stirred 30 min under a nitrogen atmosphere at rt. The mixture was poured into water (20 mL) and extracted with EtOAc (2×50 mL). The combined organic layers were washed with brine (50 mL), dried over Na$_2$SO$_4$, filtered and concentrated. The residue was purified by column chromatography (PE/EtOAc=3/1~1/1, Silica-CS 20 g, 25 mL/min, silica gel, UV 254) to afford the product (350 mg, 85%). ESI-MS m/z calcd for [$C_{19}H_{19}BrN_4O_4S$] [M+H]$^+$: 479.0; found: 479.0. $^1$H NMR (400 MHz, DMSO-$d_6$) δ 8.62-8.57 (m, 2H), 8.27-8.21 (m, 1H), 7.50-7.30 (m, 5H), 6.42 (d, J=5.2 Hz, 1H), 5.67 (s, 1H), 4.41 (d, J=2.8 Hz, 1H), 4.13-3.98 (m, 3H), 3.90-3.74 (m, 2H), 3.44 (s, 3H).

5-Cyanopyridin-3-yl 3-azido-4,6-O-benzylidene-3-deoxy-2-O-methyl-1-thio-α-D-galactopyranoside

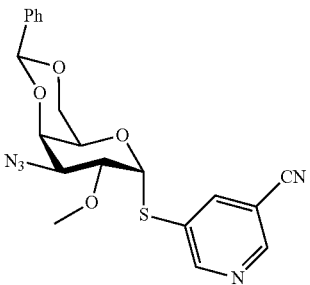

To a solution of 5-bromopyridin-3-yl 3-azido-4,6-O-benzylidene-3-deoxy-2-O-methyl-1-thio-α-D-galactopyranoside (500 mg, 1.04 mmol) in DMF (10 mL) Zn (68.2 mg, 1.04 mmol), Zn(CN)$_2$ (368 mg, 3.13 mmol), 1,1'-bis(diphenylphosphino)ferrocene (58.9 mg, 0.10 mmol) and Pd$_2$(dibenzylideneacetone)$_3$ (95.4 mg, 0.104 mmol) were added. The mixture was stirred 2.5 h at 100° C. under a nitrogen atmosphere. After diluting with water (20 mL), the mixture was extracted with EtOAc (3×10 mL). The combined organic layers were washed with brine, dried over anhydrous Na$_2$SO$_4$ and concentrated in vacuo. The residue was purified by column chromatography (PE/EtOAc=10/1~2/1, Silica-CS 12 g, 20 mL/min, silica gel, UV 254) to give the product (200 mg, 45%). ESI-MS m/z calcd for [$C_{20}H_{19}N_5O_4S$] [M+H]$^+$: 426.1; found: 426.1. $^1$H NMR (400 MHz, CDCl$_3$) δ 8.83 (d, J=2.4 Hz, 1H), 8.72 (d, J=2.0 Hz, 1H), 8.07 (t, J=2.0 Hz, 1H), 7.55-7.48 (m, 2H), 7.41-7.33 (m, 3H), 6.08 (d, J=5.2 Hz, 1H), 5.62 (s, 1H), 4.34 (d, J=2.8 Hz, 1H), 4.26 (dd, J=10.8, 5.2 Hz, 1H), 4.21 (dd, J=12.8, 1.6 Hz, 1H), 4.12 (dd, J=12.8, 1.6 Hz, 1H), 4.05 (s, 1H), 3.71 (dd, J=10.8, 3.6 Hz, 1H), 3.56 (s, 3H).

5-Cyanopyridin-3-yl 4,6-O-benzylidene-3-deoxy-3-[4-(3,4,5-trifluorophenyl)-1H-1,2,3-triazol-1-yl]-2-O-methyl-1-thio-α-D-galactopyranoside

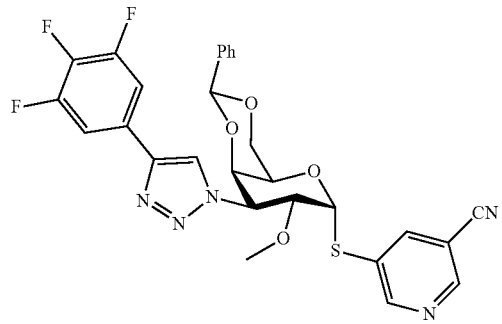

To a solution of 5-cyanopyridin-3-yl 3-azido-4,6-O-benzylidene-3-deoxy-2-O-methyl-1-thio-α-D-galactopyranoside (80.0 mg, 0.19 mmol) and trimethyl-[2-(3,4,5-trifluorophenyl)ethynyl]silane (51.5 mg, 0.23 mmol) in DMF (4.0 mL) (+)-sodium L-ascorbate (55.9 mg, 0.28 mmol) and copper(II) sulfate pentahydrate (23.5 mg, 0.094 mmol). The mixture was stirred 4 h at rt under a nitrogen atmosphere. After diluting with water (20 mL), the mixture was extracted with EtOAc (3×10 mL). The combined organic layers were washed with brine, dried over anhydrous Na$_2$SO$_4$ and concentrated in vacuo. The residue was purified by preparative HPLC (Method A) to give the product (80.0 mg, 73%) as a white solid. ESI-MS m/z calcd for [$C_{28}H_{22}F_3N_5O_4S$] [M+H]$^+$: 582.1; found: 582.1. $^1$H NMR (400 MHz, CDCl$_3$) δ 8.89 (d, J=2.0 Hz, 1H), 8.77 (d, J=1.6 Hz, 1H), 8.13 (t, J=2.0 Hz, 1H), 7.97 (s, 1H), 7.50-7.36 (m, 7H), 6.22 (d, J=5.2 Hz, 1H), 5.54 (s, 1H), 5.31 (dd, J=11.2, 3.2 Hz, 1H), 4.61-4.50 (m, 2H), 4.35-4.27 (m, 2H), 4.19-4.13 (m, 1H), 3.33 (s, 3H).

Intermediate 60

5-Cyanopyridin-3-yl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

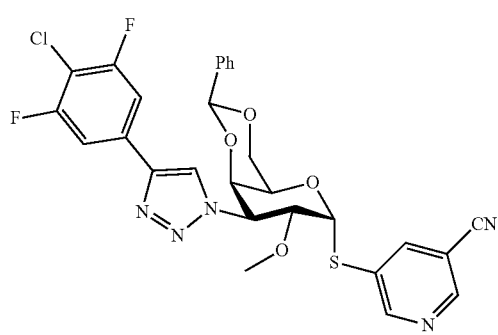

To a solution of 5-cyanopyridin-3-yl 3-azido-4,6-O-benzylidene-3-deoxy-2-O-methyl-1-thio-α-D-galactopyranoside (80.0 mg, 0.19 mmol) and trimethyl-[2-(4-chloro-3,5-difluorophenyl)ethynyl]silane (69.0 mg, 0.28 mmol) in DMF (4 mL) (+)-sodium L-ascorbate (55.9 mg, 0.28 mmol) and copper(II) sulfate pentahydrate (23.5 mg, 0.094 mmol) were added. The mixture was stirred 4 h at rt under a nitrogen atmosphere. After diluting with water (20 mL), the mixture was extracted with EtOAc (3×20 mL). The combined organic layers were washed with brine, dried over anhydrous $Na_2SO_4$ and concentrated. The residue was purified by column chromatography (PE/EtOAc=10/1~1/1, Silica-CS 12 g, 20 mL/min, silica gel, UV 254) to give the product (80.0 mg, 71%). ESI-MS m/z calcd for $[C_{28}H_{22}ClF_2N_5O_4S]$ $[M+H]^+$: 598.1; found: 598.0. $^1H$ NMR (400 MHz, $CDCl_3$) δ 9.02-8.70 (m, 2H), 8.14-8.09 (m, 1H), 8.01-7.94 (m, 1H), 7.46-7.40 (m, 7H), 6.21 (d, J=5.2 Hz, 1H), 5.55 (s, 1H), 5.31 (dd, J=11.2, 3.2 Hz, 1H), 4.58-4.47 (m, 2H), 4.33-4.27 (m, 2H), 4.20-4.11 (m, 1H), 3.33 (s, J=10.6 Hz, 3H).

Intermediate 61

5-Bromo-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-methyl-1-thio-α-D-galactopyranoside

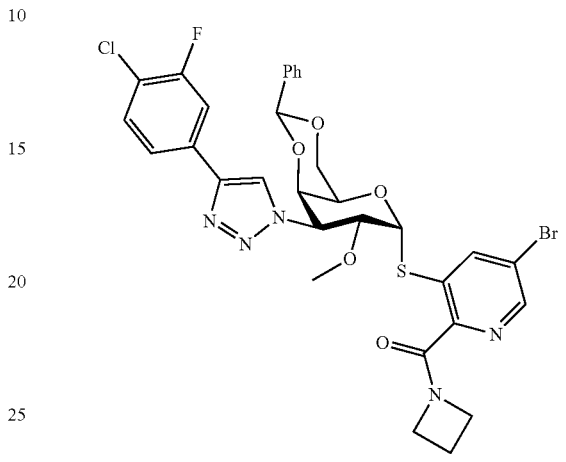

5-Bromo-2-cyanopyridin-3-yl 2,4,6-tri-O-acetyl-3-azido-3-deoxy-1-thio-α-D-galactopyranoside

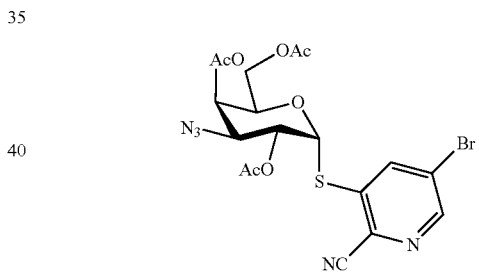

To a solution of acetyl 2,4,6-tri-O-acetyl-3-azido-3-deoxy-1-thio-α-D-galactopyranoside (4.00 g, 10.3 mmol) in DMF (30 mL) 5-bromo-3-fluoro-pyridine-2-carbonitrile (4.13 g, 20.5 mmol) and N-ethylethanamine (1.50 g, 20.5 mmol) were added at 0° C. The mixture was stirred under a nitrogen atmosphere at rt overnight. The mixture was poured into water (150 mL) and extracted with EtOAc (200 mL). The organic layer was washed with brine, dried over anhydrous $Na_2SO_4$, filtered and concentrated. The residue was purified by column chromatography (PE/EtOAc=10/1~1/1, Silica-CS 40 g, 50 mL/min, silica gel, UV 254) to afford the product (3.0 g, 55%). ESI-MS m/z calcd for $[C_{18}H_{18}BrN_5O_7S]$ $[M+H]^+$: 528.0; found: 528.1. $^1H$ NMR (400 MHz, $CDCl_3$) δ 8.66 (d, J=2.0 Hz, 1H), 8.18 (d, J=2.0 Hz, 1H), 6.11 (d, J=5.6 Hz, 1H), 5.52 (d, J=2.4 Hz, 1H), 5.31 (dd, J=11.2, 5.6 Hz, 1H), 4.60 (dd, J=7.2, 4.8 Hz, 1H), 4.17-4.11 (m, 1H), 4.04-3.98 (m, 2H), 2.24 (s, 3H), 2.18 (s, 3H), 2.02 (s, 3H).

5-Bromo-2-cyanopyridin-3-yl 3-azido-3-deoxy-1-thio-α-D-galactopyranoside

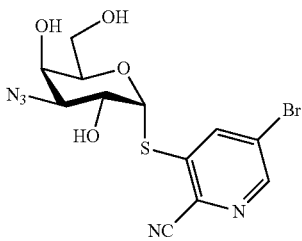

To a solution of 5-bromo-2-cyanopyridin-3-yl 2,4,6-tri-O-acetyl-3-azido-3-deoxy-1-thio-α-D-galactopyranoside (3.00 g, 5.68 mmol) in MeOH (50 mL) Et$_3$N (3.96 mL, 28.4 mmol) and water (2 mL) were added. The mixture was stirred 16 h at rt. The solvent was removed under reduced pressure and the obtained residue was washed by DCM (20 mL). The solid was collected and dried in vacuum to afford the product (1.80 g, 79%) as a white solid. ESI-MS m/z calcd for [C$_{12}$H$_{12}$BrN$_5$O$_4$S] [M+H]$^+$: 402.0; found: 402.1. $^1$H NMR (400 MHz, CD$_3$OD) δ 8.62 (d, J=2.0 Hz, 1H), 8.52 (d, J=2.0 Hz, 1H), 6.01 (d, J=5.2 Hz, 1H), 4.43 (dd, J=10.8, 5.2 Hz, 1H), 4.13 (t, J=6.0 Hz, 1H), 4.04 (d, J=2.4 Hz, 1H), 3.65-3.58 (m, 3H).

5-Bromo-2-cyanopyridin-3-yl 3-azido-4,6-O-benzylidene-3-deoxy-1-thio-α-D-galactopyranoside

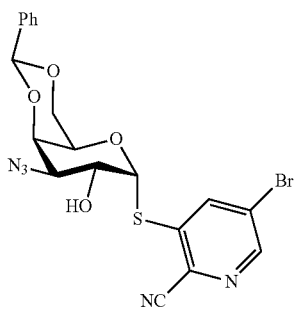

To a solution of 5-bromo-2-cyanopyridin-3-yl 3-azido-3-deoxy-1-thio-α-D-galactopyranoside (1.80 g, 4.48 mmol) in DMF (10 mL) benzaldehyde dimethyl acetal (2.04 g, 13.4 mmol) and D(+)-10-camphorsulfonic acid (312 mg, 1.34 mmol) were added. The mixture was stirred under a nitrogen atmosphere 2 h at 50° C. The mixture was cooled to rt and poured into water. The solid was collected and dried in vacuum to give the product (2.0 g, 91%). ESI-MS m/z calcd for [C$_{19}$H$_{16}$BrN$_5$O$_4$S] [M+H]$^+$: 490.0; found: 490.0. $^1$H NMR (400 MHz, CDCl$_3$) δ 8.61 (d, J=2.0 Hz, 1H), 8.24 (d, J=2.0 Hz, 1H), 7.52-7.47 (m, 2H), 7.39-7.34 (m, 3H), 5.93 (d, J=5.2 Hz, 1H), 5.64 (s, 1H), 4.67 (dd, J=10.8, 5.2 Hz, 1H), 4.43 (d, J=2.4 Hz, 1H), 4.23-3.89 (m, 3H), 3.67 (dd, J=10.8, 3.2 Hz, 1H).

5-Bromo-2-carboxypyridin-3-yl 3-azido-4,6-O-benzylidene-3-deoxy-1-thio-α-D-galactopyranoside

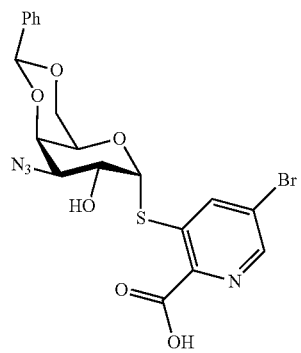

To a solution of 5-bromo-2-cyanopyridin-3-yl 3-azido-4,6-O-benzylidene-3-deoxy-1-thio-α-D-galactopyranoside (2.00 g, 4.08 mmol) in EtOH (80 mL) and water (40 mL) NaOH (2.45 mg, 61.2 mmol) was added. The mixture was kept stirring overnight at 80° C. Then EtOH was removed under reduced pressure. The mixture was acidified by 1M HCl to pH=6. The mixture was filtered, and the solid was dried in vacuum to give the product (1.20 g, 58%). ESI-MS m/z calcd for [C$_{19}$H$_{17}$BrN$_4$O$_6$S] [M+H]$^+$: 509.0; found: 509.0. $^1$H NMR (400 MHz, DMSO-d$_6$) δ 8.46 (s, 1H), 8.16 (s, 1H), 7.50-7.26 (m, 5H), 5.87 (d, J=5.2 Hz, 1H), 5.64 (s, 1H), 4.49-3.65 (m, 7H).

5-Bromo-2-(N-azetidinylcarbamoyl)-3-pyridyl 3-azido-4,6-O-benzylidene-3-deoxy-1-thio-α-D-galactopyranoside

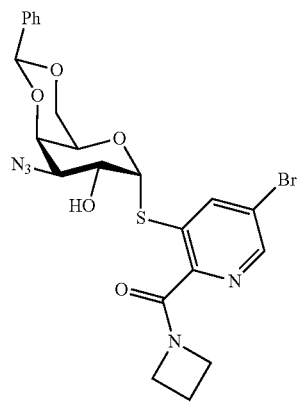

To a solution of 5-bromo-2-carboxypyridin-3-yl 3-azido-4,6-O-benzylidene-3-deoxy-1-thio-α-D-galactopyranoside (1.00 g, 1.96 mmol) in DMF (10 mL) azetidine hydrochloride (367 mg, 3.93 mmol), DIEA (1.68 mL, 9.82 mmol) and HATU (1344 mg, 3.53 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous Na$_2$SO$_4$ and concentrated. The residue was purified by column chromatography (PE/EtOAc=1/1~0/1, Silica-CS 20 g, 25 mL/min, silica gel, UV 254) to afford the product (620 mg, 58%). ESI-MS m/z calcd for [C$_{22}$H$_{22}$BrN$_5$O$_5$S] [M+H]$^+$: 548.1; found: 548.0. $^1$H NMR (400 MHz, DMSO-d$_6$) δ 8.52 (d, J=2.0 Hz, 1H), 8.35 (d, J=2.0 Hz, 1H), 7.45-7.34 (m, 5H), 6.07 (d, J=5.2 Hz, 1H), 5.67 (s, 1H), 4.50-3.64 (m, 11H), 2.26 (dt, J=15.2, 7.6 Hz, 2H).

5-Bromo-2-(N-azetidinylcarbamoyl)-3-pyridyl 3-azido-4,6-O-benzylidene-3-deoxy-2-O-methyl-1-thio-α-D-galactopyranoside

5-Bromo-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-methyl-1-thio-α-D-galactopyranoside

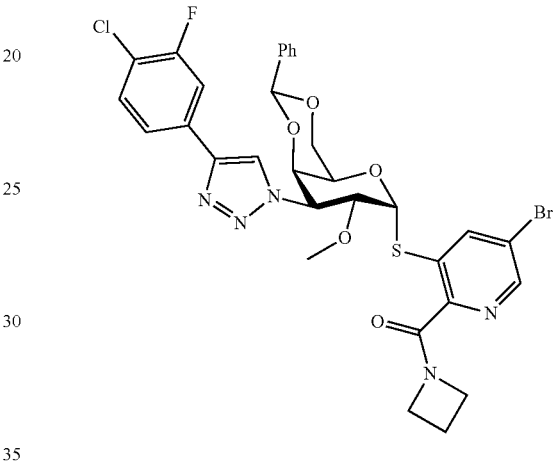

To a solution of 5-bromo-2-(N-azetidinylcarbamoyl)-3-pyridyl 3-azido-4,6-O-benzylidene-3-deoxy-1-thio-α-D-galactopyranoside (440 mg, 0.80 mmol) in DMF (5 mL) Cs$_2$CO$_3$ (523 mg, 1.60 mmol) and iodomethane (0.321 mL, 4.41 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous Na$_2$SO$_4$ and concentrated. The residue was purified by column chromatography (PE/EtOAc=10/1~1/1, Silica-CS 12 g, 20 mL/min, silica gel, UV 254) to afford the product (250 mg, 55%). ESI-MS m/z calcd for [C$_{23}$H$_{24}$BrN$_5$O$_5$S] [M+H]$^+$: 562.1; found: 562.2. $^1$H NMR (400 MHz, CDCl$_3$) δ 8.41 (d, J=2.0 Hz, 1H), 8.22 (d, J=2.0 Hz, 1H), 7.55-7.49 (m, 2H), 7.42-7.32 (m, 3H), 6.08 (d, J=5.2 Hz, 1H), 5.61 (s, 1H), 4.32-4.06 (m, 9H), 3.87 (dd, J=10.8, 3.2 Hz, 1H), 3.54 (s, J=4.0 Hz, 3H), 2.47-2.21 (m, 2H).

To a solution of 5-bromo-2-(N-azetidinylcarbamoyl)-3-pyridyl 3-azido-4,6-O-benzylidene-3-deoxy-2-O-methyl-1-thio-α-D-galactopyranoside (110 mg, 0.20 mmol) in DMF (4 mL) were added trimethyl-[2-(4-chloro-3-fluorophenyl)ethynyl]silane (66.5 mg, 0.29 mmol), copper(II) sulfate pentahydrate (47.6 mg, 0.19 mmol) and (+)-sodium L-ascorbate (37.8 mg, 0.19 mmol). The mixture was stirred under a nitrogen atmosphere at rt overnight. The mixture was poured into water (100 mL) and extracted with EtOAc (100 mL). The organic layer was washed with water (50 mL), brine (50 mL), dried over anhydrous Na$_2$SO$_4$ and concentrated. The residue was purified by column chromatography (PE/EtOAc=10/1~1/1, Silica-CS 4 g, 10 mL/min, silica gel, UV 254) to afford the product (60 mg, 43%). ESI-MS m/z calcd for [C$_{31}$H$_{28}$BrClFN$_5$O$_5$S] [M+H]$^+$: 716.1; found: 716.2. $^1$H NMR (400 MHz, CDCl$_3$) δ 8.44 (d, J=2.0 Hz, 1H), 8.20 (d, J=2.0 Hz, 1H), 8.04 (s, 1H), 7.63 (dd, J=10.0, 1.6 Hz, 1H), 7.54 (dd, J=8.4, 1.6 Hz, 1H), 7.48-7.39 (m, 1H), 7.39-7.30 (m, 5H), 6.27 (d, J=5.2 Hz, 1H), 5.49 (s, 1H), 5.40 (dd, J=11.2, 3.2 Hz, 1H), 4.61 (dd, J=11.2, 5.2 Hz, 1H), 4.51 (d, J=2.8 Hz, 1H), 4.42-4.06 (m, 7H), 3.33 (s, 3H), 2.32 (p, J=7.6 Hz, 2H).

Intermediate 62

5-Bromo-2-(N-azetidinylcarbamoyl)-3-pyridyl 4,6-O-benzylidene-3-deoxy-3-[4-(3,4,5-trifluorophenyl)-1H-1,2,3-triazol-1-yl]-2-O-methyl-1-thio-α-D-galactopyranoside

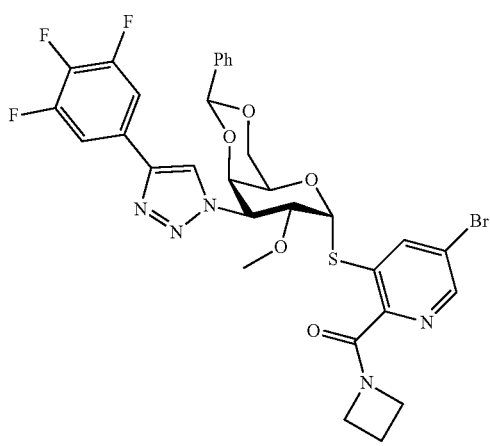

To a solution of 5-bromo-2-(N-azetidinylcarbamoyl)-3-pyridyl 3-azido-4,6-O-benzylidene-3-deoxy-2-O-methyl-1-thio-α-D-galactopyranoside (110 mg, 0.20 mmol) in DMF (4 mL) were added trimethyl-[2-(3,4,5-trifluorophenyl)ethynyl]silane (66.5 mg, 0.29 mmol), copper(II) sulfate pentahydrate (47.6 mg, 0.19 mmol) and (+)-sodium L-ascorbate (37.8 mg, 0.19 mmol). The mixture was stirred under a nitrogen atmosphere at rt overnight. The mixture was poured into water (100 mL) and extracted with EtOAc (100 mL). The organic layer was washed with water (50 mL), brine (50 mL), dried over anhydrous $Na_2SO_4$ and concentrated. The residue was purified by column chromatography (PE/EtOAc=10/1~1/1, Silica-CS 4 g, 10 mL/min, silica gel, UV 254) to afford the product (95 mg, 68%). ESI-MS m/z calcd for $[C_{31}H_{27}BrF_3N_5O_5S][M+H]^+$: 718.1; found: 718.0. $^1H$ NMR (400 MHz, $CDCl_3$) δ 8.46 (d, J=2.0 Hz, 1H), 8.20 (d, J=2.0 Hz, 1H), 8.00-7.92 (m, 1H), 7.48-7.40 (m, 2H), 7.38-7.33 (m, 5H), 6.27 (d, J=5.2 Hz, 1H), 5.50 (s, 1H), 5.40 (dd, J=11.2, 3.2 Hz, 1H), 4.59 (dd, J=5.2 Hz, 1H), 4.51 (d, J=3.2 Hz, 1H), 4.42-4.19 (m, 6H), 4.16-4.09 (m, 1H), 3.34 (s, 3H), 2.34 (p, J=7.6 Hz, 2H).

Intermediate 63

5-Bromo-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-ethyl-1-thio-α-D-galactopyranoside

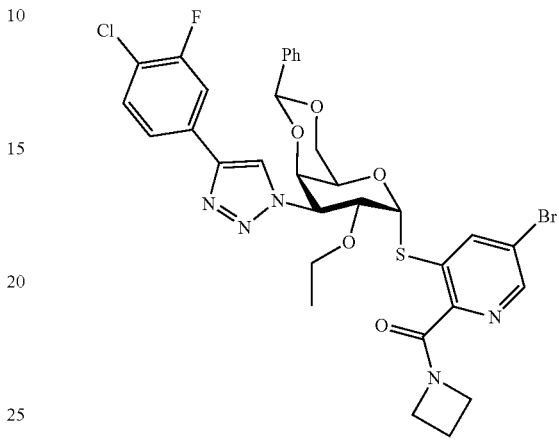

5-Bromo-2-(N-azetidinylcarbamoyl)-3-pyridyl 3-azido-4,6-O-benzylidene-3-deoxy-2-O-ethyl-1-thio-α-D-galactopyranoside

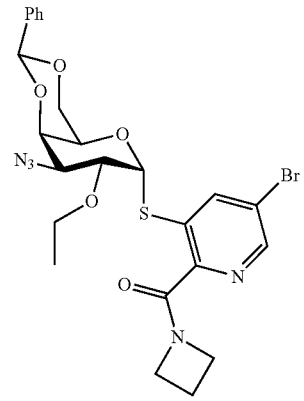

To a solution of 5-bromo-2-(N-azetidinylcarbamoyl)-3-pyridyl 3-azido-4,6-O-benzylidene-3-deoxy-1-thio-α-D-galactopyranoside (200 mg, 0.37 mmol) in DMF (5 mL) $Cs_2CO_3$ (238 mg, 0.73 mmol) and iodoethane (0.146 mL, 1.82 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous $Na_2SO_4$ and concentrated. The residue was purified by column chromatography (PE/EtOAc=10/1~1/1, Silica-CS 4 g, 10 mL/min, silica gel, UV 254) to afford the product (120 mg, 57%). ESI-MS m/z calcd for $[C_{24}H_{26}BrN_5O_5S]$ $[M+H]^+$: 576.1; found: 576.1. $^1H$ NMR (400 MHz, $CDCl_3$) δ 8.39 (d, J=2.0 Hz, 1H), 8.18 (d, J=2.0 Hz, 1H), 7.53-7.47 (m, 2H), 7.38-7.31 (m, 3H), 6.06 (d, J=5.2 Hz, 1H), 5.58 (s, 1H), 4.44-4.31 (m, 2H), 4.31-4.02

(m, 7H), 3.89 (dd, J=10.8, 3.2 Hz, 1H), 3.84-3.68 (m, 1H), 3.68-3.52 (m, 1H), 2.40-2.24 (m, 2H), 1.25 (t, J=6.8 Hz, 3H).

5-Bromo-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-methyl-1-thio-α-D-galactopyranoside

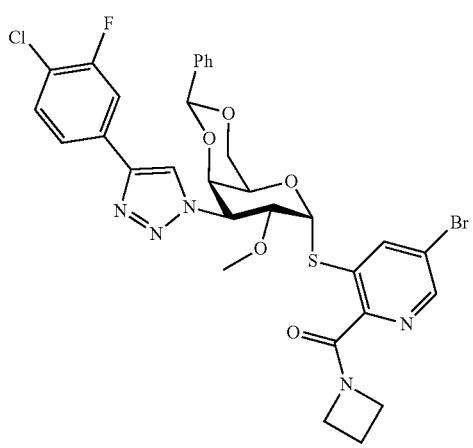

To a solution of 5-bromo-2-(N-azetidinylcarbamoyl)-3-pyridyl 3-azido-4,6-O-benzylidene-3-deoxy-2-O-ethyl-1-thio-α-D-galactopyranoside (110 mg, 0.19 mmol) in DMF (4 mL) trimethyl-[2-(4-chloro-3-fluorophenyl)ethynyl]silane (64.9 mg, 0.29 mmol), copper(II) sulfate pentahydrate (47.6 mg, 0.19 mmol) and (+)-sodium L-ascorbate (37.8 mg, 0.19 mmol) were added. The mixture was stirred under a nitrogen atmosphere at rt overnight. The mixture was poured into water (100 mL) and extracted with EtOAc (100 mL). The organic layer was washed with water (50 mL), brine (50 mL), dried over anhydrous $Na_2SO_4$ and concentrated. The residue was purified by column chromatography (PE/EtOAc=10/1~1/1, Silica-CS 4 g, 10 mL/min, silica gel, UV 254) to afford the product (90 mg, 65%). ESI-MS m/z calcd for $[C_{32}H_{30}BrClFN_5O_5S]$ $[M+H]^+$: 730.1; found: 730.0. $^1H$ NMR (400 MHz, $CDCl_3$) δ 8.48 (d, J=2.0 Hz, 1H), 8.19 (d, J=2.0 Hz, 1H), 7.99-7.95 (m, 1H), 7.63 (dd, J=10.0, 1.6 Hz, 1H), 7.54 (dd, J=8.4, 1.2 Hz, 1H), 7.46-7.33 (m, 6H), 6.23 (d, J=5.2 Hz, 1H), 5.52 (s, 1H), 5.41 (d, J=11.2 Hz, 1H), 4.65 (dd, J=11.2, 5.2 Hz, 1H), 4.58-4.05 (m, 8H), 3.78-3.64 (m, 1H), 3.38-3.23 (m, 1H), 2.50-2.21 (m, 2H), 1.01 (t, J=6.8 Hz, 3H).

Intermediate 64

2-(N-azetidinyl-carbonyl)-5-bromophenyl 4,6-O-benzylidene-3-deoxy-3-[4-(3,4,5-trifluorophenyl)-1H-1,2,3-triazol-1-yl]-2-O-methyl-1-thio-α-D-galactopyranoside

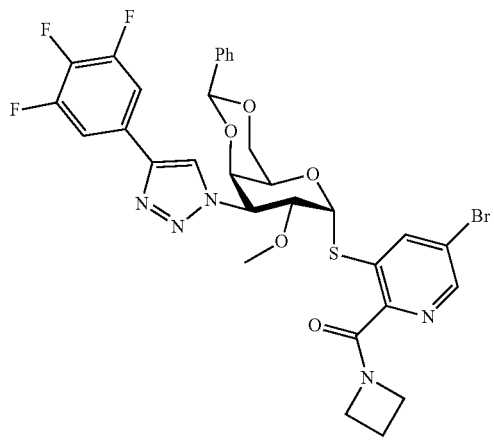

5-Bromo-2-cyanophenyl 2,4,6-tri-O-acetyl-3-azido-3-deoxy-1-thio-α-D-galactopyranoside

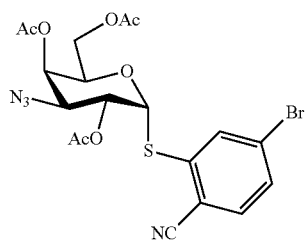

To a solution of acetyl 2,4,6-tri-O-acetyl-3-azido-3-deoxy-β-D-galactopyranosyl chloride (3.70 g, 10.6 mmol) 4-bromo-2-sulfanylbenzonitrile (4.13 g, 20.5 mmol) in DMF (25 mL) $Cs_2CO_3$ (6.89 g, 21.2 mmol) was added. The mixture was stirred at rt overnight. Water (100 mL) was added and the mixture was extracted with EtOAc (150 mL). The organic phase was washed with brine, dried and concentrated. The residue was purified by column chromatography (PE/EtOAc=10/1~3/1, Silica-CS 40 g, 20 m/min, silica gel, UV 254) to give the product (2.50 g, 45%). ESI-MS m/z calcd for $[C_{19}H_{19}BrN_4O_7S]$ $[M+H_2O]^+$:544.0; found: 544.0. $^1H$ NMR (400 MHz, $CDCl_3$) δ 7.82 (d, J=1.2 Hz, 1H), 7.59-7.46 (m, 2H), 6.06 (d, J=5.6 Hz, 1H), 5.49 (d, J=2.4 Hz, 1H), 5.29 (dd, J=11.2, 5.6 Hz, 1H), 4.75-4.48 (m, 1H), 4.12 (dd, J=11.6, 5.2 Hz, 1H), 4.00-4.05 (m, 1H), 3.97 (dd, J=10.8, 3.2 Hz, 1H), 2.21 (s, 3H), 2.16 (s, 3H), 2.01 (s, 3H).

5-Bromo-2-cyanophenyl 3-azido-3-deoxy-1-thio-α-D-galactopyranoside

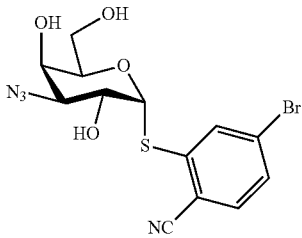

5-Bromo-2-cyanophenyl 2,4,6-tri-O-acetyl-3-azido-3-deoxy-1-thio-α-D-galactopyranoside (1.30 g, 2.47 mmol) was dissolved in a mixed solution of MeOH/Et$_3$N/H$_2$O (18 mL, v/v/v=5/3/1). The mixture was stirred overnight at rt. The solvent was removed under reduced pressure and the obtained solid was washed with DCM to afford the product (850 mg, 86%). ESI-MS m/z calcd for [C$_{13}$H$_{13}$BrN$_4$O$_4$S] [M+H$_2$O]$^+$: 418.0; found: 418.0. $^1$H NMR (400 MHz, DMSO-d$_6$) δ 8.01 (d, J=2.0 Hz, 1H), 7.74 (d, J=8.4 Hz, 1H), 7.60 (dd, J=8.4, 2.0 Hz, 1H), 6.10 (d, J=5.2 Hz, 1H), 6.00 (d, J=5.2 Hz, 1H), 5.32 (d, J=6.0 Hz, 1H), 4.62 (t, J=5.6 Hz, 1H), 4.27 (dt, J=10.4, 5.2 Hz, 1H), 3.97-3.85 (m, 2H), 3.54-3.44 (m, 2H), 3.36-3.25 (m, 1H).

5-Bromo-2-cyanophenyl 3-azido-4,6-O-benzylidene-3-deoxy-1-thio-α-D-galactopyranoside

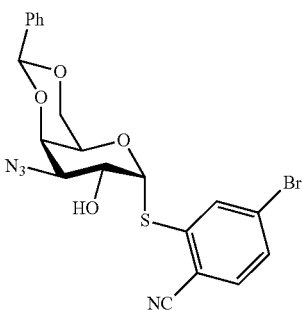

To a solution of 5-bromo-2-cyanophenyl 3-azido-3-deoxy-1-thio-α-D-galactopyranoside (850 mg, 2.12 mmol) in DMF (10 mL) benzaldehyde dimethyl acetal (967 mg, 6.36 mmol) was added followed by D(+)-10-camphorsulfonic acid (98.4 mg, 0.42 mmol). The mixture was stirred 3 h at 50° C. under reduced pressure. The mixture was neutralized with Et$_3$N and concentrated. The residue was purified by column chromatography (PE/EtOAc=5/1~3/1, Silica-CS 20 g, 20 mL/min, silica gel, UV 254) to give the product (900 mg, 87%). ESI-MS m/z calcd for [C$_{20}$H$_{17}$BrN$_4$O$_4$S] [M+H]$^+$: 489.0; found: 489.0. $^1$H NMR (400 MHz, CDCl$_3$) δ 7.92 (d, J=1.2 Hz, 1H), 7.54-7.47 (m, 4H), 7.39-7.32 (m, 3H), 5.89 (d, J=5.2 Hz, 1H), 5.63 (s, 1H), 4.64 (dd, J=10.8, 5.2 Hz, 1H), 4.42 (d, J=2.8 Hz, 1H), 4.25-4.28 (m, 2H), 4.15 (dd, J=12.4, 1.2 Hz, 1H), 3.62 (dd, J=10.8, 3.2 Hz, 1H).

5-Bromo-2-cyanophenyl 3-azido-4,6-O-benzylidene-3-deoxy-2-O-methyl-1-thio-α-D-galactopyranoside

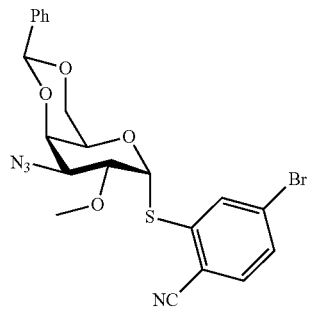

To a solution of 5-bromo-2-cyanophenyl 3-azido-4,6-O-benzylidene-3-deoxy-1-thio-α-D-galactopyranoside (450 mg, 0.92 mmol) in DMF (10 mL) Cs$_2$CO$_3$ (599 mg, 1.84 mmol) was added followed by iodomethane (653 mg, 4.60 mmol). The mixture was stirred overnight at rt and then partitioned between water and EtOAc. The organic phase was washed with brine, concentrated and purified by column chromatography (PE/EtOAc=10/1~5/1, Silica-CS 20 g, 20 mL/min, silica gel, UV 254) to give the product (226 mg, 49%). ESI-MS m/z calcd for [C$_{21}$H$_{19}$BrN$_4$O$_4$S] [M+H]$^+$: 503.0; found: 503.0. $^1$H NMR (400 MHz, CDCl$_3$) δ 7.88 (s, 1H), 7.57-7.46 (m, 4H), 7.43-7.33 (m, 3H), 6.10 (d, J=5.2 Hz, 1H), 5.61 (s, 1H), 4.33 (d, J=3.2 Hz, 1H), 4.26 (dd, J=10.4, 5.2 Hz, 1H), 4.22-4.16 (m, 2H), 4.10-4.13 (m, 1H), 3.76 (dd, J=10.8, 3.2 Hz, 1H), 3.60 (s, 3H).

2-(N-azetidinyl-carbonyl)-5-bromophenyl 3-azido-4,6-O-benzylidene-3-deoxy-2-O-methyl-1-thio-α-D-galactopyranoside

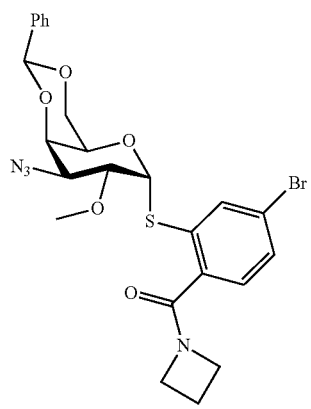

To a solution of 5-bromo-2-cyanophenyl 3-azido-4,6-O-benzylidene-3-deoxy-2-O-methyl-1-thio-α-D-galactopyranoside (226 mg, 0.45 mmol) in ethanol (18 mL) and H$_2$O (6 mL) NaOH (269 mg, 6.73 mmol) was added. The mixture was stirred overnight at 80° C. Ethanol was removed under reduced pressure, the pH of the solution was adjusted to 5-6 with 1M HCl and then extracted with EtOAc (2×30 mL). The combined organic layers were dried over Na$_2$SO$_4$ and concentrated. The obtained material was dissolved in together with azetidine hydrochloride (108 mg, 1.15 mmol)

in DMF (5 mL). To the solution HATU (335 mg, 0.88 mmol) was added followed by DIEA (0.377 mL, 2.20 mmol). The reaction was stirred 2 h at rt and then partitioned between water and EtOAc. The organic layer was dried over anhydrous $Na_2SO_4$ and concentrated. The residue was purified by column chromatography (PE/EtOAc=5/1~1/2, Silica-CS 20 g, 30 m/min, silica gel, UV 254) to give the product (130 mg, 52%). ESI-MS m/z calcd for $[C_{24}H_{25}BrN_4O_5S]$ $[M+H]^+$: 561.1; found: 561.2. $^1$H NMR (400 MHz, $CDCl_3$) δ 7.75 (d, J=1.6 Hz, 1H), 7.49-7.51 (m, 2H), 7.41 (dd, J=8.0, 2.0 Hz, 1H), 7.39-7.31 (m, 3H), 7.15 (d, J=8.0 Hz, 1H), 6.13 (d, J=5.2 Hz, 1H), 5.58 (s, 1H), 4.30 (d, J=3.2 Hz, 1H), 4.26-4.13 (m, 5H), 4.08 (dd, J=12.8, 2.0 Hz, 1H), 3.92 (td, J=8.0, 2.8 Hz, 2H), 3.77 (dd, J=10.4, 3.2 Hz, 1H), 3.56 (s, 3H), 2.37-2.27 (m, 2H).

2-(N-azetidinyl-carbonyl)-5-bromophenyl 4,6-O-benzylidene-3-deoxy-3-[4-(3,4,5-trifluorophenyl)-1H-1,2,3-triazol-1-yl]-2-O-methyl-1-thio-α-D-galactopyranoside

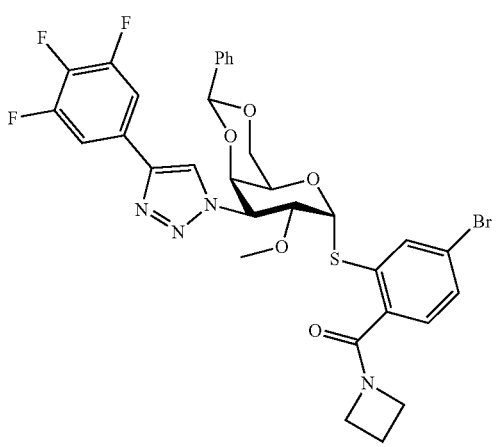

To a solution of 2-(N-azetidinyl-carbonyl)-5-bromophenyl 3-azido-4,6-O-benzylidene-3-deoxy-2-O-methyl-1-thio-α-D-galactopyranoside (130 mg, 0.23 mmol) and trimethyl-[2-(3,4,5-trifluorophenyl)ethynyl]silane (63.4 mg, 0.28 mmol) in DMF (4 mL) (+)-sodium L-ascorbate (68.8 mg, 0.35 mmol) and copper(II) sulfate pentahydrate (28.9 mg, 0.12 mmol) were added. The mixture was stirred 4 h at rt under a nitrogen atmosphere. After diluting with water (20 mL), the mixture was extracted with EtOAc (3×10 mL). The combined organic layers were washed with brine, dried over anhydrous $Na_2SO_4$ and concentrated. The residue was purified by column chromatography (PE/EtOAc=2/1~1/2, Silica-CS 20 g, 30 mL/min, silica gel, UV 254) to give the product (120 mg, 72%). ESI-MS m/z calcd for $[C_{32}H_{28}BrF_3N_4O_5S]$ $[M+H]^+$: 717.1; found: 716.7. $^1$H NMR (400 MHz, DMSO-$d_6$) δ 8.94 (s, 1H), 7.97 (d, J=2.0 Hz, 1H), 7.77 (dd, J=8.8, 6.8 Hz, 2H), 7.57 (dd, J=8.4, 2.0 Hz, 1H), 7.41-7.29 (m, 6H), 6.59 (d, J=5.2 Hz, 1H), 5.59 (s, 1H), 5.14 (dd, J=11.2, 3.2 Hz, 1H), 4.64 (dd, J=11.2, 5.2 Hz, 1H), 4.59 (d, J=3.2 Hz, 1H), 4.36 (s, 1H), 4.20-4.13 (m, 1H), 4.06 (t, J=7.7 Hz, 2H), 4.00-3.85 (m, 3H), 3.37 (s, 3H), 2.32-2.17 (m, 2H).

Intermediate 65

2-(N-azetidinyl-carbonyl)-5-bromophenyl 4,6-O-benzylidene-3-deoxy-3-[4-(3,4,5-trifluorophenyl)-1H-1,2,3-triazol-1-yl]-2-O-ethyl-1-thio-α-D-galactopyranoside

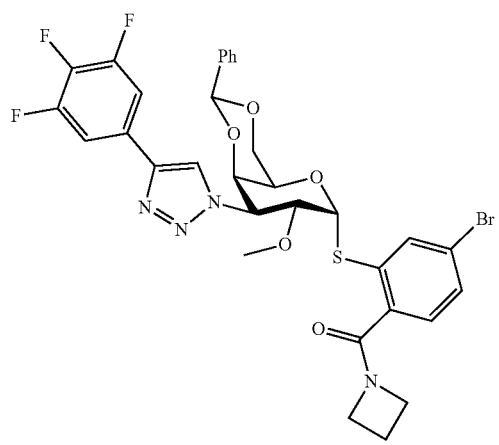

5-Bromo-2-carboxyphenyl 3-azido-4,6-O-benzylidene-3-deoxy-1-thio-α-D-galactopyranoside

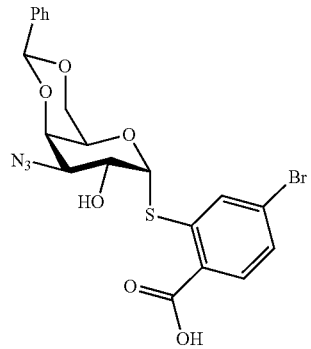

To a solution of 5-bromo-2-cyanophenyl 3-azido-4,6-O-benzylidene-3-deoxy-1-thio-α-D-galactopyranoside (400 mg, 0.82 mmol) in ethanol (18 mL) and $H_2O$ (6 mL) NaOH (490 mg, 12.3 mmol) was added. The mixture was stirred overnight at 80° C. Ethanol was removed under reduced pressure, the pH of the solution was adjusted to 5-6 with 1M HCl and then extracted with EtOAc (2×30 mL). The combined organic layers were dried over $Na_2SO_4$ and concentrated. The residue was purified by reversed-phase chromatography (MeCN/$H_2O$=1/20~3/1, C-18 column, 20 mL/min, UV 254) to give the product (300 mg, 60%). ESI-MS m/z calcd for $[C_{20}H_{18}BrN_3O_6S]$ $[M-H]^-$: 506.0; found: 506.0. $^1$H NMR (400 MHz, DMSO-$d_6$) δ 7.72 (d, J=1.2 Hz, 1H), 7.56 (d, J=8.0 Hz, 1H), 7.50-7.35 (m, 5H), 7.31 (dd, J=8.0, 1.2 Hz, 1H), 5.77 (d, J=5.2 Hz, 1H), 5.64 (s, 1H), 4.38 (d, J=2.4 Hz, 1H), 4.31 (dd, J=11.2, 5.2 Hz, 1H), 4.13-3.86 (m, 4H), 3.71 (dd, J=11.2, 3.2 Hz, 1H).

2-(N-azetidinyl-carbonyl)-5-bromophenyl 3-azido-4,6-O-benzylidene-3-deoxy-1-thio-α-D-galactopyranoside

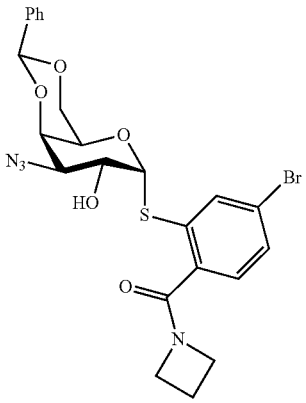

To a solution of 5-bromo-2-carboxyphenyl 3-azido-4,6-O-benzylidene-3-deoxy-1-thio-α-D-galactopyranoside (300 mg, 0.59 mmol) and azetidine hydrochloride (144 mg, 1.54 mmol) in DMF (5 mL) HATU (449 mg, 1.18 mmol) was added followed by DIEA (0.505 mL, 2.95 mmol). The mixture was stirred overnight at rt and then partitioned between water and EtOAc. The organic layer was dried, concentrated and the residue was purified by column chromatography (PE/EtOAc=5/1~1/2, Silica-CS 20 g, 30 m/min, silica gel, UV 254) to give the product (240 mg, 74%). ESI-MS m/z calcd for [$C_{23}H_{23}BrN_4O_5S$] [M+H]$^+$: 547.1; found: 546.7. $^1$H NMR (400 MHz, CDCl$_3$) δ 7.84 (d, J=2.0 Hz, 1H), 7.55-7.48 (m, 2H), 7.46 (dd, J=8.0, 2.0 Hz, 1H), 7.40-7.32 (m, 3H), 7.15 (d, J=8.0 Hz, 1H), 5.85 (d, J=5.2 Hz, 1H), 5.61 (s, 1H), 4.61 (dd, J=10.8, 5.2 Hz, 1H), 4.35-4.10 (m, 6H), 4.03-3.90 (m, 2H), 3.58 (dd, J=10.8, 3.2 Hz, 1H), 2.39-2.27 (m, 2H).

2-(N-azetidinyl-carbonyl)-5-bromophenyl 3-azido-4,6-O-benzylidene-3-deoxy-2-O-ethyl-1-thio-α-D-galactopyranoside

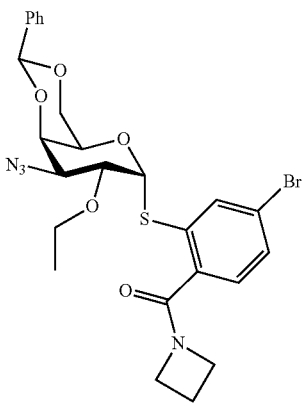

To a solution of 2-(N-azetidinyl-carbonyl)-5-bromophenyl 3-azido-4,6-O-benzylidene-3-deoxy-1-thio-α-D-galactopyranoside (240 mg, 0.44 mmol) in DMF (5 mL) Cs$_2$CO$_3$ (429 mg, 1.32 mmol) was added followed by iodoethane (342 mg, 2.19 mmol). The mixture was stirred overnight at rt, diluted with EtOAc (30 mL) and washed with water (3×30 mL). The organic layer was dried with anhydrous Na$_2$SO$_4$ and concentrated. The residue was purified by column chromatography (PE/EtOAc=5/1-1/2, Silica-CS 20 g, 20 m/min, silica gel, UV 254) to give the product (110 mg, 44%). ESI-MS m/z calcd for [$C_{25}H_{27}BrN_4O_5S$] [M+H]$^+$: 575.1; found: 574.8. $^1$H NMR (400 MHz, CDCl$_3$) δ 7.76 (d, J=1.6 Hz, 1H), 7.56-7.48 (m, 2H), 7.43 (dd, J=8.4, 2.0 Hz, 1H), 7.40-7.31 (m, 3H), 7.16 (d, J=8.4 Hz, 1H), 6.13 (d, J=5.2 Hz, 1H), 5.60 (s, 1H), 4.34 (dd, J=10.8, 5.2 Hz, 1H), 4.30 (d, J=3.2 Hz, 1H), 4.27-4.03 (m, 5H), 4.02-3.78 (m, 4H), 3.66-3.62 (m, 1H), 2.38-2.30 (m, 2H), 1.31 (t, J=6.8 Hz, 3H).

2-(N-azetidinyl-carbonyl)-5-bromophenyl 4,6-O-benzylidene-3-deoxy-3-[4-(3,4,5-trifluorophenyl)-1H-1,2,3-triazol-1-yl]-2-O-ethyl-1-thio-α-D-galactopyranoside

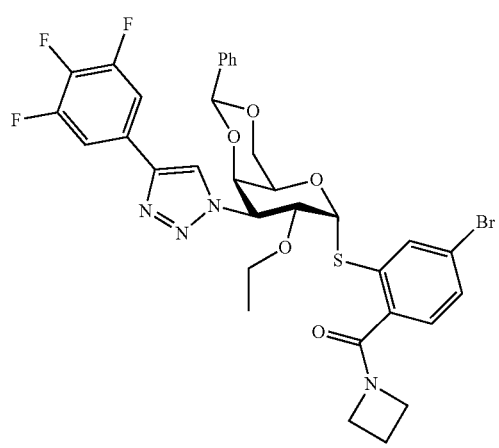

To a solution of 2-(N-azetidinyl-carbonyl)-5-bromophenyl 3-azido-4,6-O-benzylidene-3-deoxy-2-O-ethyl-1-thio-α-D-galactopyranoside (110 mg, 0.19 mmol) and trimethyl-[2-(3,4,5-trifluorophenyl)ethynyl]silane (52.4 mg, 0.23 mmol) in DMF (4 mL) (+)-sodium L-ascorbate (56.8 mg, 0.29 mmol) and copper(II) sulfate pentahydrate (23.9 mg, 0.096 mmol). The mixture was stirred 4 h at rt under a nitrogen atmosphere before diluting with water (20 mL) and extracting with EtOAc (3×10 mL). The combined organic layers were washed with brine, dried over anhydrous Na$_2$SO$_4$ and concentrated. The residue was purified by column chromatography (PE/EtOAc=2/1~1/2, Silica-CS 20 g, 30 m/min, silica gel, UV 254) to give the product (120 mg, 86%) as a white solid. ESI-MS m/z calcd for [$C_{33}H_{30}BrF_3N_4O_5S$] [M+H]$^+$: 731.1; found: 730.6. $^1$H NMR (400 MHz, DMSO-d$_6$) δ 8.93 (s, 1H), 7.95 (d, J=1.6 Hz, 2H), 7.79 (dd, J=8.8, 6.4 Hz, 2H), 7.57 (dd, J=8.4, 2.0 Hz, 1H), 7.45-7.26 (m, 5H), 6.55 (d, J=5.2 Hz, 1H), 5.58 (s, 1H), 5.13 (dd, J=11.6, 3.2 Hz, 1H), 4.71 (dd, J=11.6, 5.2 Hz, 1H), 4.59 (d, J=3.2 Hz, 1H), 4.40-4.32 (m, 1H), 4.20-4.13 (m, 1H), 4.05-4.09 (m, 2H), 3.99-3.70 (m, 4H), 3.49 (dq, J=14.0, 7.2 Hz, 1H), 2.26-2.22 (m, 2H), 0.95 (t, J=7.2 Hz, 3H).

241
Intermediate 66

5-Chloro-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-methyl-1-thio-α-D-galactopyranoside

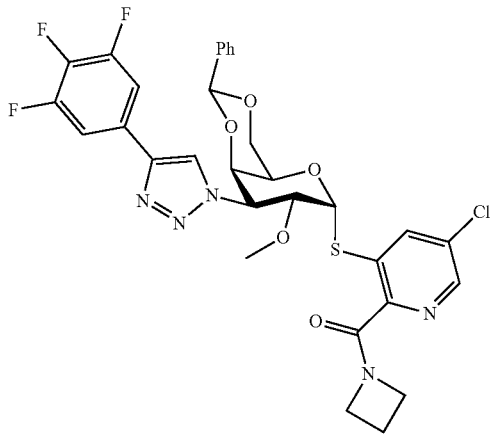

5-Chloro-2-cyanopyridin-3-yl 2,4,6-tri-O-acetyl-3-azido-3-deoxy-1-thio-α-D-galactopyranoside

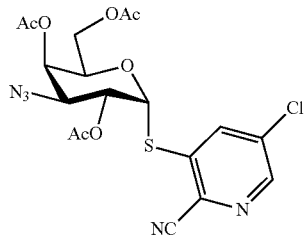

To a solution of acetyl 2,4,6-tri-O-acetyl-3-azido-3-deoxy-1-thio-α-D-galactopyranoside (4.50 g, 11.5 mmol) in DMF (30 mL) 5-chloro-3-fluoro-pyridine-2-carbonitrile (1.81 g, 11.5 mmol) and N-ethylethanamine (1.69 g, 23.0 mmol) were added at 0° C. The mixture was stirred under a nitrogen atmosphere at rt overnight. The mixture was poured into water (150 mL) and extracted with EtOAc (2×200 mL). The organic layers were washed with brine, dried over anhydrous $Na_2SO_4$, filtered and concentrated. The residue was purified by column chromatography (PE/EtOAc=10/1~1/1, Silica-CS 40 g, 50 mL/min, silica gel, UV 254) to afford the product (3.30 g, 59%). ESI-MS m/z calcd for $[C_{18}H_{18}ClN_5O_7S]$ $[M+H]^+$: 484.1; found: 484.0. $^1H$ NMR (400 MHz, $CD_3OD$) δ 8.64 (d, J=2.4 Hz, 1H), 8.28 (d, J=2.4 Hz, 1H), 6.17 (d, J=5.6 Hz, 1H), 5.54 (d, J=2.8 Hz, 1H), 5.29 (dd, J=11.2, 5.2 Hz, 1H), 4.68 (dd, J=7.6, 4.0 Hz, 1H), 4.27 (dd, J=10.8, 3.2 Hz, 1H), 4.15 (dd, J=7.6, 4.0 Hz, 1H), 3.98 (dd, J=11.6, 8.0 Hz, 1H), 2.18 (s, 3H), 2.14 (s, 3H), 2.14 (s, 3H).

242
5-Chloro-2-cyanopyridin-3-yl 3-azido-3-deoxy-1-thio-α-D-galactopyranoside

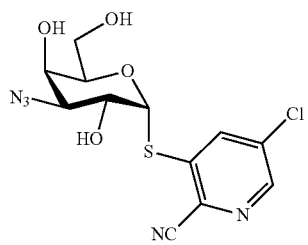

To a solution of 5-chloro-2-cyanopyridin-3-yl 2,4,6-tri-O-acetyl-3-azido-3-deoxy-1-thio-α-D-galactopyranoside (3.30 g, 6.83 mmol) in MeOH (30 mL) $Et_3N$ (12 mL, 86.2 mmol) and water (3 mL) were added. The mixture was stirred overnight at rt. The solvent was removed under reduced pressure and the obtained residue was washed by DCM (20 mL). The solid was collected to afford the product (2.20 g, 90%) as a white solid. ESI-MS m/z calcd for $[C_{12}H_{12}ClN_5O_4S]$ $[M+H]^+$: 358.0; found: 358.0. $^1H$ NMR (400 MHz, $CD_3OD$) δ 8.51 (d, J=2.0 Hz, 1H), 8.37 (d, J=2.4 Hz, 1H), 6.03 (d, J=5.2 Hz, 1H), 4.43 (dd, J=6.8, 1.6 Hz, 1H), 4.12 (t, J=6.0 Hz, 1H), 4.04 (d, J=2.4 Hz, 1H), 3.66-3.58 (m, 3H).

5-Chloro-2-cyanopyridin-3-yl 3-azido-4,6-O-benzylidene-3-deoxy-1-thio-α-D-galactopyranoside

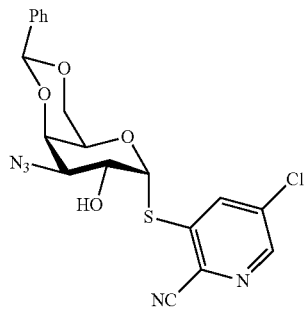

To a solution of 5-chloro-2-cyanopyridin-3-yl 3-azido-3-deoxy-1-thio-α-D-galactopyranoside (2.20 g, 6.15 mmol) in DMF (15 mL) benzaldehyde dimethyl acetal (2.81 g, 18.4 mmol) and D(+)-10-camphorsulfonic acid (429 mg, 1.84 mmol) were added. The mixture was stirred under a nitrogen atmosphere 2 h at 50° C. The mixture was cooled to rt and poured into water. The solid was collected and dried in vacuum to give the product (2.0 g, 70%). ESI-MS m/z calcd for $[C_{19}H_{16}ClN_5O_4S]$ $[M+H]^+$: 446.1; found: 446.0. $^1H$ NMR (400 MHz, $CDCl_3$) δ 8.51 (d, J=2.0 Hz, 1H), 8.08 (d, J=2.4 Hz, 1H), 7.51-7.35 (m, 5H), 5.92 (d, J=5.2 Hz, 1H), 5.64 (s, 1H), 4.66 (dd, J=10.8, 5.2 Hz, 1H), 4.44 (d, J=2.8 Hz, 1H), 4.25-4.13 (m, 3H), 3.67 (dd, J=10.8, 3.2 Hz, 1H).

5-Chloro-2-carboxypyridin-3-yl 3-azido-4,6-O-benzylidene-3-deoxy-1-thio-α-D-galactopyranoside

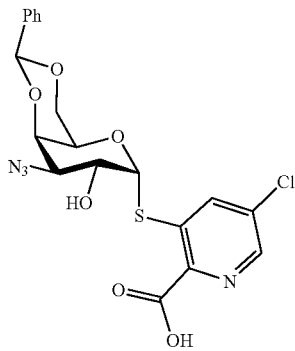

To a solution of 5-chloro-2-cyanopyridin-3-yl 3-azido-4,6-O-benzylidene-3-deoxy-1-thio-α-D-galactopyranoside (2.00 g, 4.33 mmol) in EtOH (50 mL) and water (20 mL) NaOH (2.6 mg, 64.9 mmol) was added. The mixture was kept stirring overnight at 80° C. Then EtOH was removed under reduced pressure. The mixture was acidified by 1M HCl to pH=6. The mixture was filtered, and the solid was dried in vacuum to give the product (1.80 g, 90%). ESI-MS m/z calcd for $[C_{19}H_{17}ClN_4O_6S]$ $[M+H]^+$: 465.1; found: 465.1. $^1$H NMR (400 MHz, CD$_3$OD) δ 8.34-8.28 (m, 2H), 7.49-7.34 (m, 5H), 5.94 (d, J=5.2 Hz, 1H), 5.63 (s, 1H), 4.57 (dd, J=12.0, 4.0 Hz, 1H), 4.41 (s, 1H), 4.14-4.00 (m, 3H), 3.73 (dd, J=8.4, 2.8 Hz, 1H).

5-Chloro-2-(N-azetidinylcarbamoyl)-3-pyridyl 3-azido-4,6-O-benzylidene-3-deoxy-1-thio-α-D-galactopyranoside

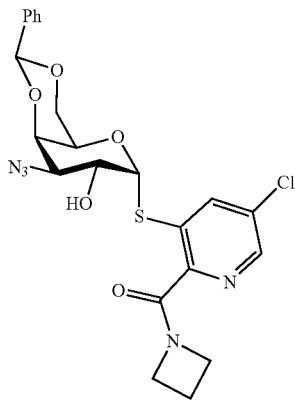

To a solution of 5-chloro-2-carboxypyridin-3-yl 3-azido-4,6-O-benzylidene-3-deoxy-1-thio-α-D-galactopyranoside (1.80 g, 3.87 mmol) in DMF (20 mL) azetidine hydrochloride (2.21 g, 5.81 mmol), Et$_3$N (2.70 mL, 19.4 mmol) and HATU (724 mg, 7.74 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous Na$_2$SO$_4$ and concentrated. The residue was purified by column chromatography (PE/EtOAc=1/1~0/1, Silica-CS 80 g, 50 mL/min, silica gel, UV 254) to afford the product (1.20 g, 55%). ESI-MS m/z calcd for $[C_{22}H_{22}ClN_5O_5S]$ $[M+H]^+$: 504.1; found: 504.1. $^1$H NMR (400 MHz, CDCl$_3$) δ 8.35 (d, J=2.4 Hz, 1H), 8.10 (d, J=2.0 Hz, 1H), 7.53-7.34 (m, 5H), 5.86 (d, J=5.2 Hz, 1H), 5.63 (s, 1H), 4.65 (dd, J=10.8, 5.6 Hz, 1H), 4.48-4.42 (m, 1H), 4.36-4.11 (m, 7H), 3.67 (dd, J=10.8, 3.2 Hz, 1H), 2.38-2.30 (m, 2H).

5-Chloro-2-(N-azetidinylcarbamoyl)-3-pyridyl 3-azido-4,6-O-benzylidene-3-deoxy-2-O-methyl-1-thio-α-D-galactopyranoside

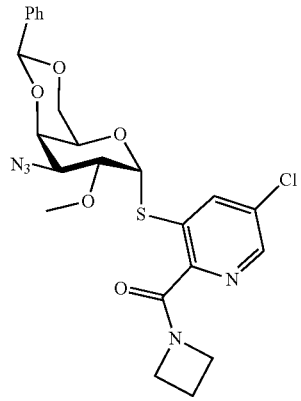

To a solution of 5-chloro-2-(N-azetidinylcarbamoyl)-3-pyridyl 3-azido-4,6-O-benzylidene-3-deoxy-1-thio-α-D-galactopyranoside (200 mg, 0.36 mmol) in DMF (8 mL) Cs$_2$CO$_3$ (348 mg, 1.07 mmol) and iodomethane (0.111 mL, 1.78 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous Na$_2$SO$_4$ and concentrated. The residue was purified by column chromatography (PE/EtOAc=10/1~1/1, Silica-CS 20 g, 25 mL/min, silica gel, UV 254) to afford the product (120 mg, 60%). ESI-MS m/z calcd for $[C_{23}H_{24}ClN_5O_5S]$ $[M+H]^+$: 518.1; found: 518.1. $^1$H NMR (400 MHz, CDCl$_3$) δ 8.31 (d, J=2.4 Hz, 1H), 8.09 (d, J=2.4 Hz, 1H), 7.54-7.26 (m, 5H), 6.09 (d, J=5.6 Hz, 1H), 5.61 (s, 1H), 4.52-4.41 (m, 1H), 4.31-4.08 (m, 8H), 3.88 (dd, J=10.8, 3.2 Hz, 1H), 3.54 (s, 3H), 2.38-2.30 (m, 2H).

5-Chloro-2-(N-azetidinylcarbamoyl)-3-pyridyl 4,6-O-benzylidene-3-deoxy-3-[4-(3,4,5-trifluorophenyl)-1H-1,2,3-triazol-1-yl]-2-O-methyl-1-thio-α-D-galactopyranoside

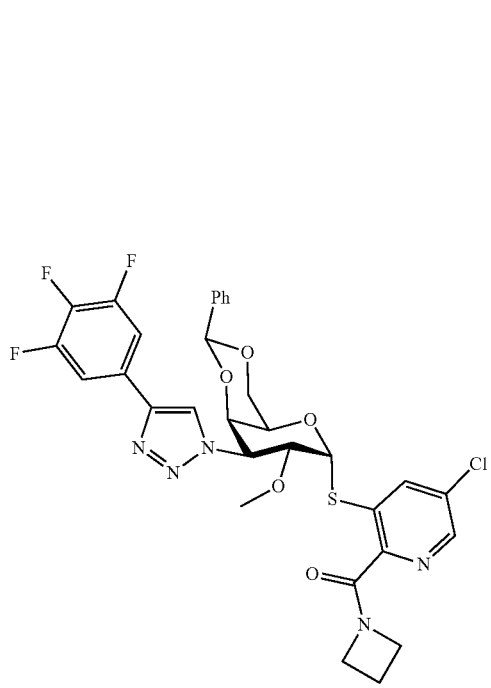

To a solution of 5-chloro-2-(N-azetidinylcarbamoyl)-3-pyridyl 3-azido-4,6-O-benzylidene-3-deoxy-2-O-methyl-1-thio-α-D-galactopyranoside (120 mg, 0.22 mmol) in DMF (8 mL) trimethyl-[2-(3,4,5-trifluorophenyl)ethynyl]silane (73.5 mg, 0.32 mmol), copper(II) sulfate pentahydrate (26.8 mg, 0.11 mmol) and (+)-sodium L-ascorbate (21.2 mg, 0.11 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous $Na_2SO_4$ and concentrated. The residue was purified by column chromatography (PE/EtOAc=10/1~1/1, Silica-CS 12 g, 20 m/min, silica gel, UV 254) to afford the product (100 mg, 63%). ESI-MS m/z calcd for $[C_{31}H_{27}ClF_3N_5O_5S]$ $[M+H]^+$: 674.1; found: 674.1. $^1H$ NMR (400 MHz, $CDCl_3$) δ 8.38 (s, 1H), 8.08 (d, J=2.0 Hz, 1H), 7.95 (s, 1H), 7.47-7.40 (m, 7H), 6.26 (d, J=5.2 Hz, 1H), 5.53 (s, 1H), 5.42 (d, J=10.8 Hz, 1H), 4.57 (dd, J=10.8, 4.8 Hz, 1H), 4.51-4.11 (m, 8H), 3.34 (s, 3H), 2.38-2.34 (m, 2H).

Intermediate 67

5-Chloro-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-ethyl-1-thio-α-D-galactopyranoside

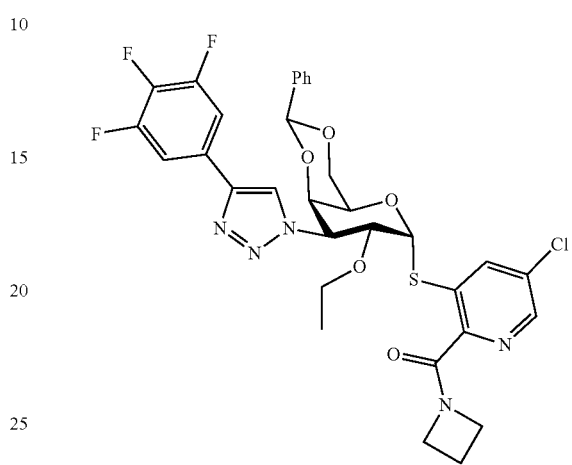

5-Chloro-2-(N-azetidinylcarbamoyl)-3-pyridyl 3-azido-4,6-O-benzylidene-3-deoxy-2-O-ethyl-1-thio-α-D-galactopyranoside

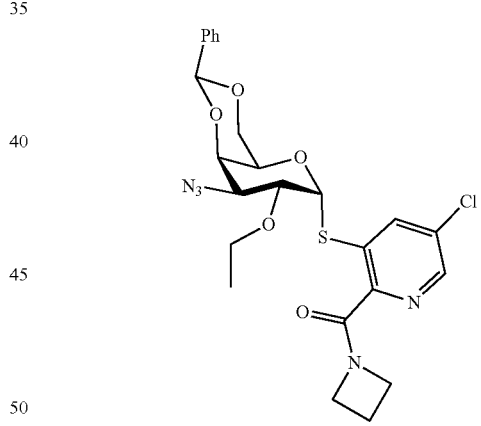

To a solution of 5-chloro-2-(N-azetidinylcarbamoyl)-3-pyridyl 3-azido-4,6-O-benzylidene-3-deoxy-1-thio-α-D-galactopyranoside (880 mg, 1.56 mmol) in DMF (16 mL) $Cs_2CO_3$ (1.02 g, 3.13 mmol) and iodoethane (732 mg, 4.69 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous $Na_2SO_4$ and concentrated. The residue was purified by column chromatography (PE/EtOAc=10/1~1/1, Silica-CS 40 g, 35 mL/min, silica gel, UV 254) to afford the product (620 mg, 71%). ESI-MS m/z calcd for $[C_{24}H_{26}ClN_5O_5S]$ $[M+H]^+$: 532.1; found: 531.8. $^1H$ NMR (400 MHz, $CDCl_3$) δ 8.30 (s, 1H), 8.05 (d, J=2.0 Hz, 1H), 7.53-7.25 (m, 5H), 6.07 (d, J=5.6 Hz, 1H), 5.59 (s, 1H), 4.46-4.06 (m, 9H), 3.91 (dd, J=10.8, 3.2 Hz, 1H), 3.84-3.77 (m, 1H), 3.64-3.57 (m, 1H), 2.38-2.30 (m, 2H), 1.28-1.24 (m, 3H).

5-Chloro-2-(N-azetidinylcarbamoyl)-3-pyridyl 4,6-O-benzylidene-3-deoxy-3-[4-(3,4,5-trifluorophenyl)-1H-1,2,3-triazol-1-yl]-2-O-methyl-1-thio-α-D-galactopyranoside

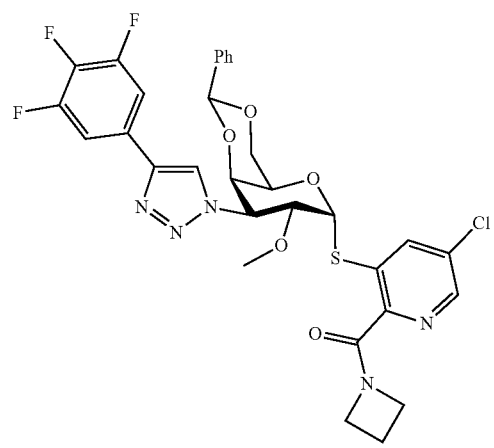

To a solution of 5-chloro-2-(N-azetidinylcarbamoyl)-3-pyridyl 3-azido-4,6-O-benzylidene-3-deoxy-2-O-ethyl-1-thio-α-D-galactopyranoside (200 mg, 0.36 mmol) in DMF (8 mL) trimethyl-[2-(3,4,5-trifluorophenyl)ethynyl]silane (122 mg, 0.54 mmol), copper(II) sulfate pentahydrate (44.6 mg, 0.18 mmol) and (+)-sodium L-ascorbate (35.4 mg, 0.18 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous Na$_2$SO$_4$ and concentrated. The residue was purified by column chromatography (PE/EtOAc=10/1~1/1, Silica-CS 12 g, 20 m/min, silica gel, UV 254) to afford the product (160 mg, 62%). ESI-MS m/z calcd for [C$_{32}$H$_{29}$ClF$_3$N$_5$O$_5$S][M+H]$^+$: 688.2; found: 687.7. $^1$H NMR (400 MHz, CDCl$_3$) δ 8.36 (d, J=2.0 Hz, 1H), 8.05 (d, J=2.0 Hz, 1H), 7.95 (s, 1H), 7.46-7.25 (m, 7H), 6.24 (d, J=5.2 Hz, 1H), 5.51 (s, 1H), 5.41 (dd, J=11.6, 3.6 Hz, 1H), 4.65 (dd, J=11.2, 5.2 Hz, 1H), 4.51 (d, J=3.2 Hz, 1H), 4.39-4.20 (m, 6H), 4.12 (dd, J=12.8, 2.4 Hz, 1H), 3.75-3.67 (m, 1H), 3.34-3.27 (m, 1H), 2.38-2.31 (m, 2H), 1.02-0.99 (m, 3H).

Intermediate 68

5-Chloro-2-(N-azetidinylcarbamoyl)-3-pyridyl 4,6-O-benzylidene-3-[4-(4-chloro-3-fluorophenyl)-1H-1,2,3-triazol-1-yl]-3-deoxy-2-O-methyl-1-thio-α-D-galactopyranoside

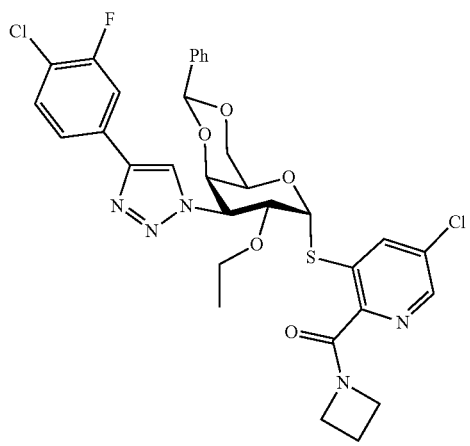

To a solution of 5-chloro-2-(N-azetidinylcarbamoyl)-3-pyridyl 3-azido-4,6-O-benzylidene-3-deoxy-2-O-ethyl-1-thio-α-D-galactopyranoside (200 mg, 0.36 mmol) in DMF (8 mL) trimethyl-[2-(4-chloro-3-fluorophenyl)ethynyl]silane (121 mg, 0.54 mmol), copper(II) sulfate pentahydrate (44.6 mg, 0.18 mmol) and (+)-sodium L-ascorbate (35.4 mg, 0.18 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous Na$_2$SO$_4$ and concentrated. The residue was purified by column chromatography (PE/EtOAc=10/1~1/1, Silica-CS 12 g, 20 m/min, silica gel, UV 254) to afford the product (145 mg, 57%). ESI-MS m/z calcd for [C$_{32}$H$_{30}$Cl$_2$FN$_5$O$_5$S] [M+H]$^+$: 686.1; found: 685.7. $^1$H NMR (400 MHz, CDCl$_3$) δ 8.37 (s, 1H), 8.05 (d, J=1.6 Hz, 1H), 7.97 (s, 1H), 7.62 (dd, J=10.0, 1.6 Hz, 1H), 7.53 (d, J=8.4 Hz, 1H), 7.46-7.36 (m, 6H), 6.23 (d, J=5.2 Hz, 1H), 5.52 (s, 1H), 5.41 (d, J=10.8 Hz, 1H), 4.66 (dd, J=11.2, 5.2 Hz, 1H), 4.52-4.11 (m, 8H), 3.72-3.68 (m, 1H), 3.33-3.16 (m, 1H), 2.39-2.32 (m, 2H), 1.03-0.99 (m, 3H).

Intermediate 69

5-Chloro-2-(N-azetidinylcarbamoyl)-3-pyridyl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

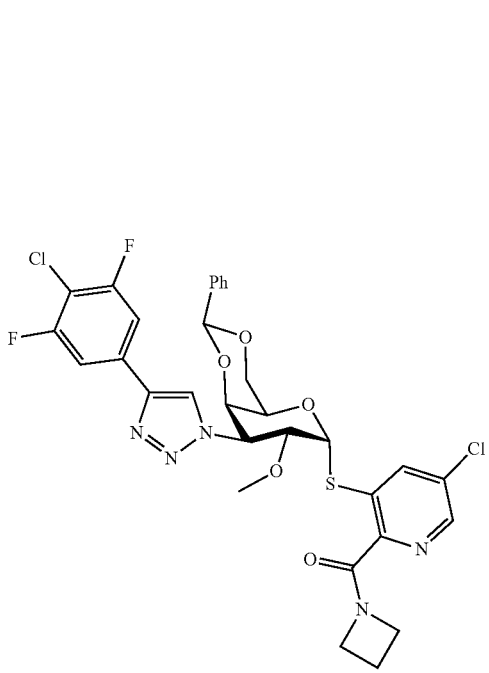

To a solution of 5-chloro-2-(N-azetidinylcarbamoyl)-3-pyridyl 3-azido-4,6-O-benzylidene-3-deoxy-2-O-ethyl-1-thio-α-D-galactopyranoside (200 mg, 0.36 mmol) in DMF (8 mL) trimethyl-[2-(4-chloro-3,5-difluorophenyl)ethynyl]silane (131 mg, 0.54 mmol), copper(II) sulfate pentahydrate (44.6 mg, 0.18 mmol) and (+)-sodium L-ascorbate (35.4 mg, 0.18 mmol) were added. The mixture was stirred under a nitrogen atmosphere at rt overnight. The mixture was poured into water (100 mL) and extracted with EtOAc (2×100 mL). The organic layers were washed with water (50 mL), brine (50 mL), dried over anhydrous $Na_2SO_4$ and concentrated. The residue was purified by column chromatography (PE/EtOAc=10/1~1/1, Silica-CS 12 g, 20 m/min, silica gel, UV 254) to afford the product (100 mg, 40%). ESI-MS m/z calcd for $[C_{32}H_{29}Cl_2F_2N_5O_5S]$ $[M+H]^+$: 704.1; found: 703.7. $^1H$ NMR (400 MHz, $CDCl_3$) δ 8.37 (d, J=2.0 Hz 1H), 8.05 (d, J=2.0 Hz, 1H), 7.98 (s, 1H), 7.47-7.44 (m, 2H), 7.41-7.25 (m, 5H), 6.23 (d, J=5.2 Hz, 1H), 5.52 (s, 1H), 5.42 (dd, J=11.2, 3.2 Hz, 1H), 4.65 (dd, J=11.6, 5.2 Hz, 1H), 4.51 (d, J=2.8 Hz, 1H), 4.59-4.20 (m, 6H), 4.12 (dd, J=12.8, 1.2 Hz, 1H), 3.74-3.67 (m, 1H), 3.34-3.26 (m, 1H), 2.39-2.31 (m, 2H), 1.02-0.99 (m, 3H).

Intermediate 70

2-(N-azetidinyl-carbonyl)-5-chlorophenyl 4,6-O-benzylidene-3-deoxy-3-[4-(3,4,5-trifluorophenyl)-1H-1,2,3-triazol-1-yl]-2-O-methyl-1-thio-α-D-galactopyranoside

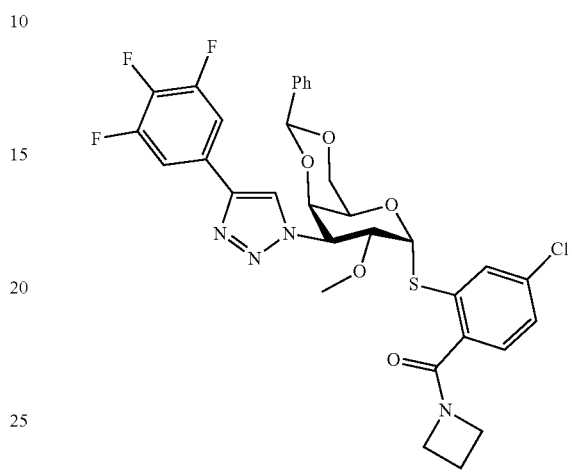

5-Chloro-2-cyanophenyl 4,6-O-benzylidene-3-deoxy-3-[4-(3,4,5-trifluorophenyl)-1H-1,2,3-triazol-1-yl]-2-O-methyl-1-thio-α-D-galactopyranoside

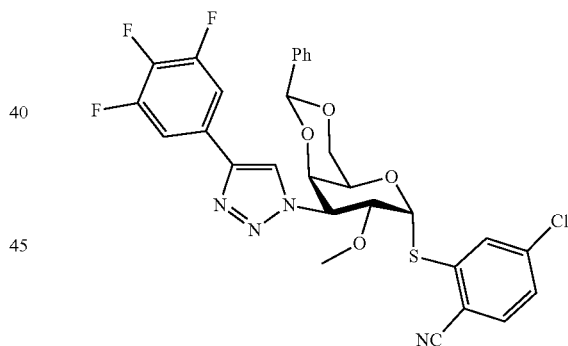

To a solution of 5-chloro-2-cyanophenyl 3-azido-4,6-O-benzylidene-3-deoxy-2-O-ethyl-1-thio-α-D-galactopyranoside (220 mg, 0.53 mmol) and trimethyl-[2-(3,4,5-trifluorophenyl)ethynyl]silane (179 mg, 0.78 mmol) in DMF (4 mL) copper(II) sulfate pentahydrate (65.4 mg, 0.26 mmol) and (+)-sodium L-ascorbate (51.8 mg, 0.26 mmol) were added. The mixture was stirred 6 h under a nitrogen atmosphere at rt. The mixture concentrated and purified by column chromatography (PE/EtOAc=10/1~1/1, Silica-CS 12 g, 20 mL/min, silica gel, UV 254) to afford the product (220 mg, 68%). ESI-MS m/z calcd for $[C_{29}H_{22}ClF_3N_4O_4S]$ $[M+H]^+$: 615.1; found: 615.0. $^1H$ NMR (400 MHz, $CDCl_3$) δ 7.94 (s, 1H), 7.75 (d, J=2.0 Hz, 1H), 7.65 (d, J=8.4 Hz, 1H) 7.46-7.36 (m, 8H), 6.22 (d, J=5.2 Hz, 1H), 5.52 (s, 1H), 5.32 (dd, J=11.6, 3.2 Hz, 1H), 4.56-4.52 (m, 2H), 4.45 (s, 1H), 4.27-4.09 (m, 2H), 3.40 (s, 3H).

2-(N-azetidinyl-carbonyl)-5-chlorophenyl 4,6-O-benzylidene-3-deoxy-3-[4-(3,4,5-trifluorophenyl)-1H-1,2,3-triazol-1-yl]-2-O-methyl-1-thio-α-D-galactopyranoside

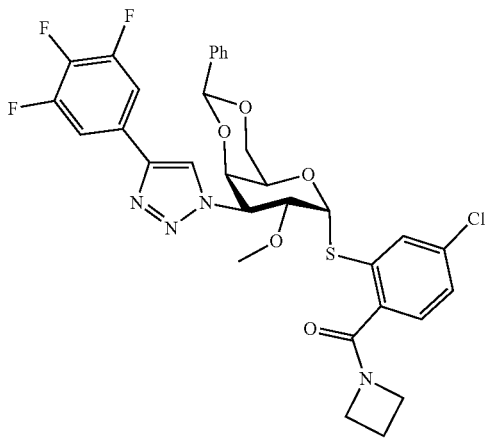

A solution of 5-chloro-2-cyanophenyl 4,6-O-benzylidene-3-deoxy-3-[4-(3,4,5-trifluorophenyl)-1H-1,2,3-triazol-1-yl]-2-O-methyl-1-thio-α-D-galactopyranoside (220 mg, 0.36 mmol) in ethanol (10 mL) and NaOH (3 M aq, 4 mL) was stirred 16 h at 80° C. After cooling to rt the mixture was concentrated to approximately 10 mL, and then acidified with HCl (3 M) to pH ~3. The solid precipitate was collected by filtration, washed with 33% aq MeOH and dried. To a solution of the obtained material, HATU (204 mg, 0.54 mmol) and Et$_3$N (109 mg, 1.07 mmol) in DMF (3 mL) azetidine hydrochloride (122 mg, 1.31 mmol) was added. The was stirred at rt overnight, and then concentrated. The residue was purified by column chromatography (PE/EtOAc=5/1~1/2, Silica-CS 12 g, 20 mL/min, silica gel, UV 254) to give the product (101 mg, 42%). ESI-MS m/z calcd for [C$_{32}$H$_{28}$ClF$_3$N$_4$O$_5$S] [M+H]$^+$: 673.1; found: 673.0. $^1$H NMR (400 MHz, CDCl$_3$) δ 7.95 (s, 1H), 7.60 (d, J=2.0 Hz, 1H), 7.44-7.29 (m, 9H), 6.26 (d, J=4.8 Hz, 1H), 5.50 (s, 1H), 5.35 (dd, J=11.6, 3.2 Hz, 1H), 4.50-4.46 (m, 2H), 4.42 (s, 1H), 4.26-4.10 (m, 4H), 3.94-3.90 (m, 2H), 3.36 (s, 3H), 3.38-3.30 (m, 2H).

Intermediate 71

3,4-Dichlorophenyl 4,6-O-benzylidene-3-[4-(4-chloro-3,5-difluorophenyl)-1H-1,2,3-triazol-1-yl]-3-deoxy-2-O-methyl-1-thio-α-D-galactopyranoside

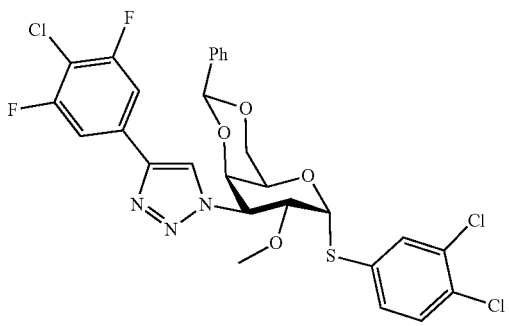

To a stirred solution of 3,4-dichlorophenyl 4,6-O-benzylidene-3-[4-(4-chloro-3,5-difluorophenyl)-1H-1,2,3-triazol-1-yl]-3-deoxy-1-thio-α-D-galactopyranoside (140 mg, 0.22 mmol) in DMF (2 mL) NaH (60% in oil, 24.0 mg, 0.63 mmol) was added at 0° C. under a nitrogen atmosphere. The mixture was stirred 10 min at 0° C., then iodomethane (0.0278 mL, 0.45 mmol) was added. The mixture was stirred 2 h at rt. After diluting with water (20 mL), the mixture was extracted with EtOAc (3×10 mL). The combined organic layers were washed with brine, dried over anhydrous Na$_2$SO$_4$ and concentrated. The residue was purified by column chromatography (PE/EtOAc=10/1~4/1, Silica-CS 12 g, 20 mL/min, silica gel, UV 254) to give the product (114 mg, 80%) as a white solid. ESI-MS m/z calcd for [C$_{28}$H$_{22}$Cl$_3$F$_2$N$_3$O$_4$S][M+Na]$^+$: 663.1; found: 663.2. $^1$H NMR (400 MHz, CDCl$_3$) δ 7.91 (s, 1H), 7.57 (d, J=2.0 Hz, 1H), 7.39-7.29 (m, 9H), 6.07 (d, J=5.2 Hz, 1H), 5.46 (s, 1H), 5.22 (dd, J=11.2, 3.2 Hz, 1H), 4.45-4.41 (m, 2H), 4.27-4.24 (m, 2H), 4.11-4.08 (m, 1H), 3.26 (s, 3H).

REFERENCES

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun.* Vol. 69: 832-837.

Barondes, S. H., Cooper, D. N. W., Gitt, M. A., and Leffler, H. (1994). Galectins. Structure and function of a large family of animal lectins. *J. Biol. Chem.* 269:20807-20810.

Blois, S. M., Ilarregui, J. M., Tometten, M., Garcia, M., Orsal, A. S., Cordo-Russo, R., Toscano, M. A., Bianco, G. A., Kobelt, P., Handjiski, B., et al. (2007). A pivotal role for galectin-1 in fetomaternal tolerance. *Nat Med* 13: 1450-1457.

Chen, W.-S., Leffler H., Nilsson, U. J., Panjwani, N. (2012). Targeting Galectin-1 and Galectin-3 Attenuates VEGF-A-induced Angiogenesis; *Mol. Biol. Cell* (suppl), Abstract No. 2695.

Cumpstey, I., Carlsson, S., Leffler, H. and Nilsson, U. J. (2005) Synthesis of a phenyl thio-β-D-galactopyranoside library from 1,5-difluoro-2,4-dinitrobenzene: discovery of efficient and selective monosaccharide inhibitors of galectin-7. *Org. Biomol. Chem.* 3: 1922-1932.

Cumpstey, I., Sundin, A., Leffler, H. and Nilsson, U. J. (2005) C$_2$-Symmetrical thiodigalactoside bis-benzamido derivatives as high-affinity inhibitors of galectin-3: Efficient lectin inhibition through double arginine-arene interactions. *Angew. Chem. Int. Ed.* 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. *Chem. Eur. J.* 14: 4233-4245.

Dam, T. K., and Brewer, C. F. (2008). Effects of clustered epitopes in multivalent ligand-receptor interactions. *Biochemistry* 47: 8470-8476.

Delacour, D., Greb, C., Koch, A., Salomonsson, E., Leffler, H., Le Bivic, A., and Jacob, R. (2007). Apical Sorting by Galectin-3-Dependent Glycoprotein Clustering. *Traffic* 8: 379-388.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. *J Med Chem* 51; 8109-8114.

Demotte, N., Wieers, G., van der Smissen, P., Moser, M., Schmidt, C., Thielemans, K., et al., (2010). *Cancer Res.* 70; 7476-7488.

Farkas, I.; Szabó, I. F.; Bognár, R.; Anderle, D. Carbohydr. Res. 1976, 48, 136-138.

Garner, O. B., and Baum, L. G. (2008). Galectin-glycan lattices regulate cell-surface glycoprotein organization and signalling. *Biochem Soc Trans* 36: 1472-1477.

Giguere, D., Patnam, R., Bellefleur, M.-A., St.-Pierre, C., Sato, S., and Roy, R. (2006). Carbohydrate triazoles and isoxazoles as inhibitors of galectins-1 and -3. *Chem Commun:* 2379-2381.

Glinsky, G. V., Price, J. E., Glinsky, V. V., Mossine, V. V., Kiriakova, G., and Metcalf, J. B. (1996). *Cancer Res* 56: 5319-5324.

Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. *Neoplasia* 11; 901-909.

Huflejt, M. E. and Leffler, H. (2004) Galectin-4 in normal tissues and cancer. *Glycoconj. J.* 20: 247-255.

Ingrassia et al. (2006) A Lactosylated Steroid Contributes in Vivo Therapeutic Benefits in Experimental Models of Mouse Lymphoma and Human Glioblastoma. *J. Med. CHem.* 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast Cancer. *Clin. Cancer Res.* 9: 2374-2383.

Kouo, T., Huang, L., Pucsek, A. B., Cao, M., Solt, S., Armstrong, T., Jaffee, E. (2015) *Cancer Immonol. Res.* 3: 412-23

Lau, K. S., and Dennis, J. W. (2008). N-Glycans in cancer progression. *Glycobiology* 18: 750-760.

Lau, K. S., Partridge, E. A., Grigorian, A., Silvescu, C. I., Reinhold, V. N., Demetriou, M., and Dennis, J. W. (2007). Complex N-glycan number and degree of branching cooperate to regulate cell proliferation and differentiation. *Cell* 129: 123-134.

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lin, C.-I., Whang, E. E., Donner, D. B., Jiang, X., Price, B. D., Carothers, A. M., Delaine, T., Leffler, H., Nilsson, U. J., Nose, V., et al. (2009). Galectin-3 Targeted Therapy with a Small Molecule Inhibitor Activates Apoptosis and Enhances Both Chemosensitivity and Radiosensitivity in Papillary Thyroid Cancer. *Mol Cancer Res* 7: 1655-1662.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.*, in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Melero, I., Berman, D. M., Aznar, M. A., Korman, A. J., Gracia, J. L. P., Haanen, J. (2015) *Nature Reviews Cancer,* 15: 457-472

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Perone, M. J., Bertera, S., Shufesky, W. J., Divito, S. J., Montecalvo, A., Mathers, A. R., Larregina, A. T., Pang, M., Seth, N., Wucherpfennig, K. W., et al. (2009). Suppression of autoimmune diabetes by soluble galectin-1. *J Immunol* 182: 2641-2653.

Pienta, K. J., Naik, H., Akhtar, A., Yamazaki, K., Reploge, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Ramos-Soriano, J.; Niss, U.; Angulo, J.; Angulo, M.; Moreno-Vargas, A. J.; Carmona, A. T.; Ohlson, S.; Robina, I. Chem. Eur. J. 2013, 19, 17989-18003.

Ruvolo, P. P. *Biochim. Biophys Acta*. Molecular cell research (2015) E-pub ahead of print, title: Galectin-3 as a guardian of the tumor microenvironment, published on-line 8 Apr. 2015: (http://www.sciencedirect.com/science/article/pii/S0167488915002700), Saegusa, J., Hsu, D. K., Chen, H. Y., Yu, L., Fermin, A., Fung, M. A., and Liu, F. T. (2009). Galectin-3 is critical for the development of the allergic inflammatory response in a mouse model of atopic dermatitis. *Am J Pathol* 174: 922-931.

Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Shah, P.; Jogani, V.; Bagchi, T.; Misra, A. Role of Caco-2 Cell Monolayers in Prediction of Intestinal Drug Absorption. *Biotechnol. Prog.* 2006, 22 (1), 186-198.

Sörme, P., Qian, Y., Nyholm, P.-G., Leffler, H., Nilsson, U. J. (2002) Low micromolar inhibitors of galectin-3 based on 3'-derivatization of N-acetyllactosamine. *Chem Bio Chem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Thijssen, V. L., Poirer, F., Baum, L. G., and Griffioen, A. W. (2007). Galectins in the tumor endothelium: opportunities for combined cancer therapy. *Blood* 110: 2819-2827.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

We claim:

1. A method for treatment of a disorder relating to the binding of a galectin-3 to a ligand in a mammal, wherein a therapeutically effective amount of at least one compound of formula (1) is administered to a mammal in need of said treatment, wherein said compound of formula (1) is a D-galactopyranose compound of formula (1)

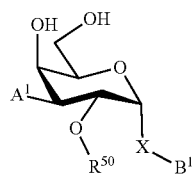
(1)

wherein
the pyranose ring is α-D-galactopyranose,
$A^1$ is selected from

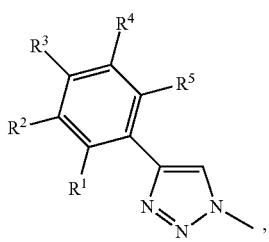
2

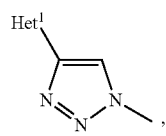
3

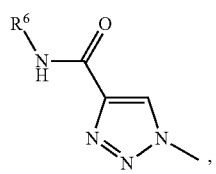
4

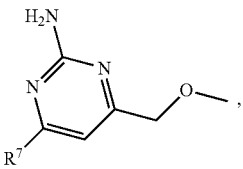
5

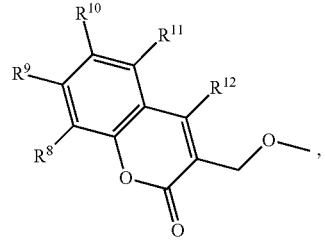
6

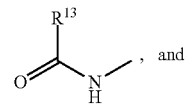
7

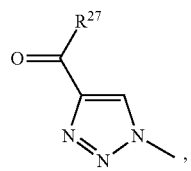
8 wherein $Het^1$ is selected from a five or six membered heteroaromatic ring, optionally substituted with a group selected from Br; F; Cl; I; CN; $NR^{19}R^{20}$, wherein $R^{19}$ and $R^{20}$ are independently selected from H, $C_{1-3}$ alkyl, cyclopropyl, iso-propyl, —C(=O)—$R^{21}$, wherein $R^{21}$ is selected from H and $C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-iso-propyl optionally substituted with a F; $OC_{1-3}$ alkyl optionally substituted with a F; and $SC_{1-3}$ alkyl optionally substituted with a F;

wherein $R^1$-$R^5$ are independently selected from H, CN, $NH_2$, Br, Cl, I, F, methyl optionally substituted with a F, $SCH_3$ optionally substituted with a F, and $OCH_3$ optionally substituted with a F;

wherein $R^6$ is selected from $C_{1-6}$ alkyl optionally substituted with a halogen, branched $C_{3-6}$ alkyl and $C_{3-7}$ cycloalkyl;

wherein $R^7$ is selected from a five or six membered heteroaromatic ring, optionally substituted with a group selected from Br, F, Cl, methyl optionally substituted with a F, and $OCH_3$ optionally substituted with a F, and a phenyl optionally substituted with a group selected from Br, F, Cl, methyl optionally substituted with a F, and $OCH_3$ optionally substituted with a F;

wherein $R^8$-$R^{12}$ are independently selected from H, F, methyl optionally substituted with a F, and $OCH_3$ optionally substituted with a F;

wherein $R^{13}$ is a five or six membered heteroaromatic ring optionally substituted with a group selected from H, OH, F, methyl optionally substituted with a F, and $OCH_3$ optionally substituted with a F, a phenyl or a naphthyl, optionally substituted with a group selected from H, OH, F, methyl optionally substituted with a F, and $OCH_3$ optionally substituted with a F;

X is selected from S, SO, SO$_2$, O, C═O, and CR$^7$R$^8$ wherein R$^7$ and R$^8$ are independently selected from hydrogen, OH, or halogen;

wherein R$^{27}$ is selected from a C$_{1-6}$ alkyl, branched C$_{3-6}$ alkyl, C$_{1-6}$ alkoxy and branched C$_{3-6}$ alkoxy;

B$^1$ is selected from a pyridinyl, optionally substituted with a group selected from a halogen; a N (2 oxa)-6-azaspiro [3.3]heptanyl; CN; —COOH; —CONR$^{24}$R$^{25}$, wherein R$^{24}$ and R$^{25}$ are independently selected from H, C$_{1-3}$ alkyl, cyclopropyl, and iso-propyl or R$^{24}$ and R$^{25}$ together with the nitrogen may form a heterocycloalkyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{30}$R$^{31}$, wherein R$^{30}$ and R$^{31}$ are independently selected from H, C$_{1-3}$ alkyl and isopropyl; OH; R$^{18}$—CONH— wherein R$^{18}$ is selected from C$_{1-3}$ alkyl and cyclopropyl; a pyrimidinyl optionally substituted with a substituent selected from CN, a halogen, methyl optionally substituted with a F, OCH$_3$ optionally substituted with a F, OCH$_2$CH$_3$ optionally substituted with a F, OH, and R$^{71}$—CONH— wherein R$^{71}$ is selected from C$_{1-3}$ alkyl and cyclopropyl; a pyridinyl optionally substituted with a substituent selected from CN, a halogen, methyl optionally substituted with a F, OCH$_3$ optionally substituted with a F, OCH$_2$CH$_3$ optionally substituted with a F, OH, and R$^{72}$—CONH— wherein R$^{72}$ is selected from C$_{1-3}$ alkyl and cyclopropyl; a tetrahydropyridinyl optionally substituted with a substituent selected from CN, a halogen, methyl optionally substituted with a F, OCH$_3$ optionally substituted with a F, OCH$_2$CH$_3$ optionally substituted with a F, OH, and R$^{73}$—CONH— wherein R$^{73}$ is selected from C$_{1-3}$ alkyl and cyclopropyl; a pyrrolinyl optionally substituted with a substituent selected from CN, a halogen, methyl optionally substituted with a F, OCH$_3$ optionally substituted with a F, OCH$_2$CH$_3$ optionally substituted with a F, OH, and R$^{74}$—CONH— wherein R$^{74}$ is selected from C$_{1-3}$ alkyl and cyclopropyl; an oxazolyl optionally substituted with a substituent selected from CN, a halogen, methyl optionally substituted with a F, OCH$_3$ optionally substituted with a F, OCH$_2$CH$_3$ optionally substituted with a F, OH, and R$^{75}$—CONH— wherein R$^{75}$ is selected from C$_{1-3}$ alkyl and cyclopropyl; a thiazolyl optionally substituted with a substituent selected from CN, a halogen, methyl optionally substituted with a F, OCH$_3$ optionally substituted with a F, OCH$_2$CH$_3$ optionally substituted with a F, OH, and R$^{76}$—CONH— wherein R$^{76}$ is selected from C$_{1-3}$ alkyl and cyclopropyl; and a C$_{2-4}$ alkynyl;

R$^{50}$ is selected from the group consisting of a) C$_{1-6}$ alkyl optionally substituted with one or more halogen, CN, OR$^{51}$, NR$^{52}$R$^{53}$, and CONH$_2$, wherein R$^{51}$ is selected from the group consisting of H, CN, a halogen, methyl optionally substituted with a F, OCH$_3$ optionally substituted with a F, OCH$_2$CH$_3$ optionally substituted with a F, OH, and R$^{54}$—CONH— wherein R$^{54}$ is selected from C$_{1-3}$ alkyl and cyclopropyl, R$^{52}$ is selected from the group consisting of H, CN, a halogen, methyl optionally substituted with a F, OCH$_3$ optionally substituted with a F, OCH$_2$CH$_3$ optionally substituted with a F, OH, and R$^{55}$—CONH— wherein R$^{55}$ is selected from C$_{1-3}$ alkyl and cyclopropyl, and R$^{53}$ is selected from the group consisting of H, CN, a halogen, methyl optionally substituted with a F, OCH$_3$ optionally substituted with a F, OCH$_2$CH$_3$ optionally substituted with a F, OH, and R$^{56}$—CONH— wherein R$^{56}$ is selected from C$_{1-3}$ alkyl and cyclopropyl, b) branched C$_{3-6}$ alkyl optionally substituted with one or more halogen, CN, OR$^{57}$, NR$^{58}$R$^{59}$, and CONH$_2$, wherein R$^{57}$ is selected from the group consisting of H, CN, a halogen, methyl optionally substituted with a F, OCH$_3$ optionally substituted with a F, OCH$_2$CH$_3$ optionally substituted with a F, OH, and R$^{60}$—CONH— wherein R$^{60}$ is selected from C$_{1-3}$ alkyl and cyclopropyl, R$^{58}$ is selected from the group consisting of H, CN, a halogen, methyl optionally substituted with a F, OCH$_3$ optionally substituted with a F, OCH$_2$CH$_3$ optionally substituted with a F, OH, and R$^{61}$—CONH— wherein R$^{61}$ is selected from C$_{1-3}$ alkyl and cyclopropyl, and R$^{59}$ is selected from the group consisting of H, CN, a halogen, methyl optionally substituted with a F, OCH$_3$ optionally substituted with a F, OCH$_2$CH$_3$ optionally substituted with a F, OH, and R$^{62}$—CONH— wherein R$^{62}$ is selected from C$_{1-3}$ alkyl and cyclopropyl, and c) cyclic C$_{3-6}$ alkyl optionally substituted with one or more halogen, CN, OR$^{63}$, NR$^{64}$R$^{65}$, and CONH$_2$, wherein R$^{63}$ is selected from the group consisting of H, CN, a halogen, methyl optionally substituted with a F, OCH$_3$ optionally substituted with a F, OCH$_2$CH$_3$ optionally substituted with a F, OH, and R$^{66}$—CONH— wherein R$^{66}$ is selected from C$_{1-3}$ alkyl and cyclopropyl, R$^{64}$ is selected from the group consisting of H, CN, a halogen, methyl optionally substituted with a F, OCH$_3$ optionally substituted with a F, OCH$_2$CH$_3$ optionally substituted with a F, OH, and R$^{67}$—CONH— wherein R$^{67}$ is selected from C$_{1-3}$ alkyl and cyclopropyl, and R$^{65}$ is selected from the group consisting of H, CN, a halogen, methyl optionally substituted with a F, OCH$_3$ optionally substituted with a F, OCH$_2$CH$_3$ optionally substituted with a F, OH, and R$^{68}$—CONH— wherein R$^{68}$ is selected from C$_{1-3}$ alkyl and cyclopropyl; or a pharmaceutically acceptable salt thereof, wherein the disorder is selected from the group consisting of: inflammation; fibrosis selected from pulmonary fibrosis, liver fibrosis, kidney fibrosis, ophthalmological fibrosis, fibrosis of the skin, and fibrosis of the heart; scarring; keloid formation; aberrant scar formation; surgical adhesions; septic shock; cancers selected from carcinomas, sarcomas, leukemias, lymphomas, and metastasising cancers; autoimmune diseases selected from psoriasis, rheumatoid arthritis, Crohn's disease, ulcerative colitis, ankylosing spondylitis, and systemic lupus erythematosus; metabolic disorders; heart disease; heart failure; pathological angiogenesis, ocular angiogenesis or a disease or condition associated with ocular angiogenesis; neovascularization related to cancer; eye diseases selected from age-related macular degeneration and corneal neovascularization; atherosclerosis; metabolic diseases; diabetes; type 2 diabetes; insulin resistens; obesity; Diastolic HF; interstitial lung diseases selected from asthma, Hermansky-Pudlak syndrome, and mesothelioma; and liver disorders selected from non-alcoholic steatohepatitis and non-alcoholic fatty liver disease.

2. The method for treatment of claim 1, wherein A$^1$ is selected from formula 3 wherein Het$^1$ is selected from a five membered heteroaromatic ring, optionally substituted with a group independently selected from H, CN, Br, Cl, I, F, methyl optionally substituted with a F, OCH$_3$ optionally substituted with a F, and SCH$_3$ optionally substituted with a F.

3. The method for treatment of claim 1, wherein X is S.

4. The method for treatment of claim 1, wherein B¹ is selected from a pyridinyl optionally substituted with a group independently selected from a Cl, Br, methyl, CF$_3$, OCH$_3$, N-(2-oxa)-6-azaspiro[3.3]heptanyl, OH, NH$_2$, CONH$_2$, —CONR$^{24}$R$^{25}$, wherein R$^{24}$ and R$^{25}$ together with the nitrogen may form a heterocycloalkyl, CN, ethynyl, pyrimidinyl, pyridinyl, tetrahydropyridinyl, pyrrolidinyl, oxazolyl, thiazolyl.

5. The method for treatment of claim 1, wherein R$^{50}$ is selected from a C$_{1-4}$ alkyl.

6. The method for treatment of claim 1, wherein the compound is selected from the group consisting of:

5-Bromopyridin-3-yl 3-deoxy-3-[4-(3,4,5-trifluorophenyl)-1H-1,2,3-triazol-1-yl]-2-O-methyl-1-thio-α-D-galactopyranoside, 5-Bromo-2-cyano-pyridin-3-yl 3-deoxy-3-[4-(3-fluoro-4-methylphenyl)-1H-1,2,3-triazol-1-yl]-2-O-methyl-1-thio-α-D-galactopyranoside, 5-Bromopyridin-3-yl 3-deoxy-3-[4-(3,4,5-trifluorophenyl)-1H-1,2,3-triazol-1-yl]-2-O-(1,1,1-trifluoro-2-hydroxyprop-3-yl)-1-thio-α-D-galactopyranoside, 5-Chloro-2-(N,N-dimethylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside, 5-Chloro-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-2-cyano-pyridin-3-yl 3-deoxy-3-[4-(3,5-difluoro-4-methylphenyl)-1H-1,2,3-triazol-1-yl]-2-O-methyl-1-thio-α-D-galactopyranoside, 5-Chloro-2-cyano-pyridin-3-yl 3-deoxy-3-[4-(3-fluoro-4-methyl-phenyl)-1H-1,2,3-triazol-1-yl]-2-O-methyl-1-thio-α-D-galactopyranoside, 5-Chloro-2-cyano-pyridin-3-yl 3-deoxy-2-O-2,2,2-trifluoroethyl-3-[4-(3,4,5-trifluoro-phenyl)-1H-1,2,3-triazol-1-yl]-1-thio-α-D-galactopyranoside, 5-Chloro-2-cyano-pyridin-3-yl 3-deoxy-2-O-ethyl-3-[4-(3,4,5-trifluoro-phenyl)-1H-1,2,3-triazol-1-yl]-1-thio-α-D-galactopyranoside, 5-Bromopyridin-3-yl 3-deoxy-3-[4-(3,4,5-trifluorophenyl)-1H-1,2,3-triazol-1-yl]-2-O-ethyl-1-thio-α-D-galactopyranoside, 5-Bromopyridin-3-yl 3-deoxy-3-[4-(3,4,5-trifluorophenyl)-1H-1,2,3-triazol-1-yl]-2-O-isopropyl-1-thio-α-D-galactopyranoside, 5-Bromopyridin-3-yl 3-deoxy-3-[4-(3,4,5-trifluorophenyl)-1H-1,2,3-triazol-1-yl]-2-O-(2-fluoroethyl)-1-thio-α-D-galactopyranoside, 5-Bromopyridin-3-yl 3-deoxy-3-[4-(3,4,5-trifluorophenyl)-1H-1,2,3-triazol-1-yl]-2-O-[2-(methylamino)ethyl]-1-thio-α-D-galactopyranoside, 5-Chloro-6-cyano-2-{N-(2-oxa)-6-azaspiro[3.3]heptanyl}-pyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-6-cyano-2-{N-(2-oxa)-6-azaspiro[3.3]heptanyl}-pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyrimidin-5-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-3-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(pyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(1,2,3,6-tetrahydropyridin-4-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(3-pyrrolin-3-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(oxazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 2,5-Bis(thiazol-2-yl)pyridin-3-yl 3-deoxy-3-[4-(3,4,5-trifluorophenyl)-1H-1,2,3-triazol-1-yl]-2-O-methyl-1-thio-α-D-galactopyranoside, 5-Chloropyridin-3-yl 3-[4-(4-chloro-3,5-difluorophenyl)-1H-1,2,3-triazol-1-yl]-3-deoxy-2-O-methyl-1-thio-α-D-galactopyranoside, 5-Bromopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloropyridin-3-yl 3-deoxy-3-[4-(3-fluoro-4-methylphenyl)-1H-1,2,3-triazol-1-yl]-2-O-methyl-1-thio-α-D-galactopyranoside, 5-Bromopyridin-3-yl 3-deoxy-3-[4-(3-fluoro-4-methylphenyl)-1H-1,2,3-triazol-1-yl]-2-O-methyl-1-thio-α-D-galactopyranoside, 5-Chloropyridin-3-yl 3-[4-(4-chloro-3-fluorophenyl)-1H-1,2,3-triazol-1-yl]-3-deoxy-2-O-methyl-1-thio-α-D-galactopyranoside, 5-Bromopyridin-3-yl 3-[4-(4-chloro-3-fluorophenyl)-1H-1,2,3-triazol-1-yl]-3-deoxy-2-O-methyl-1-thio-α-D-galactopyranoside, 6-Trifluoromethyl-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloropyridin-3-yl 3-deoxy-3-[4-(3,4,5-trifluorophenyl)-1H-1,2,3-triazol-1-yl]-2-O-methyl-1-thio-α-D-galactopyranoside, 5-Chloropyridin-3-yl 3-deoxy-3-[4-(6-fluoro-5-methylpyridin-2-yl)-1H-1,2,3-triazol-1-yl]-2-O-methyl-1-thio-α-D-galactopyranoside, 5-Chloropyridin-3-yl 3-[4-(5-chloro-6-methylpyridin-2-yl)-1H-1,2,3-triazol-1-yl]-3-deoxy-2-O-methyl-1-thio-α-D-galactopyranoside, 3-Chloro-2-cyanopyridin-5-yl 3-deoxy-3-[4-(3,4,5-trifluorophenyl)-1H-1,2,3-triazol-1-yl]-2-O-methyl-1-thio-α-D-galactopyranoside, 5-Chloro-2-cyanopyridin-3-yl 3-deoxy-3-[4-(3,4,5-trifluorophenyl)-1H-1,2,3-triazol-1-yl]-2-O-methyl-1-thio-α-D-galactopyranoside, 5-Chloro-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside, 5-Chloro-2-cyanopyridin-3-yl 3-[4-(4-chloro-3-fluorophenyl)-1H-1,2,3-triazol-1-yl]-3-deoxy-2-O-methyl-1-thio-α-D-galactopyranoside,
2-Cyano-5-methylpyridin-3-yl 3-[4-(4-chloro-3,5-difluorophenyl)-1H-1,2,3-triazol-1-yl]-3-deoxy-2-O-methyl-1-thio-α-D-galactopyranoside,
5-Bromo-2-cyanopyridin-3-yl 3-[4-(4-chloro-3,5-difluorophenyl)-1H-1,2,3-triazol-1-yl]-3-deoxy-2-O-methyl-1-thio-α-D-galactopyranoside,
5-Bromo-2-cyanopyridin-3-yl 3-[4-(4-chloro-3-fluorophenyl)-1H-1,2,3-triazol-1-yl]-3-deoxy-2-O-methyl-1-thio-α-D-galactopyranoside,
5-Chloro-2-(N-azetidinylcarbamoyl)-3-pyridyl 3-[4-(4-chloro-3,5-difluorophenyl)-1H-1,2,3-triazol-1-yl]-3-deoxy-2-O-methyl-1-thio-α-D-galactopyranoside,
5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside,
5-Ethynylpyridin-3-yl 3-[4-(4-chloro-3,5-difluorophenyl)-1H-1,2,3-triazol-1-yl]-3-deoxy-2-O-methyl-1-thio-α-D-galactopyranoside,
5-Chloro-2-cyanopyridin-3-yl 3-[4-(5-chloro-6-fluoropyridin-2-yl)-1H-1,2,3-triazol-1-yl]-3-deoxy-2-O-methyl-1-thio-α-D-galactopyranoside,
2-Cyano-5-ethynylpyridin-3-yl 3-[4-(4-chloro-3,5-difluorophenyl)-1H-1,2,3-triazol-1-yl]-3-deoxy-2-O-methyl-1-thio-α-D-galactopyranoside,
2-Cyano-5-ethynylpyridin-3-yl 3-deoxy-3-[4-(3,5-difluoro-4-methylphenyl)-1H-1,2,3-triazol-1-yl]-2-O-methyl-1-thio-α-D-galactopyranoside,
5-Cyano-6-trifluoromethylpyridin-3-yl 3-[4-(4-chloro-3,5-difluorophenyl)-1H-1,2,3-triazol-1-yl]-3-deoxy-2-O-methyl-1-thio-α-D-galactopyranoside,
5-Cyanopyridin-3-yl 3-deoxy-3-[4-(3,4,5-trifluorophenyl)-1H-1,2,3-triazol-1-yl]-2-O-methyl-1-thio-α-D-galactopyranoside,
5-Cyanopyridin-3-yl 3-[4-(4-chloro-3,5-difluorophenyl)-1H-1,2,3-triazol-1-yl]-3-deoxy-2-O-methyl-1-thio-α-D-galactopyranoside,
5-Bromo-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside,
5-Bromo-2-(N-azetidinylcarbamoyl)-3-pyridyl 3-deoxy-3-[4-(3,4,5-trifluorophenyl)-1H-1,2,3-triazol-1-yl]-2-O-methyl-1-thio-α-D-galactopyranoside,
5-Bromo-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside,
5-Chloro-2-(N-azetidinylcarbamoyl)-3-pyridyl 3-[4-(4-chloro-3-fluorophenyl)-1H-1,2,3-triazol-1-yl]-3-deoxy-2-O-methyl-1-thio-α-D-galactopyranoside,
5-Chloro-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside,
5-Chloro-2-(N-azetidinylcarbamoyl)-3-pyridyl 3-[4-(4-chloro-3-fluorophenyl)-1H-1,2,3-triazol-1-yl]-3-deoxy-2-O-ethyl-1-thio-α-D-galactopyranoside, and
5-Chloro-2-(N-azetidinylcarbamoyl)-3-pyridyl 3-[4-(4-chloro-3,5-difluorophenyl)-1H-1,2,3-triazol-1-yl]-3-deoxy-2-O-ethyl-1-thio-α-D-galactopyranoside;
or a pharmaceutically acceptable salt or solvate thereof.

7. The method for treatment of claim 1, wherein the treatment is combination therapy.

8. The method for treatment of claim 1, wherein $R^{50}$ is methyl.

9. The method for treatment of claim 1, wherein the disorder is cancer selected from the group consisting of: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia, acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, T cell leukemia, small non-small cell lung carcinoma, large non-small cell lung carcinoma, acute granulocytic leukemia, germ cell tumors, endometrial cancer, gastric cancer, cancer of the head, cancer of the neck, chronic lymphoid leukemia, hairy cell leukemia and thyroid cancer.

10. The method for treatment of claim 9, wherein the treatment is combination therapy.

11. The method for treatment of claim 10, wherein the combination treatment comprises treatment with an antifibrotic compound selected from the group consisting of pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, PAT-1251 and PBI-4050.

12. The method for treatment of claim 10, wherein the combination treatment comprises treatment with an antineoplastic chemotherapy agent selected from the group consisting of all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine, Vinorelbine, irinotecan, 5-fluorouracil, leucovorin, and oxaliplatin.

13. The method for treatment of claim 10, wherein the combination treatment comprises treatment with an immunostimulating substances selected from the group consisting of cytokines selected from GM-CSF, type I IFN, interleukin 21, interleukin 2, interleukin 12 and interleukin 15; antibodies selected from anti-CD40 antibodies and anti-CTLA-4 antibodies; regulatory T-cells; and E3 ubiquitin ligases.

14. The method for treatment of claim 10, wherein the combination treatment comprises treatment with a checkpoint inhibitor is selected from the group consisting of an Anti-PD 1 inhibitor selected from Nivolumab, Pembrolizumab, and Cemiplimab; an Anti-PD-L1 inhibitor selected from Atezolizumab, Avelumab, and Durvalumab; and an Anti-CTLA 4 inhibitor that is Ipilimumab.

15. The method for treatment of claim 10, wherein the combination treatment comprises treatment with antibodies against CTLA4.

16. The method for treatment of claim 10, wherein the combination treatment comprises treatment with one or more antibodies against PD-1, PD-L1, and/or PD-L2.

* * * * *